US012700511B2

(12) United States Patent　　　　(10) Patent No.:　US 12,700,511 B2
Senapathy et al.　　　　　　　　　　(45) Date of Patent:　　Aug. 4, 2026

(54) PRECISION MEDICINE PORTAL FOR HUMAN DISEASES

(71) Applicant: Genome International Corporation, Madison, WI (US)

(72) Inventors: Periannan Senapathy, Madison, WI (US); Sudar Senapathy, Madison, WI (US)

(73) Assignee: GENOME INTERNATIONAL CORPORATION, Madison, WI (US)

( * ) Notice: Subject to any disclaimer, the term of this patent is extended or adjusted under 35 U.S.C. 154(b) by 994 days.

(21) Appl. No.: 17/698,905

(22) Filed: Mar. 18, 2022

(65) Prior Publication Data

US 2022/0319637 A1　　Oct. 6, 2022

Related U.S. Application Data

(63) Continuation of application No. PCT/US2021/047027, filed on Aug. 20, 2021.

(Continued)

(51) Int. Cl.
　　G16B 20/50　　　　(2019.01)
　　C12Q 1/6825　　　(2018.01)
　　(Continued)

(52) U.S. Cl.
　　CPC ........... G16B 20/50 (2019.02); C12Q 1/6825 (2013.01); C12Q 1/6883 (2013.01); G16B 20/10 (2019.02);
　　(Continued)

(58) Field of Classification Search
　　CPC ........ G16B 20/50; G16B 20/10; G16B 20/20; G16B 25/10; G16B 30/00; G16B 30/10;
　　(Continued)

(56) References Cited

U.S. PATENT DOCUMENTS

2004/0267458 A1*　12/2004　Judson ................... G16B 20/40
　　　　　　　　　　　　　　　　　　　　　　　702/20
2005/0221313 A1*　10/2005　Sperling .............. A61K 48/005
　　　　　　　　　　　　　　　　　　　　　　　435/6.13
(Continued)

FOREIGN PATENT DOCUMENTS

EP　　　　2773954 B1　　3/2018
JP　　　2020525887 A　　8/2020
　　　　　　(Continued)

OTHER PUBLICATIONS

Caminsky N, Mucaki EJ, Rogan PK. Interpretation of mRNA splicing mutations in genetic disease: review of the literature and guidelines for information-theoretical analysis. F1000Res. Nov. 18, 2014;3:282. doi: 10.12688/f1000research.5654.1. PMID: 25717368; PMCID: PMC4329672. (Year: 2014).*

(Continued)

*Primary Examiner* — Sun M Li
(74) *Attorney, Agent, or Firm* — Knobbe Martens Olson & Bear LLP

(57)　　　　　　　　ABSTRACT

A method for genome analysis is provided. The method includes receiving a nucleotide string comprising a plurality of nucleotides from at least a portion of one or more individual patients' genome. The method also includes identifying a plurality of variants in said nucleotide string, assigning each identified variant a score based on a location of a variant and a predicted functional consequence, and determining a strength of a variation responsible for a trait or phenotypic manifestation of the variants. The method also includes identifying at least one phenotype, and displaying, in a graphic unit interface of a client device, said nucleotide string, the identified variants, and the at least one phenotype, in one or more genetic elements for one or more individual patients. A system and a non-transitory, computer-readable (Continued)

medium storing instructions to perform the above method are also provided.

25 Claims, 48 Drawing Sheets

Specification includes a Sequence Listing.

Related U.S. Application Data

(60) Provisional application No. 63/166,829, filed on Mar. 26, 2021, provisional application No. 63/166,803, filed on Mar. 26, 2021.

(51) Int. Cl.

| | |
|---|---|
| *C12Q 1/6883* | (2018.01) |
| *G16B 20/10* | (2019.01) |
| *G16B 20/20* | (2019.01) |
| *G16B 25/10* | (2019.01) |
| *G16B 30/00* | (2019.01) |
| *G16B 30/10* | (2019.01) |
| *G16B 40/20* | (2019.01) |
| *G16B 45/00* | (2019.01) |
| *G16H 15/00* | (2018.01) |
| *G16H 20/10* | (2018.01) |
| *G16H 50/20* | (2018.01) |
| *G16H 50/30* | (2018.01) |
| *G16H 50/70* | (2018.01) |
| *G16H 70/40* | (2018.01) |

(52) U.S. Cl.
CPC ............. *G16B 20/20* (2019.02); *G16B 25/10* (2019.02); *G16B 30/00* (2019.02); *G16B 30/10* (2019.02); *G16B 40/20* (2019.02); *G16B 45/00* (2019.02); *G16H 15/00* (2018.01); *G16H 20/10* (2018.01); *G16H 50/20* (2018.01); *G16H 50/30* (2018.01); *G16H 50/70* (2018.01); *G16H 70/40* (2018.01)

(58) Field of Classification Search
CPC ........ G16B 40/20; G16B 45/00; G16B 50/10; C12Q 1/6825; C12Q 1/6883; C12Q 1/6869; C12Q 2600/156; G16H 15/00; G16H 20/10; G16H 50/20; G16H 50/30; G16H 50/70; G16H 70/40; G16H 10/20
See application file for complete search history.

(56) References Cited

U.S. PATENT DOCUMENTS

| | | | | |
|---|---|---|---|---|
| 2016/0085909 | A1* | 3/2016 | Reese .................... | G16C 20/60 |
| | | | | 702/19 |
| 2016/0237487 | A1 | 8/2016 | Yu et al. | |
| 2016/0357903 | A1* | 12/2016 | Shendure ............... | G16B 30/00 |
| 2018/0051326 | A1* | 2/2018 | Rogan .................... | G16B 20/00 |
| 2019/0114391 | A1* | 4/2019 | Jaganathan ............ | G16B 40/20 |
| 2019/0114547 | A1 | 4/2019 | Jaganathan et al. | |
| 2019/0197401 | A1 | 6/2019 | Jaganathan et al. | |
| 2020/0152288 | A1* | 5/2020 | Srinivasan ............. | G16B 30/10 |
| 2022/0307026 | A1 | 9/2022 | Senapathy et al. | |
| 2022/0310201 | A1 | 9/2022 | Senapathy et al. | |
| 2022/0310274 | A1 | 9/2022 | Senapathy et al. | |
| 2022/0310275 | A1 | 9/2022 | Senapathy et al. | |
| 2022/0316009 | A1 | 10/2022 | Senapathy et al. | |
| 2023/0122305 | A1 | 4/2023 | Senapathy et al. | |
| 2023/0154567 | A1 | 5/2023 | Senapathy et al. | |

FOREIGN PATENT DOCUMENTS

| | | | | |
|---|---|---|---|---|
| WO | | 03-078660 A2 | 9/2003 | |
| WO | | WO-2019226804 A1 * | 11/2019 | ............ G16B 40/30 |

OTHER PUBLICATIONS

Marian AJ. Clinical Interpretation and Management of Genetic Variants. JACC Basic Transl Sci. Oct. 26, 2020;5(10):1029-1042. doi: 10.1016/j.jacbts.2020.05.013. PMID: 33145465; PMCID: PMC7591931. (Year: 2020).*

Magi A, D'Aurizio R, Palombo F, Cifola I, Tattini L, Semeraro R, Pippucci T, Giusti B, Romeo G, Abbate R, Gensini GF. Characterization and identification of hidden rare variants in the human genome. BMC Genomics. Apr. 24, 2015; 16(1):340. doi: 10.1186/s12864-015-1481-9. PMID: 25903059; PMCID: PMC4416239. (Year: 2015).*

Vreeswijk, M. P. G.; Kraan, J. N.; Van Der Klift, H. M.; Vink, G. R.; Cornelisse, C. J.; Wijnen, J. T.; Bakker, E.; Van Asperen, C. J.; Devilee, P. Intronic Variants in BRCA1 and BRCA2 That Affect RNA Splicing Can Be Reliably Selected by Splice-Site Prediction Programs. Human Mutation 2009, 30 (1), (Year: 2009).*

Garrido-Martín D, Borsari B, Calvo M, Reverter F, Guigó R. Identification and analysis of splicing quantitative trait loci across multiple tissues in the human genome. Nat Commun. Feb. 1, 2021;12(1):727. doi: 10.1038/s41467-020-20578-2. PMID: 33526779; PMCID: PMC7851174. (Year: 2021).*

Vitsios D, Dhindsa RS, Middleton L, Gussow AB, Petrovski S. Prioritizing non-coding regions based on human genomic constraint and sequence context with deep learning. Nat Commun. Mar. 8, 2021;12(1):1504. doi: 10.1038/s41467-021-21790-4. PMID: 33686085; PMCID: PMC7940646. (Year: 2021).*

International Search Report and Written Opinion mailed Dec. 20, 2021 in the corresponding PCT Application No. PCT/US2021/047025 (10 pages).

International Search Report and Written Opinion mailed Dec. 20, 2021 in the corresponding PCT Application No. PCT/US2021/047027 (8 pages).

Woods, Tony et al., "Characterizing exons and introns by regularity of nucleotide strings", Biology Direct, 2016, vol. 11, Article No. 6, pp. 1-17. (17 pages).

Abramowicz et al., Splicing mutations in human genetic disorders: Example, detection, and confirmation, J Applied Genetics. Aug. 2018; 59:253-268.

Bhasi et al., EuSplice: A Unified Resource for the Analysis of Splice Signals and Alternative Splicing in Eukaryotic Genes. Bioinform Jul. 15, 2007;23(14): 1815-1823.

Canson et al., Variant effect on splicing regulatory elements, branchpoint usage, and pseudoexonization: Strategies to enhance bioinformatic prediction using hereditary cancer genes as exemplars, Human Mut. Oct. 2020;41(10):1705-1721.

Crist et al., Pharmacogenetics of Opioid Use Disorder Treatment, CNS Drugs, 2018, vol. 32, pp. 305-320.

Daly, A. K., Genome-wide association studies in pharmacogenomics, Nature Review Genetics, Apr. 2010, vol. 11, pp. 241-246.

De Boer et al., Activation of cryptic splice sites in three patients with chronic granulomatous disease, Mol Gene Geno Med. Sep. 2019; 7(9):e854; 13 pages.

Desmet et al., Human splicing finder: An online bioinformatics tool to predict splicing signals, Nucleic Acids Res. May 1, 2009;37(9): e67; 14 pages.

Desmet et al., Bioinformatics identification of splice site signals and prediction of mutation effects, Res Adv Nucleic Acids Res. 2010:1-14.

Diederichs et al. The Dark Matter of the Cancer Genome: Aberrations in Regulatory Elements, Untranslated Regions, Splice Sites, Non-coding RNA and Synonymous Mutations. EMBO Mol Med. May 2016;8(5): 442-457.

Harris, L.W., Long Non-Coding RNAs and Human Disease, Biochem Society Trans. Aug. 1, 2012;40(4):902-906.

Houdayer et al., Evaluation of in silico splice tools for decision-making in molecular diagnosis. Human Mut. Jul. 2008; 29(7):975-982.

Hrdlickova et al., Genetic Variation in the Non-Coding Genome: Involvement of Micro-RNAs and Long Non-Coding RNAs in Disease. Biochimica et Biophysica Acta Oct. 1, 2014; 1842(10): 1910-1922.

(56) References Cited

OTHER PUBLICATIONS

Hu et al., The Role of Long Noncoding RNAs in Cancer: The Dark Matter Matters. Curr Opin Gene Develop. Feb. 1, 2018;48: 8-15.

Jaganathan et al., Predicting splicing from primary sequence with deep learning, Cell. Jan. 24, 2019;176(3): 535-548.

Lee et al., Systematic Computational Identification of Variants That Activate Exonic and Intronic Cryptic Splice Sites. Am J Human Gene. May 4, 2017;100(5): 751-765.

Mucaki et al., Prediction of mutant m RNA splice isoforms by information theory-based exon definition. Human Mutation. Apr. 2013;34(4):557-565.

NA: "User Manual—Alamut(TM) Visual Plus 1,3,4,6 v 1.0", Mar. 4, 2021; pp. 1-57, Retrieved from the Internet: URL:https://extranet. interactive-biosoftware.com/User%20Guide%20Alamut%20Visual% 20Plus%20v1.0.pdf [retrieved on Feb. 27, 2025].

Oubounyt et al., DeePromoter: Robust promoter predictor using deep learning. Front Genetics. Apr. 5, 2019; 10:286; 9 pages.

Raimondi et al. DEOGEN2: Prediction and Interactive Visualization of Single Amino Acid Variant Deleteriousness in Human Proteins. Nucl Acids Res. Jul. 3, 2017;45(W1): W201-6.

Roca et al., Intrinsic Differences Between Authentic and Cryptic 5' Splice Sites. Nucl Acids Res. Nov. 1, 2003;31(21):6321-6333.

Taft et al., Non-coding RNAs: Regulators of Disease. The J Pathol. Jan. 2010;220(2): 126-139.

Taylor et al., Genotype-phenotype correlations in hereditary familial retinoblastoma. Human Mut. Mar. 2007;28(3):284-293.

\* cited by examiner

600A

602 — Meta Data Review

604 — Patient Selection

606 — Gene Selection

Inclusion Genes          Exclusion Genes 608-1                  608-2

600B

610 — Analyze, review & formulate project plan

612 — Launch analysis

600C

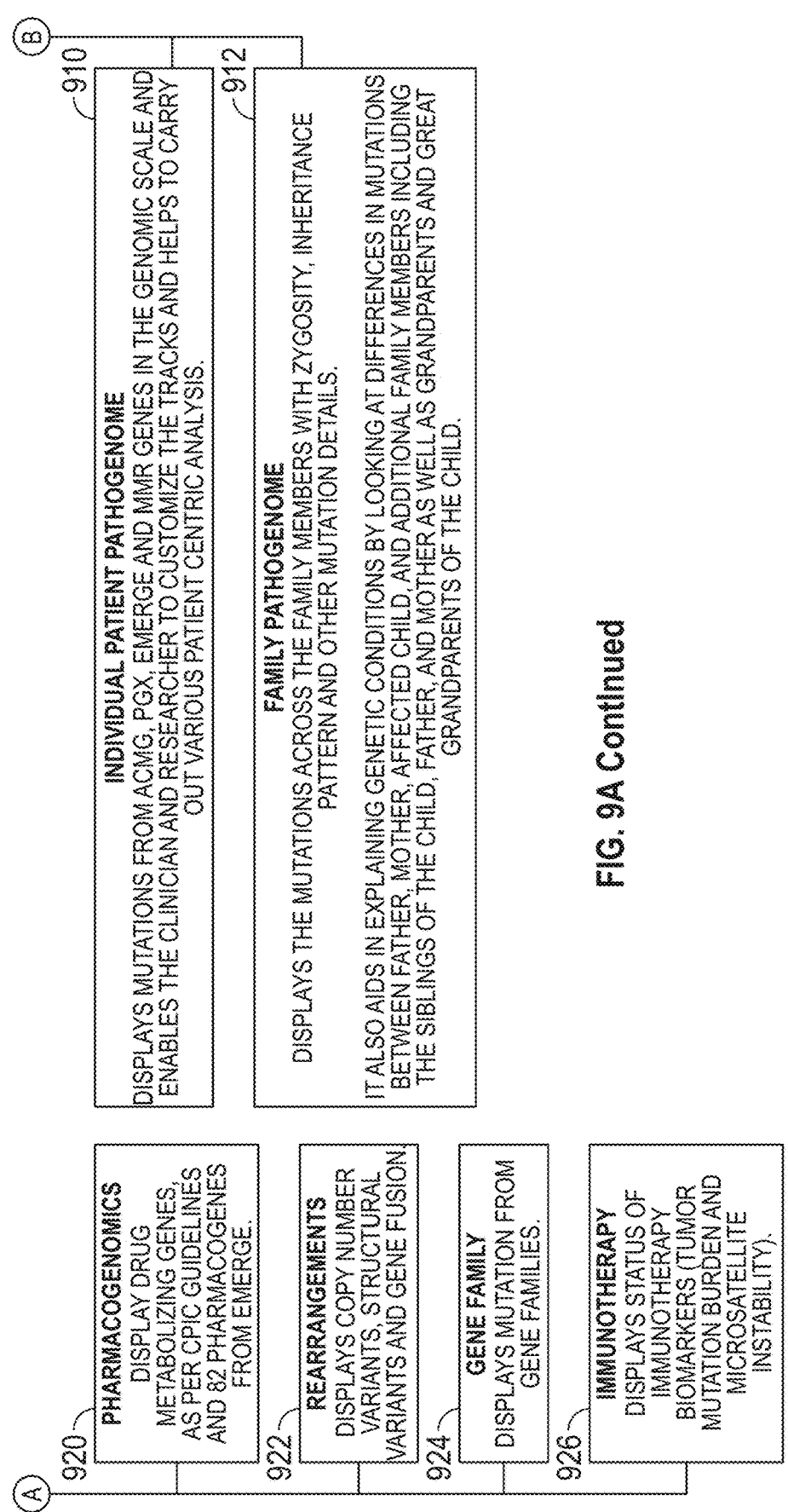

INDIVIDUAL PATIENT PATHOGENOME

DISPLAYS MUTATIONS FROM ACMG, PGX, EMERGE AND MMR GENES IN THE GENOMIC SCALE AND ENABLES THE CLINICIAN AND RESEARCHER TO CUSTOMIZE THE TRACKS AND HELPS TO CARRY OUT VARIOUS PATIENT CENTRIC ANALYSIS.

FAMILY PATHOGENOME

DISPLAYS THE MUTATIONS ACROSS THE FAMILY MEMBERS WITH ZYGOSITY, INHERITANCE PATTERN AND OTHER MUTATION DETAILS.

IT ALSO AIDS IN EXPLAINING GENETIC CONDITIONS BY LOOKING AT DIFFERENCES IN MUTATIONS BETWEEN FATHER, MOTHER, AFFECTED CHILD, AND ADDITIONAL FAMILY MEMBERS INCLUDING THE SIBLINGS OF THE CHILD, FATHER, AND MOTHER AS WELL AS GRANDPARENTS AND GREAT GRANDPARENTS OF THE CHILD.

PHARMACOGENOMICS

DISPLAY DRUG METABOLIZING GENES, AS PER CPIC GUIDELINES AND 82 PHARMACOGENES FROM EMERGE.

REARRANGEMENTS

DISPLAYS COPY NUMBER VARIANTS, STRUCTURAL VARIANTS AND GENE FUSION

GENE FAMILY

DISPLAYS MUTATION FROM GENE FAMILIES.

IMMUNOTHERAPY

DISPLAYS STATUS OF IMMUNOTHERAPY BIOMARKERS (TUMOR MUTATION BURDEN AND MICROSATELLITE INSTABILITY).

Figure 16A:
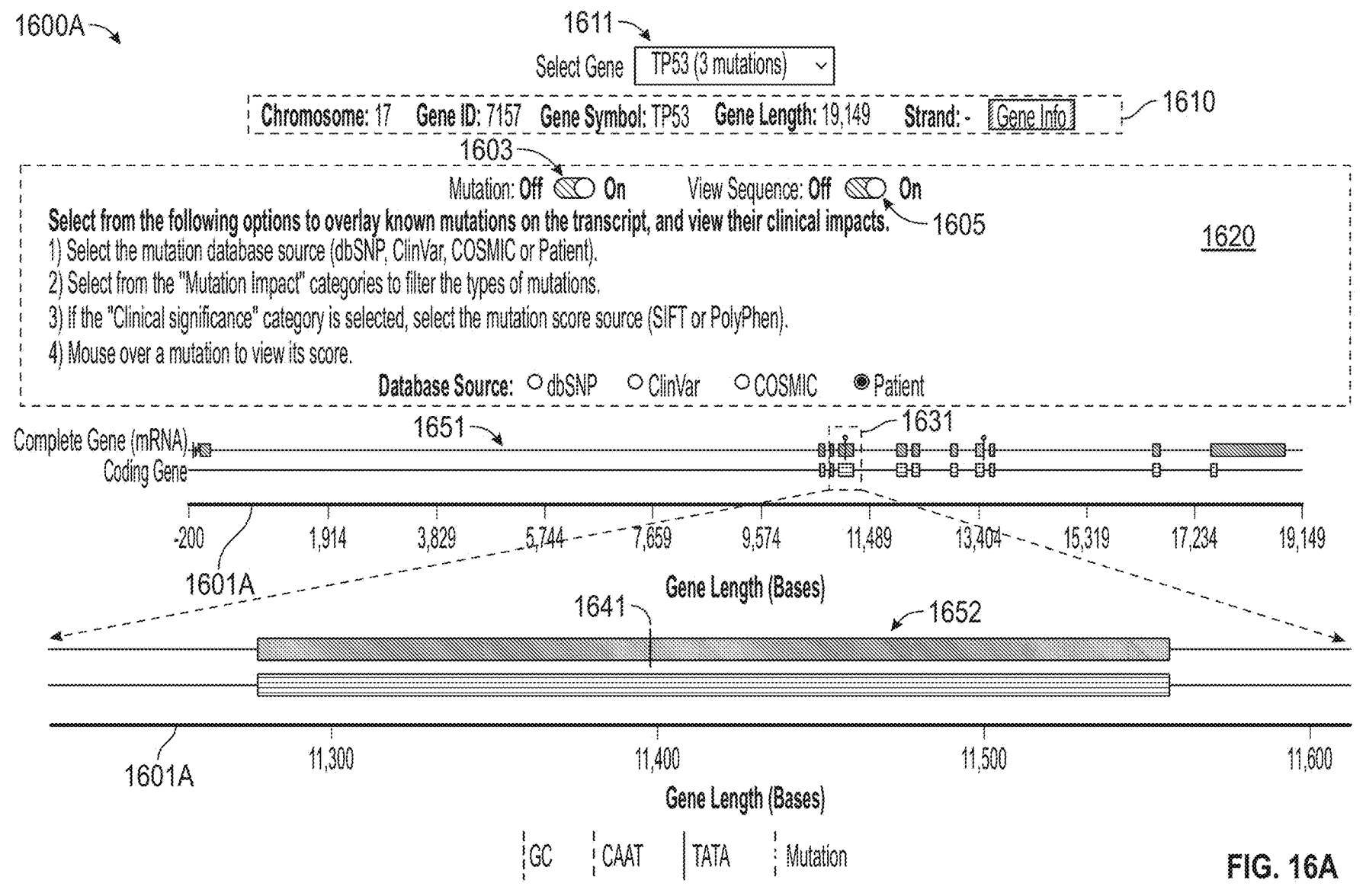

Select Gene TP53 (3 mutations) ∨

1610

Chromosome: 17 Gene ID: 7157 Gene Symbol: TP53 Gene Length: 19,149 Strand: - Gene Info

1603

1620

Mutation: Off ◯ On View Sequence: Off ◯ On

1605

Select from the following options to overlay known mutations on the transcript, and view their clinical impacts.
1) Select the mutation database source (dbSNP, ClinVar, COSMIC or Patient).
2) Select from the "Mutation impact" categories to filter the types of mutations.
3) If the "Clinical significance" category is selected, select the mutation score source (SIFT or PolyPhen).
4) Mouse over a mutation to view its score.

Database Source: ◯ dbSNP ◯ ClinVar ◯ COSMIC ⦿ Patient

1651

1631

Complete Gene (mRNA)
Coding Gene 200 1,914 3,829 5,744 7,659 9,574 11,489 13,404 15,319 17,234 19,149

Gene Length (Bases)

1601A

1641

1652

1601A 11,300 11,400 11,500 11,600

Gene Length (Bases)

GC CAAT TATA Mutation

Mutation: Off ⊘ On   Show All Poly-A Signals: Off ⊘ On [ Clear ]

Select from the following options to overlay known mutations on the transcript, and view their clinical impacts.
1) Select the mutation database source (dbSNP, ClinVar, COSMIC or Patient).
2) Select from the "Mutation Impact" categories to filter the types of mutations.
3) If the "Clinical significance" category is selected, select the mutation score source (SIFT or PolyPhen).
4) Mouse over a mutation to view its score.

Database Source: ○ dbSNP ○ ClinVar ○ COSMIC ⦿ Patient 2043C   2041C

5' and 3' UTRs   Coding Exons   ▨ Alternating Exons ▨   [ AATAAA ]   [ Mutation ]

CTGGGCGGCCGGCGGCGGCGGCGGGGAGGGGCGGGGCTCGTCGGCGGCTGCTGCTGCTCCTCGGCGCCAGGTACCATGCGGCAGGCCCGGGGCTCCT
GCTCGCGGCCGGCGGCTGAGACGGGCGGGTCAGCGCTCACGACAGCCCGCTGCCACTCTCCGGCCACCTTTCGCGATTCCCGACAGTTAACCAATGGGGAGACAT
TTGGCTTTGCCTTCTGCCTCCTTCTCTTCCAACATTTTGCAGACAGTGATGGCAGCCAACCACTTGAACACAGACTCCTCTGCTCAGTTTACACACTCG
AGTACAACGTCACCGTGCAGGAGAACTCTGCACTCGACGTAAGCACTTATCTGGGCATCCTGTTCAAGATGCGGTGTTTACATTACACATCCACGGTGGGAAGTAAG
GTACAAAAATTGTTTCCGGAGACAGTGAAAAAACCTGTTCAAAGCTGAAGAGTACATTCTCGGAGACACTTTTGCTTTCTAAGAAATAAGGACCAAAGGAGGAAAT
ACAGCTATTCTTAATAGAGAAGTGAAGGATCACTACACATTGATGAGTGAAAAAAAAATACTAAGTGAGGCGGCGAACAAAGGTCAGGGTGC
AGGTGCTGGCATACAAATGACTTGAGACCGGTTATTCTCACCCACCTCATCAGCGTTTCTTTACCTTGAAAAACACACGCTATAAGGACCAGTATCGCAAGAGT
CAGCGCCACGGATGCAGACATAGGAACCAACGGCGGAAGTTTTACTACAGTTTTAAAGATCGAACAGATATGTTTGCTATTCACCCACCAGTGGTGTCGATA
GTGTTAACTGGTACACTTGATTACCTAGAGACCAAGCTCTATGCATGATCGGAATCCTCGCTCGGCGGATGAAGTTGTATCGGAGCAGTGGGCATCA
GCAGGCATGCCAAGCTAACGGTCGCACATCGAACAGGGCCAATGAAGTGTCCTCCGGGTATAACAGCAGTCTTTAAGCACGTGCAGGTGACCTTTCTCCAGCAGTTTAGA
AGCATATGCAATTGTGACACGTGGATGACTGCGATCAGGGTGCCAATGGTGCCATTCGGTGCAGCAGTCAGTCGGCTACAATCTCACACTACAGG
ACAGTGAGGTCCTTTTCCAGGGAGTAAGGAGTATAAAAGTCAAAGCCATCGGTGACATCGGTCATTGATTGGGACCAGCAGTCCTTTCGGCTACAATCTCACACTACAGG
CTAAAGATAAAGGAACTCCGCCCCCCAGTTCTTCTTCTTCTGTTAAAGCATTCAGCTTAAAGCTCTTCCCCACACGTTCAAAGCCGGCCAGTCAGTTTGAAAAGGATGT
TTACAGAGCCAGAAATAAGTGAATTTGCTCCTCCCAACACACCTGGTCATGGTGTAAAGGCCATTCCTGGCTTATTCCCTATTGGTGTATCTTAAAAGT
ACACCTGGAAAAGCTAATTCAGTTTAAATTACAACACTGGTCTCATTTCTATTTTAGAACCAGTTAAAAGACACAGGCCAGGCAGCCCCATTTTGAACTTGAAG
TAACAACAAGTGACAGAAAAGCGTCCACCAAGGTCTTGGTGAAAGTCTTAGGTGCAAATAGCAATCCCCCTGAATTTACCCAGAACAGCGTACAAAGCTGC
TTTTGATGAATGAAACGTGCCCATTGGTACTACTGTCATGAGCCTGATGAGCTGCCGTAGTGACTGCCGTAGGACGTAGCGTGACATACCAGTATCGCAAAT
TTAAATCAATGNGCCGTTTGCCAATTCACCAATTCACTCGGTGCCGTGAGTAGGTCAGAAAACCTGGACGTTAGACAGTTAGTCCTCGGGTTTATACTCTCAGGA
TTCGTGCATCGACTGGGGCTTGCCGTACCGCCGGGAAGTCGAAGTCCTTGCTACGAAGTCCTTGCTACCAATTACTCAATAACTTGAATGACAACACCACTTTTGTTTCAGAA
AATAAATTGTGAAGGGACAATTCCCAGAGATCTAGGCCGTGGGAGGAGCAAATAACCACTGTTTCTCGCTATTGAATGCAGATGAACTTCAGTTGGTACAGTAT

SEQ ID NO: 43

FIG. 20C

Transcript Length (Bases)

Fully Coding Exon  5' Partially Coding Exon  3' Partially Coding Exon  Non-Coding Exon
Cryptic Acceptor  Cryptic Donor  Real Donor  Real Acceptor  Mutation

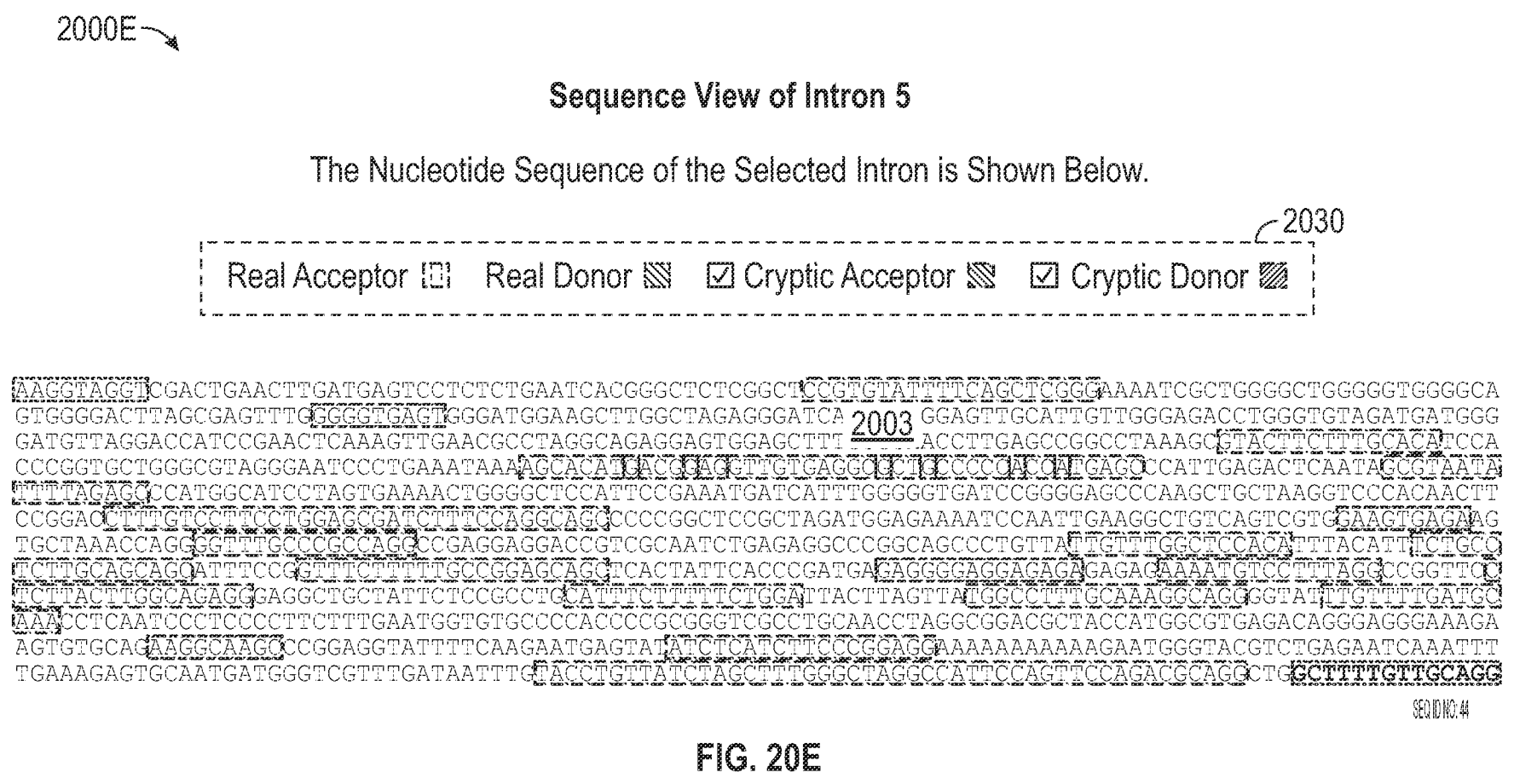

Sequence View of Intron 5

The Nucleotide Sequence of the Selected Intron is Shown Below.

Real Acceptor ⊡    Real Donor ▨    ☑ Cryptic Acceptor ▨    ☑ Cryptic Donor ▨

FIG. 20E

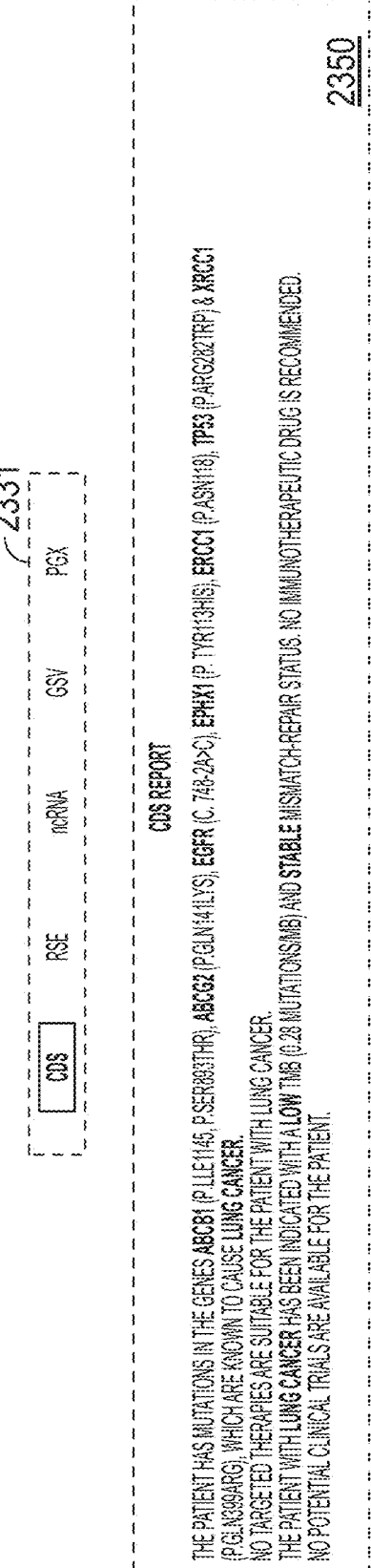

2331

CDS | RSE | mRNA | GSV | PGX

CDS REPORT

THE PATIENT HAS MUTATIONS IN THE GENES ABCB1 (P.ILE1145, P.SER893THR), ABCG2 (P.GLN141LYS), EGFR (C. 748-2A>C), EPHX1 (P. TYR113HIS), ERCC1 (P.ASN118), TP53 (P.ARG282TRP) & XRCC1 (P.GLN399ARG), WHICH ARE KNOWN TO CAUSE LUNG CANCER.
NO TARGETED THERAPIES ARE SUITABLE FOR THE PATIENT WITH LUNG CANCER.
THE PATIENT WITH LUNG CANCER HAS BEEN INDICATED WITH A LOW TMB (0.20 MUTATIONS/MB) AND STABLE MISMATCH-REPAIR STATUS. NO IMMUNOTHERAPEUTIC DRUG IS RECOMMENDED.
NO POTENTIAL CLINICAL TRIALS ARE AVAILABLE FOR THE PATIENT.

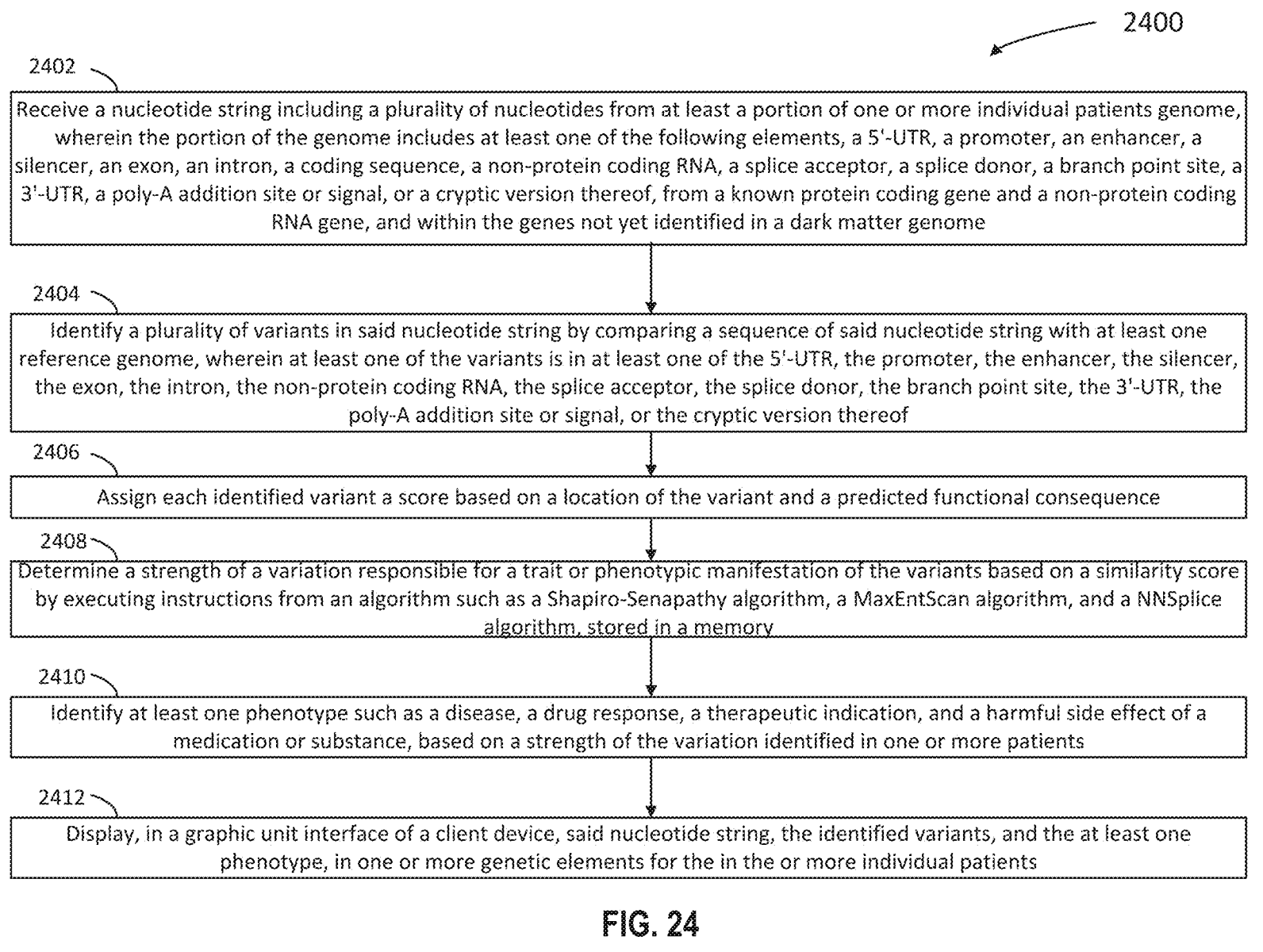

2402 — Receive a nucleotide string including a plurality of nucleotides from at least a portion of one or more individual patients genome, wherein the portion of the genome includes at least one of the following elements, a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a dark matter genome 2404 — Identify a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof 2406 — Assign each identified variant a score based on a location of the variant and a predicted functional consequence 2408 — Determine a strength of a variation responsible for a trait or phenotypic manifestation of the variants based on a similarity score by executing instructions from an algorithm such as a Shapiro-Senapathy algorithm, a MaxEntScan algorithm, and a NNSplice algorithm, stored in a memory 2410 — Identify at least one phenotype such as a disease, a drug response, a therapeutic indication, and a harmful side effect of a medication or substance, based on a strength of the variation identified in one or more patients 2412 — Display, in a graphic unit interface of a client device, said nucleotide string, the identified variants, and the at least one phenotype, in one or more genetic elements for the in the or more individual patients

FIG. 24

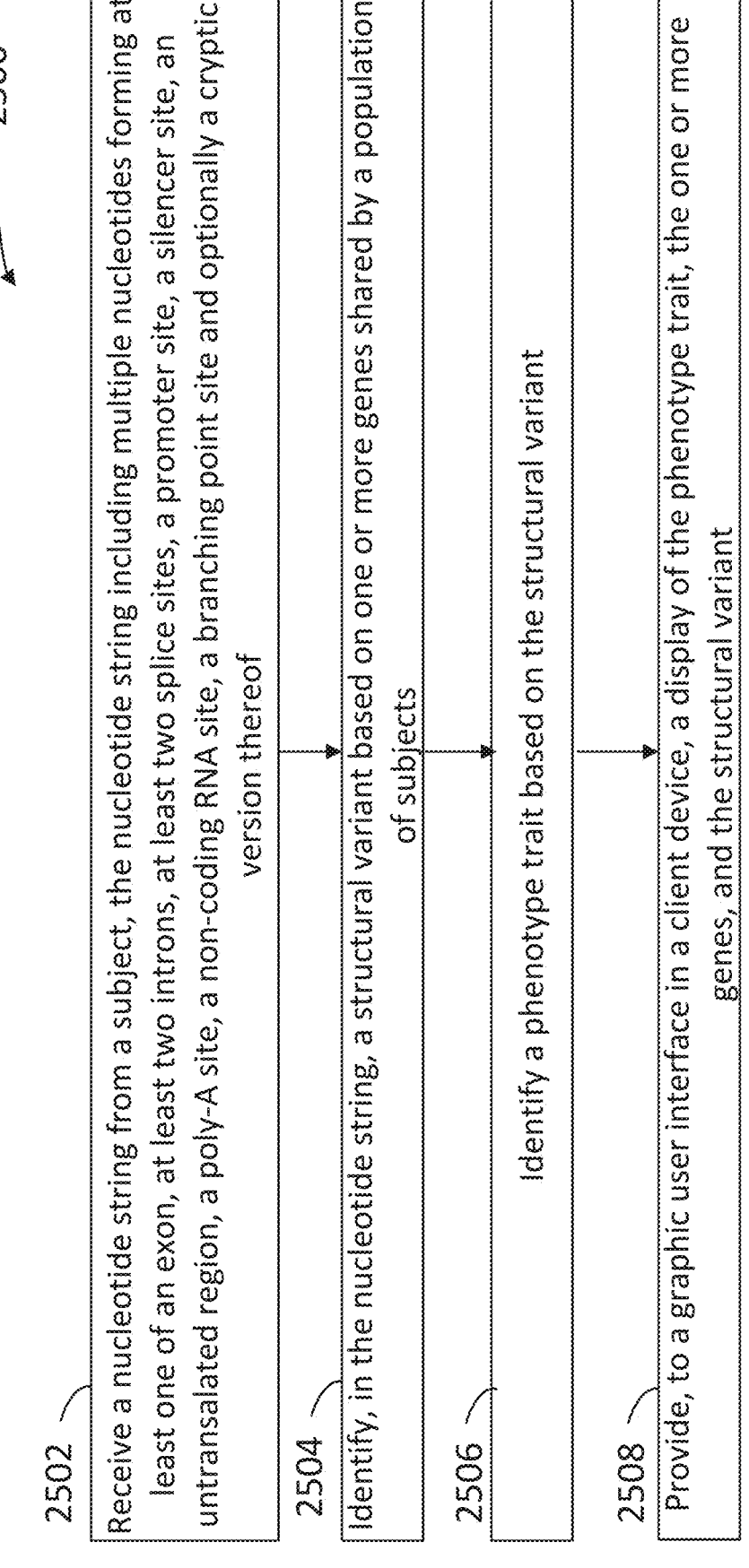

2500

2502 Receive a nucleotide string from a subject, the nucleotide string including multiple nucleotides forming at least one of an exon, at least two introns, at least two splice sites, a promoter site, a silencer site, an untranslated region, a poly-A site, a non-coding RNA site, a branching point site and optionally a cryptic version thereof 2504 Identify, in the nucleotide string, a structural variant based on one or more genes shared by a population of subjects 2506 Identify a phenotype trait based on the structural variant 2508 Provide, to a graphic user interface in a client device, a display of the phenotype trait, the one or more genes, and the structural variant

FIG. 25

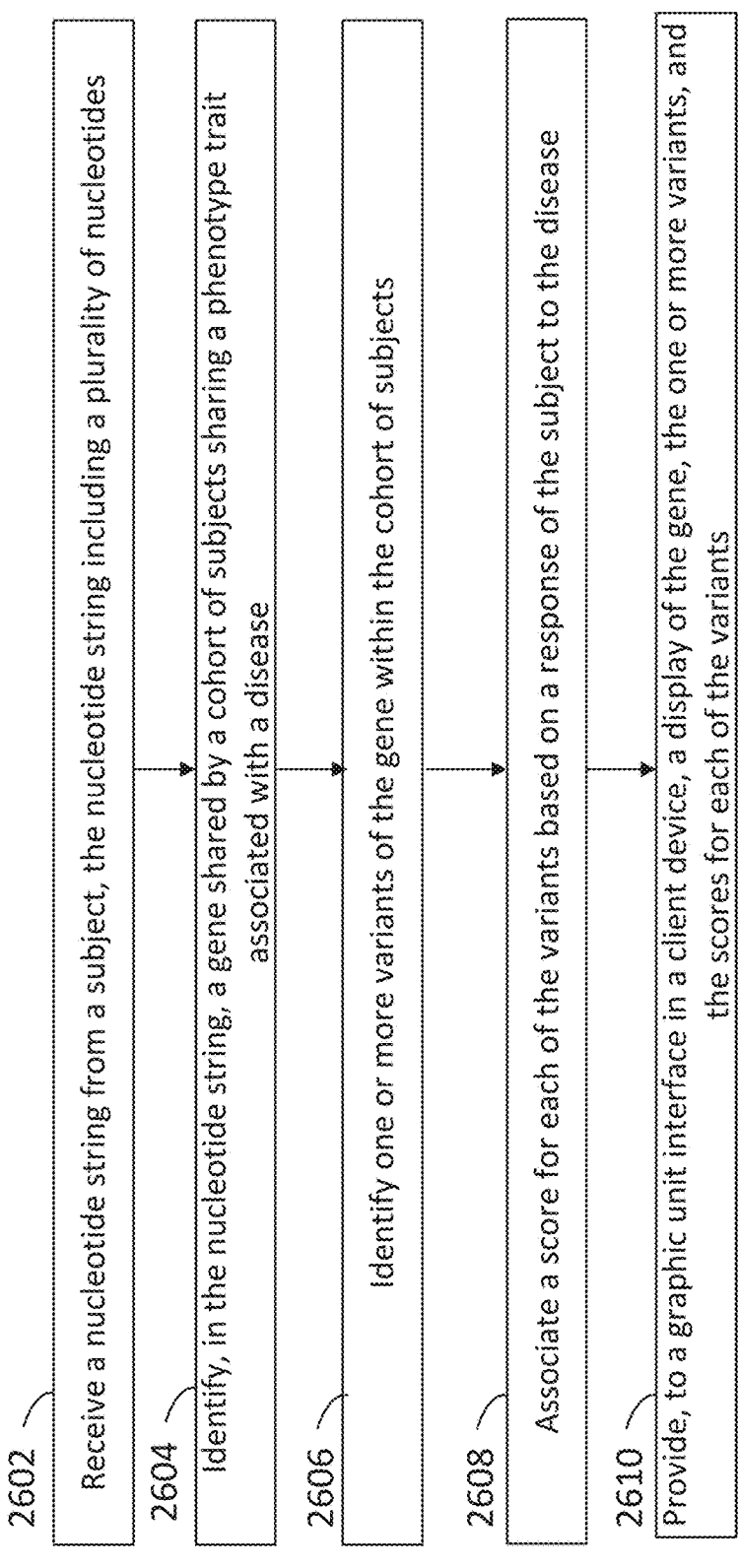

2600

2602  Receive a nucleotide string from a subject, the nucleotide string including a plurality of nucleotides 2604  Identify, in the nucleotide string, a gene shared by a cohort of subjects sharing a phenotype trait associated with a disease 2606  Identify one or more variants of the gene within the cohort of subjects 2608  Associate a score for each of the variants based on a response of the subject to the disease 2610  Provide, to a graphic unit interface in a client device, a display of the gene, the one or more variants, and the scores for each of the variants

FIG. 26

SEQUENCE LISTING

```
<160> NUMBER OF SEQ ID NOS: 45

<210> SEQ ID NO 1
<211> LENGTH: 97
<212> TYPE: DNA
<213> ORGANISM: Artificial Sequence
<220> FEATURE:
<223> OTHER INFORMATION: Synthetic

<400> SEQUENCE: 1
aggtggggct gggcctgggt tctgtgcagg tggggctggc tgacacccgg cttccgtgtc        60
tccacctgga aaagtgactc tgtgtctctg cttagga                                 97

<210> SEQ ID NO 2
<211> LENGTH: 810
<212> TYPE: DNA
<213> ORGANISM: Artificial Sequence
<220> FEATURE:
<223> OTHER INFORMATION: Synthetic

<400> SEQUENCE: 2
gatgggattg gggtttttccc ctcccatgtg ctcaagactg gcgctaaaag ttttgagctt        60
ctcaaaagtc tagagccacc gtccagggag caggtagctg ctgggctccg gggacacttt       120
gcgttcgggc tgggagcgtg ctttccacga cggtgacacg cttccctgga ttggcagcca       180
gactgccttc cgggtcactg ccatggagga gccgcagtca gatcctagcg tcgagccccc       240
tctgagtcag gaaacatttt cagacctatg acttcctgaa aacaacgttc tggaaacttc       300
ccccttgccg tcccaagcaa tggatgattt gatgctgtcc ccggacgata ttgaacaatg       360
gttcactgaa gacccaggtc cagatgaagc tcccagaatg ccagaggctg ctcccccccgt       420 ggcccctgca ccagcagctc ctacaccggc ggcccctgca ccagcccccct cctggcccct       480 gtcatcttct gtcccttccc agaaaaccta ccagggcagc tacggtttcc gtctgggctt       540
cttgcattct gggacagcca agtctgtgac ttgcacgtac tcccctgccc tcaacaagat       600
gttttgccaa ctggccaaga cctgccctgt gcagctgtgg gttgattcca caccccccgcc       660 cggcacccgc gtccgcgcca tggccatcta caagcagtca cagcacatga cggaggttgt       720
```

-continued

```
gaggcgctgc ccccaccatc agcgctgctc agatagcgat ggtctggccc ctcctcagca       780
tcttatccga gtggaaggaa atttgcgtgt                                        810
```

<210> SEQ ID NO 3
<211> LENGTH: 156
<212> TYPE: DNA
<213> ORGANISM: Artificial Sequence
<220> FEATURE:
<223> OTHER INFORMATION: Synthetic

<400> SEQUENCE: 3

```
gcgcagctct tcgcgcagag ctacaactcc agcgccgaac aggtcctgtt ccagagcgtg        60
gccgccagct gggcgcacga caccaacatc accgcggaga atgcaagccg ccaggaggaa       120
gcagccctgc tcagccagga gtttgcggag gcctgg                                 156
```

<210> SEQ ID NO 4
<211> LENGTH: 53
<212> TYPE: PRT
<213> ORGANISM: Artificial Sequence
<220> FEATURE:
<223> OTHER INFORMATION: Synthetic

<400> SEQUENCE: 4

```
Ala Gln Leu Phe Ala Gln Ser Tyr Asn Ser Ser Ala Glu Gln Val Leu
1               5                   10                  15

Phe Gln Ser Val Ala Ala Ser Trp Ala His Asp Thr Asn Ile Thr Ala
            20                  25                  30

Glu Asn Ala Arg Arg Gln Glu Glu Ala Ala Leu Leu Ser Gln Glu Phe
        35                  40                  45

Ala Glu Ala Glu Trp
    50
```

<210> SEQ ID NO 5
<211> LENGTH: 42
<212> TYPE: PRT
<213> ORGANISM: Artificial Sequence
<220> FEATURE:
<223> OTHER INFORMATION: Synthetic

<400> SEQUENCE: 5

```
Tyr Tyr Tyr Thr Tyr Tyr Val Trp Tyr Trp Tyr Trp Tyr Tyr Trp Pro
1               5                   10                  15

Trp Trp Trp Trp Tyr Tyr Trp Val Tyr Tyr Tyr Tyr Tyr Tyr Tyr Trp
            20                  25                  30

Tyr Tyr Gln Tyr Trp Ser Trp Tyr Trp Arg
        35                  40
```

<210> SEQ ID NO 6
<211> LENGTH: 39
<212> TYPE: PRT
<213> ORGANISM: Artificial Sequence
<220> FEATURE:
<223> OTHER INFORMATION: Synthetic

<400> SEQUENCE: 6

```
Trp Pro Trp Ser Trp Thr Arg Trp Arg Trp Trp Ser His Tyr Ser Arg
1               5                   10                  15

Arg Trp Trp Pro Thr Trp Trp Trp Trp Trp Trp Val Trp Trp Pro
            20                  25                  30

Trp Thr Arg Pro Trp Thr Pro
        35
```

```
<210> SEQ ID NO 7
<211> LENGTH: 39
<212> TYPE: PRT
<213> ORGANISM: Artificial Sequence
<220> FEATURE:
<223> OTHER INFORMATION: Synthetic

<400> SEQUENCE: 7

Thr His Pro Arg Thr Pro Met Val Gln Pro Asn Pro Glu Gln Met Pro
1               5                   10                  15

Pro Pro Pro Leu Ser Pro Val Ser Thr Ser Pro Arg Pro Pro Ser His
            20                  25                  30

Arg Pro Pro Lys Thr Pro Asn
            35

<210> SEQ ID NO 8
<211> LENGTH: 42
<212> TYPE: PRT
<213> ORGANISM: Artificial Sequence
<220> FEATURE:
<223> OTHER INFORMATION: Synthetic

<400> SEQUENCE: 8

Ser Gly Gly Gln Ser His Leu Pro Arg Cys Pro Pro His Met Asn Asp
1               5                   10                  15

Met Cys Met Leu Met Gln Lys Arg Leu Thr Pro Pro Arg Met Pro Met
            20                  25                  30

His Pro Asp Pro Leu Asn Gly Pro Met Gly
            35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic

<400> SEQUENCE: 9

Arg Phe Cys Pro Arg Phe Ile Asn Gln Tyr Asn Asn Cys His His Tyr
1               5                   10                  15

Leu Tyr His Lys Gly Pro Ile Gln His Pro Met Ile Gln Gly Asn Leu
            20                  25                  30

Asp Gly Cys Met Ile Lys Cys Asn Gly Asp
            35                  40

<210> SEQ ID NO 10
<211> LENGTH: 42
<212> TYPE: PRT
<213> ORGANISM: Artificial Sequence
<220> FEATURE:
<223> OTHER INFORMATION: Synthetic

<400> SEQUENCE: 10

Gln Cys Val Asn Gln Cys Cys Met Pro Val His Lys Val Cys Asp Trp
1               5                   10                  15

Gly Val Cys His Cys Asn His Pro Gly Asn His His Pro Phe His Ile
            20                  25                  30

Cys Cys Tyr Lys His Gly Tyr Met Phe Cys
            35                  40

<210> SEQ ID NO 11
```

```
<211> LENGTH: 42
<212> TYPE: PRT
<213> ORGANISM: Artificial Sequence
<220> FEATURE:
<223> OTHER INFORMATION: Synthetic

<400> SEQUENCE: 11

Pro Trp Thr Met Pro Trp Tyr Lys Met Thr Gly His Thr Val Cys Val
1               5                   10                  15

Glu Thr Tyr Gly Val Met Phe Asn Phe His Gly Gly Met Cys Gly His
            20                  25                  30

Val Val Trp Ile Phe Asp Val Phe Cys Tyr
        35                  40

<210> SEQ ID NO 12
<211> LENGTH: 42
<212> TYPE: PRT
<213> ORGANISM: Artificial Sequence
<220> FEATURE:
<223> OTHER INFORMATION: Synthetic

<400> SEQUENCE: 12

Asn Val Ser Leu Asn Val Trp Gly Leu Ser Phe Glu Ser Thr Tyr Thr
1               5                   10                  15

Asp Arg Val Phe Thr Leu Cys Met Val Gly Phe Asp Lys Val Glu Cys
            20                  25                  30

Thr Thr Val His Asp Cys Thr Asp Tyr Trp
        35                  40

<210> SEQ ID NO 13
<211> LENGTH: 42
<212> TYPE: PRT
<213> ORGANISM: Artificial Sequence
<220> FEATURE:
<223> OTHER INFORMATION: Synthetic

<400> SEQUENCE: 13

Met Thr Arg Lys Lys Ser Thr Asp Lys Arg Cys Asp Arg Ser Val Ser
1               5                   10                  15

Tyr Gln Thr Glu Ser His Tyr Leu Thr Phe Asp Cys Phe Thr Asp Tyr
            20                  25                  30

Ser Arg Thr Glu Cys Tyr Ser Cys Val Val
        35                  40

<210> SEQ ID NO 14
<211> LENGTH: 42
<212> TYPE: PRT
<213> ORGANISM: Artificial Sequence
<220> FEATURE:
<223> OTHER INFORMATION: Synthetic

<400> SEQUENCE: 14

Lys Ser Gln His His Arg Ser Tyr Ile Gln Ala Cys Gln Arg Thr Arg
1               5                   10                  15

Val Pro Ser Asp Arg Gly Val Lys Ser Cys Cys Val Cys Ser Cys Thr
            20                  25                  30

Arg Gln Ser Cys Tyr Trp Arg Val Ser Thr
        35                  40

<210> SEQ ID NO 15
<211> LENGTH: 42
<212> TYPE: PRT
<213> ORGANISM: Artificial Sequence
```

<220> FEATURE:
<223> OTHER INFORMATION: Synthetic

<400> SEQUENCE: 15

His Arg Asn Gly Gly Gln Arg Val His Pro Thr Tyr Asn Gln Arg Gln
1               5                   10                  15

Ser Asn Gln Cys Gln Phe Thr Ile Arg Ser Val Ser Val Arg Val Ser
            20                  25                  30

Gln Asn Arg Val Val Val Gln Ser Arg Ser
        35                  40

<210> SEQ ID NO 16
<211> LENGTH: 52
<212> TYPE: PRT
<213> ORGANISM: Artificial Sequence
<220> FEATURE:
<223> OTHER INFORMATION: Synthetic

<400> SEQUENCE: 16

Phe Gln Met Glu Glu Asn Gln Ser Gly Asn Ser Val Met Pro Gln Asn
1               5                   10                  15

Arg Leu Asn Tyr Asn Glu Ser His Gln Cys Ser Phe Glu Phe Gly Gln
            20                  25                  30

Pro Glu Gln Arg Thr Arg Thr Gln Thr Arg Asn Met Asn Thr Ser Thr
        35                  40                  45

Asn Arg Gln Gln
    50

<210> SEQ ID NO 17
<211> LENGTH: 52
<212> TYPE: PRT
<213> ORGANISM: Artificial Sequence
<220> FEATURE:
<223> OTHER INFORMATION: Synthetic

<400> SEQUENCE: 17

Glu Asn Leu Asp Asp Met Asn Gln Phe Leu Arg Thr Leu Leu Met Met
1               5                   10                  15

Pro Lys Leu Val Leu Asp Arg Gly Asn Tyr Asn Glu Cys Glu Phe Pro
            20                  25                  30

Asn Asp Asn Gln Arg Gln Asn Asn Ser Gln Met Leu Met Ser Arg Gln
        35                  40                  45

Met Gln Asn Met
    50

<210> SEQ ID NO 18
<211> LENGTH: 52
<212> TYPE: PRT
<213> ORGANISM: Artificial Sequence
<220> FEATURE:
<223> OTHER INFORMATION: Synthetic

<400> SEQUENCE: 18

Asp Met Lys Cys Cys Leu Lys Leu Cys Lys Gln Ser Lys Lys Leu Leu
1               5                   10                  15

Asn Ile Lys Thr Lys Cys Gln Glu Met Ser Leu Asp Ala Asp Glu Asn
            20                  25                  30

Leu Cys Met Met Gln Asn Leu Leu Gln Asn Leu Lys Leu Gln Gln Met
        35                  40                  45

Leu Leu Leu Leu
    50

```
<210> SEQ ID NO 19
<211> LENGTH: 49
<212> TYPE: PRT
<213> ORGANISM: Artificial Sequence
<220> FEATURE:
<223> OTHER INFORMATION: Synthetic

<400> SEQUENCE: 19

Cys Leu Ile Tyr Val Lys His Ile Thr Ile Met Met Ile Ile Lys Lys
1               5                   10                  15

Ser Ile Val Asn Asp Lys Gln Ile Cys Tyr Cys Asp Leu Lys Ala Leu
            20                  25                  30

Leu Asn Met Ile Lys Met Lys Lys Ile Lys Asn Asn Leu Ile Lys Lys
        35                  40                  45

Lys

<210> SEQ ID NO 20
<211> LENGTH: 49
<212> TYPE: PRT
<213> ORGANISM: Artificial Sequence
<220> FEATURE:
<223> OTHER INFORMATION: Synthetic

<400> SEQUENCE: 20

Val Lys His Trp Met Ile Gly His Ser His Leu Leu Gly Gly Ile Ile
1               5                   10                  15

Gln His Thr Met Cys Ile Asn Gly Ala Ser Val Cys Lys His Thr Lys
            20                  25                  30

Lys Leu Leu His Ile Leu Gly Ile His Ile Leu Met Ile His Ile Ile
        35                  40                  45

Ile

<210> SEQ ID NO 21
<211> LENGTH: 52
<212> TYPE: PRT
<213> ORGANISM: Artificial Sequence
<220> FEATURE:
<223> OTHER INFORMATION: Synthetic

<400> SEQUENCE: 21

Leu Ile Phe Val Leu Gly Phe Phe Asn Gly Lys Ile Phe Phe Gly Gly
1               5                   10                  15

His Phe Phe Asn Phe Ser Gly Ala Glu His Phe Val Asn Met Ala His
            20                  25                  30

Phe Asn Ile Ile Lys Lys Gly His Lys Phe Gly Phe Gly Gly Lys His
        35                  40                  45

Phe His His His
    50

<210> SEQ ID NO 22
<211> LENGTH: 51
<212> TYPE: PRT
<213> ORGANISM: Artificial Sequence
<220> FEATURE:
<223> OTHER INFORMATION: Synthetic

<400> SEQUENCE: 22

Ile Glu Glu Ile Glu Glu Glu Glu Ile Gly Glu Glu Phe Phe Phe
1               5                   10                  15

Glu Glu Met Glu Lys Glu Tyr Asp Gly Glu Thr His Leu Thr Glu Glu
```

-continued

```
           20              25              30

Leu Glu Glu Ile Phe Glu Glu Ile Glu Phe Glu Phe Phe Gly Phe Glu
        35              40              45

Gly Glu Phe
    50

<210> SEQ ID NO 23
<211> LENGTH: 52
<212> TYPE: PRT
<213> ORGANISM: Artificial Sequence
<220> FEATURE:
<223> OTHER INFORMATION: Synthetic

<400> SEQUENCE: 23

Gly Asp Asp Phe Phe Asp Asp Cys Asp Asp Glu Phe Asp Asp Glu Cys
1               5               10              15

Cys Asp Asp Ile Asp Ile Asp Trp Cys Phe Asp Ser Phe Ile Ser Asp
            20              25              30

Asp Lys Asp Asp Glu Glu Asp Asp Phe Asp Glu Asp Glu Asp Glu Glu
        35              40              45

Asp Glu Asp Glu
    50

<210> SEQ ID NO 24
<211> LENGTH: 52
<212> TYPE: PRT
<213> ORGANISM: Artificial Sequence
<220> FEATURE:
<223> OTHER INFORMATION: Synthetic

<400> SEQUENCE: 24

Ala Ala Ala Ala Ala Ala Ala Ala Ala Ala Asp Ala Ala Ala Ala Ala
1               5               10              15

Ala Ala Ala Ala Ala Ala Ala Phe Ala Ala Ala Asn Asp Ala Asn Ala
            20              25              30

Ala His Ala Ala Ala Ala Ala Ala Ala Ala Ala Ala Ala Ala Ala Ala
        35              40              45

Ala Ala Ala Ala
    50

<210> SEQ ID NO 25
<211> LENGTH: 80
<212> TYPE: DNA
<213> ORGANISM: Artificial Sequence
<220> FEATURE:
<223> OTHER INFORMATION: Synthetic

<400> SEQUENCE: 25
cccagcgtca tcttgtctcc cagcgtcatc ttgtctccca tcttgtctcc cagcgtcatc      60
ttgtctccca gcgtccagca                                                  80

<210> SEQ ID NO 26
<211> LENGTH: 1200
<212> TYPE: DNA
<213> ORGANISM: Artificial Sequence
<220> FEATURE:
<223> OTHER INFORMATION: Synthetic

<400> SEQUENCE: 26
agttgctaga aagcaatgcg cctattcaca tggagaatct tccctttcct ctaaaattac      60
ttagtgcctc atcactaaac accccagct ccacaccatg ggtgttggat atcttcctca       120
```

```
ccttggtgtt tgccctgggg ctcttcttcc tattactccc ctacttctct tacctccgtt     180
gtgacaaccc accctcacca tcgcctagga agagaaaggt aaggagctct cagtccagac     240
ccacagagct tgattctctt ctttcttttt attattagtt ccacctttcc aaatccagtg     300
gagacttctg cgatgggaag tctcaggaga gaccagaaca gcatgcttcc agggagaggc     360
agggcagcca ggggttggta ggggtagatc gtgtactggg atttccatcc caagctctca     420
gtccatctgt gggggagcca ggaggcatga aggcaaaatc aaacccgtgg gctcagcggc     480
caggaccggt catgagacgg gggaggtctc tggtcatgag acgggaggtc tctgtccgag     540
gccaggccct gagccctggc tcatcagtcc cttcctgggg caggtggctc gggacccagc     600
ctcttctgtg tggggtgata tggggcctgt gctgggcccc cgaggggcct cccaccgggc     660
ctggcatctc ctctggtctc ctggcaagca gaatgctacc tgacagctca gtggtgcctg     720
cgggcctgag cctgggtgtt cctggagcag aggaacaggg actgatggcg tccatggtgg     780
acctcatatt gaaaatccct gtgtgtgtgc gtgtgtgttt gtgtgttatt tttatttatt     840
ttgttttttg tgcaggctgc agtgaaatga agcgataccg gctcagtgcc acctttgctt     900
ccagagttca agctattctc ctgtcttagc gtcctgagta gctggggatt acaggcgccc     960
gccaccacgc ctggctaatt ttcgtatttt tagtagagat ggggtttcac catggccagg    1020
ctggtctcaa actcttgacc tcaggtgatc cacctgcctc ggcctcccaa agtgcttgga    1080
ttataggcgt gagccaccgc acccgacccc ctcttcctgt ttttctaaga aaagcagttt    1140
atcatccatt taaacatgag tgggagggga gaaagcacac agagctccct gagcaagaca    1200
```

```
<210> SEQ ID NO 27
<211> LENGTH: 105
<212> TYPE: DNA
<213> ORGANISM: Artificial Sequence
<220> FEATURE:
<223> OTHER INFORMATION: Synthetic

<400> SEQUENCE: 27
atggagaatc ttccctttcc tctaaaatta cttagtgcct catcactaaa cacccccagc      60
tccacaccat gggtgttgga tatcttcctc accttggtgt ttgcc                     105
```

```
<210> SEQ ID NO 28
<211> LENGTH: 35
<212> TYPE: PRT
<213> ORGANISM: Artificial Sequence
<220> FEATURE:
<223> OTHER INFORMATION: Synthetic

<400> SEQUENCE: 28

Met Glu Asn Leu Pro Phe Pro Leu Lys Leu Leu Ser Ala Ser Ser Leu
1               5                   10                  15

Asn Thr Pro Ser Ser Thr Pro Trp Val Leu Asp Ile Phe Leu Thr Leu
            20                  25                  30

Val Phe Ala
        35
```

```
<210> SEQ ID NO 29
<211> LENGTH: 1200
<212> TYPE: DNA
<213> ORGANISM: Artificial Sequence
<220> FEATURE:
<223> OTHER INFORMATION: Synthetic

<400> SEQUENCE: 29
```

-continued

```
agttgctaga aagcaatgcg cctattcaca tggagaatct tccctttcct ctaaaattac      60
ttagtgcctc atcactaaac accccccagct ccacaccatg ggtgttggat atcttcctca     120
ccttggtgtt tgccctgggg ttcttcttcc tattactccc ctacttctct tacctccgtt     180
gtgacaaccc accctcacca tcgcctaaga agagaaaggt aaggagctct cagtccagac     240
ccacagagct tgattctctt ctttcttttt attattagtt ccacctttcc aaatccagtg     300
gagacttctg cgatgggaag tctcaggaga gaccagaaca gcatgcttcc agggagaggc     360
agggcagcca ggggttggta ggggtagatc gtgtactggg atttccatcc caagctctca     420
gtccatctgt gggggagcgc aggaggcatg aaggcaaaat caaacccgtg ggctcagcgg     480
ccaggaccgg tcatgagacg ggggaggtct ctggtcatga gacggggggag gtctctgtcc    540 gaggccaggc cctgagccct ggctcatcag tcccttcctg gggcaggtgg ctcgggaccc     600
agcctcttct gtgtggggtg atatggggcc tgtgctgggc ccccgagggc ctcccaccgg     660
ggcctggcat ctcctctggt ctcctggcaa gcagaatgct acctgacagc tcagtggtgc     720
ctgcgggcct gagcctgggt gttcctggag cagaggaaca gggactgatg gcgtccatgg     780
tggacctcat attgaaaatc cctgtgtgtg tgcgtgtgtg tttgtgtgtt atttttattt     840
attttgtttt ttgtgcaggc tgcagtgaaa tggagcgata ccggctcagt gccacctttg     900
cttccagagt tcaagctatt ctcctgtctt agcgtcctga gtagctgggg attacaggcg     960
cccgccacca cgcctggcta attttttgtat ttttagtaga gatggggttt caccatggct    1020
aggctggtct caaactcttg acctcaggtg atccacctgc ctcagcctcc caaagtgctg     1080
ggattatagg cgtgagccac cgcaccgtga gccactgcac ccgaccccct cttcctgttt     1140
ttctaagaaa agcagtttat catccattta aacatgagtg ggaggggagg aagcacacag     1200
```

<210> SEQ ID NO 30
<211> LENGTH: 105
<212> TYPE: DNA
<213> ORGANISM: Artificial Sequence
<220> FEATURE:
<223> OTHER INFORMATION: Synthetic

<400> SEQUENCE: 30

```
atggagaatc ttccctttcc tctaaaatta cttagtgcct catcactaaa caccccccagc     60 tccacaccat gggtgttgga tatcttcctc accttggtgt tgcc                       105
```

<210> SEQ ID NO 31
<211> LENGTH: 35
<212> TYPE: PRT
<213> ORGANISM: Artificial Sequence
<220> FEATURE:
<223> OTHER INFORMATION: Synthetic

<400> SEQUENCE: 31

```
Met Glu Asn Leu Pro Phe Pro Leu Lys Leu Leu Ser Ala Ser Ser Leu
1               5                   10                  15

Asn Thr Pro Ser Ser Thr Pro Trp Val Leu Asp Ile Phe Leu Thr Leu
            20                  25                  30

Val Phe Ala
        35
```

<210> SEQ ID NO 32
<211> LENGTH: 1200
<212> TYPE: DNA
<213> ORGANISM: Artificial Sequence -continued
<220> FEATURE:
<223> OTHER INFORMATION: Synthetic
<400> SEQUENCE: 32

```
agttgctaga aagcaatgcg cctattcaca tggagaatct tccctttcct ctaaaattac      60
ttagtgcctc atcactaaac acccccagct ccacaccatg ggtgttggat atcttcctca     120
ccttggtgtt tgccctgggg ctcttcttcc tattactccc ctacttctct tacctccgtt     180
gtgacaaccc accctcacca tcgcctagga agagaaagcg tcatcttgtc tcccagcgtc     240
cagcagggcg gaggggaggg cccagaggca ggatgaaaaa ccacagtctg agagggtaag     300
gctctgccag ggcacactag agttaatttg atctcatctg tccgggaggg aactgactct     360
gaagaagtca gttgaaaaaa cctgaggtgg gggctcctag gaaggaaatc agaaccctgg     420
gtccttctca gattctgtgc cgccggaatg aagccatggt gggccaggga ctgagcgtta     480
cccagcaggg ggcagtgtgt gtgtcctggg gagaccaatg cctgcctgga tgcggagggg     540
ggtgaggggc ctcccgctcc ctgggaacag ctgttcaact ctgctaaggc tgattcctct     600
ctgagaccac cccagtcctt tctcctcaca ggcgagttgt gaggaccgtg ggggtggagg     660
gtctgtgtgt ggaagccctt tgtgaatgac aaagccctgt cctctatgcc ttgctattac     720
cgtcggggcc atgtggcttt ggacacagat gggtgggttc cagggtctaa ttccccatgg     780
tcttccctaa agaaacatac actcagcctc ctgtgagatc ccaagcccct ccctcactgc     840
cctaacccgg tctgatttcc agcttgtaga gagtgcccga gaggcctgga ggagacttgg     900
gacctgcttt cacaactgca gaggtgaggc acttcccctt ccctgcgtcc ttcctaccag     960
ggctgggacg tgaccccagg gccacaggca gcctggagtc gacctgggat ggagagacca    1020
gggggacaga ggatgggagt aaagccctgg ggcgaggggt agcaggagaa ttgggtggtc    1080
agggtgtggc gtggtggagg ggctgtggcc caagcgccca ctctgccctg gcaacccatc    1140
tgctcctggc tgcagcttgt gcctcctgtc tcctgcagcc tcctggggcc acaccttgaa    1200
```

<210> SEQ ID NO 33
<211> LENGTH: 102
<212> TYPE: DNA
<213> ORGANISM: Artificial Sequence
<220> FEATURE:
<223> OTHER INFORMATION: Synthetic
<400> SEQUENCE: 33

```
atggagaatc ttccctttcc tctaaaatta cttagcgtca tcttgtctcc cagcgtccag      60
ggcggagggg gaggcccaga ggcaggatga aaaaccacag tc                        102
```

<210> SEQ ID NO 34
<211> LENGTH: 34
<212> TYPE: PRT
<213> ORGANISM: Artificial Sequence
<220> FEATURE:
<223> OTHER INFORMATION: Synthetic
<400> SEQUENCE: 34

```
Met Glu Asn Leu Pro Phe Pro Leu Lys Leu Leu Ser Val Ile Leu Ser
1               5                   10                  15

Pro Ser Val Gln Gln Gly Gly Gly Gly Gly Pro Glu Ala Gly Lys Thr
            20                  25                  30

Thr Val
```

<210> SEQ ID NO 35

-continued

```
<211> LENGTH: 7
<212> TYPE: DNA
<213> ORGANISM: Artificial Sequence
<220> FEATURE:
<223> OTHER INFORMATION: Synthetic

<400> SEQUENCE: 35 gagaaat                                                                                          7

<210> SEQ ID NO 36
<211> LENGTH: 12
<212> TYPE: DNA
<213> ORGANISM: Artificial Sequence
<220> FEATURE:
<223> OTHER INFORMATION: Synthetic

<400> SEQUENCE: 36
cgtggccgag cc                                                                                    12

<210> SEQ ID NO 37
<211> LENGTH: 12
<212> TYPE: DNA
<213> ORGANISM: Artificial Sequence
<220> FEATURE:
<223> OTHER INFORMATION: Synthetic

<400> SEQUENCE: 37
cccgagaaat ga                                                                                    12

<210> SEQ ID NO 38
<211> LENGTH: 14
<212> TYPE: DNA
<213> ORGANISM: Artificial Sequence
<220> FEATURE:
<223> OTHER INFORMATION: Synthetic

<400> SEQUENCE: 38
cagggactgg ggct                                                                                  14

<210> SEQ ID NO 39
<211> LENGTH: 14
<212> TYPE: DNA
<213> ORGANISM: Artificial Sequence
<220> FEATURE:
<223> OTHER INFORMATION: Synthetic

<400> SEQUENCE: 39
agggactggg gctc                                                                                  14

<210> SEQ ID NO 40
<211> LENGTH: 14
<212> TYPE: DNA
<213> ORGANISM: Artificial Sequence
<220> FEATURE:
<223> OTHER INFORMATION: Synthetic

<400> SEQUENCE: 40
tttgggtccg ggcg                                                                                  14

<210> SEQ ID NO 41
<211> LENGTH: 14
<212> TYPE: DNA
<213> ORGANISM: Artificial Sequence
<220> FEATURE:
<223> OTHER INFORMATION: Synthetic

<400> SEQUENCE: 41
```

```
ttgggtccgg gcgg                                                              14

<210> SEQ ID NO 42
<211> LENGTH: 14
<212> TYPE: DNA
<213> ORGANISM: Artificial Sequence
<220> FEATURE:
<223> OTHER INFORMATION: Synthetic

<400> SEQUENCE: 42
tgggtccggg cggg                                                              14

<210> SEQ ID NO 43
<211> LENGTH: 2000
<212> TYPE: DNA
<213> ORGANISM: Artificial Sequence
<220> FEATURE:
<223> OTHER INFORMATION: Synthetic

<400> SEQUENCE: 43
ctgggcggcc gggcgcgggg agagggcgcg ggagcggctc gtgcggcagg taccatgcgg         60
acgcgcgagc ccggcgaggg ccccggcagg cccggtccct gctcgggggc gcgctgagac        120
ggcgggtgag ctccacgaga gcgccgtcgc cacttcgggc caactttgcg attcccgaca        180
gttaagcaat ggggagacat ttggctttgc tcctgcttct gctccttctc ttccaacatt        240
ttggagacag tgatggcagc caacgacttg aacagactcc tctgcagttt acacacctcg        300
agtacaacgt caccgtgcag gagaactctg cagctaagac ttatgtgggg catcctgtca        360
agatgggtgt ttacattaca catccagcgt gggaagtaag gtacaaaatt gtttccggag        420
acagtgaaaa cctgttcaaa gctgaagagt acattctcgg agactttgc tttctaagaa         480 taaggaccaa aggaggaaat aacagctatt cttaatgaga agtgaaggat cactacacat        540
tgatagtgaa agcacttgaa aaaaatacta atgtggaggc gcgaacaaag gtcagggtgc        600
aggtgctgga tacaaatgac ttgagaccgt tattctcacc cacctcatac agcgtttctt        660
tacctgaaaa cacagctata aggaccagta tcgcaagagt cagcgccacg gatgcagaca        720
taggaaccaa cggggaattt tactacagtt ttaaagatcg aacagatatg tttgctattc        780
acccaaccag tggtgtgata gtgttaactg gtacacttga ttacctagag accaagctct        840
atgagatgga aatcctcgct gcggaccgtg gcatgaagtt gtatgggagc agggcatcat        900
gcagcatggc caagctaacg gtgcacatcg aacaggccaa tgaatgtgct ccggtgataa        960
cagcagtgac attgtcacca tcagaactgg acagggaccc ggagcatatg caattgtgac       1020
agtggatgac tgcatcaggg tccaatggtg acatagcatc tttaagcatc gtggcaggtg       1080
accttctcca gcagtttaga acagtgaggt cctttccagg gagtaaggag tataaagtca       1140
aagccatcgg tggcattgat tgggacagtc atccttttcgg ctacaatctc acactacagg      1200
ctaaagataa aggaactccg ccccagttct cttctgttaa agtcattcac gtgacttctc       1260
cacagttcaa agccgggcca gtcaagtttg aaaaggatgt ttacagagca gaaataagtg       1320
aatttgctcc tcccaacaca cctgtggtca tggtaaaggc cattcctgct tattcccatt      1380
tgaggtatgt ttttaaaagt taacacctgg aaaagcaatt cagtttaaat tacaacactg       1440
gtctcatttc tattttagaa ccagttaaaa gacagcaggc agcccatttt gaacttgaag       1500
taacaacaag tgcacagaaaa gcgtccacca aggtcttggt gaaagtctta ggtgcaaata      1560 gcaatcccccc tgaatttacc cagacagcgt acaaagctgc ttttgatgag aacgtgccca     1620
```
ttggtactac tgtcatgagc ctgagtgccg tagaccctga tgagggtgag aacgggtacg      1680
tgacatacag tatcgcaaat ttaaatcatg tgccgtttgc gattgaccat ttcactggtg      1740
ccgtgagtac gtcagaaaac ctggactacg aactgatgcc tcgggtttat actctgagga      1800
ttcgtgcatc agactggggc ttgccgtacc gccgggaagt cgaagtcctt gctacaatta      1860
ctctcaataa cttgaatgac aacacacctt tgtttcagaa aataaattgt gaagggacaa      1920
ttcccagaga tctaggcgtg ggagagcaaa taaccactgt ttctgctatt gatgcagatg      1980
aacttcagtt ggtacagtat                                                   2000

<210> SEQ ID NO 44
<211> LENGTH: 1190
<212> TYPE: DNA
<213> ORGANISM: Artificial Sequence
<220> FEATURE:
<223> OTHER INFORMATION: Synthetic

<400> SEQUENCE: 44
aaggtaggtc gactgaactt gatgagtcct ctctgaatca cgggctctcg gctccgtgta        60
ttttcagctc gggaaaatcg ctggggctgg gggtggggca gtggggactt agcgagtttg       120
ggggtgagtg ggatggaagc ttggctagag ggatcaggag ttgcattgtt gggagacctg       180
ggtgtagatg atggggatgt taggaccatc cgaactcaaa gttgaacgcc taggcagagg       240
agtggagctt taccttgagc cggcctaaag cgtacttctt tgcacatcca cccggtgctg       300
ggcgtaggga atccctgaaa taaaagcaca tgacggaggt tgtgaggcgc tgcccccacc       360
atgagcccat tgagactcaa tagcgtaata ttttagagcc catggcatcc tagtgaaaac       420
tggggctcca ttccgaaatg atcatttggg ggtgatccgg ggagcccaag ctgctaaggt       480
cccacaactt ccggaccttt gtccttcctg gagcgatctt tccaggcagc ccccggctcc       540
gctagatgga gaaaatccaa ttgaaggctg tcagtcgtgg aagtgagaag tgctaaacca       600
ggggtttgcc cgccaggccg aggaggaccg tcgcaatctg agaggcccgg cagccctgtt       660
attgtttggc tccacattta catttctgcc tcttgcagca gcatttccgg tttcttttttg      720 ccggagcagc tcactattca cccgatgaga ggggaggaga gagagagaaa atgtccttta       780
ggccggttcc tcttacttgg cagagggagg ctgctattct ccgcctgcat ttctttttct       840
ggattactta gttatggcct ttgcaaaggc aggggtattt gttttgatgc aaacctcaat       900
ccctcccctt ctttgaatgg tgtgccccac cccgcgggtc gcctgcaacc taggcggacg       960
ctaccatggc gtgagacagg gagggaaaga agtgtgcaga aggcaagccc ggaggtattt      1020
tcaagaatga gtatatctca tcttcccgga ggaaaaaaaa aaagaatggg tacgtctgag      1080
aatcaaattt tgaaagagtg caatgatggg tcgtttgata atttgtacct gttatctagc      1140
tttgggctag gccattccag ttccagacgc aggctggctt ttgttgcagg               1190

<210> SEQ ID NO 45
<211> LENGTH: 61
<212> TYPE: DNA
<213> ORGANISM: Artificial Sequence
<220> FEATURE:
<223> OTHER INFORMATION: Synthetic

<400> SEQUENCE: 45
attcataaac ccgccctttg taggaggaag cggtgaacca cggggcgtgg tcattcgtgt        60
c                                                                        61

PRECISION MEDICINE PORTAL FOR HUMAN DISEASES

CROSS-REFERENCE TO RELATED APPLICATIONS

This application is a continuation of International Application No. PCT/US2021/047027, filed on Aug. 20, 2021, entitled "A PRECISION MEDICINE PORTAL FOR HUMAN DISEASES", which claims priority under Article 8 of the PCT to U.S. Provisional Application No. 63/166, 803, entitled "A UNIFIED PORTAL FOR REGULATORY AND SPLICING ELEMENTS FOR GENOME ANALYSIS," to Sudar Senapathy, filed on Mar. 26, 2021, and to U.S. Provisional Application No. 63/166,829, entitled "A PRECISION MEDICINE PORTAL FOR HUMAN DISEASES," to Periannan Senapathy, filed on Mar. 26, 2021, the contents of both applications incorporated herein by reference in their entirety, for all purposes.

This application is related to International Application No. PCT/US2021/047025 filed Aug. 20, 2021, which claims the benefit of U.S. Provisional Patent Application No. 63/166,803, filed Mar. 26, 2021, and U.S. Provisional Patent Application No. 63/166,829, filed on Mar. 26, 2021, each of which is owned by Applicant and is incorporated herein by reference and which is not admitted to be prior art with respect to the present invention by its mention in the cross-reference section.

SEQUENCE LISTING

The instant application contains a Sequence Listing which has been filed electronically in ASCII format and is hereby incorporated by reference in its entirety. Said ASCII copy, created on May 10, 2022, is named 112503-0023 SEQ.txt and is 26,092 bytes in size.

BACKGROUND

Field

The present disclosure relates generally to a platform of networked computing devices for performing a comprehensive use of gene regulation in the human genome. More specifically, the present disclosure provides a platform for use in pharmaceutical and therapeutic applications, as well as in biological and anthropological research, for the use of gene mutations and their phenotypical manifestation in the development of personalized medicine, new drugs and treatments to cure disease, and for understanding social and behavioral traits in different human communities over time.

Related Art

The traditional expectation in clinical genomics has been that most disease-causing mutations occur in the protein-coding regions (exons, which are protein-coding sequences called CDS), as they directly affect the proteins. The vast majority of cancer-causing mutations in the TP53 gene, for example, are thought to be caused by the CDS mutations (missense, nonsense, and Frameshift), The widely used clinical genome sequence analysis software focuses on the coding sequence mutations. In addition, the American College of Medical Genetics (ACMG) guidelines largely focus on CDS variants and classify them as Pathogenic (P), Likely Pathogenic (LP), Benign (B), Likely Benign (LB), and Variants of Unknown Significance (VUS), which are universally followed in the clinical genomics field. However, a vast majority of the genome includes non-coding portions, which are largely ignored or considered secondary information sources, in state of the art approaches.

SUMMARY

In a first embodiment, a computer-implemented method for genomic analysis includes receiving a nucleotide string comprising a plurality of nucleotides from at least a portion of one or more individual patients genome, wherein the portion of one or more individual patient's genome includes at least one of: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a Dark Matter genome. The computer-implemented method includes identifying a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof. The computer-implemented method also includes assigning each identified variant a score based on a location of a variant and a predicted functional consequence. The computer-implemented method also includes determining a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory. The computer-implemented method also includes identifying at least one phenotype such as a disease, a drug response, a therapeutic indications, and a harmful side effects of a medication or substance, based on the strength of the variation identified in one or more patients, and displaying, in a graphic unit interface of a client device, said nucleotide string, the identified variants, and the at least one phenotype, in one or more genetic elements for one or more individual patients.

In a second embodiment, a system includes a memory storing instructions, and one or more processors configured to execute the instructions to cause the system to receive a nucleotide string comprising a plurality of nucleotides from at least a portion of one or more individual patients genome, wherein the portion of one or more individual patients genome includes at least one of: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a Dark Matter genome. The one or more processors also execute instructions to cause the system to identify a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof. The one or more processors also execute instructions to cause the system to assign each identified variant a score based on a location of a variant and a predicted functional consequence, and to determine a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory. The one or more processors also execute instructions to cause the system to identify at least one phenotype such as a disease, a drug response, a therapeutic indications, and a harmful side effects of a medication or substance, based on the strength of the variation identified in one or more patients, and to display, in a graphic unit interface of a client device, said nucleotide string, the identified variants, and the at least one phenotype, in one or more genetic elements for one or more individual patients.

In a third embodiment, a non-transitory, computer-readable medium stores instructions which, when executed by a processor, cause a computer to execute a method for genome analysis. The method includes receiving a nucleotide string comprising a plurality of nucleotides from at least a portion of one or more individual patients genome, wherein the portion of one or more individual patients genome includes at least one of: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a Dark Matter genome. The method includes identifying a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof. The method also includes assigning each identified variant a score based on a location of a variant and a predicted functional consequence. The computer-implemented method also includes determining a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory. The method also includes identifying at least one phenotype such as a disease, a drug response, therapeutic indications, and a harmful side effects of a medication or substance, based on the strength of the variation identified in one or more patients, and displaying, in a graphic unit interface of a client device, said nucleotide string, the identified variants, and the at least one phenotype, in one or more genetic elements for one or more individual patients.

BRIEF DESCRIPTION OF THE DRAWINGS

FIGS. 9A-9C illustrates a chart of a pathogenome module in a genome sequence analysis engine, according to some embodiments.

FIG. 10 illustrates a chart with mutation distributions for genes having pharmacologic impact, according to some embodiments.

FIGS. 13A-13D illustrates a customizing framework configured to provide a cohort pathogenome frequency plot, a pathogene frequency plot, and an individual pathogenome plot in a genome sequence analysis engine, according to some embodiments.

FIGS. 16A-16B illustrates the structure of an entire gene in a compact and expanded view provided by a genome sequence analysis engine, according to some embodiments.

FIGS. 19A-19C-1 through -3, illustrate a gene fusion mutation event leading to a chimeric gene, according to some embodiments.

FIGS. 20A-20G illustrate mutation visualizations provided by a genome sequence analysis engine, according to some embodiments.

FIG. 24 illustrates steps in a method for studying a disease or other inherited trait using a gene explorer platform, according to some embodiments.

FIG. 25 illustrates steps in a method for developing a therapeutic procedure using a gene explorer platform, according to some embodiments.

FIG. 26 illustrates steps in a method for applying a genome explorer platform to identify structural variants and phenotypic traits in a population cohort, according to some embodiments.

Figure 1:
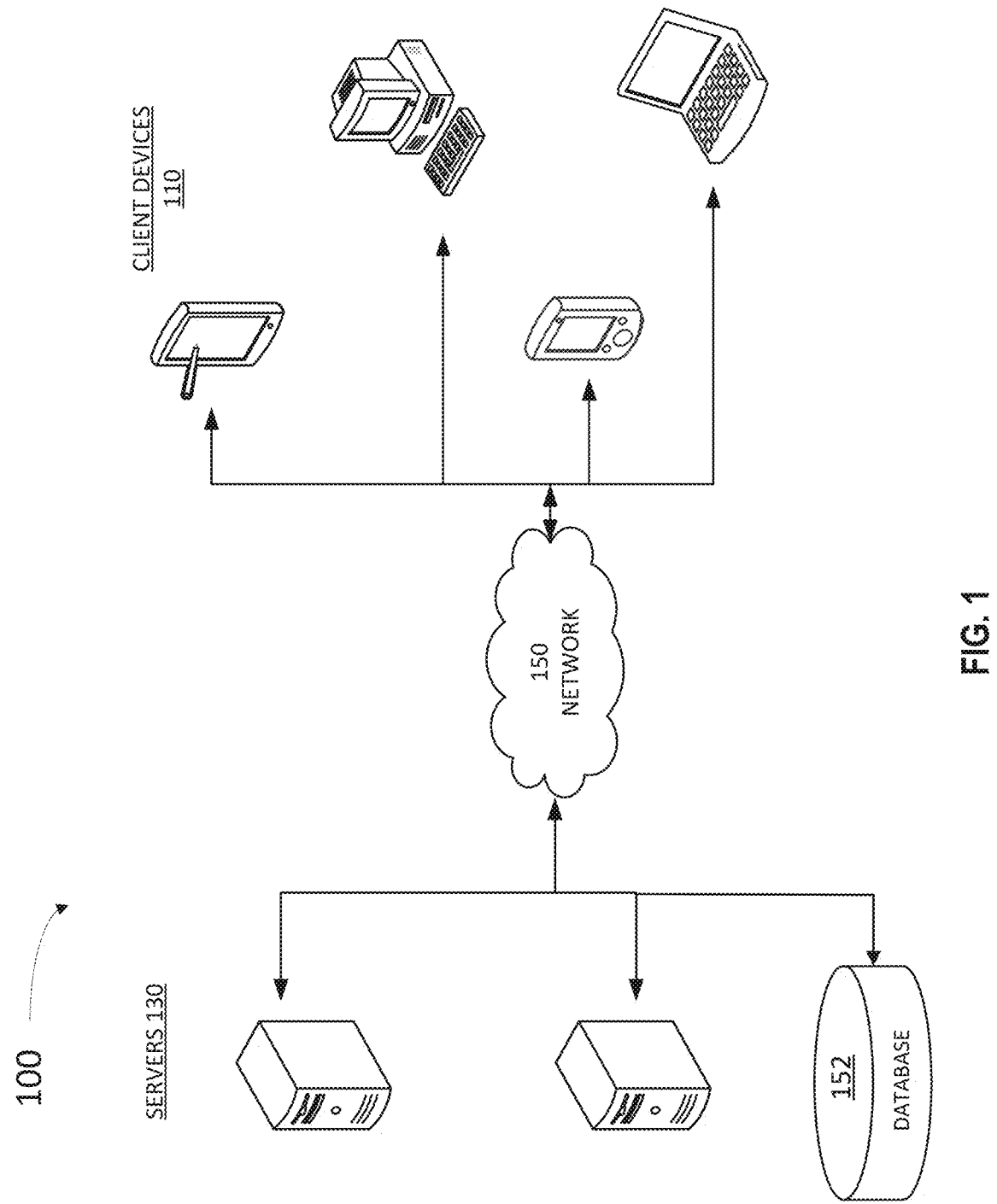
FIG. 1 illustrates an architecture of devices and systems for providing a personalized product service, according to some embodiments.

In the figures, elements or steps having the same or similar labels are associated with features or processes having the same or similar description, unless otherwise stated.

DETAILED DESCRIPTION

In the following detailed description, numerous specific details are set forth to provide a full understanding of the present disclosure. It will be apparent, however, to one ordinarily skilled in the art, that the embodiments of the present disclosure may be practiced without some of these specific details. In other instances, well-known structures and techniques have not been shown in detail so as not to obscure the disclosure.

The field of clinical genomics has largely focused on the coding sequence of genes to predict and diagnose the disease-causing mutations. However, it is increasingly clear that the majority of these mutations occur outside of the coding regions and in the regulatory and splicing regions. Some embodiments of the present disclosure include identifying the mutations in coding and non-coding regions and their cryptic versions, in the human genome. Some embodiments are able to predict disease-causing mutations in different regulatory and splicing regions and their cryptic versions in a gene, which may occur across patients exhibiting a particular disease, combine them to identify the genes and mutations that cause various disease and drug response phenotypes, and apply these discoveries to precisely diagnose individual patients. Some embodiments also include scans and analysis in uncharted regions of the genome called the dark matter genome to further identify the mutations within the potential additional genes and the regulatory regions that cause disease. Some embodiments enable the identification of the complete pathology of the genome and the comprehensive diagnosis of potential diseases and drug response phenotypes in a patient. The present disclosure thus accurately decodes and prioritizes disease-causing genes and mutations for cancers and non-cancer disorders, and assists the healthcare providers in clinical decisions.

Embodiments as disclosed herein also relate to the dark matter of the genome, which encompasses 98% of the human genome that does not code for the proteins. Only 1-2% of the human genome encodes proteins (exons), and the remaining 98% consists of non-coding RNA genes, untranslated regions, splice sites, branch sites, enhancers and silencers, regulatory elements, cryptic sites of all of the regulatory elements, and introns. It is thought that these elements are extremely important in the function of the genome, and mutations in them are involved in causing disease and drug response phenotypes. In addition, there are many new genes within the intergenic regions or spaces (i.e., between the known genes), which are yet to be discovered, and mutations in them also can lead to diseases. Genome Explorer focusses on these areas of the genome to unravel their hidden wealth and to enable the discovery of important genetic information that will advance the understanding of the disease and drug response, ultimately benefiting the practice of medicine.

The platform is automated for analyzing a patient's DNA, and the genomes of multiple patients from a trio, family, cohort, and clinical trials. It has unique modules and platforms for analyzing the whole genome, exomes, gene panels, and individual genes in various ways with finer and granular visualization of every gene from every patient in a clinically relevant setting. Genome Explorer is divided into several major platforms including Patient Genomics™, Family Genomics™, Cohort Genomics™, Clinical Trials Genomics™, EHR Genomics™, and Dark Matter Genomics™. The platform has expanded further into additional platforms and modules for individual diseases such as hypertrophic cardiomyopathy or neuroblastoma, or groups of diseases such as lung cancer, colon cancer, cardiological disorders, neurological disorders, and many other diseases including newborn, fetal, infertility and women's diseases.

The disclosure includes a wide range and automated sequencing data analysis platform for oncology and non-neoplastic inherited disorders, which seamlessly provides a unified treatment approach specific to the individual based on the variations present in the individual's genome. The platform identifies many possible genetic alterations such as Single Nucleotide Variations (SNV), Insertions and Deletions (InDels), Copy Number Variations (CNV), Structural Variations (SV), Gene Fusions, Splice acceptor and Splice donor variations, variations at the promoter and poly-Adenylated sites, backed by the tissue-specific gene expression levels. The promoter, poly-A, and intronic mutations are indicated as per the Shapiro-Senapathy algorithm to have a high mutation impact.

In some embodiments, an evidence-driven platform incorporates standard practice guidelines from the Association for Molecular Pathology (AMP), the ACMG, and the College of American Pathology (CAP). The drug-metabolizing phenotypes are defined as per the Clinical Pharmacogenetics Implementation Consortium (CPIC) guidelines for the patient's sequence variants. The platform generates predictions based on the clinical history and patient presentation available in the electronic healthcare record (EHR) data to facilitate informed decision making From the disease incidence and progression history, and various pathology, laboratory, imaging, and/or genomic sequencing and reports in the patient's EHR, the present disclosure comprehensive framework simplifies and enhances personalized approaches starting from diagnosis through therapeutics and dosage recommendations.

Thus, the field has largely ignored the regulatory mutations, giving them a low priority, and consolidated tools to address these regions have been mostly lacking. However, recent findings indicate that the majority of disease-causing variants occur outside of the coding regions, and it is increasingly becoming apparent that mutations in regulatory and splicing elements are responsible for upwards of 60% of many diseases. The present disclosure fulfills this need and enables the systematic analysis of the mutations in many of the regulatory and splicing elements. In addition, the platform aims to discover novel disease-causing genes and diagnosing additional patients based on mutations in different regulatory regions throughout the gene, in addition to the CDS regions.

Some of the features for rationale, logic, algorithms, methodologies, and discoveries implemented in some embodiments may include:

i) Detecting causal genes for cancers and other disorders: GE's methodology to identify the genes causal of a disease is to determine that deleterious mutations occur within multiple regulatory and coding elements of a gene across many patients. The expectation or the principle is that, if the defectiveness of a gene is a primary cause of the disease, then a deleterious mutation at any of the regulatory or coding elements of that gene should be able to cause the disease individually and independently. Thus, mutations in different regulatory elements in the same gene individually should cause the disease in different patients. For example, in a particular gene with 20 exons, a mutation at the donor site of exon 17 in one patient, a mutation at the acceptor site of exon 6 of another patient, a cryptic mutation at the branch point site of exon 14 in a 3rd patient, a mutation at the promoter site in a 4th patient, or a particular amino acid mutation in a coding sequence in a 5th patient, and so on, can cause the same disease in each of these patients independently. This approach of identifying mutations in multiple regulatory elements of the same gene across multiple patients in a cohort analysis is the basis to discover genes causing a disease that underlies the patient cohort by a platform as disclosed herein. The present disclosure thus has formulated a principle that a combination of different mutations in different regulatory elements in the same gene in different patients would lead to a particular disease by making that gene defective and thus would enable the discovery of that gene in a cohort analysis. Furthermore, although the manner in which the mutations at the different regulatory or coding elements lead to the defect in the protein, they make the same protein defective. Thus, embodiments in the present disclosure are able to identify the mechanism of a mutation causing the gene and protein defect and present it to the clinicians.

ii) Gene signature as a predictor of a disease: The present disclosure can bring out the complete pathology of the genome of patients that are indicative of many potential diseases including cancers and non-cancer disorders. GE expects that each specific cancer or any other disease should have a unique gene signature. GE has the ability to bring out the gene signature specific for different cancers and other diseases. Even though majorly cell structure, function, and regulatory genes are mostly affected, sets of genes that are expressed in specific organs vary. It is expected that there will be a core cancer gene signature for any cancer and a sub-signature specific to different tissues and organs. Thus, GE aims to find these signatures based on its ability to uncover disease-causing mutations within the CDS and many of the different regulatory elements. The platform produces specific signatures of genes that exhibit deleterious mutations from cohort studies of different cancers and diseases, which could be diagnostic marker signatures for the different diseases. As a corollary, the presence of a set of mutated genes or a gene signature in a patient's DNA would signify or diagnose a particular disease in the patient. Thus, the present disclosure is able to predict or diagnose a disease from the genomic data obtained from the blood cells, or any type of cell/tissue source, or from the cell-free DNA or circulating tumor DNA from a patient. It would thus be able to predict any cancer possible in the future in a newborn, or cancer that is present in any of the tissue or organs in a patient, unknown to the patient. This ability can also be used as a diagnostic approach to predict any cancer from the data obtained from a blood sample in a patient at any stage of the tumor growth.

Some embodiments include a combination of certain types of genes that are often required to cause particular cancer or a non-cancer disease. For instance, causing cancer requires multiple genetic and molecular steps: 1) a cell should lose its cell division control to make it divide uncontrollably, 2) the cell should be able to detach itself from its current position and float in the circulatory system, 3) the cell should be able to attach itself at another location in the body, and 4) the tumor that grows from this cell should be able to establish its growth environments including blood circulation, growth of blood vessels, and so on. Thus, multiple genes have to be mutated for a cell to become cancerous, metastasize, and establish tumors growing at other locations in the body. The present disclosure determines, based on its cohort studies by using its approach of detecting mutations across multiple genetic elements, that certain necessary types of genes are required to become defective (due to mutations in gene expression regulation, splicing, or CDS): 1) a gene that is required to stop or control the cell division cycle, 2) a gene that is required in cell structure (e.g., cytoskeleton stability), 3) a gene that is required for extracellular matrix and/or cell-cell adhesion, 4) a gene that is required for cell detachment and motility, 5) a gene that is required for anchoring the cancer cell in another location, and 6) a gene that is required for establishing the growth environment, and so on. Some embodiments determine that a gene signature should contain the combination of one or more defective genes from each of these types of gene/cell functions to cause cancer and metastasis. For example, the TP53, TAF3, or OBSCN gene that is involved in transcriptional regulation, a PCDH, DNAH, or KIF gene that is involved in cell structure, and MT1E and NNMT in cell migration.

iii) Family genomics: The present disclosure performs the Next-Generation Sequencing (NGS) based genomic family analysis including father, mother, and child (trio), or siblings, grandparents, and other relatives such as aunts and uncles for multiple generations (family), providing a strategy for the identification of causal variants and genes for inherited diseases that run in the family, and congenital disorders. The trio analysis pipeline within the platform accurately helps to identify variants inherited from the parents causing recessive diseases or dominant diseases and the drug response phenotypes. It has the potential to identify disease-causing variants based on the zygosity of many family members and the mode of inheritance (MOI), which otherwise is not possible by individual patient analysis. Trio/Family analysis can be performed using either whole genome, whole exome, or from the targeted gene panels and analyzing complete variant/mutation information such as SNVs, indels, real and cryptic splice sites, branch sites, enhancers and silencers, UTRs, promoters, transcription initiators, poly-A sites (many within exons, introns, regulatory elements, and throughout the gene) and ncRNAs (tRNA, rRNA, miRNA, siRNA, snoRNA, snRNA, and lncRNA) supported by gene tissue expression data (wherever applicable). They can also be performed based on structural variants, CNVs, Gene Fusions, and other chromosomal aberrations and rearrangements. The family analysis can be a standard routine test in patients with common diseases, rare genetic conditions, or having atypical clinical presentations or undiagnosed genetic disorders, where the cause and mode of inheritance are not ascertained. In addition, it can aid in determining the carrier gene status of various diseases or drug response phenotypes. The present disclosure relates to processes for characterizing and screening for genes that are the cause for the existence or predisposition to inherited disorders or denovo (congenital) disorders, and ADRs, in the subject, and also relates to therapies for prevention, therapeutics, and/or reducing the severity. The family analysis reports the deleterious genetic alterations at genomic regions like exons, introns, promoters, UTRs, poly-A sites, and splice regions among the family members. The downstream molecular effects of SNPs, small Indels, large genomic rearrangements like gene fusion, copy number variants, and structural variants can be easily analyzed and visualized. The alterations observed at the coding, exonic, promoter, poly-A, splice site, intronic, and deep intronic sites are compared among the family members based on the genotype, zygosity, and mode of inheritance to identify the disease-associated mutations, genes, domains, and pathways. The distribution of mutated genes, domains, pathways, and actionable drugs in individual patients, parents, and the trio or family are provided to determine the mutation lineage. Mutations in the spectrum of poly-A regions, promoter regions (e.g., TATA box, CAAT box, GC box, and initiator regions), along with the real acceptor, real donor, cryptic splice acceptor, cryptic splice donor, branch regions, and cryptic exons, are analyzed to provide comprehensive and novel insights of these regions towards disease pathogenesis. The platform also provides options to scan many human gene families, protein domains, and gene super-families, and cell structure/function, and gene-expression regulation genes, which helps in understanding the mutation inheritance pattern across genes or multiple genes within a family.

iv) Mode of inheritance patterns in the proband: The zygosity and mode of inheritance of many of the different mutations in the coding and regulatory elements are assessed throughout the gene, multiple genes, or many of the genes in the genome. They are also determined based on if the gene itself is normal or has become defective due to one or more deleterious mutations in any of these coding and/or regulatory elements within the gene (cis-acting) or from outside the gene itself (transacting). The various types of inheritance are determined based on the mutations in the various genetic elements as follows.

v) Denovo: The denovo mode of inheritance includes new mutations present in an affected child but not in either parent. The affected child must have unaffected parents and the affected child must be heterozygous (RV) while the parents must be homozygous (RR or VV) at variant positions.

vi) Autosomal dominant: The autosomal dominant mode of inheritance i.e., an affected child must be heterozygous (RV) and have at least one affected parent. A person with an autosomal dominant disorder has a 50 percent chance of having an affected child with one mutated gene (dominant gene) and a 50 percent chance of having an unaffected child with two copies of normal genes (recessive genes). It affects males and females in the same way.

vii) Autosomal recessive: The autosomal recessive mode of inheritance i.e., any affected person must be homozygous to alternate allele (VV). This DNA change occurs when both copies of the gene are mutated. A person with an autosomal recessive disorder inherits two mutated genes, one from each parent. These disorders are usually passed on by two carriers having a 25 percent chance of an unaffected child with two normal genes, a 50 percent chance of having an unaffected child (carrier), and a 25 percent chance of having an affected child with two recessive genes. It affects males and females in the same way.

viii) Compound heterozygous: The compound heterozygous mode of inheritance e.g., an affected child must be heterozygous (Rr) at both sites whereas one of the parents must be heterozygous (RV) and the other parent must be reference homozygous (RR) or vice versa at the variant site.

xix) X-linked recessive: The x-linked recessive mode of inheritance i.e., these mutations are present in genes on the X chromosome. In affected males, one altered copy of the gene is sufficient to cause the condition; whereas, in affected females, a mutation would have to occur in both copies of the gene to cause the disorder. Because it is unlikely that females will have two altered copies of this gene, males are affected by X-linked recessive disorders much more frequently than females. A characteristic of X-linked inheritance is that an affected father cannot have an affected son (e.g., no male-to-male transmission).

x) X-linked dominant: In the x-linked dominant mode of inheritance, the affected males are heterozygous or variant allele homozygous, the affected females must be heterozygous, and the unaffected must be reference allele homozygous. The girls of the affected dad must be affected and the boys of the affected dad must be unaffected; whereas, the mothers of affected males must be heterozygous and affected. Also, at least one parent of affected females must be heterozygous and affected.

xi) X-linked de-novo: The x-linked denovo mode of inheritance i.e., these are the new mutations present in the affected child but not in either parent in sex chromosomes. The selection of variants based on the inheritance patterns where the affected child must have unaffected parents and the affected female child must be heterozygous (RV) and the affected male child must be homozygous to alternate allele (VV) while the parents must be reference homozygous (RR) at variant positions.

xii) Y-linked: The variants exhibit a Y-linked mode of inheritance i.e., these mutations are present on the Y chromosome of an affected male child which can be passed from an affected father only. Selection of variants is based on the inheritance patterns where the affected child must have an affected father. Since only males have a Y chromosome, Y-linked traits are passed only from affected father to son and rarely occur in females.

In some embodiments, a genome analysis engine as disclosed herein performs a differential gene expression analysis directed to genome-wide messenger RNA (mRNA) expression data. Accordingly, a platform as disclosed herein provides higher resolution data and explicit measurement of transcripts level for studying gene expression via mRNA. Consequently, analyzing gene expression values provides deep insight into the interplay between intrinsic cellular processes and stochastic gene expression to explore biological conditions. The expression levels for each gene are compared between the case and control samples of a patient and the genes that carry certain statistical cutoffs are selected for further interpretation and validation. This type of analysis has been used as the basis for understanding the expression level of genes that drive physiological and disease mechanisms.

The mutations in the promoter regions of the genome, including the different promoter boxes and transcription initiation box are known to affect the expression of a gene's transcripts, which are known to lead to various diseases and traits. For example, Manganese superoxide dismutase (MnSOD) is known to prevent cancer progression, but the expression level of MnSOD can be reduced due to defects in the promoter region.

In addition, mutations in the 5' and 3' UTRs also are known to be causal of various diseases and traits. The promoter, UTR, poly-A, splicing, and other regulatory mutations in one gene can affect the expression of not only this gene but also genes that are regulated by its protein product. Thus, the ability to identify the mutations in the promoters, UTRs, splicing, poly-A, and regulatory regions, and to determine their corresponding effects on the levels of transcripts of a gene or the target genes that are regulated by a gene, would enable the correlations to disease conditions.

The advent of high throughput RNA sequencing technology facilitates the efficient detection of intergenic fusion events and acts as the most useful resource for the identification of fusion transcripts. Gene fusions are important in the cancer research field because of their potential as carcinogenic drivers. The RNA gene fusion module aims at detecting the intergenic fusion variants, unsupervised and supervised fusion transcripts, homology scores, quality metrics, and fusion frame classification. Identifying the gene fusion by whole genomic or exome sequencing assays is greatly interrupted by the large intronic segments and requires extra effort for exome enrichment analysis respectively. However, detecting the fusion events by RNA sequencing is fast and accurate in discovering biologically relevant fusions. Also, the present disclosure uses a dual-mapping strategy that enhances sensitivity and sharpens the analytical endpoints.

In some embodiments, a platform as provided herein investigates the causality of variants in the non-coding (nc) RNA genes which is gaining interest with the rapid discovery of correlations between mutations in these regions and diseases like cancers, and multisystemic disorders. The mutations that disrupt the cellular functions which are dependent on non-coding RNAs or the factors required for these RNA functions can be deleterious. The ncRNA genes like tRNA, rRNA, miRNA, siRNA, snoRNA, snRNA, and lncRNA are considered for the analysis of the pathogenicity of these variations, which are of major diagnostic importance. Most of these ncRNAs are also processed from their original genomic sequences to shorter forms, often using splicing signals (e.g., in tRNAs), and thus mutations that cause errors in the processing of these RNAs will also be deleterious and cause disease or Adverse Drug Reactions (ADRs). The ncRNA module in the present disclosure provides the possibility to visualize the processing of these ncRNAs from the genome, in tabular, graphical, and sequence illustrations. Approaches are also provided to examine the splicing patterns of mutant ncRNAs, other processing mechanisms, and/or the processes by which they may lead to disease. Identifying SNPs and Indels at the miRNA-related functional regions such as 3'-UTRs, pre-miRNAs and others collectively called MirSNPs represents a novel category of functional molecules that targets gene dysregulation resulting in susceptibility to or onset of human diseases. The deleterious mutations of mitochondrial transfer RNA (mt-tRNA) and mitochondrially encoded rRNA (mt-rRNA) genes are the commonest mitochondrial (mtDNA) mutations to cause many genetic diseases. Defects in oxidative phosphorylation in mitochondria are often associated with impairment of processes such as replication, transcription, or translation of mtDNA, which can be due to mutations in either of the mtDNA-encoded RNAs (tRNAs and rRNAs). Diseases caused by mt-tRNA mutations can also affect very specific tissue types, as in the case of neurosensory non-syndromic hearing loss, diabetes mellitus, and a diverse range of clinical phenotypes. Identification of disease-causing alleles at the region of si-RNA that promotes alteration in the gene expression level is also important to understand these diseases. In many cases, RNAs may provide a more readily accessible target for therapy than the defective or deficient proteins they regulate. Thus, discovering the disease-causing mutations at the RNA genes has the potential benefit especially for cancer specialists who focus on circulating RNA cancer biomarkers and also produce a wealth of new therapeutic targets, with a growing understanding of RNA biology.

In some embodiments, a platform as disclosed herein identifies a branch point sequence (BPS) is a highly conserved splicing signal essential for spliceosome assembly and lariat intron formation. These are typically located within 30-50 nucleotides upstream of the 3' splice site and are required for precise exon joining and are recognized through RNA-RNA and RNA-protein interactions with components of the spliceosome. Mutations within the sequences that disrupt these interactions are responsible for 9-10% of the genetic diseases that are caused by point mutations. Mutations localized in the branch point sequence might lead to an exon skipping due to improper binding of the SF1 and U2 snRNP splicing proteins and disruption of the natural acceptor splicing site. Mutations in the branch point sequence can also cause intron retention (whole or its fragment) if they create a new 3' splice site. The platform identifies many possible mutation events within these highly conserved regions, and/or associates the findings with publicly available disease and annotation databases. The platform can also be ideal to discover novel branch point mutations utilizing its cohort analysis or family analysis modules. It also enables the identification of cryptic branch point sites and the mutations within them throughout the gene and throughout the genome. This approach of detecting the mutations within the branch points acts as an effective strategy for the clinicians and researchers in analyzing the splicing defects associated with the disease. Also, branch point mutations establish a valuable resource for further investigations into the genetic encoding of splicing patterns and interpreting the impact of common and disease-causing human genetic variation on gene splicing.

Regulation and selection of splice sites is done by trans-acting splicing activator and splicing repressor proteins as well as cis-acting elements within the pre-mRNA itself such as exonic splicing enhancers (ESEs) and exonic splicing silencers (ESSs). These sequences are located within both exons and introns that either enhance or suppress splicing. ESEs and ESSs activate or repress splicing, respectively, from within exons while intronic splicing enhancers (ISEs) and silencers (ISSs) function from within introns. The cis-regulatory elements, e.g., exonic and intronic splicing enhancers (ESE and ISE, respectively) and exonic and intronic splicing silencers (ESS and ISS, respectively) are recognized by specific splicing repressors and activators (trans-acting elements) that help to properly carry out the splicing process.

In embodiments as disclosed herein, splicing enhancers are sites to which splicing activator proteins bind, increasing the probability that a nearby site will be used as a splice junction. These also may occur in the intron (intronic splicing enhancers, ISE) or exon (exonic splicing enhancers, ESE). An exonic splicing enhancer (ESE) is a DNA sequence motif consisting of ~6 bases within an exon that directs, or enhances, accurate splicing of pre-mRNA into messenger RNA (mRNA). Most of the activator proteins that bind to ISEs and ESEs are members of the SR protein family Such proteins contain RNA recognition motifs and arginine and serine-rich (RS) domains. Likewise, splicing silencers are sites to which splicing repressor proteins bind, reducing the probability that a nearby site will be used as a splice junction. These can be located in the intron itself (intronic splicing silencers, ISS) or in a neighboring exon (exonic splicing silencers, ESS). An exonic splicing silencer (ESS) is a short region (usually 4-18 nucleotides) of an exon and is a cis-regulatory element. ESSs inhibit or silence the splicing of the pre-mRNA and contribute to constitutive and alternative splicing. The majority of splicing repressors are heterogeneous nuclear ribonucleoproteins (hnRNPs) such as hnRNPA1 and polypyrimidine tract binding protein (PTB).

Point mutations in exons that inactivate an exonic splicing enhancer (ESE) can create an exonic splicing silencer (ESS), which in turn can lead to alternative events like exon skipping and eventually a truncated protein resulting in genetic disorders. Mutations in these regions are of very high significance as these are implicated in numerous cancers and non-cancer disorders. Also, the adaptive significance of splicing silencers and enhancers is further attested by multiple studies showing that there is a strong selection in human genes against mutations that produce new silencers or disrupt existing enhancers. Enhancers are cis-acting sequences that can greatly increase transcription rates from promoters regions and activate the transcription, while the silencer sequences that are bound by repressors have the opposite effect by inhibiting activators and reducing transcription. Enhancers and silencers are organized as a series of cis-acting sequences that are bound by trans-acting regulatory proteins similar to promoter-proximal regions. The group of transcription factor binding sites (enhancers and silencers) allows cells to perform logic operations and combine different sources of information to "decide" whether to express a gene.

The present disclosure defines untranscribed regions as sequences upstream of the gene start and downstream of the gene end up to several 1000 bases. It is known that promoter regions with multiple binding sites occur for over several 1000 bases upstream of the transcription initiation site where multiple proteins bind to regulate the gene. Similarly, gene-regulating sequences occur for over 1000s of bases downstream of the end of the coding sequence. The present disclosure can identify novel and known mutations in these highly conserved enhancer and silencer regions, untranscribed regions, and also cryptic sites and mutations in them, and can help in understanding gene regulation, gene expression, and splicing processes and their defects in disease and ADRs.

DNA methylation is a major epigenetic modification that is strongly involved in the physiological control of genome expression. Aberrant methylation may lead to the silencing of important genes, such as tumor suppressor genes, affecting their related transcriptional pathways, activating proto-oncogenes, and ultimately leading to cancer. Despite tremendous advances in treatment for cancer, the ability to detect cancer from tumor cfDNA fragments in blood using DNA methylation could help overcome the limitations of organ-specific screening tests and enable the clinical sensitivity needed for early cancer detection. The methylation pattern is specific for the different tissues in the body and a Methylseq database is created containing tissue-specific methylation patterns with and without cancer. The blood sample from an individual contains the cfDNA fragments that reflect the tissue of their origin. cfDNA fragments are sequenced and targeted methylation-based analysis helps in recognizing the differences in the methylation patterns in cell-free DNA fragments released by tumor cells in the blood. The tissue-specific methylation patterns are used to map the location of abnormally methylated cfDNA in the body. Detecting gene-specific DNA methylation signature in different stages of cancer cells identifies prognostic and predictive markers and improves treatments, thus extending the survival rate in cancer patients. The present disclosure enables the identification of methylation patterns in cfDNA and correlation with the mutations in the regulatory elements of genes. It also makes it possible to analyze these combinations of methylation patterns and the deleterious mutations in genes to study the inter-relationships between the two biological phenomena in producing the disease phenotypes.

Circulating tumor cells (CTCs) analysis is an effective tool in molecular profiling of cancer cells developed as a non-invasive, cost-effective alternative to tissue biopsy. Higher amounts of preoperative circulating tumor cells are known to be associated with disease recurrence and decreased overall survival. However, circulating tumor nucleic acids (DNA/RNA) in the liquid biopsy are constituents of circulating cell-free (plasma/serum) which is highly diluted by nucleic acids, extracellular vesicles, proteins, and metabolites from cancer and non-cancer cells, thus limiting the detection of variant allele frequencies. The sequenced and uniquely tagged cfDNA fragments are mapped against the human reference genome (GrCh37/hg19) and then the generated BAM is processed by Pisces variant caller. It identifies the small variants (single nucleotide variants (SNVs) and insertions and deletions (indels)) while filtering for mismatches due to sequencing or sample preparation errors and includes a collapsing algorithm to rescue variants broken up by the read boundaries. The quality of the variants is re-calibrated with variant QScore and distinguishes the true variants from cfDNA sequencing data against the background noise. The reference and variant sequences (e.g., A to C SNV, or AG to A deletion), the frequency, and a QScore are provided for each variant indicating the confidence rate that the variant is indeed present in the sample. Thus, low-frequency variant calling in NGS data from a liquid biopsy can be performed with higher confidence.

Nucleic acids secreted by the tumor cells can serve as predictive and prognostic biomarkers. CTCs as a source of tumor DNA/RNA can be molecularly profiled to detect informative genomic or mRNA expression signatures for cancers and to identify genetic mutations that predict response to targeted therapies. The present disclosure enables the detection of deregulated gene expression resulting in uncontrolled cell proliferation, immune regulation, and stromal remodeling that defines cancer. Discrete alteration in circulating RNA reflects dysregulation of cancer immunity, cell growth, proliferation, and stromal interaction. The mutations present in the ct or cf DNA, within the coding and many of the regulatory regions from the genome of a patient or cohort of patients, are detected, thus enhancing the ability to relate these mutations with the disease. It combines the mutations from the different regulatory regions to detect the most probable genes causal of disease or ADR, and also in combination with the coding regions. The pathways are identified based on the frequently mutated genes (FMGs) and significantly mutated genes (SMGs) to discover the molecular networks such as MAPK/RAS pathway, p53 signaling pathway, and signaling pathways affecting basic cell structure, cell signaling, cell divisions, and actions. These analyses provide a broadly applicable approach for non-invasive detection of early-stage tumors that may be useful for screening and management of patients with diseases. Early detection and intervention are likely to be the most effective means for reducing morbidity and mortality of human diseases. This non-invasive cancer biomarker detection in the present disclosure will provide a more effective and patient-friendly method for the detection, monitoring, and treatment of cancer.

In some embodiments, a platform as disclosed herein provides a gene expression signature. Accordingly, a database may host manually curated gene expression data gathered from multiple public resources and are annotated with biological conditions and ontology terms. The platform can find the differentially expressed genes that are up or down-regulated for different cancer types and across tumor stages. Tissue-specific gene expression data were collected from non-diseased tissue sites for each gene and treated as a control dataset. Similarly, disease-specific gene expression data were collected and treated as a disease cohort. The expression values (FPKM) are compared between healthy and disease datasets to find the case-control Gene Expression Ratio (GER). The top 20 up-regulated and down-regulated genes constitute the expression signature that will be unique for different diseases and across tumor stages for a given cancer. The platform is also able to determine the effects of mutations in the promoters, UTRs, poly-A, splice, and other regulatory regions which affects the gene's expression and correlates the corresponding effects on the levels of transcripts of a gene or the target genes and the patterns of expression (signatures) that are regulated by a gene in various diseases from RNA sequencing data including mRNA, cfRNA, and ctRNA. In some embodiments, the mutations and DNA methylation profiles are integrated with RNA-sequencing data to correlate methylation variation across tissues with differential gene expression levels. An RNA sequencing technique is employed for the analysis of the transcriptome and its quantification for measuring gene expression. The transcriptional levels are represented at the logarithmic scale for FPKM and Transcripts Per Million (TPM) for each identified gene. The majority of differentially expressed genes are then compared with the significant changes in DNA methylation, indicating that DNA methylation plays an essential role in mediating tissue differentiation. The platform employs an in-built algorithm to investigate the profiles of mutations, gene expression, and methylation mainly on the promoter, transcription start sites, and other regulatory and splicing regions whether DNA mutations, methylation, and gene expression have correlations across each other in disease causation.

In some embodiments, a platform as disclosed herein may be used to predict a likelihood of a disease in a newborn. The likelihood of a patient getting a disease depends on the particular gene(s) affected by pathogenic mutations, which can be a single gene to multiple genes. In addition, the zygosity and MOI of each mutation and the gene(s) themselves are also determinants of the causation of disease. The affected or carrier state of each of the deleteriously mutated genes in an individual can be determined based on the mutations in one or more genetic elements in one or more genes in one or more patients, and tabulated and graphically illustrated. The likelihood for a disease possibility in a patient can be determined and assigned a score, based on the total number of affected genes from a gene signature or a panel for a disease. This score information can then be used to predict one or more diseases in a patient based on the particular genes deleteriously mutated in the genome of a new patient.

In some embodiments, a platform as disclosed herein may be used for prediction of disease and other drug phenotypes. There are several methods we have developed to identify the genes indicating a disease: Doublet or triplet gene signatures, Cell structure-function based gene signatures, diagnosing disease in asymptomatic people using weighted scores, and finding scores based on the number of genes indicating the "Affected" status. We can combine the scores for these different methods in a single patient and define a combination method or algorithm to provide a FINAL SCORE of disease(s). The top scoring diseases should be indicative of the diseases that the individual may develop in the future, even a newborn. The validity of this method can be tested in individuals with multiple diseases from the EHR of a hospital system. The WGS from the blood cells should indicate the diseases by this method. This set of diseases can be verified by the actual diseases that the individuals have from the EHR. Scores can be given for the accuracy of the findings in each patient, and in a large number of patients in total. If this cumulative score average is high enough, like 80 or 90%, then this method can be effectively used to predict diseases in new patients. This is similar to the CVC method we use for CDS by combining multiple known methods and taking the average score to predict the deleterious mutations.

In some embodiments, a platform as disclosed herein may be configured to perform a method to form cancer gene signatures by analyzing a large number of patients using known gene panels for different cancers: First determine the mutated genes from the gene panels of a particular disease or cancer (or from different gene panels from different cancers) in one or more patients and collect the mutated genes for each patient. This will give a list of genes and their combinations (gene signatures) either single, double, or higher numbers, occurring in every patient. The frequency of patients including each of these combinations are determined and sorted in descending order. The combinations whose frequency is higher than a threshold are only considered and these combinations of genes with high frequency in a large population of patients will form multiple gene-combination signatures, which can then be used to predict that disease in a new patient. The combinations whose standard deviations (SD) are greater than or equal to a high SD can be valid signatures indicative of a disease.

Example System Architecture

FIG. 1 illustrates an architecture 100 of devices and systems for providing a map of genes and mutations thereof for an individual or a cohort of individuals, according to some embodiments. A server 130 may be coupled with a database 152 storing a genome sequence log for each of multiple users handling client devices 110. Servers 130, database 152, and client devices 110 may be communicatively coupled with each other via a network 150.

Servers 130 may interact and communicate with other devices in network 150 via any one of multiple interfaces and communications protocols (e.g., wired, cable, wireless, and the like). More specifically, servers 130 and client devices 110 may include an appropriate processor, memory, and communications capability, configured to interact with network 150 via a digital interface. Client devices 110 may include, for example, desktop computers, mobile computers, tablet computers (e.g., including e-book readers), a digital stand in a retailer store, mobile devices (e.g., a smartphone or PDA), wearable devices (e.g., smart watch and the like), or any other devices having appropriate processor, memory, and communications capabilities for accessing one or more of servers 130 through network 150. In some embodiments, client devices 110 may include a Bluetooth radio or any other radio-frequency (RF) device for wireless access to network 150. The memory in the client device from the retailer may include instructions from an application programming interface (API) hosted by server 130 (e.g., downloaded from, updated by, and in communication with server 130). The API in client devices 110 may be configured to cause client devices 110 to execute steps consistent with methods disclosed herein.

Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like.

Figure 2:
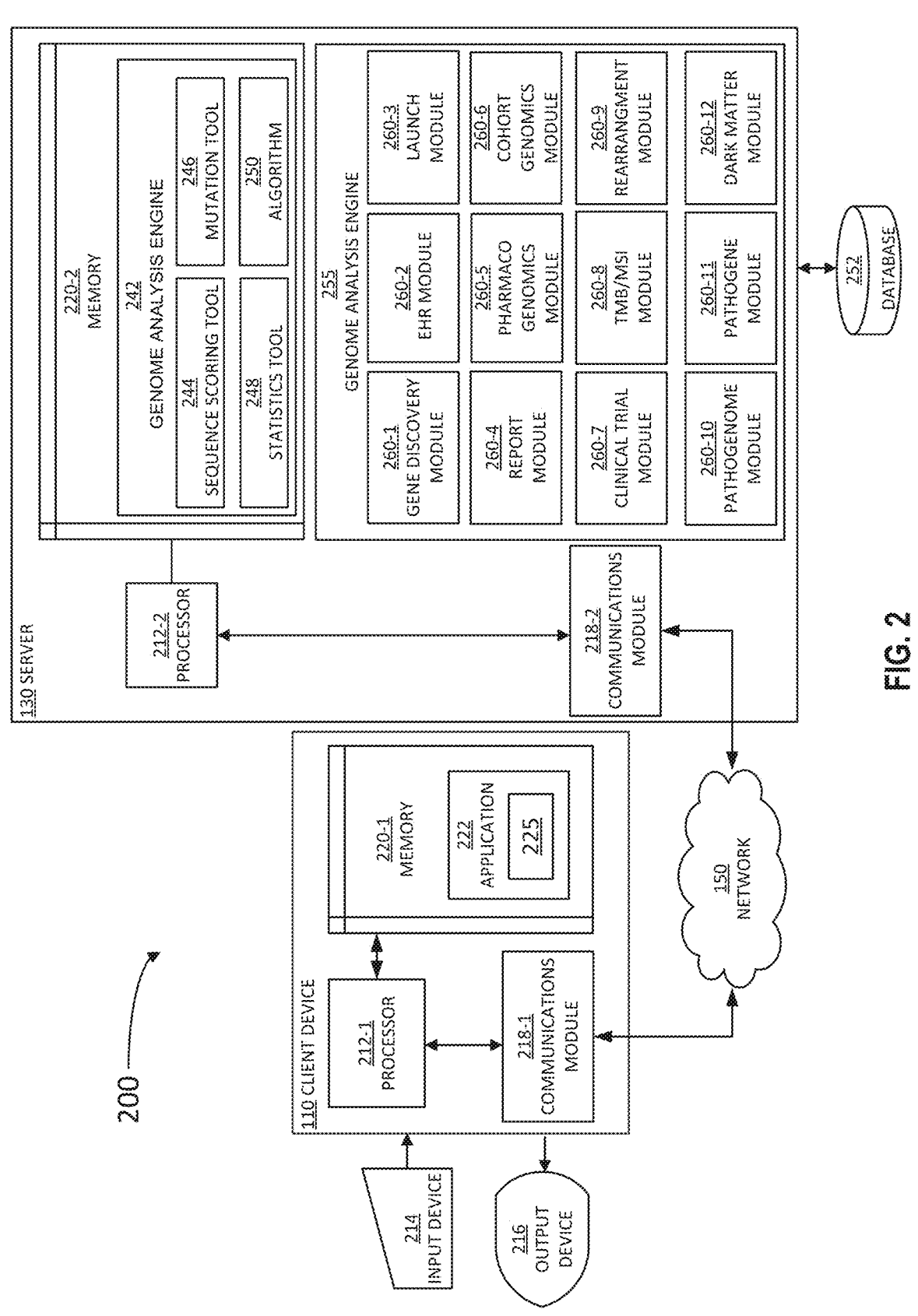
FIG. 2 illustrates the details for devices and systems in the architecture of FIG. 1, according to some embodiments.

FIG. 2 is a block diagram 200 illustrating an example server 130 and client device 110 in architecture 100, according to certain aspects of the disclosure. Client device 110 and server 130 are communicatively coupled over network 150 via respective communications modules 218-1 and 218-2 (hereinafter, collectively referred to as "communications modules 218"). Communications modules 218 are configured to interface with network 150 to send and receive information, such as data, requests, responses, and commands to other devices on the network. Communications modules 218 can be, for example, modems or Ethernet cards. Client device 110 may be coupled with an input device 214 and with an output device 216. Input device 214 may include a keyboard, a mouse, a pointer, or even a touch-screen display that a user may use to interact with client device 110. Likewise, output device 216 may include a display and a speaker with which the user may retrieve results from client device 110. Client device 110 may also include a processor 212-1, configured to execute instructions stored in a memory 220-1, and to cause client device 110 to perform at least some of the steps in methods consistent with the present disclosure. Memory 220-1 may further include an application 222, including specific instructions which, when executed by processor 212-1, cause a graphic payload 225 hosted by server 130 to be displayed for the user in output device 216. Graphic payload 225 may include multiple graphic illustrations of a nucleotide sequence requested by the user to server 130. The user may store at least some of the illustrations and partial nucleotide sequences from graphic payload 225 in memory 220-1.

In some embodiments, application 222 includes a voice navigation feature within the user interface, such that a user can navigate everything about a patient or a cohort without having to click any button. A set of voice commands that aids in the navigation of the disclosed platform has been incorporated within the application. Accordingly, application 222 may include a clinical genomics intelligence program that detects the appropriate events for the voice commands provided and enables navigation to the results swiftly based on built-in data connections. This functionality enables the user to use voice commands to know the details of any gene such as gene name, length, number of exons, number of domains, protein length, and gene function, and further enabling the user to stop or know more details of the same or different genes, mutations, disease, drugs, therapeutics, and harmful side effects. It involves designing, implementing, and enabling clinic-centric, patient-centric, clinician-centric, and genome-centric questions and answers through voice.

In some embodiments, memory 220-1 may include an application 222, configured to display and process the contents in graphic payload 225. Application 222 may be installed in memory 220-1 by server 130, together with the installation of an operating system that controls many hardware operations of client device 110.

Server 130 includes a memory 220-2, a processor 212-2, and communications module 218-2. Processor 212-2 is configured to execute instructions, such as instructions physically coded into processor 212-2, instructions received from software in memory 220-2, or a combination of both. Hereinafter, processors 212-1 and 212-2 will be collectively referred to as "processors 212," and memories 220-1 and 220-2 will be collectively referred to as "memories 220." Memory 220-2 includes a genome sequence analysis engine 242. In some embodiments, genome sequence analysis engine 242 includes a sequence scoring tool 244, a mutation tool 246, a statistics tool 248, and an algorithm 250 to manipulate genome sequence data and create charts and reports for graphic payload 225. Sequence scoring tool 244 parses at least a portion of a nucleotide sequence from a genome sequence to identify a splicing site therein. Accordingly, applications 222 may be installed by server 130 and perform scripts and other routines provided by server 130 to display graphic payload 225 provided by genome sequence analysis engine 242. Mutation tool 246 may be configured to identify protein domains affected by mutations in the nucleotide sequence that may alter the splicing sites (according to sequence scoring tool 244).

In some embodiments, mutation tool 246 may access a mutation log in database 252, to identify a recurring mutation over a cohort or a population of individuals. Statistics tool 248 may perform a frequency analysis over the splice sites and the mutations identified by sequence scoring tool 244 and mutation tool 246. In some embodiments, statistics tool 248 may use mutation logs and gene sequencing logs in database 252 to evaluate statistical data on a nucleotide sequence for an individual or a cohort of individuals, for analysis. Algorithm 250 may be a linear or non-linear algorithm, including a neural network, machine learning, or artificial intelligence algorithm used to identify and score splicing sites (e.g., for sequence scoring tool 244). For example, in some embodiments, algorithm 250 may include the Shapiro-Senapathy algorithm to score a nucleotide sequence as a splice site (e.g., a 'donor' site or an 'acceptor' site).

In some embodiments, database 252 includes a Regulatory Elements Disease Database (REDDB). REDDB is a database of the genes and signatures that it has identified based on the frequency of patients with mutations in multiple different regulatory elements and their cryptic versions in a cohort of patients, separately for the genes within the white matter genome (currently known genes in the human genome) and the genes within the dark matter genome. It also includes the genes based on the coding sequences. Based on cohort studies, the platform has discovered: 1) a set of genes that are already known to cause a particular cancer (e.g., prostate cancer), 2) a set of genes that can be defined as novel cancer genes, and 3) a set of genes that are known to cause one or more non-cancer diseases (e.g., Parkinson's disease or Fructose intolerance). The latter set of genes can be confidently defined as novel cancer genes or genes that are known to cause particular non-cancer disorders, as they occur in a high frequency in the cohort of cancer patients. The database includes them appropriately as either potential novel cancer genes, or genes causal of another particular disease that occurs in association with particular cancer. The platform applies the information that has accumulated in the REDDB to predict the genes that cause disease in a given patient. Thus, it predicts and reports these genes and the details of mutations in the clinical report of a patient with a particular disease, or a newborn, or any individual without any apparent disease. It can also predict genes responsible for different stages of cancer in patients who do not yet have the knowledge of the disease. The REDDB enables a robust backend processing, and a user-friendly front end with various capabilities for searching and analyzing the information of the genes, many of the genetic and regulatory elements, mutations, patients, diseases, and other relevant data and information. It is also linked with the modules of individual Patient Genomics, Family Genomics, Cohort Genomics, and Clinical Trials Genomics in the present disclosure, such that the data can be utilized in the different modules as required. From the fact that there are several other genes with these mutations that occur in a high number of patients, the platform determines that these genes have a high probability of being causal of the particular disease, or another disease that occurs in association with the primary disease. Thus, genome analysis engine 255 assigns a high score of being causal of cancer or a secondary disease and integrates them within the REDDB. Furthermore, some genes are known to cause one or more non-cancer diseases with high frequency in the cohort of cancer patients. REDDB includes such genes as either potential cancer genes that are novel, or genes causal of a particular disease that occurs in association with particular cancer.

Server 130 may further include a genome analysis engine 255. Genome analysis engine 255 may include multiple modules, such as gene discovery module 260-1, an EHR module 260-2, a launch module 260-3, a report module 260-4, a pharmacogenomics module 260-5, a cohort genomic module 260-6, a clinical trial module 260-7, a tumor mutation burden and microsatellite instability (TMB/MSI) module 260-8, a rearrangement module 260-9, a pathogenome module 260-10, a pathogene module 260-11, and a dark matter module 260-12 (hereinafter, collectively referred to as "modules 260").

Gene discovery module 260-1 provides gene discovery including the analysis of deleterious genetic alterations that are commonly seen among the individuals of the cohort and interpreted with the functional understanding of those mutations affecting the protein structure and function, gene families, protein domains, biological pathways, and drug response. In this perspective, the platform presents the opportunities for analyzing large-scale cohort studies to investigate the downstream molecular effects of SNVs and Indels in different regions including the coding regions, exons, introns, promoters, poly-A sites, and the various regulatory genetic elements within the genes and the genome. It also enables the analysis of large genomic rearrangements including gene fusion, copy number variants, and structural variants from the cohort of patients, and makes informed conclusions concerning their disease relationship.

Gene discovery module 260-1 may perform comparative genomic analysis to provide top recurring genetic mutations affecting protein domains, pathways, and potentially actionable drugs. Also, the alterations observed at the promoter, poly-A, splice site, exonic, intronic, and deep Intronic cryptic sites and cryptic exons in genes are compared among the individuals in a cohort that helps to identify the disease-associated domains and to group the affected proteins into a pathway, which can provide an insight into how this information is connected to the disease at molecular and clinical levels.

Gene discovery module 260-1 also identifies real and cryptic regulatory elements including promoter, poly-A, splice sites, branch points, enhancers and silencers, and UTR, exonic, intronic, and deep intronic mutations. Accordingly, gene discovery module 260-1 identifies the causality of variants in regulatory regions like promoters (TATA box, CAAT box, GC box, and initiator), untranslated regions on the 5' and 3' region of the coding sequence (UTRs), poly-A, splice site, exonic, intronic, and deep intronic cryptic splice, branch points and cryptic exon mutations in the cohort individuals. Gene discovery module 260-1 also reports the mutations observed in different samples derived from each individual of the cohort. The regulatory site mutations are scored using the Shapiro-Senapathy algorithm and its adaptation to fit the length, sequence, and position weight matrices (PWMs) of the different elements, and other relevant algorithms to identify the potential real and cryptic splice sites, promoter and poly-A boxes, branch sites, and other genetic elements. The scores are calculated for the genetic variants identified at the real and cryptic sites in the individuals of the study and compared with the original scores to detect the alterations in the potential regulatory sites. The mutations in these regulatory regions are known to lead to pathological effects at the level of RNA splicing and gene expression, which can explain the clinical phenotypes observed in human genetic disease.

Gene discovery module 260-1 identifies genes with mutations across multiple genetic elements of exons, splice sites, branch points, enhancers and silencers, promoters, and UTRs. In some embodiments, the regulatory elements that are mutated and falling under the various combinations of the coding region, splice sites, promoter regions, initiators, and poly-A sites and other regulatory elements within a gene across the cohort population are discovered and illustrated. Although aberrations in these elements are found to be a major cause of human diseases, there is only a very limited understanding of how regulatory element genotypes lead to specific phenotypes. This section thus may be integrated as a single processing component for interpreting the genetic alterations at the coding and regulatory regions of genes occurring in various individuals from the study to provide a better understanding of the functional roles of how these elements can be associated with specific phenotypes/genotypes in a population. It also provides the unique ability to understand and discover genes that have higher probability of being the causative agents of the disease or trait across the cohort population by virtue of occurring in multiple genetic elements of particular genes, rather than by relying or focusing on the coding sequence as the main source or cause of the disease or other phenotypes in the cohort.

The various "sites" for different regulatory elements (e.g., splice sites, branch sites, enhancers and silencers, promoters, transcription initiators, poly-A sites), and their cryptic sites are identified throughout the exons, introns, UTRs, and other elements, throughout the gene, and throughout multiple genes or many genes in a genome. The present disclosure works on the concept that the probability of identifying the gene causative of disease, trait, condition, or drug response from a cohort of patients increases when the results from these mutations are combined from multiple genetic and regulatory elements, and thus enables this approach for multiple elements from a patient or cohort of patients, and multiple genes or many genes in a genome.

Gene discovery module 260-1 identifies splicing mutations and aberrations. In some embodiments, gene discovery module 260-1 identifies splice sites (real acceptors and donors, cryptic acceptors and donors, real and cryptic branch points, real and cryptic splice enhancers and silencers, and cryptic exons) mutations classified based on pathogenicity scores. As illustrated, the splice sites are scored using the Shapiro-Senapathy algorithm to identify the potential splice sites. The genetic alterations identified in the cohort study at the splice sites are calculated for scores and compared with the original scores. The pathogenicity is thus assigned for each variant based on differences between original and observed scores. This section provides genes with different types of splice site variants classified as "Pathogenic," "Likely Pathogenic," and "Unknown" (based on the score difference of the mutated site compared to the original site) from the study along with the statistics of reported samples and patients. In a similar manner, the cryptic sites for many of the regulatory elements including the promoters (promoter boxes), transcription initiators, enhancers and silencers, splice donor, acceptor and branch sites, and poly-A sites, throughout the genes, intergenic regions, and the genome are identified and the mutations within them are determined.

The following are the additional statistical data for the genes handled by gene discovery module 260-1: A total number of splice mutations is a unique count of splice mutations reported in the study, a total number of unique genes is a unique count of genes with splice mutations reported in the study, a real acceptor is a unique count of real acceptor mutations reported in the study, a real donor is a unique count of real donor mutations reported in the study, a cryptic acceptor is a unique count of cryptic acceptor mutations reported in the study, a cryptic donor is a unique count of cryptic donor mutations reported in the study, a real and cryptic branch site count indicates the number of real and cryptic branch sites in the genes.

Gene discovery module 260-1 also identifies promoter mutations. In some embodiments, gene discovery module 260-1 identifies promoter mutations (TATA, CAAT, CG, and Initiator boxes) classified based on the pathogenicity scores calculated. Pathogenicity scores may be calculated for the promoter mutations by employing the Shapiro-Senapathy algorithm adapted from the algorithm for splice sites. This section also provides statistical information for the genes in different pathogenicity statuses (e.g., Pathogenic, Likely Pathogenic, and Unknown). The information provided in this section aids the researcher to understand and explain the regulatory functions of these mutations in a diseased condition. The following are the additional statistical information collected and processed by gene discovery module 260-1:

A total number of promoter mutations is the count of promoter mutations present in the cohort study, a total number of unique genes is the number of unique genes which consists of promoter mutations, a TATA box is a measure of the TATA box mutations present in the cohort study, a GC box indicates a count of GC box mutations present in the cohort study, a CAAT box indicates the number of CAAT box mutations present in the cohort study, an initiator box is the count of initiator box mutations present in the cohort study, a Poly-A mutation that leads to alterations in the mRNA 3'-end processing mechanisms. These changes are implicated as a common characteristic among many endocrine, hematological, oncological, immunological, and neurological diseases. Gene discovery module 260-1 also provides further evidence of these mutations and their impact on several physiological conditions. The following are the additional statistical information provided by gene discovery module 260-1: A total number of poly-A mutations: Count of poly-A mutations present in the cohort, a total number of unique genes: Unique count of the genes which contain poly-A mutations. Additionally, gene discovery module 260-1 identifies the top mutated genes that belong to a gene family, which are based on common structures and functions of genes and proteins, and aids in understanding gene groups and families that may be involved in disease or traits in a cohort.

Gene discovery module 260-1 is configured to discover top genes and domains, and summarizes and helps to visualize the most frequently mutated genes across the cohort, based on the affected protein domains present in the selected study cohort. Gene discovery module 260-1 also summarizes the top genes containing particular domains or group(s) of domains based on the basic structure and/or function of the domain. Gene discovery module 260-1 has enabled the discovery that genes that cause various cancers fall under three major groups, genes that build the basic cell structure, genes that enable the basic functions of the cell, and the genes that are involved in transcriptional regulation (gene expression) in the cell. For example, protein domains such as cadherins, dyneins, collagens, and kinesins are involved in maintaining the structure of the cell, providing the skeleton and stability for the cell. They are also involved in cell adhesion, extracellular matrix, and cell motility. Mutations in the genes containing these domains will affect the basic structure and function of the cell, or gene regulation, leading to cancers and non-cancer diseases. Identifying these genes that are frequently mutated in a cohort of individuals with a particular disease or trait will uncover the type of genes potentially responsible for these phenotypes.

Gene discovery module 260-1 enables the identification of the top genes based on the occurrence of mutations in these genes in multiple genetic elements including the CDS and the various genetic regulatory elements and their cryptic forms, and the grouping of these genes into few major categories of cell structure, function, and gene regulation. In some embodiments, gene discovery module 260-1 identifies top genes (based on cell structure, function, and gene regulation). Genome analysis engine 255 views cancers as the defect of the cell structure and function and not as a defect of an organ, and that, cancer is a disease of the cell, not the disease of the organ. It enables the discovery that the mutations in the coding and the several regulatory sequences of genes from particular gene families that affect the basic cell structure such as the cytoskeleton, cell-cell adhesion, and extracellular matrix, and cell functions such as signal transduction and transcriptional regulation, are actually the basic cause of cancer, and potentially non-cancer diseases. This discovery potentiates the development of therapeutic drugs by targeting these cell structure, function, and transcriptional regulating genes, proteins, and their domains. Thus, this cohort platform enables the grouping of different genes belonging to a family or one of the few groups unearthed in the Gene Discovery module, such as the protocadherins or dyneins, or transcription regulating genes, a group of genes rather than single genes, and using the combination of these genes as the most frequently mutated genes in a cohort in one approach of diagnosis, treatment, or drug development.

Gene discovery module 260-1 also identifies gene signatures for different cancers and other diseases caused by the participation of multiple genes that have become defective due to mutations and are called polygenic or multi-gene disorders. The cohort platform enables the discovery of the multiple genes that are necessary and/or sufficient for causing disease, as it enables the identification of more numbers of relevant genes and gene groups based on the combination of mutations across multiple genetic and regulatory elements. This makes it easy to form gene signatures with deleterious mutations present in an individual and across multiple patients, especially based on genes that belong to a gene group such as cell structure genes (e.g., cadherins, dyneins, and kinesins), cell function genes such as kinases and phosphates, and gene regulation genes such as TP53, TAF, and FAT. The platform provides several tabular details of genes based on cell structure, function, gene regulation, domains, gene families, and gene signatures across patients, for the user to carry out various analyses that enable the determination of the disease-causing genes, gene groups, and gene signatures.

Gene discovery module 260-1 may include analytical capabilities such as tabular details of genes, including the number of patients, samples, and mutations for every genetic element such as real splice donor, real splice acceptor, cryptic donor, cryptic acceptor, each of the promoter boxes, branch site, and the other genetic regulatory elements, and their cryptic versions, are provided. Users can analyze these genes and the frequencies of patients and other parameters associated with each gene by scrolling and page views, and by searching and sorting, for many of the genes with mutations in every genetic element. In addition, genes with mutations in CDS based on frequently mutated genes (FMG) and significantly mutated genes (SMG) are also provided in separate tables. The list of affected domains, pathways, and drugs with responses are provided in separate tables for every genetic element. The user can easily compare the details across multiple tables for different genetic elements, thus enabling analysis, conclusion, and discovery. Genes with frequent mutations in multiple genetic elements in the same gene across the cohort of patients are also provided with several tabular details, and their graphical illustrations to identify the most clinically relevant genes causal of a disease.

Various toggle buttons are provided to choose multiple levels of different parameters. For example, the user can choose the different score thresholds for cryptic sites (e.g., splice, branch, promoter) from a score ranging from 50 to 100 for displaying the genes with mutations in the different cryptic sites of splice sites, branch sites, promoter boxes, and other elements throughout the gene. The user can also choose Pathogenic, Likely Pathogenic, and/or Unknown mutations to display each type of regulatory element mutations. The module also enables filter options to filter genes and details in a particular table from another table. There exist ~3,000 genes that have overlapping sequence regions between two or more genes. The module provides the ability to remove the overlapping genes, enabling tables of genes with and without the overlaps. Furthermore, we identified that cryptic regulatory elements that occur in many places throughout the genes exhibit overlaps within the same type of element (e.g., one cryptic acceptor with another cryptic acceptor), or between different types of elements (e.g., a cryptic donor with a cryptic acceptor). The module provides the ability to analyze the details of genes and genetic regulatory elements with mutations with and without such overlaps.

Gene discovery module 260-1 provides illustrations for the above instances and statistical information are provided with tabular, graphical, and sequence views of genes, including the mutations, their effects, and disease connections. Gene discovery module 260-1 may also be configured to score and rank the causality of genes and patient risk of disease in a cohort and its application in individual patients' diagnosis. Genome analysis engine 255 defines and assigns scores and ranks to genes and patients based on mutations in regulatory and coding elements, using the various approaches. These approaches use the data from the total number of mutations from different regulatory elements of genes, and the total number of patients with such mutations, in the genomic sequences of patients within the cohort. Relevant genomics test reports from whole exome, whole genome, or targeted resequencing strategies are readily accessible through gene discovery module 260-1.

Electronic health record (EHR) module 260-2 includes a large amount of data fulfilling numerous parameters for a large number of patients. Currently, only a small subset of these patients' genomes have been and are being sequenced. In some embodiments, EHR module 260-2 works with an institutional EHR, and it may not modify any of these parameters or write new data into their EHR. In some embodiments, EHR module 260-2 is independent of an institutional EHR, to address several such issues. EHR module 260-2 will be able to accommodate many of these issues and provide a seamless interface between the IEHR and many of the present disclosure modules.

EHR module 260-2 can contain millions of patients of different age, gender, race, ethnicity, disease, drug usage, drug efficacy, adverse reactions, treatment outcomes, geographical regions, and time-interval. This information enables family genomics, cohort genomics, and clinical trial genomics. The EHR genomics module is integrated within the Genome Explorer platform and can also be a standalone EHR platform for all EHR functionalities, with a focus on integrating with genomics and precision medicine for the patient, clinician, clinical researchers, and clinical institution. The module provides an interface for a systematized collection of electronically-stored health information in a digital format of a patient's electronic health records including clinical metadata, pathology reports, and genomic reports. These records can be shared through network-connected, enterprise-wide information systems across various clinical departments like cardiology and neurology, pharmacies, and pathology labs, and across various clinical institutions.

Based on given parameters such as gender, age range, disease, drug treatment, efficacy and side effects outcomes, including specific efficacy and side effects, and the genome sequence, EHR module 260-2 may identify patients fitting these parameters. EHR module 260-2 processes the genome data for this patient cohort (e.g., genes and biomarkers for the particular phenotype(s)). In some embodiments, EHR module 260-2 uses a patient selection module within genome analysis engine 255 to retrieve patient data. In some embodiments, EHR module 260-2 uses the voice navigation feature to capture the parameters. As the different parameters are not given in a highly defined or structured manner, we need to use special algorithms to capture these parameters from the unstructured data from the EHR of different patients, which have been input by various clinicians and healthcare providers, which thus will have a lot of variations.

EHR module 260-2 includes patient metadata including the patient's age, gender, habits such as smoking, alcohol, and drug usages, diseases that the patient has been suffering from, and medicines that the patient has been taking, and pathology data including the tissue sections images, Immunohistochemistry (IHC), Fluorescence in situ hybridization (FISH), and other relevant information. The EHR includes the information on whether the DNA from the patient has been sequenced, the nature of the DNA (WGS, WES, TRS), the sequence format (MAF, VCF, FASTQ), and a link for their locations.

Based on given parameters such as gender, age range, disease, drug treatment, efficacy and side effects outcomes, including specific efficacy and side effects, and the genome sequence, we can isolate the patients who fit these parameters. We can subject the genome data for this patient cohort through the disclosed platform and get the genes and the biomarkers for the particular phenotype(s). We can use the patient selection module within GE or the Voice Navigation to capture the parameters. As the different parameters are not given in a highly defined or structured manner, we need to use special algorithms to capture these parameters from the unstructured data from the EHR of different patients, which have been input by various clinicians and healthcare providers, which thus will have a lot of variations.

EHR module 260-2 may also include meta information with patient demographics, medical history, medication, allergies, risks, habits, immunization status, vital signs, and personal statistics like age, BMI, and billing information.

EHR module 260-2 enables access to relevant patient information from and into the EHR including the patient meta information, disease, drug, and genomic sequences (DNA and/or RNA) or its weblinks in an automated way. Additionally, it has automated the use of this information in processing, analysis, and reporting of the patient's genomic data and his or her clinical, disease, and drug response outcomes. Once the genetic/genomic test is ordered by the clinician and the corresponding genomic sequencing has been completed, and the data links become available in EHR module 260-2, the platform automatically locates the sequenced data and starts the analysis. Based on the test and input file format, the platform automatically selects the analysis pipeline with the most suitable parameters and integrates the clinical report to EHR module 260-2, upon completion of the analysis.

In addition, different institutions have different EHR systems (e.g., Cerner, Epic), and it will be difficult to customize different requirements in each of them. To resolve this, EHR module 260-2 interfaces between genome analysis engine 255 and each of the EHRs from different Health Systems.

In some embodiments, EHR module 260-2 is spread across various categories and modules such as EHR, Order Sequence, Launch Analysis, Clinical Report, Pharmacogenomics module (PGx), TMB/MSI, Rearrangement, Pathogene, and Pathogenome. Clinician centric user interface that includes a navigation pane, and a drop-down menu showing different platforms (e.g., Patient genomics, Family genomics, Cohort genomics, and Clinical trial genomics) and modules to conduct various types of clinical, translational, and genomic analyses using a given patient's genome data.

In some embodiments, EHR module 260-2 automatically downloads data from the IEHR into the GE EHR system that are relevant to genomics, and to provide various kinds of analytical capabilities and metrics for the administration personnel and researchers. Thus, EHR module 260-2 enables various genomics related analysis to the clinical researchers, and department/hospital administrators and executives. For example, EHR module 260-2 retrieves and sorts a variety of data such as the number of sequenced patients in various common and rare diseases, number of patients with WGS, WXS, and TRS sequences, and the number of cohort studies or clinical trials carried out. In addition, EHR module 260-2 provides a standalone EHR system for patient administration for small to medium clinics and primary healthcare facilities that are emerging in the US to serve a large population of patients.

Launch module 260-3 launches a genome analysis when the sequencing for a chosen genomic library strategy is completed and the raw data is linked to the patient EHR. In some embodiments, launch module 260-3 provides a genomic test report once the analysis is completed successfully.

Report module 260-4 includes pathology reports including various reports of diagnosis for a disease like Immunohistochemistry (IHC), biopsy, magnetic resonance imaging (MRI), Fluorescent In-situ hybridization (FISH), and radiology images along with regular blood, urine, and saliva laboratory test reports.

Pharmacogenomics (PGx) module 260-5 enables the discovery of a patient's response to a drug that may be taken based on the patient's genomic variations within the genes that transport or metabolize, or in any way react with the drugs within the patient, even before the patient has taken the medicine. In some embodiments, PGx module 260-5 determines the pharmacogenomic status of the drug-metabolizing genes to predict the response of the patient as recommended by Clinical Pharmacogenetics Implementation Consortium (CPIC) guidelines (panel of 11 genes) and the eMERGE-PGx network (panel of 82 genes). PGx module 260-5 expands further with more genes, more pathogenic mutations, and information for more drugs that ensue in the future.

In some embodiments, PGx module 260-5 produces a report including mutations in the drug-metabolizing genes and their corresponding metabolizing-phenotype of normal, intermediate, rapid, or poor metabolizers as identified in the patient are indicated. The drugs are flagged to avoid use, use with caution, or use as directed based on the clinical association. Table I illustrates a list of pharmacogenomics tests available in PGx module 260-5 to analyze the drug-metabolizing genes and predict the drug response.

TABLE I

| Pharmacogenomics Test For Drug Responses |
|---|
| The pharmacogenomics analysis includes 11 genes (CYP1C9, CYP2C19, CYP2D6, CYP3A5, CYP4F2, DPYD, NUDT15, SLCO1B1, TMPT, UGT1A1 and VKORC1) as per the recommendations of the Clinical Pharmacogenetics Implementation Consortium (CPIC) guidelines. Based on the genotype of these drug metabolizing genes, the diplotypes are computed to determine the metabolizing phenotypes The genes reported below were found to be mutated and shown to have clinical association with drug metabolism for different medication categories. |

| Gene | Variant | Haplotype | Diplotype | Priority |
|---|---|---|---|---|
| CYP2C19 Poor Metabolizer | rs12769205 | No function | *35/*35 | High Risk |
| CYP4F2 Intermediate Metabolizer | rs2108622 | Normal Function Decreased Function | *1/*3 | High Risk |
| TPMT Normal Metabolism | r2842934 | Normal Function | *1S/*1S | Low Risk |

PGx module 260-5 determines a drug metabolizer status and drug dosage based on mutations in a combination of multiple genes. In some embodiments, the drug metabolizer status of a gene is determined based on the combination of variants and the haplotypes/diplotypes. In some embodiments, a method for determining a drug metabolizer status uses the pathogenicity of mutations to first determine if a gene becomes defective and, if it does, it is considered as a non-metabolizer. The method equates this status to a poor-metabolizer. In some embodiments, the method includes information on the zygosity of mutations, wherein deleterious mutation in one allele is an intermediate metabolizer and in both alleles is a non-metabolizer.

In some embodiments, the metabolizer status of a gene is determined based on the mutations in at least one of the genetic elements in the drug metabolizing genes. When a drug metabolizing gene has at least one pathogenic mutation in any one of the genetic elements and is homozygous deleterious allele (VV), then it becomes a non-metabolizer (poor). Whereas, if that mutation is heterozygous, it is an intermediate metabolizer, since one allele has become defective and the other allele is normal. Using this approach, some embodiments determine the metabolizer status of a combination of more than one gene, and also determine the dose of the drug based on this combination. As an example, PGx module 260-5 may perform the following sequence of steps: A drug is metabolized by two genes—CYP2D6, DYPD;

CYP2D6 is mutated (VV or RV). When CYP2D6 is VV or RV and DYPD is not mutated, then the metabolism status of the drug based on combination of genes is "intermediate." When both genes are mutated, CYP2D6 has one VV and DYPD has only RV, then PGx module 260-5 determines a status as between "poor" and "intermediate" metabolizer. When both genes are mutated, CYP2D6 has one VV and DYPD has one VV, then PGx module 260-5 identifies the status as a "non-metabolizer," or a "poor" metabolizer.

In some embodiments, PGx module 260-5 includes a quantity of a drug metabolized per unit time by different genes. For instance, when the gene DYPD metabolizes 100 units of a particular drug, and the gene CYP2D6 metabolizes 20 units of the same drug, then PGx module 260-5 incorporates this information to determine the dose, in addition to the metabolizer status of a combination of different genes. When a VV variant is present in both genes, PGx module 260-5 may drastically reduce the medication dose to about $\frac{1}{100}$th to $\frac{1}{10}^{th}$ of a regular dose. When a VV variant is present in one gene and an RV variant is present in the other gene, PGx module 260-5 may reduce the dose to $\frac{1}{4}$th of the regular dose. When the two genes have an RV variant, PGx module 260-5 may determine a $\frac{1}{2}$ reduced dose relative to the regular dose. When one gene has an RR variant and the other gene has an RV variant, PGx module 260-5 may determine a $\frac{3}{4}$ of a regular dose. When more than 3 genes are involved in the metabolic chain for a given drug, PGx module 260-5 applies a similar analysis using the total number of genes and the number of alleles with Pathogenic mutations.

Cohort genomics module 260-6 enables genomic research of cohorts of patients exhibiting specific diseases with the aim of finding the genes and their defects that are causative of the disease or adverse drug reactions in the patients. The basic concept employed in the GE cohort genomics platform is that the disease-causing mutations can occur in any part of a gene including CDS or any of the several genetic regulatory elements. It facilitates the discovery of various details of these defects in particular genes, including within different types of genetic elements such as exons, introns, splice sites, branch sites, promoters, poly-A sites, cryptic versions of many of these regulatory motifs and elements, and 5' and 3' UTRs. By enabling the identification of genes containing a combination of deleterious mutations within multiple genetic elements across different patients, this platform has the potential to uncover the genes with the highest probability of causing the disease, trait or conditions, and the adverse drug reactions (ADRs) in a cohort of patients than focusing mainly on the coding sequence (CDS) of the protein.

In some embodiments, cohort genomics module 260-6 interacts with gene discovery module 260-1, EHR module 260-2, launch module 260-3, and pathogenome module 260-10 to prepare a cohort report. The cohort report may include visual elements provided to application 222 in graphic payload 225, and may also include tabulated information for storage in database 252. The elements in the cohort report provide knowledge about the characteristics of the patients in the cohorts and the study, listed as follows: Disease: Disease/phenotype of the individuals present in the cohort; Number of Patients: Total number of patients involved in the study; Unique Mutations: Total number of unique mutations observed in the patients; Unique Mutated Genes: Total number of unique mutated genes observed in the patients; and PubMed Id: The identifier of the published article if the data is sourced from a published source.

The cohort report is a comprehensive report of many of the findings from the cohort analysis in tabular, graphical, and sequence illustrations. They include the tabular details for the mutations in CDS and each of the different regulatory elements and their cryptic versions. For each table, graphical illustrations are provided depicting the details of the genes, patients, mutations, and other relevant information with popup windows and mouse overs. The cohort report also gives summary findings in graphical and tabular forms. In some embodiments, the cohort report includes summary statistics: This section presents the statistics of frequently occurring causal mutations distributed across genes in the group of individuals. The section also delivers complete details of those mutations affecting the domains, gene families, pathways, and actionable drugs. Thus, it provides the identification of the presence of causal and driver mutations in population data sets which is of clinical and biological interest. In some embodiments, the cohort report includes key genomic findings from cohort analysis: This section provides the distribution of mutated genes among the individuals affecting protein domains, pathways, and potential actionable drugs. The top recurring genes with more mutations provide an insight into those driver genes and mutations responsible for the phenotypes or certain characteristic behavior of the disease associated with the cohort individuals. The protein domains encoded by top recurring mutated genes can be a traceable target for new drug development. The pathways affected by the commonly recurring genes deliver information about the molecular mechanisms which regulate the disease. The section also provides the statistics of domains, pathways, and actionable drugs commonly observed in the cohort study. In some embodiments, the cohort report includes comprehensive characterization of mutated genes: This section summarizes the distribution of genes having actionable mutations, affected pathways, and protein domains. Additionally, it gives the drug information applicable to the particular gene. The availability of this information illustrates the clinical significance of the gene in a cohort. In some embodiments, the cohort report includes a distribution of affected domains: This section summarizes the top domains which occur commonly within the mutated genes in the cohort. It aids in sharpening the functional interpretation of the impact of domains, as they are the embodiment of the entire gene. Thus, facilitating the identification of hotspot mutations in actionable protein domains provides insights to the researcher on the relationship between the gene, domain, protein, and disease. In some embodiments, the cohort report includes top genes (based on mutation frequency): This section summarizes and helps to analyze and visualize the frequently mutated genes among the cohort, within different genetic elements individually or in combination. In some embodiments, the cohort report includes top genes (based on domain): This section summarizes and helps to analyze and visualize the frequently mutated genes, based on the affected protein domains present in the selected study cohort. In some embodiments, the cohort report includes top genes (based on pathway): This section summarizes and helps to analyze and visualize the top mutated genes based on the affected pathways in the selected cohort study. It also facilitates in unraveling the disease-causing mechanism and provides a deeper understanding to the researcher about the molecular functions of the particular gene and the affected pathway.

In some embodiments, cohort genomics module 260-6 produces a mutational landscape report. The mutational landscape report provides a multitude of analysis and visualization features to advance our understanding of the large-scale genomic data from the patient cohorts. The cohort-based large-scale characterizations often produce large amounts of data in the form of somatic single-nucleotide variants (SNV) and small insertion/deletions (indels). These data provide a baseline for many analyses such as driver gene detection, pathway analysis, mutational signatures, gene interactions, and survival analysis. On the other hand, visualization of these complex and heterogeneous data plays key roles in genomic studies, when the clinicians find it difficult to interpret the clinical significance of the data. In some embodiments, the mutational landscape report includes co-occurrence and mutual exclusivity and refers to two or more mutated genes that tend to be positively or negatively correlated among different samples in a cohort. A pair-wise Fisher's Exact Test is used to detect such a significant pair of genes. The test is used to support co-occurrence when the number of samples with alterations in both genes is significantly higher than expected by chance. Likewise, it suggests mutual exclusivity when the number of samples with alterations in both genes is significantly lower. The efficacy of this test depends on the hypothesis that the genes' alterations across samples are independent and identically distributed. In some embodiments, the mutational landscape report includes the transition-transversion ratio and refers to the distribution of two types of genetic mutations in the cohort of patients considered to have distinct effects on gene regulation and protein-coding factors. Transitions are DNA mutations that specifically exchange a one-ring pyrimidine with another pyrimidine or a two-ring purine for another purine. Transversion, in contrast, are mutations that change the nucleotide base from a purine to a pyrimidine or vice versa. It is well known that Transitions are enriched over Transversion in protein-coding regions of the human genome. This plot summarizes SNVs from 12 types of transitions and transversions into six different categories that start with 'C' or 'T' in the opposite strand. The stacked bar plot (bottom) shows the distribution of mutation spectra for every sample in the MAF file. In some embodiments, the mutational landscape report includes the significant pathways that control cell cycle progression, apoptosis, and cell growth, based on the frequent genetic alterations distributed across the patients in the cohort that are reported. The fraction of genes with at least one alteration in each of the pathways is computed based on the total number of genes (N) involved in the pathway. The fraction of samples with at least one alteration in each of the pathways are also evaluated. A sample was considered as altered in a given pathway if one or more genes in the pathway contained a recurrent or known driver alteration. The plots are shown for the fraction of affected genes in each pathway and the fraction of samples having mutated pathway genes. In some embodiments, the mutational landscape report includes significantly mutated driver genes that are identified from the patient cohort. The concept is based on the fact that most of the variants in disease-causing genes are enriched at hot-spots. Protein altering mutations of each gene across the cohort are evaluated looking for those protein residues having multiple mutations barely expected by chance. Second, these positions are thereafter grouped to form mutation clusters or hotspots. Third, each cluster is scored with a figure proportional to the percentage of the gene mutations that are enclosed within that cluster and inversely related to its length. The gene clustering score is obtained as the sum of the scores of many clusters (if any) found in that gene. Finally, each gene clustering score is compared with the background model to obtain a significance value. The background model is obtained performing the same steps as above but assessing only coding silent mutations. In some embodiments, the mutational landscape report includes a survival analysis. To prepare the survival analysis, cohort genomics module 260-6 is configured to group samples based on the survival status (alive or deceased), the survival time, and the mutation status of significantly mutated genes across the cohort. Kaplan-Meier estimate is used to measure the fraction of subjects living for a certain amount of time after treatment. The effect of an intervention is assessed by measuring the number of subjects survived or saved after that intervention over a period of time.

In some embodiments, cohort genomics module 260-6 includes a family genomics report. The family genomics report includes a trio/family analysis of detailed clinical report depicting variants or identifying shared chromosomal regions among affected family members along with the mode of inheritance and pedigree information which represents the familial relationships, gender, ethnicity, and phenotypic information of the individuals in the given family. This helps in analyzing hereditary patterns and phenotypic factors of genomic variants/mutations to quickly identify and understand these patterns in the patient's family history. The family genomics report includes patient meta-information, testing indications, key findings or absence of findings, conclusions, and recommendations. A clinical summary of the genomic findings precedes the clinical report that compiles the primary diagnosis based on the disease indications, secondary findings based on the ACMG 59 genes, and the present disclosure's proprietary disease panels, pharmacogenomic indications, therapeutic indications, and the suggested clinical trials. The detailed information about the variants such as the affected genes, variant's consequence, variant allele frequency, and zygosity for each family member, mode of inheritance, and the associated phenotypes of the specific variants are provided along with the minor allele frequency, and pathogenicity class including the ACMG 2015 guidelines and the present disclosure's pathogenicity criteria based on the score differences for regulatory elements from the reference sequences and genes. The mutational consequences are overlaid on the genome-scale illustration and displayed across the family members showing the pattern of inheritance along with the relevant mutation details. The mutations can also be selected based on the pathogenicity, type of genetic elements including coding (CDS), regulatory and splicing elements, particular genetic elements, disease panels, or the mode of inheritance as an interactive visualization. These variants are also reported as per the HGVS nomenclature along with Refseq accession numbers, genome build, and official gene names, as per Human Genome Organization (HUGO) guidelines. Actionable variants are highlighted along with therapies approved by regulatory agencies like the FDA. The clinical report is divided into sections of summary statistics, test performed block, therapeutic indications, promoter, poly-A, exonic, intronic, and deep intronic mutations, variant interpretation, ACMG incidental findings, drug details, gene details, and variants of uncertain significance (VUS). For significant variants not included in the system generated clinical report in the diagnosis, the clinician can bookmark variants for the disease which is considered important for the disease, and edit any portion of the clinical report and customize the clinical report. These findings can positively impact clinical decisions and can modify treatments and clinical care. Mutations identified within the family are stacked and overlaid on the genome-scale illustration as a pathogenome frequency plot with multiple options for interactive visualization. The mutations can be selected by disease, consequences, domain, pathway, gene family, and can be grouped by either gene or mutation. The mutation position and frequency are plotted for individual genes as a Pathogene Frequency Plot. Mutations for one individual within the family are plotted on an illustration with multiple tracks like consequence, pathogenicity, ACMG, MMR, PGx, and eMERGE for deeper analysis in individual patient pathogenome. This feature enables the selection of a particular patient from a group of patients in the Family, Cohort, or Clinical Trials modules, and displays the Pathogenome visualization plot for that patient. Similarly, the genes and mutations are stacked for many individuals within the family together for a comprehensive view in the Family Pathogenome illustrations.

Cohort genomics module 260-6 includes the information on mutations within the genetic elements in one or more patients in the EHR. This dashboard will be connected to the institutional EHR (IEHR) and EHR (GE-EHR) in such a way that when a new patient is processed in genome analysis engine 255, his/her sequence details and clinical reports will be automatically updated in the cohort genomics dashboard. Thus, it becomes a repository of clinical reports of each of the processed patients through the present disclosure. This repository can be used to perform several cohort, family, and clinical trial projects for diagnosis, therapeutics, or PGx in real time for any disease, drug, or side effect phenotypes at any given time. Cohort genomics module 260-6 illustrates metrics about different genetic elements and can be viewed in real time for one patient or 1000 patients directly uploaded from a real-time EHR.

In some embodiments, cohort genomics module 260-6 provides a real-time interaction with pathogenome module 260-10. Cohort genomics module 260-6 analyzes real-time data in the framework of pathogenome module 260-10. Additionally, it has the ability to visualize one or more patients in a Pathogenome framework, wherein, when a single patient is chosen, the Individual Pathogenome framework will be executed, and when more than one patient is chosen, then a Cohort Pathogenome framework will be executed.

In some embodiments, cohort genomics module 260-6 displays the metrics and statistics of each of the genetic elements for each of the 20,000 genes from one or more patients in various ways in real time, including frequency plots of various parameters as in a pathogenome plot both graphically and in tabular form. In some embodiments, cohort genomics module 260-6 graphically depicts each of the multiple patients in bands on a single line and highlights the ones having mutations in the genes or genetic elements. In addition, it enables the selection of various gene panels based on several criteria such as diseases, gene families, domains, and pathways.

In some embodiments, cohort genomics module 260-6 enables the selection of various gene panels based on several criteria such as diseases, gene families, domains, and pathways. Furthermore, it enables the selection of patients based on various parameters such as disease, drugs taken, gender, age, tumor or disease stage, drug response phenotypes, and tissue type, to carry out cohort analysis. It also provides statistics of many of the parameters from the EHR and in real-time. For each element, a table icon provided will enable the respective table with many of the details of genes, mutations, and patients.

Cohort genomics module 260-6 may include several sub-modules as follows:

Cohort Builder sub-module: a component that facilitates to select variant call files such as VCF or MAF files of patients in combination with patient metadata and other relevant information from GE EHR or public resources and create a cohort. The patients can be searched automatically by GE's pre-defined rules or based on user-defined criteria like disease, age, gender, race, ethnicity, drug usage, ADRs, drug efficacy, or any other available metadata to create super-cohort or divided into sub-cohorts based on user discretion. The cohort builder can also use the "Bulk upload" feature to upload multiple VCF or MAF files together from S3, FTP, HTTPS, or from the local computer. The selected VCF files are converted to MAF files or vice-versa and processed along with the attached metadata for the cohort analysis. The cohort builder can also split the cohort MAF or VCF file(s) into individual patient VCF files and can produce clinical reports for each patient from the cohort in an automated manner.

Launch sub-module: performs identifying the group of patients with a particular condition, disease, and drug or other treatment from the EHR data that forms the cohort, the set of genes that will be tested across the cohort, super-cohort or sub-cohort of patients, and the tissue, blood, saliva or other samples from each patient from which the DNA/RNA will be studied. The launch sub-module may include several panels, as follows. Somatic cancer gene panel: A panel of somatic cancers with the associated genes. Germline cancer gene panel: A panel of hereditary cancers with the associated genes. Non-cancer Inherited Disorders gene panel: A panel of inherited non-cancer disorders with the associated genes. Industrial gene panel: Various disease/research gene panels from IonAmpliseq, Illumina, and Oncomine. ACMG 59 gene panel: The list of 59 genes from the American College of Medical Genetics and Genomics (ACMG). Specific mutations in these genes are known to be causative of disorders with defined phenotypes. Drug metabolizing gene panel: The genetic variants in the drug-metabolizing genes produce various impacts on the degree of converting the drugs into water-soluble metabolites. Based on the impact of mutations in these genes, the metabolizer. The status of these genes is classified as "Normal Metabolizers," "Poor Metabolizers," "Intermediate Metabolizers," and "Indeterminate." Human genes panel: Researchers can select any gene or all genes from the available "All human gene" panel, listing all ~20,000 human genes.

Patient/Sample & Gene selection sub-module: enables the analysis between a specific set of genes and a specific set of patients from the cohort to facilitate biomarker discovery.

Patient Group creation sub-module: enables the creation of a user-defined patient group (cohort) or subgroup (sub-cohort) from the EHR. EHR in a health institution would contain a large number of patients with various conditions or diseases (including cancers or non-cancer disorders), who have been, or are undergoing different types of treatment (e.g., drugs, surgery or other treatment), and have undergone various tests (e.g., blood, biopsy, imaging, immunohistochemistry). The user can search the EHR data and select patients that satisfy various conditions (e.g., males, females, smokers, non-smokers, patients with a specific disease or condition such as heart attacks or lung cancer, or have undergone various treatments such as warfarin or clopidogrel), and create one or more patient groups (as shown below). The patient group creation sub-module also enables the selection of user-defined sample(s) for specific patients and creates sample subgroups, to study the sample-specific characteristics, including the comparison between primary vs metastatic cancer biopsy or blood/saliva/lymph samples from patients, timeline experiments of disease progression or therapy (e.g., chemotherapy), mutational differences over different TNM stages, tumor heterogeneity, tumor microenvironment(s) and sub-clonal studies.

Gene Group creation sub-module: creates user-defined gene groups or subgroups and/or selection of standard industry gene panels, which facilitates the clinical researcher for targeted biomarker discovery. The inclusion and exclusion category facilitates the researcher to select, add, and/or exclude particular genes from all or subsets of human genes, based on the research requirements.

Clinical trial module 260-7 combines the gene discovery platform with pharmacogenomics for a cohort study. The analysis to outline and study the drug responses from a patient cohort is enabled by a user-driven patient identifier and the gene panel input from the meta-information. Meta information becomes a matrix of individual patient EHR, combined into a tabular format to present the clinical presentations, disease condition, disease (e.g., cancer) stage, various pathological test statuses, disease-relapse, surgical resection, blood workup, drug efficacy, etc., for all the patients present in the cohort study. This gives a focused view of the broad spectrum of variables in determining drug response. The analysis results are presented in the clinical trial report, cohort report, and the pathogenome as statistical evaluations or visualization modules.

Clinical trial module 260-7 unifies cohort disease and genomic-data led research and/or discovery of varied drug responses and reactions. The key influencing factors like age, personal habits (exposure to smoke, previous chemotherapeutic therapies, previous radiotherapies, and the like), genomic mutations, blood profiles, cancer stages, etc., for short-term exposure, can be explored to predict the drug efficacy responders and disease regression, and adverse drug reactions and antagonistic reactions in responders and non-responders with disease progression. Long-term implications such as drug tolerance, drug safety, and accumulation of toxicity based on the genomic signatures to elucidate progression-free survival duration of the disease relapse can be scrutinized for evidence-based clinical interpretation. Clinical trial module 260-7 enables cohort-based drug efficacy and adverse drug response prediction for both established and investigational drugs from a group of patients with the same clinical presentations, and personalized therapeutic indications based on the individual's genomic information.

Clinical trial module 260-7 includes the following features: Disease: disease diagnosis of the patients populating the cohort. Number of Patients: number of patients populating the cohort. Unique Mutations: total number of unique mutations reported in the cohort. Unique Mutated Genes: total number of unique mutated genes reported in the cohort. PubMed Id: Article identifier of the published study reporting the cohort metadata, clinical presentation, methodology of various investigations performed, and their outcomes when the study is based on a published report.

Clinical trial module 260-7 is configured to group a subject cohort based on the efficacy and side effects of a drug consumed by two or more patients during a clinical trial. In some embodiments, clinical trial module 260-7 determines the frequently mutated genes in each group to find mutations and genes that are effective for a drug and cause side effects in patients having these mutations, during a clinical trial. In some embodiments, clinical trial module 260-7 is configured to collect data from multiple EHRs from various institutions and integrate it into a single EHR to perform clinical trial studies from patients with a particular disease or drug response phenotype across multiple institutions, thus paving the way for interoperability and cohort of cohort studies. In some embodiments, clinical trial module 260-7 is configured to graphically visualize a variety of data such as the number of sequenced patients exhibiting various common and rare diseases, number of patients using a particular drug with a specific type of drug response, number of patients with WGS, WXS, and TRS sequences, and the number of cohort studies or clinical trials carried out.

Tumor mutation burden and microsatellite instability (TMB/MSI) module 260-8 provides a diagnostic immunotherapy biomarkers (TMB and MSI) status from a subject's sequence. In some embodiments, TMB/MSI module 260-8 measures a number of somatic protein-coding mutations occurring in a tumor specimen per million base pairs. For example, in some embodiments, TMB/MSI module 260-8 may classify results as TMB-High: with above 20 mutations per megabase (mutations/Mb), TMB-Intermediate: about 6-19 mutations/Mb, whereas TMB-Low may be about 5 mutations/Mb, or less. An MSI is an FDA-approved immunotherapy biomarker across many major solid tumor types. In some configurations, MSI is caused by insertion or deletion of repeating bases during DNA replication. In some configurations, MSI results from the failure of the mismatch repair system (MMR) to correct DNA replication errors, resulting in an abnormally high frequency of genetic mutations. Accordingly, TMB/MSI module 260-8 classifies results as: MSS (Microsatellite stable) status, and MSI-H (Microsatellite Instability—High) status. Based on the TMB and MSI status of the patient, the response to immune checkpoint inhibitors is predicted. TMB/MSI module 260-8 enables the study of the mismatch repair genes (MMR genes) or many human genes.

Rearrangement module 260-9 is configured to display the details of the patient's defects in each gene in the regions where a structural variation (e.g., translocation, transversion, inversion, deletion, and insertion) has occurred in graphical displays, depicting the details of the variation at the macro- and molecular level as to the point of the variation within one or more genes, and further drilling down into the sequence views of the structural alteration, with many of the elements of the involved chromosome(s) and genes displayed on the gene sequence, representing them in different color codes, with the pre-alteration and post-alteration details. Rearrangement module 260-9 is also configured to display the details of the patient's defects in each gene in the regions where a copy number variation (CNV) has occurred in graphical displays including the genomic or genetic regions that have been amplified (or deleted), and depicting the details of the amplification (or deletion) at the macro- and molecular level, and further drilling down into the sequence views of the amplification (or deletion), with many of the elements of the CN Vs displayed on the genome and gene sequence, representing them in different color codes, with the pre-CNV and post-CNV details. Rearrangement module 260-9 is also configured to display the details of the patient's defects of the two genes that are fused together in graphical displays and depicting the details of each gene at the macro- and molecular level, and further drilling down into the nucleotide and protein sequence views of each gene and fused chimeric gene, with many of the elements of the fused breakpoint displayed on the genome and gene sequence, Rearrangement module 260-9 is also configured to visualize many of the chromosomal rearrangements identified in the particular patient. The breakpoints of rearrangements are labeled and the gene/sequence structures that are affected due to chromosomal rearrangements (SV, CNV, and gene fusions) are shown with graphical, tabular, and sequence illustrations.

Pathogenome module 260-10 integrates genomic data visualization with extensive patient records. Pathogenome module 260-10 enables the discovery of genes causal of disease and adverse drug reactions (ADRs). This approach enables the illustration and visualization of the deleterious mutations in many of the genes in the genome depicted to scale in one view. Pathogenome module 260-10 also enables the frequency of the deleterious mutations and genes from a cohort of individuals. Thus, pathogenome module 260-10 enables the visualization of particular molecular and clinical data types by taking into account complex relationships between patients in a family or cohort.

Pathogenome module 260-10 supports the interactive analysis, creation, and refinement of patient groups, disease groups, and genetic elements groups, and visualizes the corresponding landscape of genes, mutations, and genetic elements on the genome-scale. It encompasses the whole genome details to successively finer levels of the chromosome, gene, and genetic elements, down to the level of sequence.

Pathogenome module 260-10 enables the visualization and analysis of the genes and genetic elements that are causal or involved in disease from the whole human genome in a simplified manner, and the navigation from the whole genome to chromosomes to single genes. Pathogenome module 260-10 also illustrates different genetic elements and the sequences of genes and genetic elements that incorporate the variants and mutations at different levels.

Pathogenome module 260-10 provides visualization approaches including and beyond particular molecular and clinical data types, taking into account complex genomic relationships between patients in a family or cohort, and the commonalities of genes and mutations that are causal or contributing to the particular disease, trait, or ADR in the cohort of patients or population. It further facilitates the unraveling of mysteries hidden in the gene and the genome with the help of modules such as Gene, Protein, Promoters, Splice sites, Poly-A site, Branch Sites, Cryptic sites, Gene Fusion, CNV, and SV views for many of the protein-coding genes, and many of the ncRNA genes in the genome, by depicting the various kinds of mutations within them.

Pathogenome module 260-10 illustrates genetic alterations identified in the patients' genes under each genetic or genomic category such as the regulatory regions, coding regions, pharmacogenes, MMR (Mismatch Repair) genes, TMB (Tumor Mutation Burden), and Microsatellite instability (MSI), enabling high-resolution analysis. With the high influx of genomic data from patient cohorts, the frequency of the mutations is visualized along with the zygosity, inheritance patterns of genes, and mutations in the individual or in the cohort of patients from the whole genome in one view.

Pathogenome module 260-10 empowers unraveling the various abnormalities identified in the individual's genome to facilitate the clinician in the decision-making process. The module is a one-stop solution for the users to visualize the summary of genetic alterations identified in the individual from the whole genome in one view. The variants identified in the individual's genes under each genetic category across the whole genome, such as coding and many of the regulatory elements, Pharmacogenes, MMR (Mismatch Repair) genes, TMB (Tumor Mutation Burden), and Microsatellite instability (MSI), or gene panels from medical guidelines such as ACMG or the present disclosure's gene panels or user-specified panels can be visualized, providing high-resolution analysis. Non-coding RNA genes and the mutations within them in a patient genome are also illustrated in genome-scale on the Pathogenome platform. With the high influx of genomic data, Pathogenome facilitates answers to numerous disease-related queries.

Pathogenome module 260-10 may include a gene family section to display tracks specific to gene families. The mutations in genes from each gene family are plotted in the tracks with a statistical view on gene families and pathogenicity. This helps the researchers or clinicians to get a better understanding of the various gene families which might be responsible for the disease and drug response pathogenesis. Pathogenome module 260-10 may include a protein domain section to display tracks specific to genes that contain particular protein domains. The mutations in genes from different protein domain groups are plotted in the tracks with a molecular view on the domains and pathogenicity. This helps the researchers and clinicians to get a better understanding of mutations in the genes containing various domains that might be responsible for disease and drug response pathogenesis. Pathogenome module 260-10 may include genes for cell structure, function, and gene regulation section to display tracks specific to genes that specify cell structure, function, or gene regulation such as transcriptional regulation. The mutations in these types of genes are known to cause many diseases including cancer and non-cancer diseases. Mutations in these genes are plotted in the tracks with molecular views to determine its impact on the cell structure, function, or gene regulation and disease pathogenesis. This helps the researchers or clinicians to get a better understanding of the various ways the disease is caused, and thus predict the mechanisms which might be responsible for the disease and drug response pathogenesis, and to define precise diagnosis and treatment.

Pathogene module 260-11 helps to visualize the mutated genes, proteins, and many of the regulatory elements such as splice, promoter, and poly-A mutations in a particular patient or a patient group along with the supporting evidence. In this approach, the module acts as an ingenious visualization portal for genetic variations like SNPs, Indels in exons, introns, genes, protein domains, regulatory elements, UTR, promoters, splice sites, as calculated by algorithms such as the Shapiro-Senapathy, and supported by various public databases. The visualization framework of the pathogene module is similar for any of the four modules (Patient Genomics, Family Genomics, Cohort Genomics, and Clinical Trials Genomics). Pathogene module 260-11 provides a visualization portal for genetic variations like SNPs, Indels in genes, proteins, regulatory elements such as promoters, splice sites, branch points, poly-A, and other structural rearrangements for every gene from every patient in various Pathogene tabs enabling a high-resolution analysis. In some embodiments, pathogene module 260-11 aids in representing genes and structural elements showing different types of mutations from the patient, and the known mutations from the different databases such as dbSNP, ClinVar, and COSMIC depicting the CDS, and many of the regulatory elements, and categorizing them into clinical significance, molecular consequence, and variation type, and pathogenicity based on the SIFT and/or PolyPhen scores. By accessing pathogene module 260-11, clinicians can easily review the meta-information, pathology reports, and available genomic reports to decide the appropriate sequencing strategy required for disease prognosis.

A dark matter module 260-12 performs operations and searches in a portion of the genome known as the "Dark Matter Genome." Genes occur within the dark matter genome at high frequency, exhibiting high scores for many of the coding and regulatory elements and their cryptic versions in these genes, just as they occur within the currently known genes in the NCBI/ENSEMBL data sources. This discovery provides a high level of confidence for the existence of genes within the dark matter genome, in addition to the currently annotated genes in the human genome. Thus, the present disclosure approaches this problem with the same methodologies to find genes causing different disease and drug response phenotypes by exploring the dark matter genomes of cohorts of patients with various diseases.

Dark matter module 260-12 focuses on the clinical application of the dark matter genome to discover the genetic information that relates to disease and drug response in patients with various diseases, and applies this information in clinical practice and research. It aims to decipher the important coding and regulatory regions within the dark matter genome and discover the mutations that occur within them in different diseases, by uncovering them in patient cohorts with various underlying diseases.

In addition to identifying the disease-causing mutations in the currently annotated genes in NCBI/ENSEMBL resources, dark matter module 260-12 approaches this problem by detecting the deleterious mutations from many of these elements within the genes occurring in the dark matter genome. Dark matter module 260-12 utilizes the S&S method and other relevant algorithms that are used for detecting the splice sites and mutations in them and modifies them appropriately to develop unique scoring methods for the different regulatory elements by applying the unique PWMs based on the consensus sequences and the specific lengths of the respective elements. With this basic approach, dark matter module 260-12 identifies deleterious mutations enriched within the different regulatory regions of particular genes in the dark matter genome in different diseases. Furthermore, it discovers the deleterious mutations that are also enriched in cryptic sites for the different regulatory elements that occur throughout the sequences of various genes in the dark matter genome.

Dark matter module 260-12 works on its basic principle that deleterious, disease-causing mutations would be enriched in the genes that cause the disease in a patient cohort across many of the genetic elements including the CDS and the different regulatory elements in the gene, such as the promoter, UTR, splice donor, acceptor, and branch sites, enhancers and silencers, and poly-A sites, and their cryptic versions throughout the gene sequence. Thus, the platform approaches the discovery of disease-causing genes by identifying the deleterious mutations in multiple different regulatory elements and their cryptic versions throughout a gene across the patient cohort, and throughout many of the genes in both dark and white matter genomes of the patients in the cohort.

In some embodiments, dark matter module 260-12 is configured to identify the regulatory motifs and elements, including the promoters, splice acceptors, and donors, enhancers and silencers, and poly-A, and their cryptic versions, and CDS, using the S&S and other relevant algorithms and their modified versions in the genes from the dark matter genome. In some embodiments, dark matter module 260-12 is configured to identify the deleterious mutations in the CDS, and many of the different regulatory motifs and elements, from the genetic variants present in the patient's sequence, using the S&S and other relevant algorithms and their modified versions in the genes from the dark matter genome. In some embodiments, dark matter module 260-12 is configured to identify the dark matter genes that are frequently mutated in the CDS and the regulatory regions in a cohort of patients with a given disease. In some embodiments, dark matter module 260-12 is configured to accumulate many of the mutation information from many of the different genetic and regulatory elements and their cryptic versions in different genes, including the frequency of patients and frequency of mutations within each gene and the details of each of the regulatory mutations within each regulatory element, in addition to the CDS mutations. In some embodiments, dark matter module 260-12 is configured to combine the set of genes from the white matter genome and the new dark matter genome to present integrated information of the potentially disease-causing genes for the cohort. In some embodiments, dark matter module 260-12 is configured to create a database for the dark matter genes and for the integrated genes from different cohorts with the same underlying disease, and for many cancer and non-cancer diseases. In some embodiments, dark matter module 260-12 is configured to create a database for the dark matter genes and for the integrated genes from different cohorts with the same underlying disease, and determining a gene signature for each of the different cancers and non-cancer diseases. In some embodiments, dark matter module 260-12 is configured to identify cell structure, cell function, and transcriptional regulator genes from the dark matter genome. In some embodiments, dark matter module 260-12 is configured to determine the signatures of causal genes for disease within the white and dark matter genomes, based on the requirement of genes for the basic cell structure, function, and regulation to become defective by deleterious mutations. In some embodiments, dark matter module 260-12 is configured to identify mutational signatures in the different regulatory elements and CDS in particular genes in the white and dark matter genomes.

Figure 3:
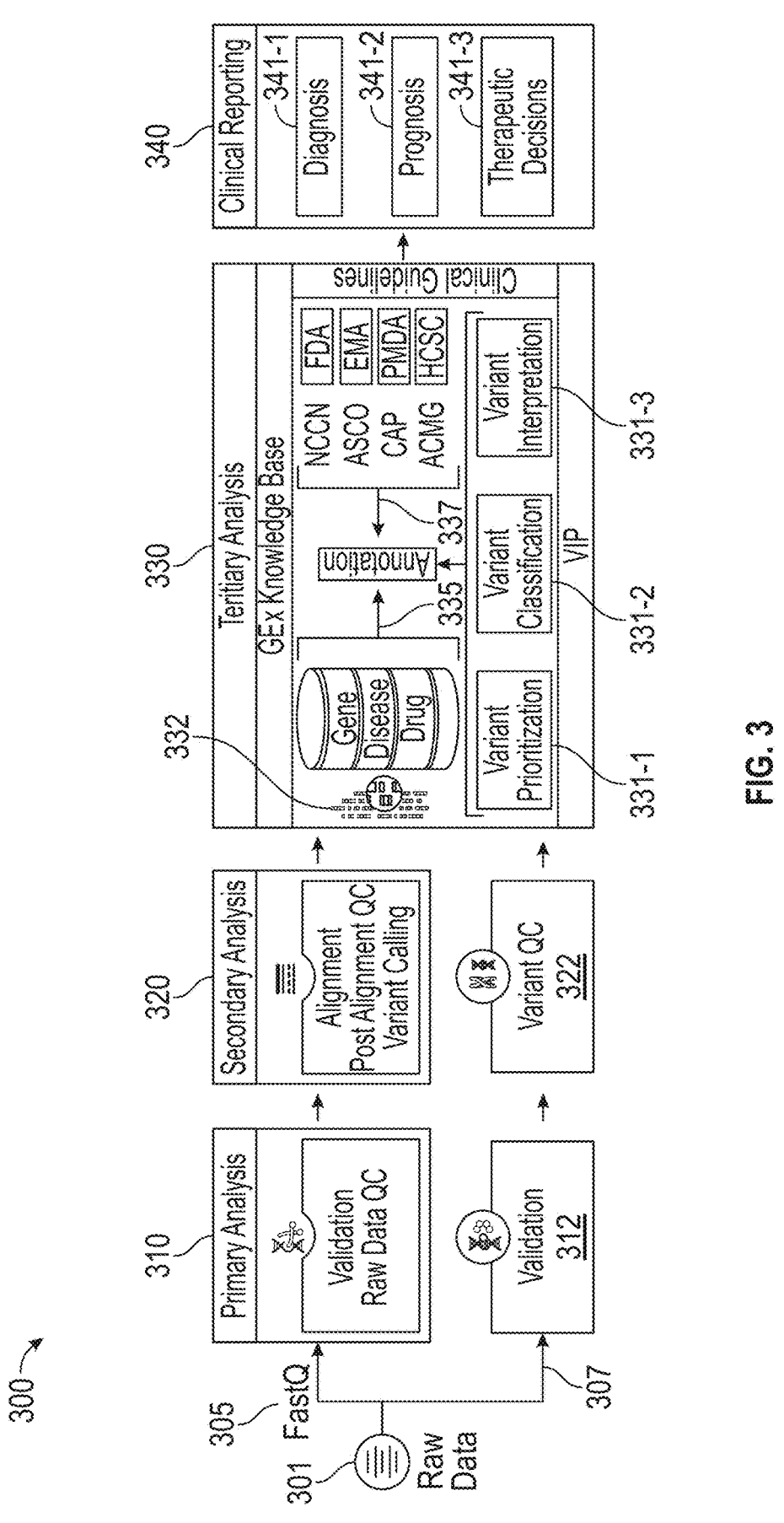
FIG. 3 is a block diagram illustrating a genome sequence analysis strategy, according to some embodiments.

FIG. 3 is a block diagram illustrating a genome sequence analysis strategy 300, according to some embodiments. The patient genomics platform is for analyzing an individual patient's genome (DNA or RNA), raw data 301, and determining the pathogenic mutations in each of the ~20,000 protein-coding genes and several thousand non-coding (nc) RNA genes within the human genome. The platform identifies the variants in the genes, transcripts, proteins, and ncRNAs and correlates their impact on potential diseases that the patient might currently have or will have in the future. The platform may also provide insight into gene expression by looking at customized high-throughput NGS analysis of messenger RNA (mRNA) sequencing data and performs a quality check to ensure the quality of raw data, route 305. The module provides a QC report which can spot biases in the library material or during sequencing and compiles important statistics on NGS data, such as per-base and per-sequence quality scores and GC content. The platform provides a comprehensive clinical report of the patient, with key genomic, diagnostic, and therapeutic findings, and a customized list of key suggestions for the primary and secondary diseases, drug dosage and treatment, Adverse Drug Reactions (ADRs), and further genomic-based suggestions that would provide support for clinical decisions, and validation 312 of the same.

The platform is enabled with customized high-throughput NGS analysis workflows for individual samples, case-control, family analysis, cohort analysis, and clinical trial analysis. The analysis can be performed using raw sequencing data 305 or variants VCF file format 307. Relevant, clinically useful genomic details are given in the clinical report to aid the healthcare providers in clinical practice. Several visualizations are provided for the clinicians and researchers to gain a deeper understanding of the genes, mutations, and clinical outcomes.

A primary analysis 310 involves a quality check of the raw genomic data to avoid data anomalies. A QC report translates any biases in the sequence library material, sequencing errors, contamination of the data via other biological sources, and any remaining adapter contents. In some embodiments, the QC report includes: a Sequence length distribution, a Per base sequence quality, a Per sequence quality, a Per base sequence content, a Per sequence GC content, a KMER content, and an Adapter content. Anomalies can be removed using automated trim/filter options with the default and customizable parameters. The output is then ready for processing in secondary analysis 320.

Secondary analysis 320 involves alignment, variant identification, and annotation required for the tertiary downstream analyses. Alignment includes mapping the cleaned sequence reads against the human reference genome (GRCh37/hg19) and is performed using a fast and accurate read aligner BWA-MEM, based on the Burrows-Wheeler Transformation (BWT) algorithm. Read alignment information is reported in SAM/BAM format, which is used for calculating the depth of coverage and calling variants. Post-alignment QC includes examining sequencing alignment data according to the features of the mapped reads and their genomic properties. This performance assessment provides an overall view that helps detect biases in the sequencing and/or mapping, which must be removed before calling the variants. The unaligned reads are removed before variant calling and used to estimate any possible non-human contamination. The aligned reads are processed to de-noise by removing duplicate reads and reads mapping to multiple positions, followed by sorting and indexing the BAM file. Post-Alignment QC improves the accuracy and quality of the further variant analysis. Variant calling includes identifying high-quality Single Nucleotide Variants (SNVs) and small insertions and deletions (InDels), using variant callers like GATK, VarScan, Freebayes, Pisces, and Samtools. The likelihood data for each genotype is calculated and variants 322 in each sample are identified with respect to the reference genome. The variants are reported in the standard Variant Call Format (VCF) file.

Secondary analysis 320 may also include variant annotation, which includes a functional annotation of high-quality variants and is performed using Ensembl VeP (Variant Effect Predictor) to predict the effects of variants on genes and classify them into synonymous, non-synonymous, missense, or silent consequences. Multiple in-silico prediction algorithms are utilized to grade the variants for their level of penetrance and classify the variants as deleterious or benign. The present disclosure integrates well-curated population databases such as ExAC, ESP, and 1000 Genomes; Disease annotation Databases such as dbSNP, dbNSFP, COSMIC; Phenotype Databases such as ClinVar, OMIM, HPO, MONDO; Drug databases such as PharmGKB and Drug regulations such as FDA, EMA, PMDA, HCSC, and clinical trials. The annotated VCF file is compressed and stored in a MySQLite database, facilitating readily accessible and easy data extraction using simple SQL queries.

In some embodiments, genome sequence analysis strategy 300 may include the following features to assign the functional information for the variants: A Genomic annotation, e.g., UCSC Reference genome—GRCh37/hg19, ENSEMBL and Variant Effect Predictor (VEP); functional consequences, wherein variants are annotated using ENSEMBL VEP to determine the consequences viz. synonymous, non-synonymous, nonsense, splice acceptor, splice donor, or frameshift events; population databases, wherein a minor allele frequency of variants across healthy population databases helps distinguish common polymorphisms from disease-causing variants.

Some databases used in genome sequence analysis strategy 300 may include 1000 Genomes (1KG)—Phase 3, NHLBI Exome Sequencing Project (ESP), and Exome Aggregation Consortium (ExAC).

Genome sequence analysis strategy 300 may also access disease databases to identify variants with known disease associations, as established in disease and phenotype databases to enhance the differential diagnosis. Some examples of these databases may include: ClinVar, Catalogue of Somatic Mutations in Cancer (COSMIC), dbNSFP, dbSNP, Online Mendelian Inheritance in Man (OMIM), and Human Phenotype Ontology (HPO). In addition to the above, other variant information like conservation, computational predictions, and PubMed evidence are compiled and classified for clinical reporting.

A tertiary analysis 330 may include variant prioritization 331-1, variant classification 331-2, and a variant interpretation 331-3, based on the consensus from pathogenicity classifiers, clinical significance as reported by well-established databases 332 (e.g., genes, diseases, and drugs), appropriately annotated 335, and professional practice guidelines. In some embodiments, variant prioritization 331-1 identifies disease-causing variations among dozens or hundreds of detected variants and identifies a functional impact of variants.

Variant prioritization 331-1 employs many major in-silico classifiers to determine the likelihood of the variants being pathogenic or benign. Disease-causing potential of variants is calculated based on amino acid structural substitutions using physical and comparative considerations, protein functions, and evolutionary conservation of amino acids. Multiple in-silico pathogenicity classifiers are used to rank variants based on weighted deleteriousness scores, and predicts the functional impact, such as FATHMM, LRT (Likelihood Ratio Test), MetaLR, MetaSVM, Mutation Assessor, Mutation Taster, Polyphen2, PROVEAN, and SIFT.

Variant classification 331-2 classifies variants as per the ACMG evidence and classification guidelines, which specify that clinical reporting must clearly distinguish Benign and Likely Benign variants from Variants of Uncertain Significance (VUS) and Pathogenic variants. The present disclosure four-tiered variant classification system specifies the amount and quality of evidence required to classify genetic variants as per the Joint Consensus Recommendation of the Association for Molecular Pathology (AMP), American Society of Clinical Oncology (ASCO), and College of American Pathologists (CAP). Table II below lists some of the codes provided in variant classification step 331-2, associated with pathogenic evidence—Strong, Moderate- or benign evidence, and the like (e.g., as per ACMG-AMP).

TABLE II

| Strong Pathogenic Evidence |
| --- |
| VS1 Null variant (nonsense, frameshift, canonical +− 2 splice sites, initiation codon, single or multi-exon deletion) in a gene where LOF is a known mechanism of disease |

TABLE II-continued

| S1 | Same amino acid change as a previously established pathogenic variant regardless of nucleotide change |
| S2 | De novo (both maternity and paternity confirmed) in a patient with the disease and no family history |
| S3 | Well-established in vitro or in vivo functional studies supportive of a damaging effect on the gene or gene product |
| S4 | The prevalence of the variant in affected individuals is significantly increased compared with the prevalence in controls |

Moderate Pathogenic Evidence

| M1 | Located in a mutational hot spot and/or critical and well-established functional domain (e.g., the active site of an enzyme) without benign variation |
| M2 | Absent from controls (or at extremely low frequency if recessive) in Exome Sequencing Project, 1000 Genomes Project, or Exome Aggregation Consortium |
| M3 | For recessive disorders, detected in trans with a pathogenic variant |
| M4 | Protein length changes as a result of in-frame deletions/insertions in a non-repeat region or stop-loss variants |
| M5 | Novel missense change at an amino acid residue where a different missense change determined to be pathogenic has been seen before |
| M6 | Assumed de novo, but without confirmation of paternity and maternity |

Supporting Pathogenic Evidence

| P1 | Co-segregation with disease in multiple affected family members in a gene definitively known to cause the disease |
| P2 | A missense variant in a gene that has a low rate of benign missense variation and in which missense variants are a common mechanism of disease |
| P3 | Multiple lines of computational evidence support a deleterious effect on the gene or gene product (conservation, evolutionary, splicing impact, etc.) |
| P4 | Patient's phenotype or family history is highly specific for a disease with a single genetic etiology |
| P5 | A reputable source recently reports variant as pathogenic, but the evidence is not available to the laboratory to perform an independent evaluation |

Strong Benign Evidence

| A1 | Allele frequency is >5% in Exome Sequencing Project, 1000 Genomes Project, or Exome Aggregation Consortium |
| S1 | Allele frequency is greater than expected for the disorder |
| S2 | Observed in a healthy adult individual for a recessive (homozygous), dominant (heterozygous), or X-linked (hemizygous) disorder, with full penetrance expected at an early age |
| S3 | Well-established in vitro or in vivo functional studies show no damaging effect on protein function or splicing |
| S4 | Lack of segregation in affected members of a family |

Supporting Benign Evidence

| P1 | A missense variant in a gene for which primarily truncating variants are known to cause disease |
| P2 | Observed in trans with a pathogenic variant for a fully penetrant dominant gene/disorder or observed in cis with a pathogenic variant in any inheritance pattern |
| P3 | In-frame deletions/insertions in a repetitive region without a known function |
| P4 | Multiple lines of computational evidence suggest no impact on gene or gene product (conservation, evolutionary, splicing impact, etc.) |
| P5 | The variant found in a case with an alternate molecular basis for disease |
| P6 | A reputable source recently reports variant as benign, but the evidence is not available to the laboratory to perform an independent evaluation |
| P7 | A synonymous (silent) variant for which splicing prediction algorithms predict no impact to the splice consensus sequence nor the creation of a new splice site AND the nucleotide is not highly conserved |

Variant interpretation step 331-3 may be implemented as recommended by the professional practice guidelines from NCCN, ASCO, ESMO, and ACMG. Variant interpretation step 331-3 ensures that the disclosed platform adheres to professional practice guidelines and evidence-based guidelines from clinical regulatory bodies for validation and reporting of NGS-based diagnostics in regular clinical practice. The variants are classified in tiers based on clinical pathogenicity and drug ability as per ACMG guidelines which are seamlessly incorporated to inform management decisions and interventions (cf. Table II). In order to prioritize and interpret the variants, the biomarkers with therapeutic, prognostic, and/or diagnostic significance are reported to empower clinicians and other healthcare decision-makers around the world. Some of the clinical guidelines may include the following professional organizations and groups: the National Comprehensive Cancer Network (NCCN), the American College of Medical Genetics (ACMG), the College of American Pathologists (CAP), and the American Society of Clinical Oncology (ASCO).

Variant interpretation 331-3 provides automated variant interpretation for the pathogenic and likely pathogenic mutations identified by the present disclosure processing workflow (as outlined in the workflow). The interpretation explains the mutation consequences (e.g., missense, nonsense, synonymous, splice acceptor, splice donor, frameshift and In-frame InDels, etc.), mutation type (single nucleotide variation, insertion, deletion), and its effect on the protein in the CAP suggested HGVS syntaxes. The interpretations are supported by the consensus of in-silico pathogenicity prediction tools, ClinVar expert panel review, PubMed evidence, and the minor allele frequencies from the healthy population databases such as 1000 Genomes, ExAC, or ESP. Table III below demonstrates the ability of the platform to designate the variant, and providing the detailed interpretation of the variant with its zygosity, pathogenicity, frequency, and other relevant details. More specifically, Table III includes a stop gained single nucleotide transversion mutation in the BRCA2 gene of a subject, classified as pathogenic due to variant consequences reviewed by ClinVar experts or having major consensus across most widely used in-silico pathogenicity prediction tools. Some variants may be reviewed by a ClinVar expert panel, and may be cited in medical art publications. The variant is not hitting any domain and may be present in the conserved region. The variant may be reported in the ACMG list of incidental findings and COSMIC-Cancer Gene Census. The variant is present in the healthy population databases such as 1000 Genomes, ExAC, or ESP with 0.0001 minor allele frequency.

TABLE III

| BRCA2 | | | | | |
| --- | --- | --- | --- | --- | --- |
| | Variant | Consequences | rs ID | VAF | Zygosity |
| P | Chr13:32,914,137 C > A ENSP00000439902.1: p.Ser1882Ter | Stopped Gained | Rs80359785 | Case: 72% | Heterozygous |

Curated assertions and drug labels, and approval statements 337 for the targeted therapeutic, prognostic, and diagnostic biomarkers as approved by following regulatory agencies and making it an accurate, intuitive, and efficient tool for clinicians to improve patient care: the Food and Drug Administration, USA (FDA), the European Medicines Agency (EMA), Health Canada (HCSC), and the Pharmaceuticals and Medical Devices Agency, Japan (PMDA).

In some embodiments, genome sequence analysis strategy 300 prioritizes potential clinical trials for the targeted variants, empowering the clinician with current evidence-backed options. Tertiary analysis step 330 enables a health-care provider or a clinical or pharmaceutical researcher to conduct a deep analysis of many of the variants, pathogenic mutations, and diseases hidden within the genome of the patient. Detailed information accounting for many possible mutation types (splice mutations, promoter mutations, poly-A, coding mutations, DNA Gene Fusion, Structural Variants, and Copy number variants) are provided and supported by various quality metrics (Variant statistics, Alignment statistics, Raw data QC) and are provided in this module. These variants can be further evaluated and bookmarked to be included in the customized clinical report.

In some embodiments, tertiary analysis step 330 for mRNA employs the reads that were previously aligned to the reference genome into transcript structure (transcript assembly process) and estimates the abundance levels of genes and transcripts. The expression levels are reported in terms of Fragments Per Kilobase of Exon per Million mapped fragments (FPKM) and Transcripts Per Million (TPM) units. FPKM is a normalized estimation of gene expression calculated from the number of reads mapping to each particular gene sequence by taking into account gene length and sequencing depth. The expression values of genes and transcripts are compared across samples post-transcript-assembly process. The differentially expressed genes are identified from the merged transcript GTF file of case and control samples. The significant changes in the gene/transcript level expression between the samples are annotated and reported.

A clinical reporting step 340 includes a comprehensive clinical report of the patient, with key genomic, diagnostic, and therapeutic findings, a customized list of key suggestions for the primary and secondary diseases, drug dosage and treatment, Adverse Drug Reactions (ADRs), and further genomic-based suggestions that would provide support for clinical decisions. Clinical reporting step 340 incorporates industry best practices in the implementation of NGS-based diagnostics that live up to the highest technical standards, quality controls, secondary findings, and variant interpretation and prioritization. Genome sequence analysis strategy 300 follows recommendations outlined by clinical regulatory bodies for pipeline development, validation, quality management, and regular updates, and interfaces seamlessly with hospital EHRs, and genetic counselors. In some embodiments, genome sequence analysis strategy 300 meets and exceeds clinical reporting best practices by integrating clinical reporting guidelines established by professional regulatory bodies like CAP and ACMG, depending on the patient's disease.

A clinical report includes a diagnosis 341-1, a prognosis 341-2, and therapeutic decisions 341-3. In some embodiments, at-a-glance relevant details are in a clear, concise format, including patient meta-information, testing indications, key findings or absence of findings, conclusions, and recommendations. A clinical summary of the genomic findings precedes the clinical report that compiles the primary diagnosis 341-1 based on the disease indications, secondary findings based on the ACMG 59 genes and proprietary disease panels, pharmacogenomic indications, therapeutic indications, immune checkpoint inhibitors based on the immunotherapy biomarker status, and the suggested clinical trials. The variants are tier-classified and Tier-I, II, and III are reported in descending order of potential significance. Tier-IV variants (Benign/Likely benign) are not included in the report, as per CAP guidelines. The variants are reported as per the HGVS nomenclature along with Refseq accession numbers, genome build, and official gene names, as per Human Genome Organization (HUGO) guidelines. The clinical report clearly differentiates somatic and germline variants and provides Zygosity information and mode of inheritance. Actionable variants are highlighted along with therapies approved by various regulatory agencies and suggested by professional guidelines.

The clinical report may include sections such as clinical report summary, test performed block, therapeutic indications, immunotherapy markers, promoter, 5' & 3' UTR, poly-A and exonic, intronic, and deep intronic splicing mutations, variant interpretation, ACMG incidental findings, copy number variants report, structural variants, gene fusions, PGx report, drug details, gene details, and variants of uncertain significance (VUS) as detailed below. For variants not included in the system generated clinical report for the diagnosis, the clinician can bookmark any variant of their choice and add such variants to the report. The clinical report can further be customized by editing the clinical summary, case history and findings, testing indications, variant interpretations, and therapeutic indications to suit the clinician's requirements.

In some embodiments, the clinical report prepared in step 340 may include multiple sections, as follows. A clinical report summary may include a synopsis of clinical findings identified in a patient and described in the clinical report. The section contains key information such as primary diagnosis, secondary diagnosis, targeted therapy, immunotherapy, pharmacogenomics, and clinical trials. A primary diagnosis may identify and illustrate deleterious genes and variants that are causal for the disease and are analyzed in various aspects and clinically interpreted referring to the condition to which the majority of the signs, symptoms, and clinical phenotype of an individual are applied. A secondary diagnosis contains the ACMG and secondary findings which impose the co-existing phenotypes in a patient or develop subsequently and have the potential to impact a patient's severity of illness and risk of mortality Immunotherapy includes the status for two emerging diagnostic biomarkers, Tumor Mutation Burden (TMB) and Microsatellite Instability (MSI) are provided which plays an important role in predicting response to immune checkpoint inhibitors across various tumor types. Pharmacogenomics may include the drug-metabolizing phenotypes of 11 major drug-metabolizing genes and the gene set from the eMERGE consortium, and their effect on different medications are provided as per the recommendations of the Clinical Pharmacogenetics Implementation Consortium (CPIC) guidelines. These predicted drug responses can help clinicians to make informed drug administration decisions. Targeted therapy and Clinical Trials may indicate disease-associated therapeutic procedures approved by various drug regulatory agencies like FDA, EMA, PMDA & HCSC, and are provided along with available contraindicated and/or investigational therapies associated with the targeted mutations identified in the patient. The available clinical trials of the suggested drugs are described suggesting the clinical phases of targeted therapy. A summary of statistics presents the analysis outcomes and reports the unique number of genomic alterations, applicable Immuno-marker status, therapies (approved, contraindicated, investigational), and the potential clinical trials. Table IV, below, illustrates the summary tags of the clinical report briefing the statistics of mutations, immunomarker status, suggested therapies, and available clinical trials.

TABLE IV

| Genomic Findings | | Immunomarkers | | Therapy | | | Clinical |
|---|---|---|---|---|---|---|---|
| Tier 1 | Tier II | TMB (mut/MB) | MSI | Approved | Investigation | Contraindicated | Trials |
| 2 | 0 | 127 | Stable | 2 | 0 | 0 | 1 |

Table V is a tabular reporting of the biomarkers indicated as pathogenic, likely pathogenic, or drug response for the patient's disease, their respective tier classifications, mutation consequences, Zygosity, and phenotype (wherever applicable). The actionable and significant variants are tagged for enhanced user understanding. Table V indicates the framework to report the biomarkers identified in the genomic test along with the consequences, and other relevant details.

TABLE V

Test Performed For Breast Cancer
Genomic testing was performed to detect the presence of point mutations, short insertion/deletions in the protein-coding regions, and exon-intron boundaries associated with Breast Cancer, 2 gene(s) (shown below) found to be mutated in this sample.

| | Biomarkers | | Tier | Consequences |
|---|---|---|---|---|
| P | BRCA2 | p.Ser1882Ter | Tier 1 | Stop Gained |
| P | NCOR1 | p.Glu1860Ter | Tier 1 | Stop Gained |

Table VI is a tabular reporting of the targeted therapeutic indications and is provided for the patient's disease-specific genomic alterations classified as approved, contraindicated, or investigational therapy. The contraindications or the drugs which need to be avoided are suggested as per the guidelines. Therapies are reported with respect to the specific biomarker variants, approved agencies, other approved cancer types, and the clinical trials. Table VI depicts the targeted therapies suggested for each genomic alteration identified in the patient. The module provides therapies approved by drug regulatory agencies, contraindicated, and investigational therapies.

TABLE VI

Therapeutic Indications

| Therapy | Biomarkers | Approved Agencies | For Other Cancer(s) | Clinical Trials |
|---|---|---|---|---|
| Talazoparib | BRCA2 p.Ser1882Ter | FDA EMA | Pancreatic, Prostrate, Ovarian | II(1) |
| Otaparib | BRCA2 p.Ser1882Ter | NCCN FDA EMA HCSC PMDA | Pancreatic, Prostrate, Ovarian | — |
| Therapies With Potential Benefit | | | | |
| Olaparib, Talazoparib | | | | |
| Therapies With Lack of Benefit | | | | |
| No relevant therapies are available | | | | |
| Investigative Therapies | | | | |
| No relevant therapies are available | | | | |

Table VII illustrates immunotherapy markers such as TMB, as a measure of the number of somatic protein-coding mutations occurring in a tumor specimen per million base pairs, and the MSI caused by frameshift mutations of dinucleotide repeat bases during DNA replication and the failure of the mismatch repair system (MMR) to correct these error status are calculated in the patient's genome. More specifically, Table VII illustrates the immune biomarkers (TMB and Microsatellite status) identified in the patient. Based on these biomarkers, immunotherapies are recommended for the patient to enhance the clinical outcomes.

TABLE VII

| Tumor Mutation Burden (TMB) | Microsatellite Instability Status |
|---|---|
| HIGH | STABLE |

In some embodiments, clinical reporting step 340 includes reporting mutations located in the splice sites (exon-intron boundaries), cryptic splice sites within exons and introns, untranslated regions (UTRs), poly-adenylation sites (Poly-A), and/or promoter regions, that lead to defective or non-functional proteins. The splicing mutations (real and cryptic splice acceptor and donor mutations) are scored using the Shapiro-Senapathy algorithm (S&S algorithm), the promoter, branch point, UTR, and poly-A mutations are scored using algorithms built on S&S and other established scoring algorithms, and those that are determined to be pathogenic and likely pathogenic are reported.

Some portions of the report provided in clinical reporting step 340 may be as follows. An ACMG Incidental findings section reports 59 curated genes for reporting of incidental findings in clinical exome and genome sequence analysis as recommended by the American College of Medical Genetics and Genomics (ACMG) which are known to be implicated in a number of diseases including cancers and non-cancer disorders with potentially actionable outcomes. The platform identifies pathogenic and likely pathogenic mutations in these genes in a patient and reports the ACMG indicated diseases.

A copy number variants (CNV) section includes copy number variation and involves alterations in the number of copies in specific regions of an individual's DNA, which can either be amplified or deleted. Such events are identified from the patient DNA in the analysis and reported for disease association. CNV involves alterations in the number of copies in specific regions of an individual's DNA, which can either be amplified or deleted. The copy number changes are inferred by processing the reads aligned against the reference genome (hg19). The candidate breaks are identified and supporting read depths are normalized to the reference and corrected for several systematic biases to calculate log 2 copy ratios. A built-in segmentation algorithm is used to infer discrete copy number segments with the default threshold value for amplification (>=0.2 log 2 ratio) and deletion events (<=−0.25 log 2 ratio).

A structural variants (SV) section includes by deletions, insertions, duplications, or inversions of chromosomal segments, or rearrangements of the chromosomal locations either to other chromosomes (interchromosomal rearrangement) or within a chromosome (intrachromosomal rearrangement). Such events are identified in the analysis and reported for disease association. Structural variation refers to large-scale structural differences in the genomic DNA, as a result of chromosomal rearrangements like deletion, duplication, insertion, inversion, and inter- and intra-chromosomal translocations. These structural variants are predicted using read pairs that are mapped with unexpected separation distances or orientation. The module estimates the parameters of the insert size distribution and goes through reads to identify Discordant Read Pairs (DRPs) i.e., reads with abnormal orientations or insert sizes (either too small or too large) and clusters them to identify the structural variants in the patient.

A gene fusion (GF) events section includes gene fusion events. Gene fusion is a phenomenon in which the whole or parts of two genes are juxtaposed and fused into a single chimeric gene. The fusion can result from structural rearrangements like translocations, inversion, amplification, or deletions. Such events are captured in the analysis and reported under individual known gene fusions for the indicated disease and novel gene fusion tables under this section. A pharmacogenomics report reveals the drug response by identifying the individual's genotype and its effect on different medications. These findings help clinicians make informed drug and dose administration decisions based on the patient's drug metabolizer status, e.g., normal, intermediate, poor, or rapid metabolizer. A drug details section outlines the drug information for those indicated as suitable for the patient in terms of the trade name, adverse drug reaction, pathway information, approved annotation labels, and ongoing clinical trials. The side effects due to the prolonged usages of the drugs are also provided as per the PubMed evidence. A gene details section provides details for many of the mutated genes indicated in the patient and are summarized under this section as per the definition and functional implications reported by NCBI. A variant of uncertain significance (VUS) section includes mutations whose connection to diseases have not been established and are classified as variants of uncertain significance as per the ACMG guidelines. These mutations are thus recommended to be reported as per the good clinical practices under CAP guidelines.

A variant report may include a well-structured mutation-centric report that outlines many of the variants present in the patient classified based on the pathogenicity. Each variant is infused with evidence derived from well-established databases—both healthy and disease-centric. The entire report can be explored using various filters to cater to specific user needs. The clinician can bookmark to add any biomarker variants for the disease which is deemed important for the disease. A regulatory genetic elements report includes a well-structured splice, poly-A, and deep intronic mutation report that culminates many of the pathogenic and likely pathogenic mutations scored using the S&S and other algorithms Each variant is reported with its reference and mutated base sequences, and the percentage difference scores are calculated by the algorithms that translate into the significance of disease causation. A splice site mutations report includes mutations in the boundary of an exon and an intron (splice sites) and cryptic splice sites that exist throughout the gene including exons and introns, or changes in the activity of splicing events by mutations in the spliceosome proteins and RNA, and leads to a profound impact on the regulatory and accuracy of the function of the proteins leading to pathogenesis and disease progression. The real and cryptic splice acceptor and donor and cryptic exon mutation events and aberrations are identified using the Shapiro-Senapathy algorithm and prioritized based on the percentage score difference. A promoter mutations report includes mutations in the promoter regions and can disrupt the normal gene activation and transcriptional initiation and alter the binding ability of DNA-sequence motifs by various protein factors that functionally interact with them, thus leading to disease pathogenesis. The pathogenic promoter defects are identified based on an algorithm adapted from the Shapiro-Senapathy algorithm suited to the length and sequence of the promoter and other elements and prioritized on the percentage score difference. A UTR mutations report includes mutations in the untranslated regions and can disrupt the normal gene translation, and thus lead to disease pathogenesis. The pathogenic 5' UTR and 3' UTR defects are identified based on the Shapiro-Senapathy algorithm and prioritized on the percentage score difference. A Poly-A mutations report includes mutations in the 3'-untranslated region having the polyadenylation sites that contributes to mRNA stability, translation control, nuclear export, and cellular functions of growth proliferation and differentiation, thus becoming one of the critical events that regulate diverse molecular aspects of mRNA metabolism. Therefore, a disruption in these sites has been known to cause diseases where the pathogenesis has been outlined to include a varied concentration of mRNA processing factors, RNA-binding proteins, and the global transcriptome changes of the cellular signaling pathway. The mutations in the 3'-UTR affecting the signals, as well as those identified by the adaptation of the Shapiro-Senapathy algorithm, are prioritized as pathogenic events. A DNA gene fusion report includes DNA fusion events that are identified by locating the candidate breaks with two or more clipped reads. The breaks supported by at least three unique discordant reads with one of the two pairs longer than 10 bp and matching more than 70% of the split length is considered as a fusion event. The functional consequences of genomic fusions are annotated with genes, fusion domains in a strand-specific manner, and frequency of the events in disease databases like cosmic. The known fusion event(s) that are likely to have an association with the disease is reported along with the novel fusion events. The reported gene fusion events are described with the breakpoints, fusion orientation, potential targeted therapy, and the clinical trials.

In some embodiments, the report includes an expression level of the genes, annotated, and with the log fold change and p-value estimating the significance level of expression. The top significant up-regulated and down-regulated genes are differentiated and visualized as a volcano plot with the log fold change and p-value which refers to the analysis and interpretation of differences in the abundance of gene transcripts within a transcriptome. The log of fold-change is used so that changes in both directions (up and down) appear equidistant from the center, whereas the data points with low p-values (highly significant) appear towards the top of the plot. It enables visual identification of the most meaningful and statistically significant genes. The corresponding transcripts, coverage, FPKM, and Transcripts Per Million (TPM) levels of each identified gene are reported. The functional enrichment analysis (Gene Ontology and Pathway analysis) is also performed for the top significant differentially expressed genes and based on the level of gene expression, the affected pathways, molecular function, cellular components, and biological processes are reported with the significant p-value.

Other elements in the report provided in clinical reporting step 340 may include the following. A variant statistics including statistics and quality metrics are summarized to indicate the chromosome-wise variant summary, mutation spectrum, amino acid spectrum, top 50 mutated genes, ts/tv count, and distribution of functional consequences along with the depth and quality distribution of variants identified in the patient. An alignment statistics is summarized to indicate the chromosome-wise distribution of aligned sequence reads, coverage, mapped bases, and insert-size distribution in the patient's sequence alignment map. A raw data QC including various sequence read statistics and quality metrics are summarized to indicate the per-base sequence content, per-base quality scores, GC content, sequence quality, length distribution, Kmer content, and adapter content in the patient's sequenced reads. PGx genes including patient mutations in the drug-metabolizing genes are plotted, and interactive graphical interpretations are shown together on the gene structure and sequence landscape for a comprehensive representation of many of the possible mutation types (splice mutations, promoter mutations, UTR, poly-A, and coding mutations). eMERGE genes including the metabolizing functions of 82 or more pharmacogenes which are critical for the implementation of "precision medicine" are provided as per the study outcome of the eMERGE-PGx project. The detailed sequence view and various genic properties of these pharmacogenes are shown using interactive visuals. MMR genes including the patient mutations in the Mismatch repair genes (MMR) are plotted on the gene structure and genomic sequence map on the chromosomal scale for many of the possible mutation types (splice mutations, promoter mutations, poly-A, and coding mutations) for comprehensive visualization. Many genes including the patient's mutated genes are sorted in descending order so that the genes with the highest number of mutations are prioritized. Many of the possible mutations (splice mutations, promoter mutations, poly-A, and coding mutations) in a given gene are plotted and shown together on the gene structure and sequence landscape for an encyclopedic view.

Figure 4:
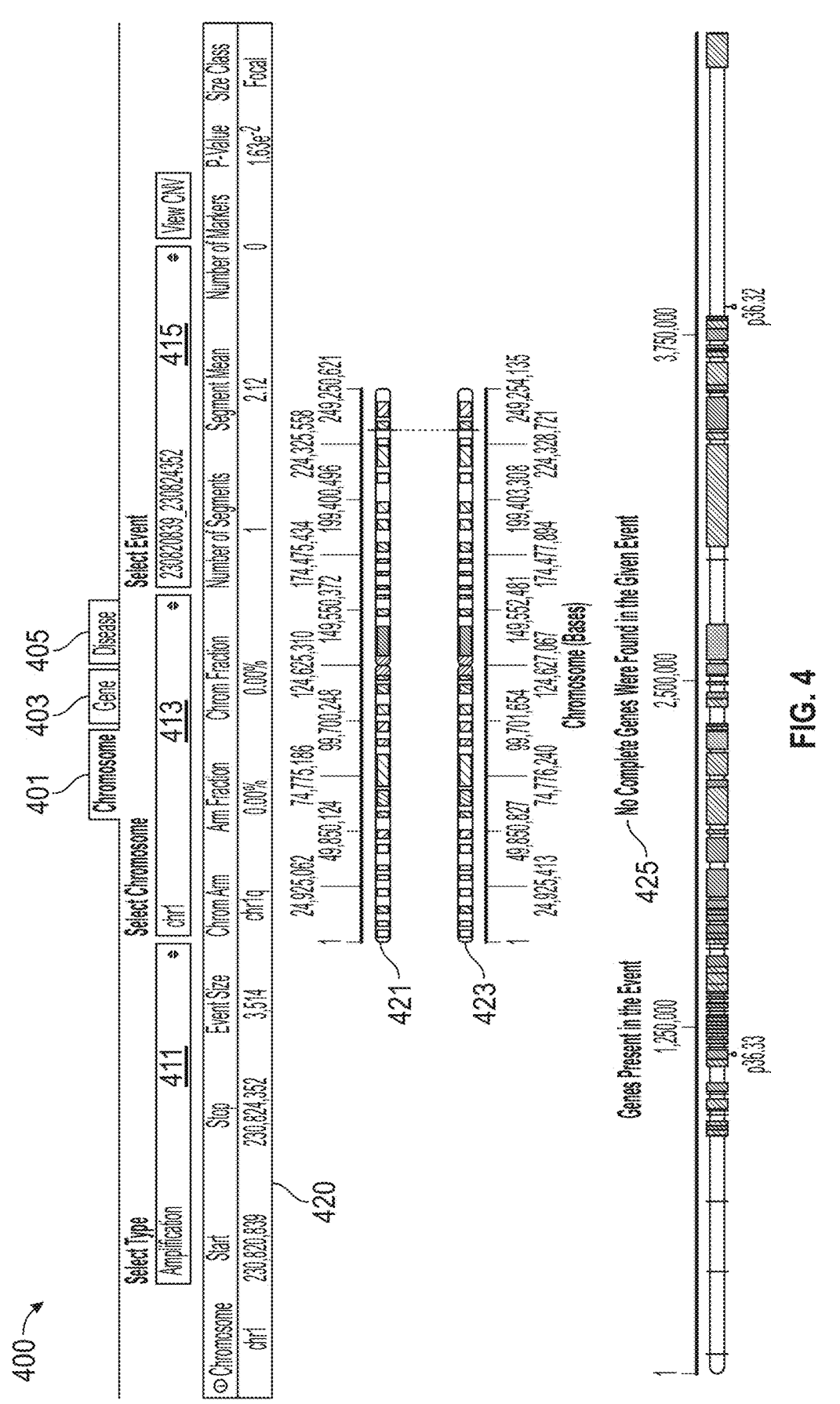
FIG. 4 illustrates copy number variants and associated genes in a chromosome, according to some embodiments.

FIG. 4 illustrates copy number variants 400 and associated genes 403 in a chromosome 401 for a selected disease or trait 405, according to some embodiments. The present disclosure can diagnose the patient genome for various genomic rearrangements that encompass structural variants, copy number variants, and gene fusions. These rearrangement events are visualized on the genomic scale in an interactive graphical interpretation. The events are also shown at the sequence level, depicting the exact points of rearrangements.

Copy number variation (CNV) involves alterations in the number of copies in specific regions of an individual's DNA, which can either be amplified or deleted. The chromosome wise events 415 reported from the patient's genome can be visualized on the chromosomal structure and the corresponding genes that are partially and completely amplified or deleted through interactive visualization before amplification 421 or after amplification 423. The type of event to be selected (e.g., amplification, partial amplification deletion, and the like) is selected via tab 411. The chromosome to be analyzed may be selected through tab 413, and the CNV events are selected through tab 415.

In some embodiments, a message 425 may indicate that no complete genes have been found for the selected event in tab 415. Gene tab 403 gives the details of genes in the genomic location that are present at a variable copy number in comparison with a reference genome. The copy number variants at the genomic location refer to the part of the genome that is either amplified or deleted at large-scale. Gene tab 403 provides information about the genes that are duplicated or deleted due to copy number alterations. It is thought that large-scale chromosomal rearrangements also give rise to various genetic diseases, which can be viewed through disease tab 405. With reliable detection of CNVs, the driver mutations for various diseases are identified for a single subject, helping in developing personalized medicines when integrating with other genomic features.

A detailed result table 420 indicates the chromosome, the start and stop nucleotide location of the CNV event, the size (e.g., number of nucleotides involved), the chromosome arm, the arm fraction, the chromosome fraction of the segment mean, the number of markers, the P-value, and the size class involved in the event.

Figure 5:
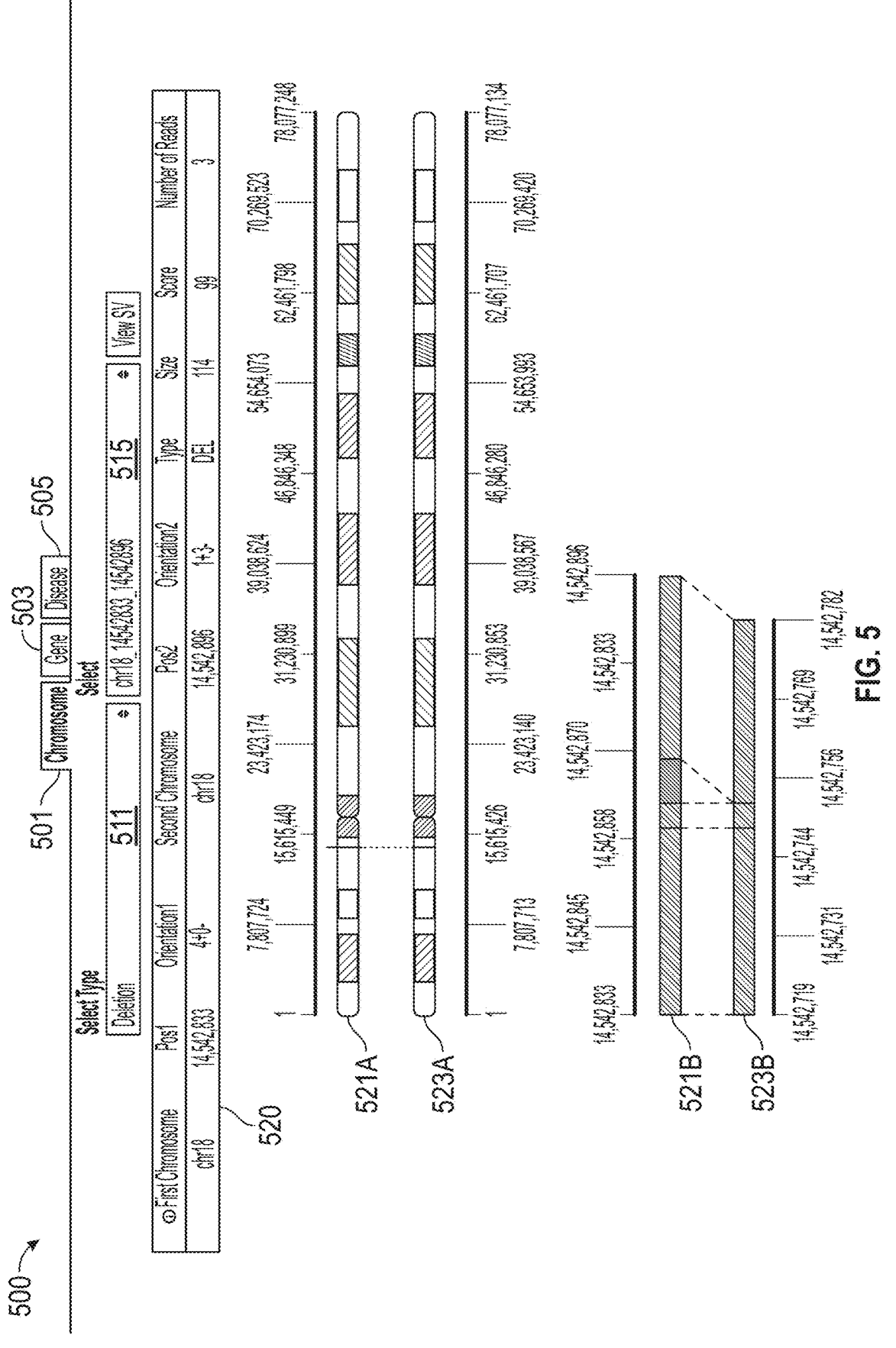
FIG. 5 illustrates structural variants and associated genes in a chromosome, according to some embodiments.

FIG. 5 illustrates structural variants 500 and associated genes in a chromosome, according to some embodiments. The view may be toggled between chromosome 501, gene 503, and disease 505. Structural variations (SV) are characterized by type 511 such as deletions, insertions, duplications, or inversions of chromosomal segments or rearrangements of the chromosomal locations either to other chromosomes (interchromosomal rearrangement) or within a chromosome (intrachromosomal rearrangement). SV events 515 reported from the patient's genome can be visualized on the chromosomal structure with the corresponding genes that are partially and completely amplified or deleted.

SV events 515 are also reported based on SV containing genes and on the basis of diseases. Gene tab 503 lists the genes present in the genomic location where deletions, insertions, duplications, or inversions of chromosomal segments between the chromosomes (interchromosomal rearrangement) or within a chromosome (intrachromosomal rearrangement) are identified in a patient. Gene tab 503 provides information about genes affected due to structural alterations between or within the chromosomes. Disease tab 505 aids in providing the clinical phenotypes that are caused by structural alterations. For example, the Philadelphia chromosome is the first recurrent genetic alteration found to be associated with human cancer, chronic myeloid leukemia (CML). This occurs due to interchromosomal translocation involving the ABL gene on chromosome 9, a tyrosine kinase, and the BCR gene on chromosome 22.

A view of the chromosomes before deletion 521A and after deletion 523A illustrates the specific portions deleted in the nucleotide string (see positions in the chromosomes). An expanded view before deletion 521B and after deletion 523B clearly indicates the missing portion of the sequence. A detailed result table 520 indicates the position and orientation of the first and second chromosome involved in this specific deletion event, and the type and size of the deletion, a score value, and a number of reads.

Figure 6A:
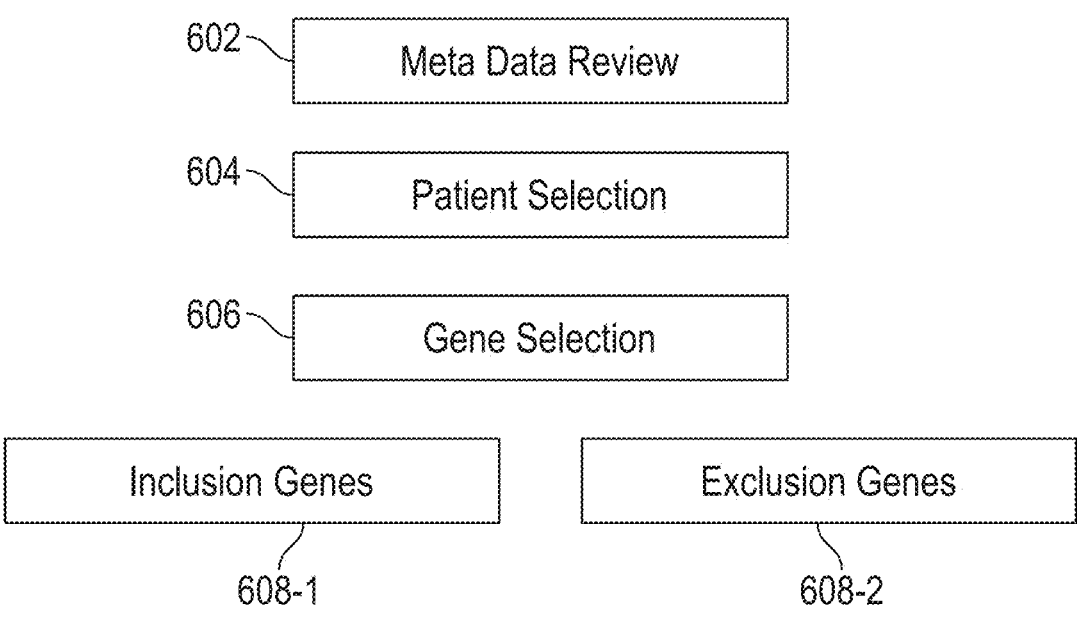
FIGS. 6A-6C illustrates block diagrams in a cohort and family genomics application of a genome sequence analysis engine, according to some embodiments.
Figure 6B:
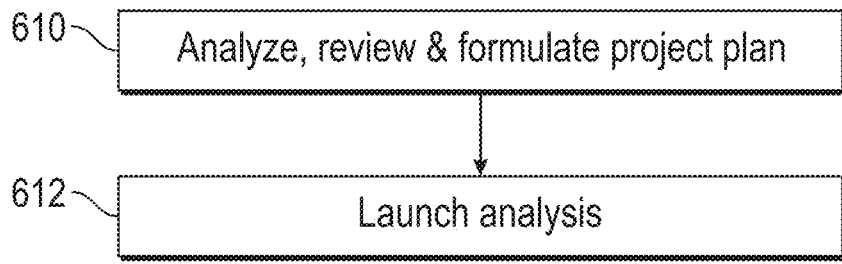
Figure 6C:
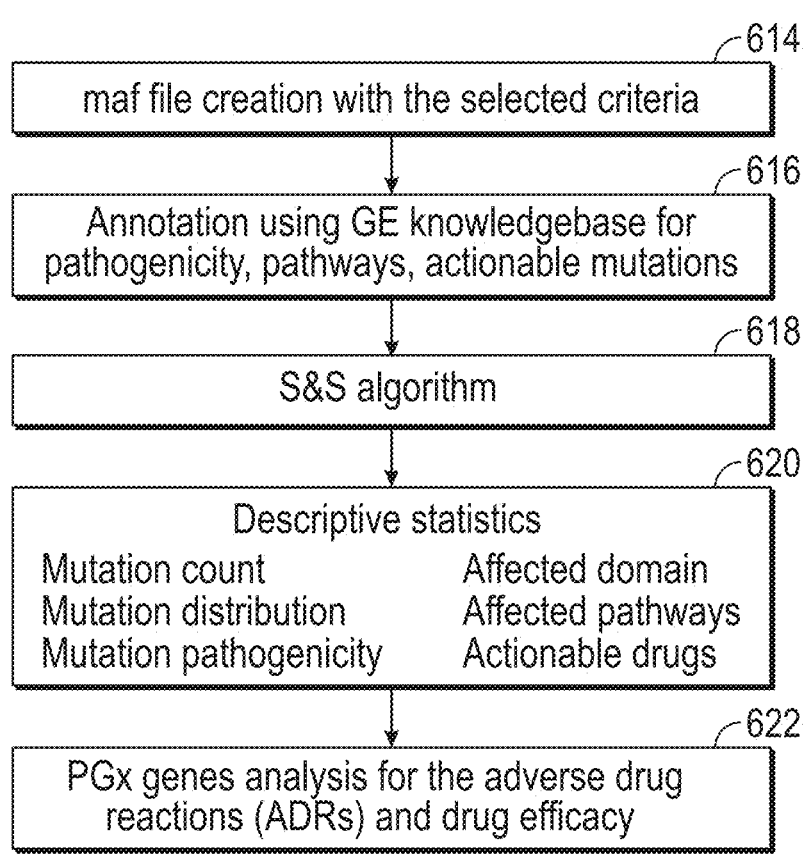

FIGS. 6A-C illustrate block diagrams for methods of processing 600A, analyzing 600B, and reporting 600C genomic data from multiple patients in a cohort and family genomics application of a genome sequence analysis engine, according to some embodiments. Genomic data from multiple patients in a cohort are extracted via the EHR interface, enabling the framework for formulating the project plan, processing the data by parsing into various implemented modules, and illustrating and visualizing the results in an interactive framework.

Family genomics as disclosed herein contains meta-information of family members where the next-generation sequencing (NGS) based genomic family analysis can be performed between father, mother, and child (trio), or siblings, grandparents, and other relatives such as aunts and uncles for multiple generations. The module facilitates testing for the inheritance pattern of deleterious mutations that are causal for the disease and carried across the family members. It comprises various sections enabling the user to select the individuals from a family and panel of genes satisfying the study parameters.

A patient group creation section provides the meta-information of all the individuals from a family in a tabular format facilitating the user to select the patients based on the study design. The user is given the option to create multiple groups within a family and multiple analyses can be performed within a family. A gene group creation section allows the user to select the genes or create a gene panel upon which the analysis to be performed to derive the Zygosity or mode of inheritance of the mutations on these disease-associated genes across the family members. A patient and group selection section manages the created patient groups and gene groups can be chosen as per the study design and analysis can be launched for the Family Genomics module.

FIG. 6A illustrates an electronic health record review method 600A that includes: a metadata review 602, a patient selection 604, and a gene selection 606. The genes may be separated into inclusion genes 608-1 and exclusion genes 608-2.

FIG. 6B illustrates an analysis launch method 600B that includes: analyzing, reviewing, and formulating a project plan 610, and launching the analysis 612.

FIG. 6C illustrates a processing method 600C that includes: creating a mutation annotation file (MAF) with selected criteria 614. The MAF is a tab-delimited file format which contains the mutation information from the VCF (Variant Call Format) files.

Step 616 includes annotating actionable mutations using the gene explorer engine knowledge base. Step 616 includes annotating information such as mutation pathogenicity, gene pathway, gene mutation actionable drugs, protein domains, and splicing (site) annotations are added to the MAF file. Step 616 also includes annotating pathogenicity criteria based on the consequences, implications, and in silico pathogenicity scores for the identified SNPs and Indels. Step 616 includes calculating a pathogenicity status for each variant identified in the individuals of the cohort study as per the ACMG guidelines. In some embodiments, step 616 includes selecting at least one of the following pathogenicity criteria: Pathogenic; Likely Pathogenic; Drug Response; Variants of Uncertain Significance (VUS); Benign; Likely Benign. Step 616 may also include identifying pathways, actionable drugs, and domains. Accordingly, in some embodiments, step 616 includes collecting information on the affected domains, pathway, and actionable drugs and facilitates a deeper understanding of the functions of the mutations identified in the cohort. Step 616 may include adding this information into the MAF file with the help of the genome analysis engine curated knowledgebase. The genome analysis engine knowledgebase is an aggregated data collected from several publicly available databases to provide comprehensive genomic information and is inbuilt in the present platform.

In some embodiments, step 616 includes processing the clinical trial cohort and annotating relevant information like pathogenicity, pathway, actionable drug, domain indications, and regulatory and splice information. In some embodiments, step 616 may also include the following steps:

Analyzing drug-metabolizing genes as per the recommendations and rules outlined by Clinical Pharmacogenetics Implementation Consortium (CPIC) guidelines for 11 genes. Furthermore, different gene sets such as the eMERGE genes or any other gene sets that are determined to have drug response/metabolizing associations, or the set of many genes in the genome are also analyzed for frequently mutated genes exhibiting associations with drug response phenotypes, such as high, medium, or low drug efficacy or adverse drug reactions (ADRs), and different grades and intermediates between the high and low phenotypes.

Outlining, based on the haplotype, diplotype significance of the mutations, drug metabolizer status (normal, intermediate, and poor metabolizers) classification rules. Scanning each of the individual genomic signatures against these criteria and the drugs indicated to be "use as directed," "use with caution," and "drugs to avoid" are assigned.

Associating genes to drugs: For many of the mutated drug-metabolizing genes reported, the corresponding drug categories, sub-categories, and drug members (monotherapy and combination therapy) are reported in a tabular format. They are presented in different sections as per the drug-metabolizing status of normal (low risk), intermediate (medium risk), and poor metabolizers (high risk) through a risk selection drop-down. Based on the chosen risk criteria, the user can study a few specific genes with the metabolizing impact as per convenience. Analyzing the data based on the genes and mutations associated with high, medium, and low drug efficacy and adverse drug reactions, and the combinations such as high efficacy/low ADR, low efficacy/high ADR, and other permutations and combinations of drug responses. Table VIII illustrates a framework providing the status of drug-metabolizing genes and their impact on different categories of drugs.

TABLE VIII

| Gene Drug Association |
|---|
| This section provides the reported drug-metabolizing genes and their impact on drugs along with the drug-categories. |
| Select Risk |
| Low Risk |
| Show 10 entries |

| Gene symbol Search | Drug Search | Category Search | Sub-Category Search |
|---|---|---|---|
| CYP2C19 | Drospirenone + Ethinyl Estradiol | Hormonal Contraceptives | |
| CYP2C19 | Iguratimod | Rheumatology | — |
| CYP2C19 | Leflunomide | Rheumatology | — |
| CYP2C19 | Donepezil | Psychiatry | Acetylcholinesterase (AchE) inhibitor |
| CYP2C19 | Carisoprodol | Pain Management | Analgesic, Anesthesiology |

In some embodiments, step 616 includes annotating splice mutations. In some embodiments, the pathogenicity for the splice mutations is calculated by employing the S&S algorithm. The bases ranging for the real and cryptic splice sites (acceptors and donors) are scored using the Shapiro-Senapathy algorithm. The sites scoring more (or less) than user-specified or inbuilt score threshold (cut-off) within exons and introns are determined as potential cryptic splice sites. The chromosomal positions of the identified splicing mutations are scanned against the original cryptic and real splice sites positions built into the present disclosure or user-specified, and if matched, the scores are calculated for the mutated splice sites. The original scores and observed scores are analyzed for assigning the pathogenicity depending on how they vary from the original sites.

Step 618 includes applying a sequence analysis algorithm (e.g., the S&S algorithm, and the like).

Step 620 includes preparing and providing descriptive statistics. The descriptive statistics may include a mutation count, a mutation distribution, a mutation pathogenicity, affected domains and pathways, and actionable drugs for selected diseases. In some embodiments, step 620 includes measuring various features of genes, mutations, domains, genetic elements, pathways, patients, and other factors to estimate the probability of the factors associated with disease and the clinical genotypes and phenotypes distributed among the individuals in the cohort. Additionally, in some embodiments, step 620 includes evaluating the number of patients reported with the respective mutations and genes with mutations. This factor provides an understanding of how the mutations or genes with mutations are distributed among the individuals with similar disease phenotypes. These types of mutations might act as a driving factor for the study of phenotypes or associated traits of the population. In some embodiments, step 620 includes evaluating unique protein domains which are commonly affected across the patient group or cohort. This provides an understanding of the functional part of the protein in the associated study phenotype. The domain can be a targetable region which can be studied in drug discovery. In some embodiments, step 620 includes evaluating the number of unique actionable drugs from the mutations observed in individuals. This leads to an understanding of potentially actionable variants in the group of individuals exhibiting similar phenotypes. As the root of precision medicine, this can initiate the experimentation of the effectiveness of a drug that is approved for a particular phenotype caused by a genotype (variant) for its effectiveness on a different phenotype caused by the same genetic variant or by different mutations causing a defect in the same gene or underlying biochemical function. In some embodiments, step 620 includes evaluating unique pathways affected by the commonly mutated genes. This aids in understanding the multiple commonly affected pathways that associate with the disease, determining the molecular mechanisms of the disease phenotype in the group of individuals with the underlying disease, and targeting drug development. This platform systematically identifies the pathway(s) affected by the specific gene mutations that may be involved in the cause of the disease. In some embodiments, step 620 includes evaluating the number of unique mutations in the regulatory regions: promoters, 5' and 3' UTR, splice sites, branch sites, cryptic splice sites, cryptic branch sites, cryptic exons, enhancers (ESEs, ISEs) and silencers (ESSs, ISSs), and poly-A sites, in the genes across the patient group. The mutations in these sites are implicated in a large fraction of human diseases, and diseases in other animals, plants, and microbial organisms. Understanding the importance of the regulatory regions and the impact of mutations in them will enable the identification of the molecular causes of disease in the cohort. This will enable the development of targeted diagnosis and treatment.

In some embodiments, step 620 includes measuring various features to estimate the uncertainties of the factors associated with disease and the clinical phenotypes distributed among the individuals in the cohort. The analysis supports to evaluate the following statistics: a number of patients reported with the respective mutations; a number of unique protein domains which are commonly affected; a number of unique actionable drugs for the mutations observed in individuals; a number of unique pathways affected by the commonly mutated genes; a number of unique mutations in regulatory regions (promoters, splice sites, branch sites, cryptic splice, branch points, enhancer/silencer sites, and Poly-A sites); a number of unique mutations in the pharmacogenes is computed to indicate the number of mutations affecting the DMG for unique patient identifiers. Many of these statistics are determined for a group of genes or many genes from the genome.

In some embodiments, step 620 includes preparing a pharmacogenomic summary statistics report including an exhaustive statistical reporting of the pharmacogenomics genes analyzed. The genes mutated with the metabolizing status, the risk status, and the number of patients presented with the mutation, and other details concerning the mutations, patients, and type of genetic elements, are reported in a tabular format. Table IX illustrates a framework providing the statistics of the drug-metabolizing status of the genes based on the mutations in patient cohorts.

TABLE IX

| Pharmacogenomic Summary Statistics |
|---|
| The module provides statistics of the drug metabolizer status for genes associated with different drug categories in the patient cohorts. |
| Show 10 ▾ entries |

| Gene symbol Search | Metabolizer Status Search | Priority Search | Number of Patients Search |
|---|---|---|---|
| CYP2C19 | Intermediate Metabolizer | Low Risk | 1 |

Step 622 includes analysis of pharmacogenomics genes for adverse drug reactions (ADRs) and drug efficacy.

Figure 7:
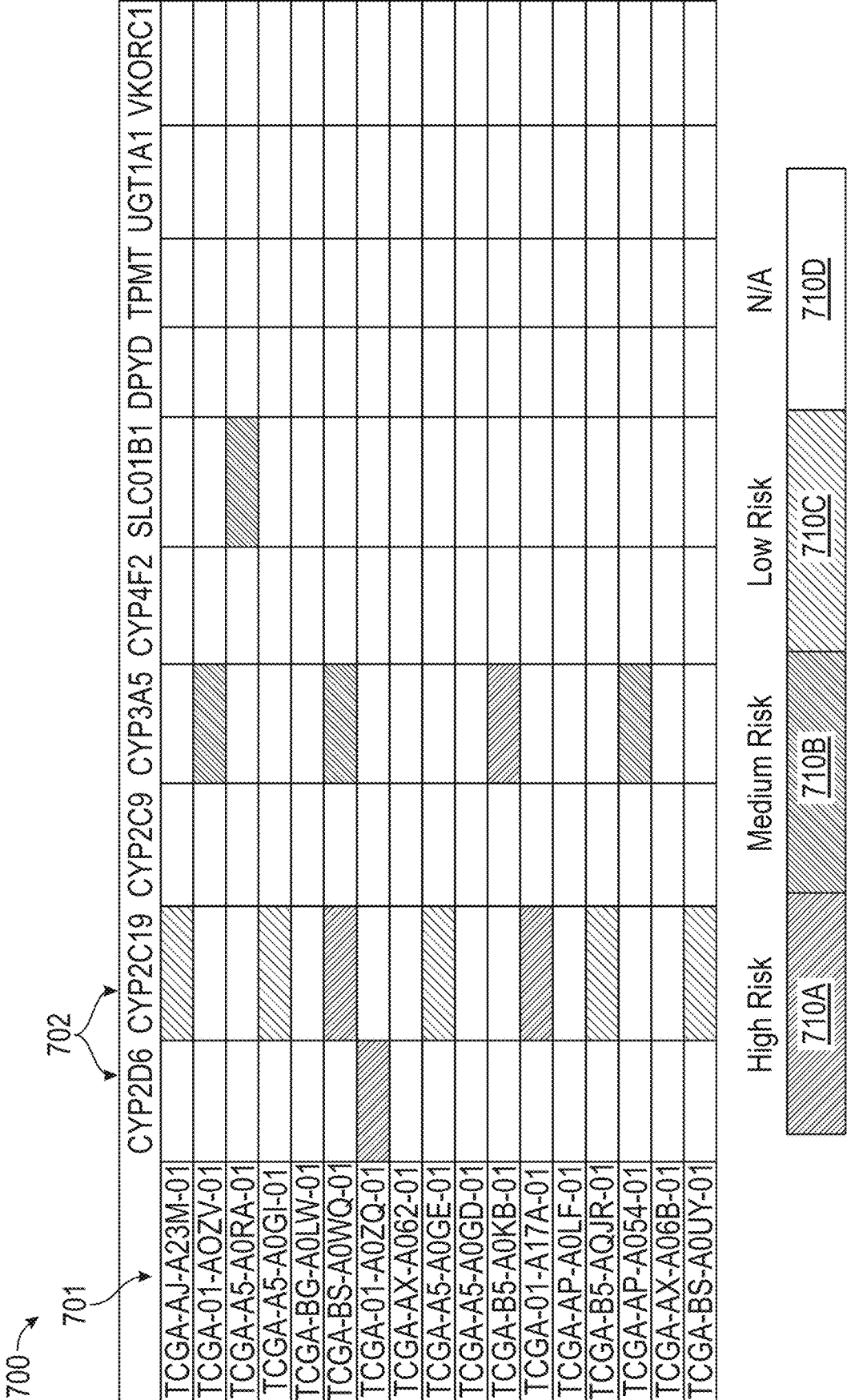
FIG. 7 illustrates a patient risk assessment chart based on a genome analysis, according to some embodiments.

FIG. 7 illustrates a patient risk assessment chart 700 based on a genome analysis, according to some embodiments. Column 701 lists different patients, and columns 702 indicate a selected drug-metabolizing gene (DMG). For many of the patients represented vertically, a respective gene map is reported horizontally, and those patients which carry mutations in any of the DMG are indicated for their risk assessment as per a color-coded key to enable a panoramic view of the pharmacogene status: 710A for high risk (Red), 710B for medium risk (green), 710C for low risk (Yellow), and no risk assessed 710D may also be included. In some embodiments, genes and mutations in the different groups of patients who have been assessed to exhibit low 710C, medium 710B, or high 710A ADRs (side effects) are determined to be the causative of these drug response phenotypes. Details of these mutations and the coding elements, regulatory elements, and ncRNA genes in which they occur and associate with the different patient groups are provided for analysis in tabular, graphical, and sequence views, and the tools for these analyses.

In some embodiments, risk assessment chart 700 may be provided a clinical trial module (e.g., clinical trials module 260-7). Risk assessment chart 700 accounts for the mutations present in the patient group concerning the metabolizing status of affected genes. The genes that are responsible for metabolizing the drugs are analyzed in the patient group. Depending on the impact of mutations, the risk of a patient for the respective drugs is classified as "High," "Medium," or "Low." The drugs are further categorized as "Use as Directed by Physician," "Drugs to avoid," and "Use with caution" based on the patient's risk towards the drugs. The data from a clinical trial cohort, and from multiple similar trials for a drug, are accumulated and appended to a database of drug response genes and details, which can be used in treating individual patients.

Figure 8:
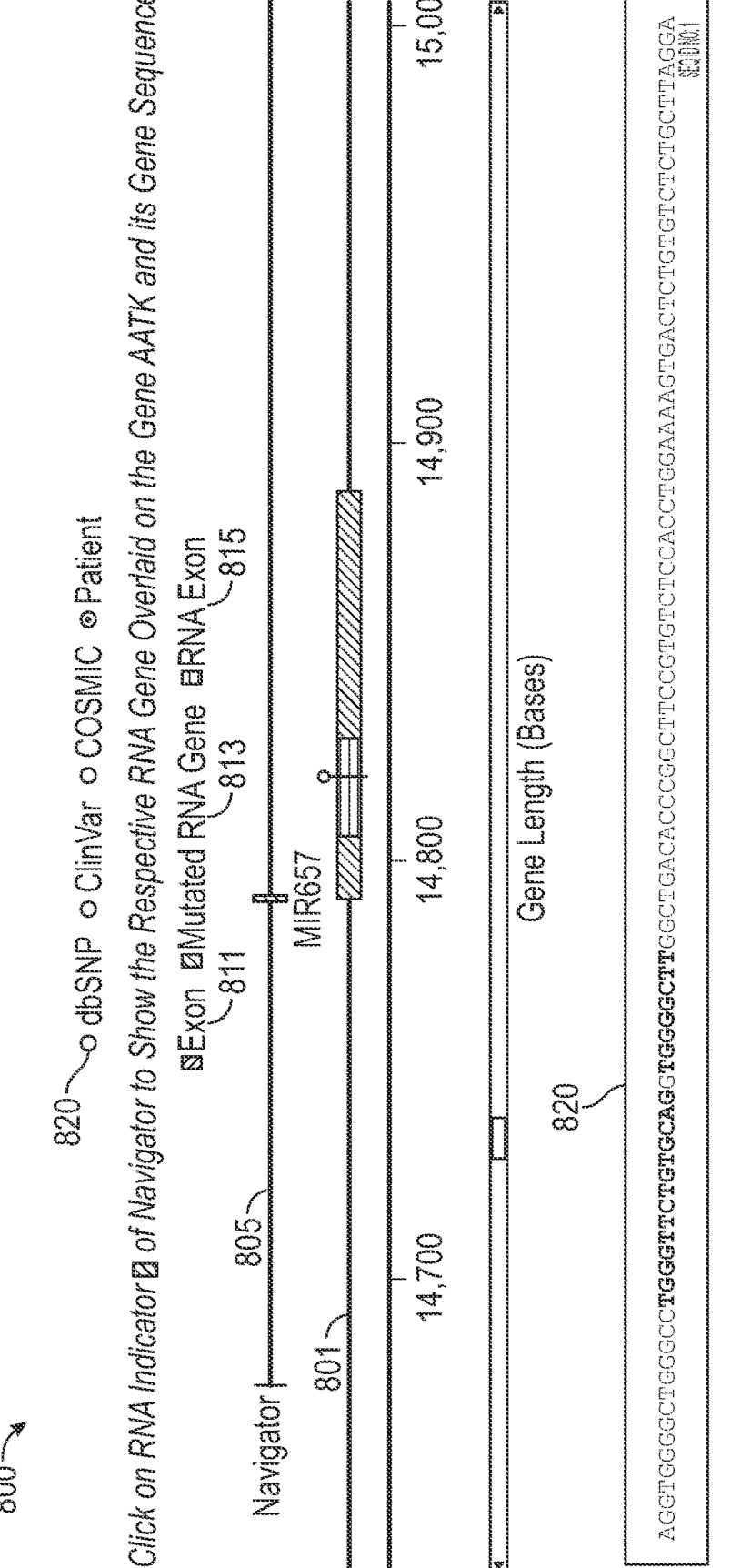
FIG. 8 illustrates a map of non-coding RNA provided by a genome sequence analysis engine, according to some embodiments.

FIG. 8 illustrates a map 800 of an mRNA gene sequence containing an exon, and a mutation overlaid on it, provided by a genome sequence analysis engine, according to some embodiments. A selector 820 enables the user to select a database source. A navigator 805 over an RNA gene 801 enables the user to view the different components such as an Exon 811, a mutated RNA gene 813, and an RNA exon 815. Map 800 also includes a sequence view 821 of RNA gene 801.

An mRNA gene sequencing module processes the paired-end sequencing data of the case sample and aligns it to the human reference genome (hg19/GRCh37) and transcriptome. The resulting BAM file is remapped from transcriptome locations to genomic locations and the quality scores are recalibrated for the paired BAM file. This allows the reads to align with the known transcript sequences, including exon junctions and unannotated mRNAs. This dual mapping strategy retrieves only the best alignment reads, including those reads mapping to multiple locations (both transcriptomic and genomic) and collapsing into single genomic coordinates. The fusion genes are identified based on discordant read pairs (reads mapping to different protein-coding genes) and junction spanning reads (reads mapping to the exon-exon junctions) from RNA sequence data, and filter out the fusion candidates observed in normal controls lookup, and the fusion candidates with highly similar patterns in sequence (BlastN e-value≤0.001). The remaining fusion events are annotated using an in-house developed ensemble-based SQLite database to provide the frame, affected domains, and the estimated oncogenic potential of newly discovered gene fusions. This module uses several hallmark features and utilizes a bayesian classifier to provide the probability of a given gene fusion being a driver mutation. The identified fusion events are parsed against the manually curated disease fusion repository and visualized along with the transcript and coverage details. The mRNA gene sequencing may also be combined with gene fusion, as disclosed herein.

In some embodiments, a genome analysis engine as disclosed herein (e.g., genome analysis engine 255) may include RNA sequencing to quantify the expression levels of alternatively spliced genes and the identification of differentially regulated isoforms or exons across samples. The RNA isoform expression quantification uses Bayesian inference to compute the probability of reads originated from a particular isoform and enables a more extensive and accurate analysis of alternative splicing, at either the exon or isoform level. The isoforms are commonly referred to as different forms of a gene that perform similar or different functions. They often play a distinct role in cancer-related hemostatic and non-hemostatic pathophysiologic processes, such as thrombosis, angiogenesis, tumor growth, and metastasis, and act as cancer biomarkers in predicting drug response. The reads from either the single or paired-end RNA sequencing data are aligned to the human reference genome (hg19) and pre-computed human alternative splice junctions. The insert length distribution and standard deviation are calculated for the paired-end sequencing data. The aligned reads are then mapped to isoforms and represented as binary matrices corresponding to the compatible isoforms. By computing the probability distribution (psi) from the matrix over the given reads, the exon/isoform expression levels (psi) are calculated along with the confidence intervals using Bayes rule. Bayes rule states that this distribution is proportional to the product of our expectation about the value (delta psi) and the likelihood of observing the reads given psi. Thus, the significance and magnitude of changes (isoforms) are computed using Bayes rule. The set of events that meet the Bayes rule may be displayed graphically as differentially expressed exons/isoforms.

Using mRNA sequencing, a genome analysis engine as disclosed herein may perform exon-centric analysis: Accordingly, the genome analysis engine estimates expression levels of exons, and determines the alternative splicing at the level of individual splicing events, e.g., the inclusion levels of a particular cryptic exon, or the use of a particular alternative splice site. The genome analysis engine may also perform isoform-centric analysis. Accordingly, the genome analysis engine may estimate an expression level of whole transcripts, and estimates the expression level of each individual isoform of a gene.

The genome analysis engine may summarize the differentially expressed isoforms and exons identified in the sample with the following features: chromosomal coordinates of mRNA isoforms, and the number of reads mapping to isoforms along with the confidence interval. The Sashimi plot highlights the differentially expressed isoforms of alternative splicing sites at 3' and 5' end, exons, and retained introns. With the spliced alignments of reads from a sample, a region of interest is visualized in a Sashimi plot as (i) Representing the read densities (normalized by genomic region coverage and length) from the alignment of exons. (ii) The splice junction reads are drawn as arcs connecting a pair of exons, where arc width is drawn proportional to the number of reads aligning to the junction (or to the log of this number). The aberrant isoforms in a patient or a cohort are reported based on mutations in many of the genes in the genome of a patient in many of the genetic elements including the regions of promoters, donor splice sites, acceptor splice sites, branch point sites, exon, and intron splicing enhancers (ESEs & ISEs) or silencers (ESSs & ISSs), poly-A sites and regions, and the cryptic sites of many regulatory elements, individually and in various combinations. Accordingly, a genome sequence analysis module as disclosed herein determines the isoforms and the mutational sources of these isoforms across the genes and the genome, and to illustrate these events in detailed graphical representations, tabular descriptions, and sequence illustrations that are useful to the practicing clinicians, and clinical and pharmaceutical researchers.

Figure 9A:
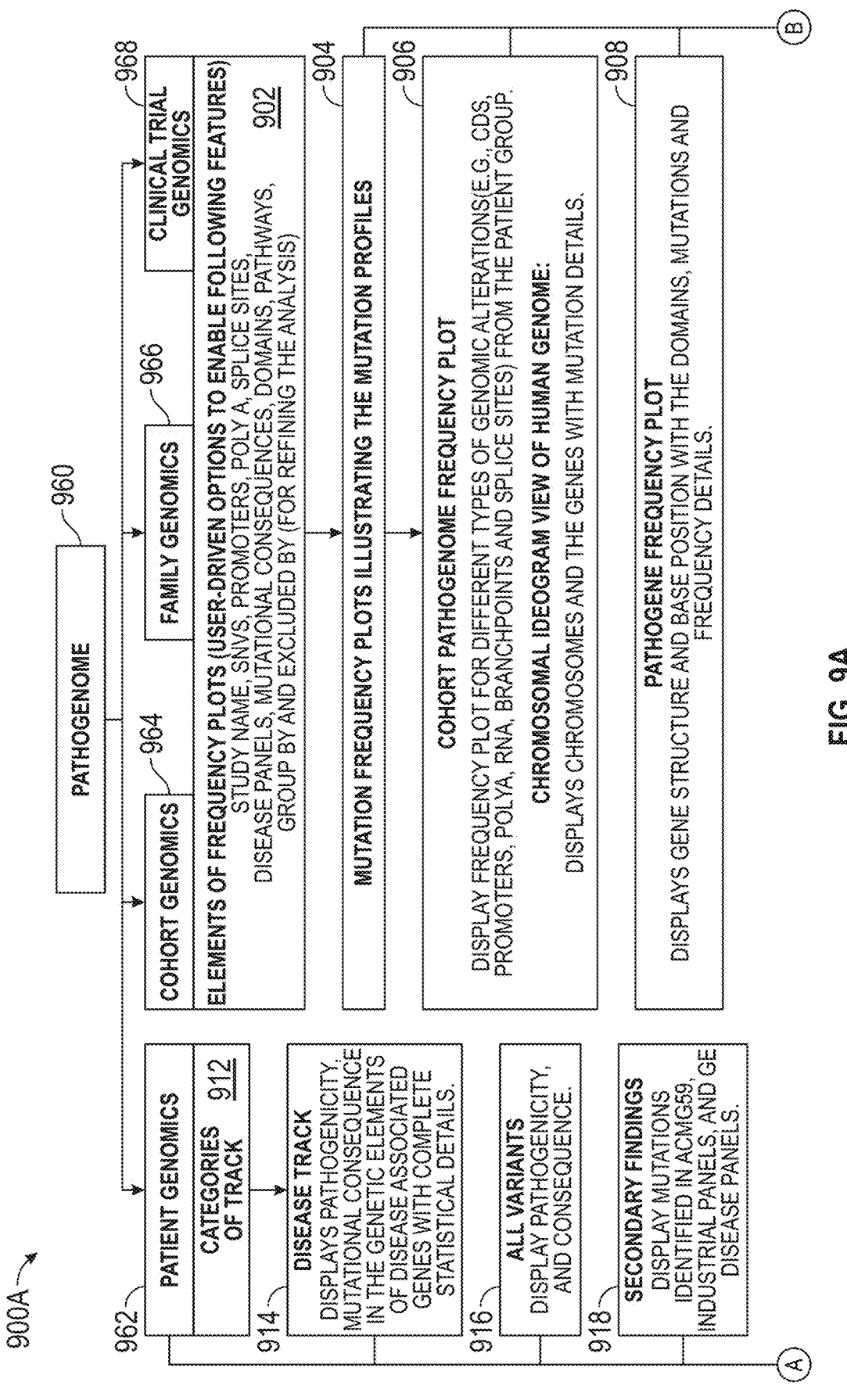
Figure 9B:
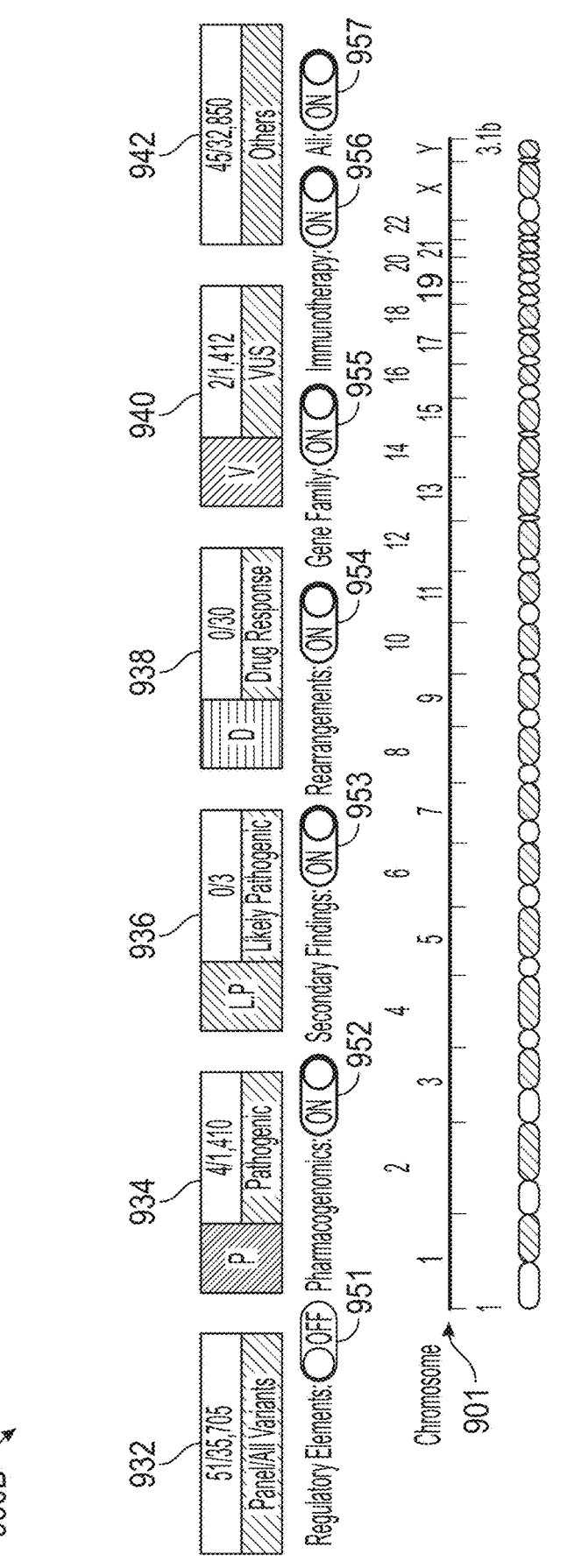
Figure 9C:
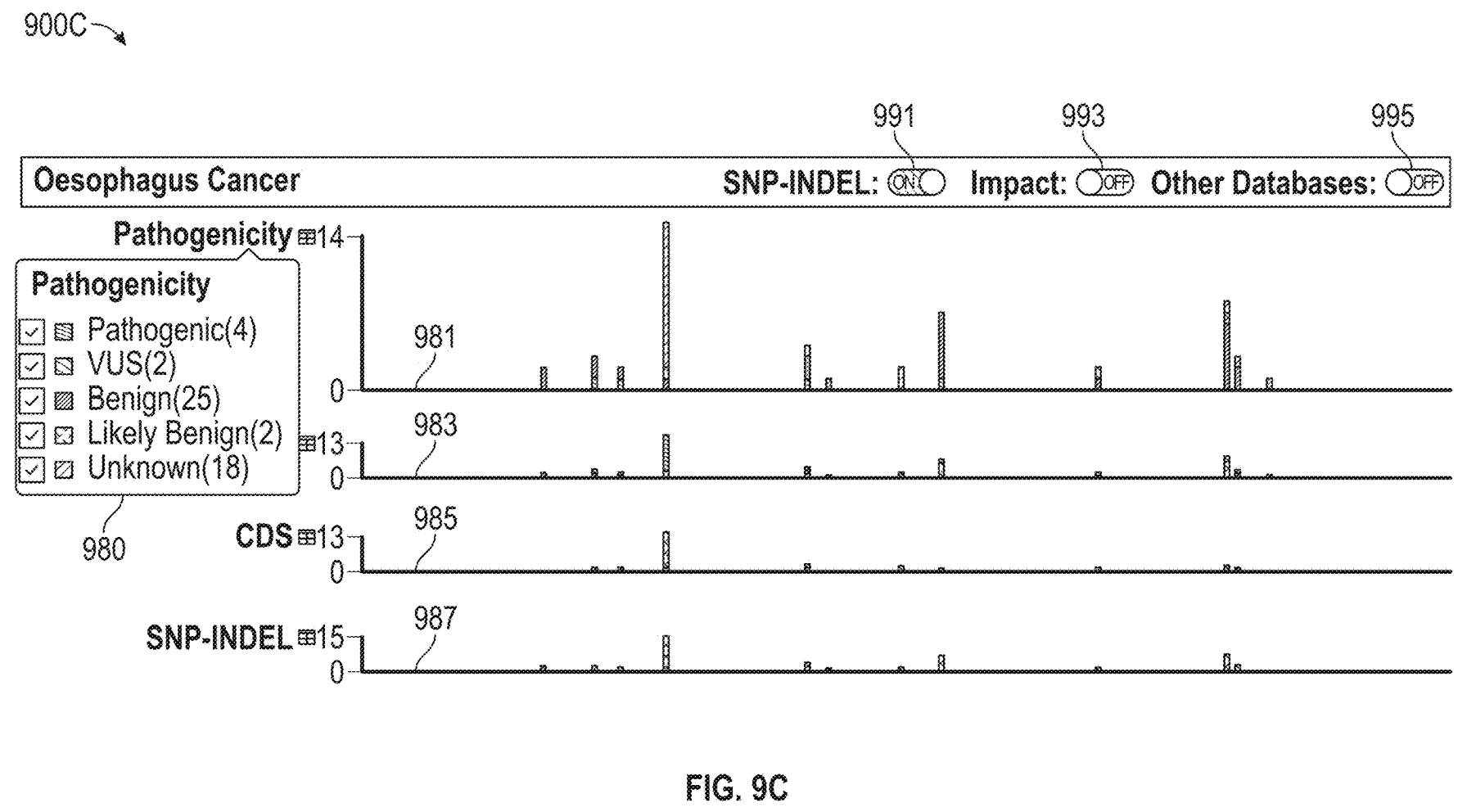

FIGS. 9A-C illustrate workflow chart 900A and displays 900B and 900C, respectively, of a pathogenome module (e.g., pathogenome module 260-10) in a genome sequence analysis engine, according to some embodiments. Workflow chart 900A is for a pathogenome 960 procedure that includes patient genomics 962, cohort genomics 964, family genomics 966, and clinical trial genomics 968.

FIG. 9A illustrates workflow chart 900A, wherein patient genomics 962 includes tracking categories 912, such as: disease track 914, which displays pathogenicity, mutational consequence in the genetic elements of disease associated genes with complete statistical details. All variants track 916 displays pathogenicity and consequence for gene variants. Secondary findings track 918 displays mutations identified in ACMG59, industrial panels, and GE disease panels.

Pharmacogenomics track 920 displays drug-metabolizing genes, as per CPIC guidelines and 82 pharmacogenes from eMERGE database. Rearrangements track 922 displays copy number variants, structural variants, and gene fusion events. Gene family track 924 displays mutations from gene families Immunotherapy track 926 displays the status of immunotherapy biomarkers (e.g., TMB and MSI). In some embodiments, patient genomics 962 is further divided into different modules including EHR, Launch, Report, PGx, TMB/MSI, Rearrangement, Pathogene, and Pathogenome, each of which are subdivided into additional modules. The workflow and descriptions of each platform and module are described below.

Cohort genomics 964, family genomics 966, and clinical trial genomics 968 may include the following steps:

Step 902 includes determining elements of frequency plots, e.g., by receiving user options to enable features: study name, SNVs, promoters, Poly-A sites, splice sites, disease panels, mutational consequences, domains, pathways, and group excluded by (for refining the analysis).

Step 904 performs mutation frequency plots illustrating the mutation profiles.

Step 906 includes preparing a cohort pathogenome frequency plot. In some embodiments, step 906 includes displaying frequency plots for different types of genomic alterations (e.g., CDS, promoters, Poly-A, RNAs, branch points, and splice sites) from the patient group.

Step 908 includes preparing a pathogene frequency plot and displaying gene structure and base position with the domains, mutations, and frequency details.

Step 910 includes providing an individual patient pathogenome that displays mutations from ACMG, PGx, eMERGE, and MMR genes in the genomic scale, enabling the clinician and researcher to customize the tracks and helps to carry out various patient-centric analysis.

Step 912 includes preparing a family pathogenome that displays the mutations across the family members with zygosity, inheritance patterns, and other mutation details. In some embodiments, step 912 includes displaying the differences in mutation between father, mother, affected child, and additional family members including the siblings of the child, father, and mother as well as grandparents and great grandparents of the child.

FIG. 9B illustrates display 900B including statistics of variants identified in the individual under each pathogenicity criteria: all variants 932, pathogenic 934, likely pathogenic 936, drug response 938, VUS 940, and others 942. Display 900B provides a pathogenicity plot to visualize the pathogenicity of the mutations for the selected patient. The gene name, pathogenicity, and the number of mutations are displayed on the mouse over of the bar plot.

Display 900B illustrates the entire nucleotide string 901, including all the chromosomes (per user selection). Options to turn ON/OFF the visualization for each following category include several features, as follows. Regulatory Elements 951, which represent the mutations in real and cryptic splice sites, real and cryptic branch sites, enhancers and silencers, promoter regions, UTRs, and poly-A regions. SNPs/Indels in these regions are known to be implicated in drug response and/or disease. Also, these mutations have the potential to alter the level of gene expression. Pharmacogenomics 952, which represent the mutations in 11 PGx genes and 82 eMerge pharmacogenes identified in the individual. Secondary Findings 953, which displays the mutations reported in the ACMG59 gene panel and GE disease panels that are outside of the disease of the patient. Rearrangements 954, which represent the copy numbers (amplification and deletion), structural chromosomal aberrations (inversions, translocations, insertions, and deletions), and intergenic fusions identified in the individual. Gene family 955, a schematic representation of many of the variants in a patient's genome in one view, overlaid against each of the 23 chromosomes juxtaposed consecutively. The location of many of the ~20,000 human genes and interspersed elements are represented to scale on the line representing the length of the human genome, and against the chromosomes consecutively represented to scale. Different categories of genetic and genomic features are depicted as tracks to represent the genome-wide distribution of these elements. This view thus includes the visualization of the patient's variants in many of the genes in the human genome, and the diseases and other conditions that may be associated with these genes, elements, variants, and mutations. Immunotherapy 956, which represents the status of immunotherapy markers of the individual and status of MMR genes shown as a track with pathogenicity of mutations reported in the individual. In the All category 957, all chromosomes are included in display 900B.

FIG. 9C includes display 900C with a pathogenome illustration showing the pathogenicity of genes in a patient's genome. In some embodiments, display 900C may enable the user to visualize and analyze multiple tracks for different modules implemented in the present disclosure. It facilitates the understanding of the key features and distribution of the patient's variants and mutations from particular genes in a genome. Each of the tracks is in the form of a bar-plot representing the different kinds of variants within a gene. Each track is named and shown with the legends on the mouse over. On clicking the legends, a statistical and colorful visualization appears in a separate pop-up showing complete details of the specific tracks like the gene distribution and pathogenicity distribution with the table containing the details of the reported genes in the track. Based on the pathogenicity categories of the mutation present, the bars in each track are color-coded. The following are the tracks which can be visualized in this section.

In some embodiments, a disease track displays the pathogenicity, mutational consequence, and mutations identified in the CDS. The pathogenicity track plots many of the categories of the disease-associated genes with complete statistical details. The consequence and CDS track bar plots representing the mutations are colored based on the following consequences: Start retained Variant; Start lost; Synonymous (silent) Variant; Missense Variant; Inframe Insertion; Inframe Deletion; Stop gained; Frameshift Variant; Coding Sequence Variant; Stop lost; Stop retained Variant; Incomplete terminal codon Variant; Protein altering Variant.

Display 900C may support many variants, and display the pathogenicity 980, and consequence of many genes reported in the patient. Pathogenicity track plots 981, 983, 985, and 987 illustrate many of the categories of the disease-associated genes with complete statistical details. The type of mutations observed in various regions of the whole genome can be tracked from here. The SNP-indel 991, impact 993, and other database toggle options 995 are shown, to view the mutations falling under any of these categories.

The genes and mutations reported in the patient are scanned against various panels like ACMG59, industrial panels, and GE disease panels and plot them on the genomic scale. This track indicates the mutations that are most likely to be associated with that individual's set of signs and symptoms and thus provides a medical benefit by preventing or better managing health conditions. It also depicts the genes that indicate the potential diseases that the patient may not currently exhibit, but may express in the future. The variants identified in these genes would indicate the "Secondary Findings" in the particular patient. The bar plot representing the mutations in these genes are color-coded to explain the consequences of variations and mutations in the genetic sequences from the patient.

Figure 10:
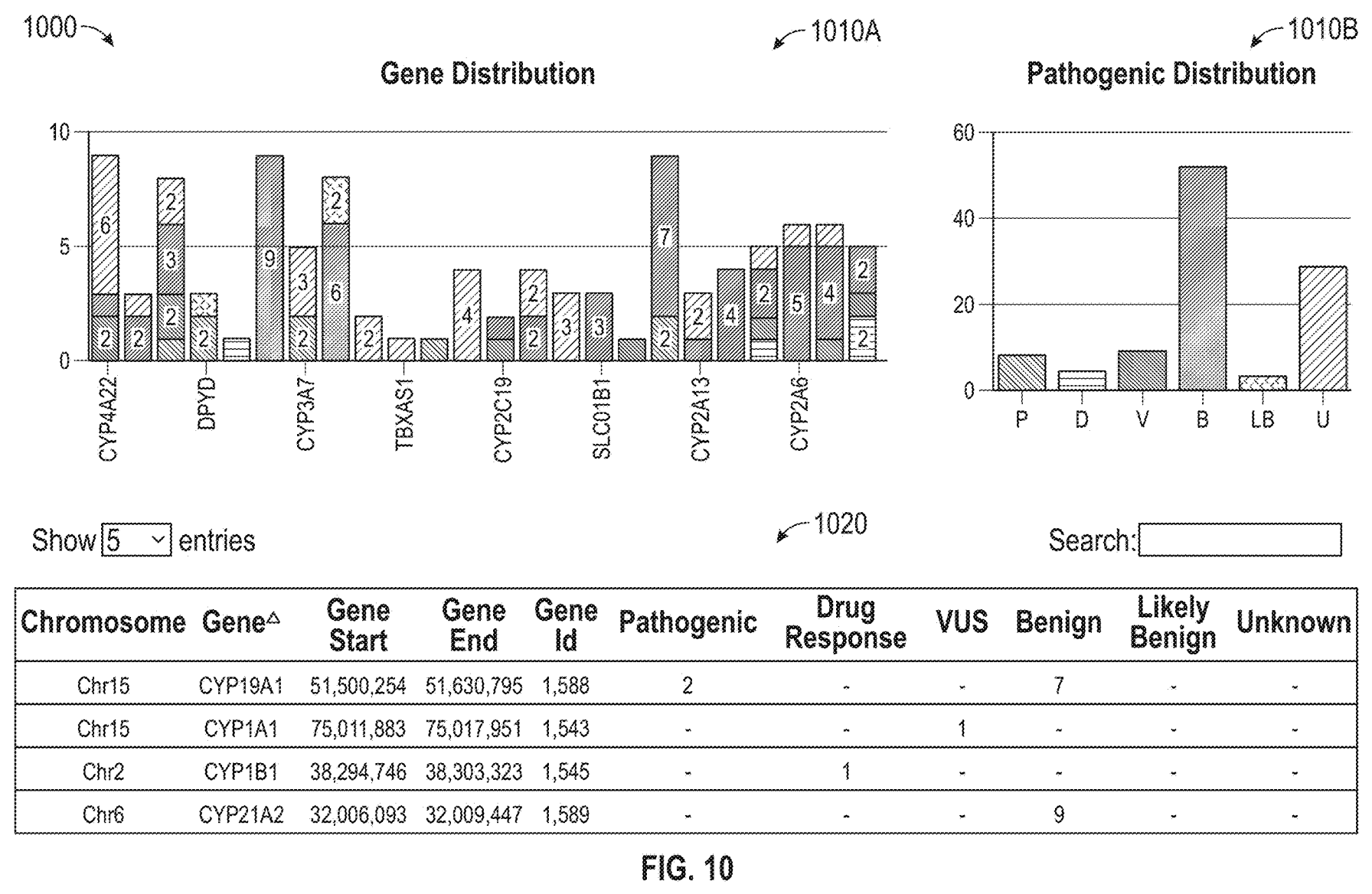

FIG. 10 illustrates a chart 1000 with mutation distributions for genes 1010A having pharmacologic impact, according to some embodiments. Chart 1000 is a statistical representation of mutations occurring in pharmacogenes based on pathogenicity 1010B. A pharmacogenomics table 1020 aids in visualizing the variants identified in 11 drug-metabolizing genes as per the recommendations of the Clinical Pharmacogenetics Implementation Consortium (CPIC) guidelines and the set of 82 pharmacogenes from the eMERGE-PGx project. This section also helps in educating the clinician and the researcher about the functional outcomes of the mutations and their impact on drug metabolism, which would indicate the patient's response to various drugs.

Figure 11:
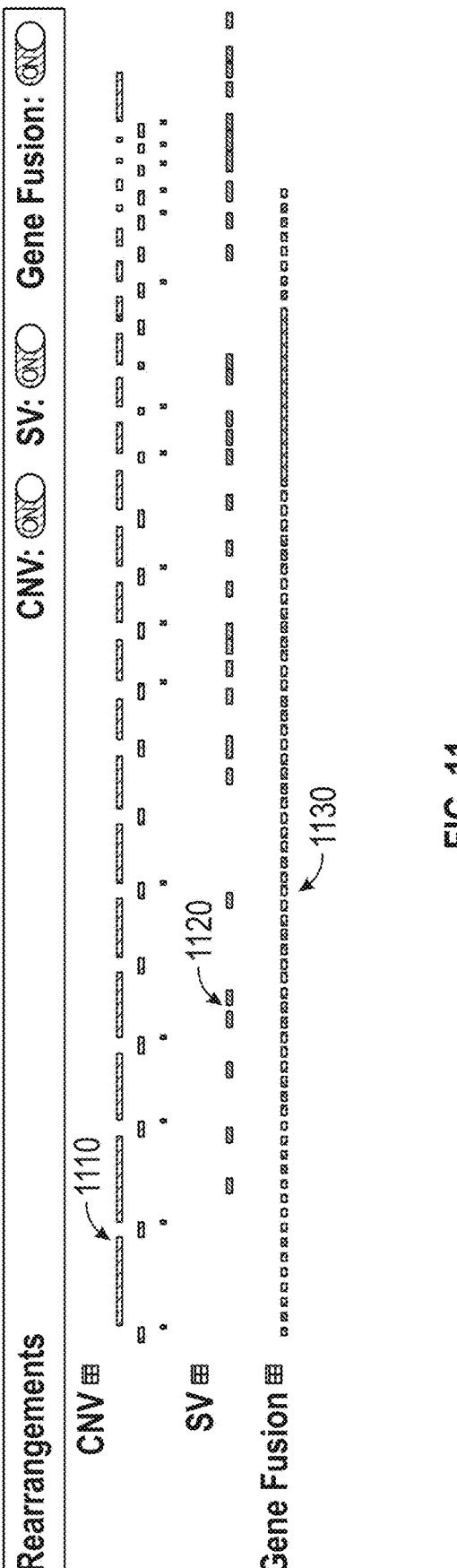
FIG. 11 illustrates tracks for copy number variants, structural variants, and gene fusions in a nucleotide sequence provided by a genome sequence analysis engine, according to some embodiments.

FIG. 11 illustrates tracks for rearrangements 1100 in the genomic structure such as copy number variants (CNV) 1110, structural variants (SV) 1120, and gene fusions (GF) 1130 provided by a genome sequence analysis engine, according to some embodiments. Rearrangements 1100 provide a visualization of the tracks for copy number variants, structural variants, and gene fusions identified in the patient's genome, depicted on a genomic scale. This track is displayed in the form of tiles instead of the default bar-plot, where on mouse over the type of event and position information can be studied. This section aids in visualizing the different types of intergenic fusions that occur in the individuals. The molecular details of gene fusions are differentiated and color-coded along with the original genes and orientation details. This section also aids in visualizing different types of structural variants reported in the individuals. The types of structural variants are differentiated and color-coded and provided with the chromosomal position details. This visualization can assist in understanding the genetic and genomic changes due to CNVs, which can be predictive of disease prognosis and therapeutics. Many of these events are illustrated in detail in tabular, graphical, and sequence views, with easy guides to each of the different events and molecular details.

Figure 12:
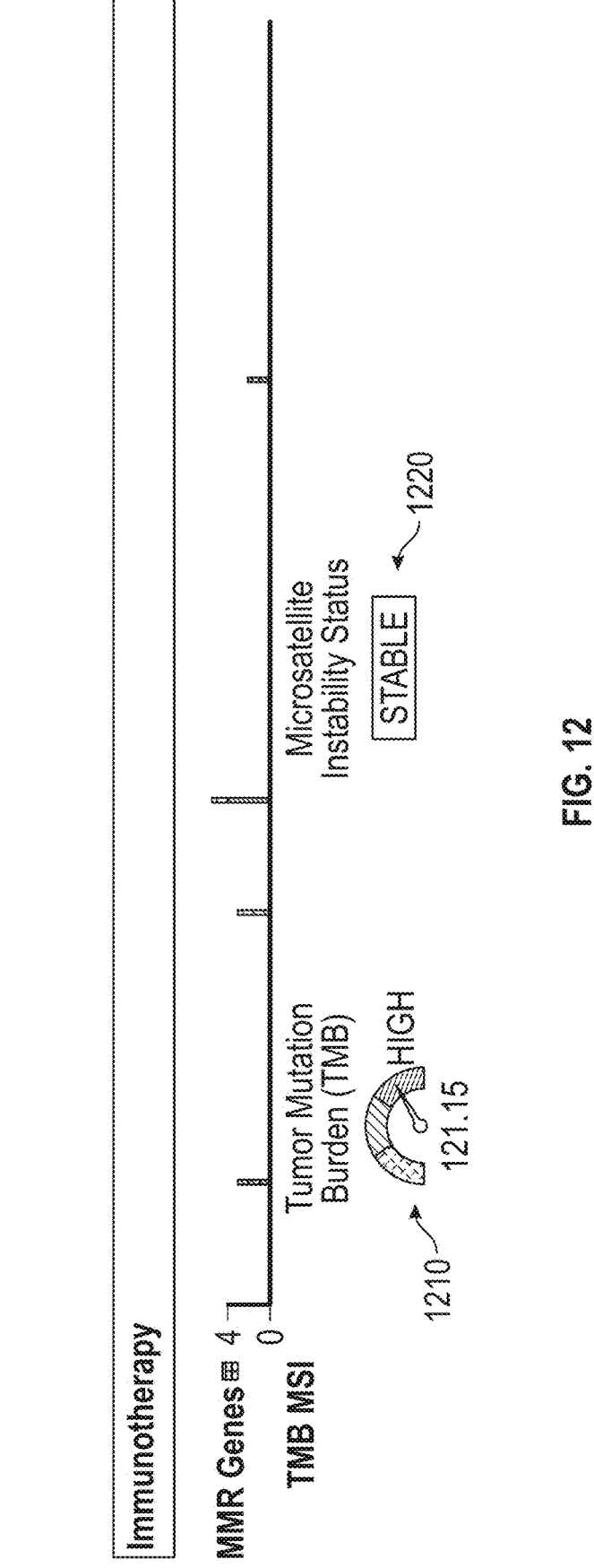
FIG. 12 illustrates an immunotherapy track including tumor mutation burden and microsatellite instability status, according to some embodiments.

FIG. 12 illustrates an immunotherapy track 1200 including a tumor mutation burden (TMB) indicator 1210 and a microsatellite instability status (MSI) indicator 1220, according to some embodiments Immunotherapy track 1200 aids in assessing the status of immunotherapy biomarkers (e.g., TMB indicator 1210 and MSI indicator 1220) in the individual Immunotherapy track 1200 provides insights into the context of cancer immunotherapy biomarkers in each individual's genetic makeup, their behavior, and interactions with the immune system. This analysis aids the clinicians to determine if the individual can benefit from immunotherapies. This track also aids in visualizing the mutations in the Mismatch Repair (MMR) genes depicted on the genomic scale. Mismatch repair is a process that facilitates the identification and repairing of erroneous changes in the genome. The genes involved in this biological process are said to have the utmost clinical significance, as a small change in this set of genes can lead to the accumulation of mutations in many genes and adverse disease conditions. This track helps in understanding the functions of the mutations identified in the MMR genes, and their adverse outcomes, within an immuno-therapy analysis. A status track of mismatch repair (MMR) genes including immune biomarkers, according to some embodiments may help track the status of MMR genes depicted on a genomic scale and provide the status of immune biomarkers (TMB and MSI).

FIGS. 13A-D illustrate a customizing framework 1300A configured to provide a cohort pathogenome frequency plot 1300B, a pathogene frequency plot 1300C, and an individual pathogenome 1300D (hereinafter, collectively referred to as "frequency plots 1300"), according to some embodiments.

Figure 13A:
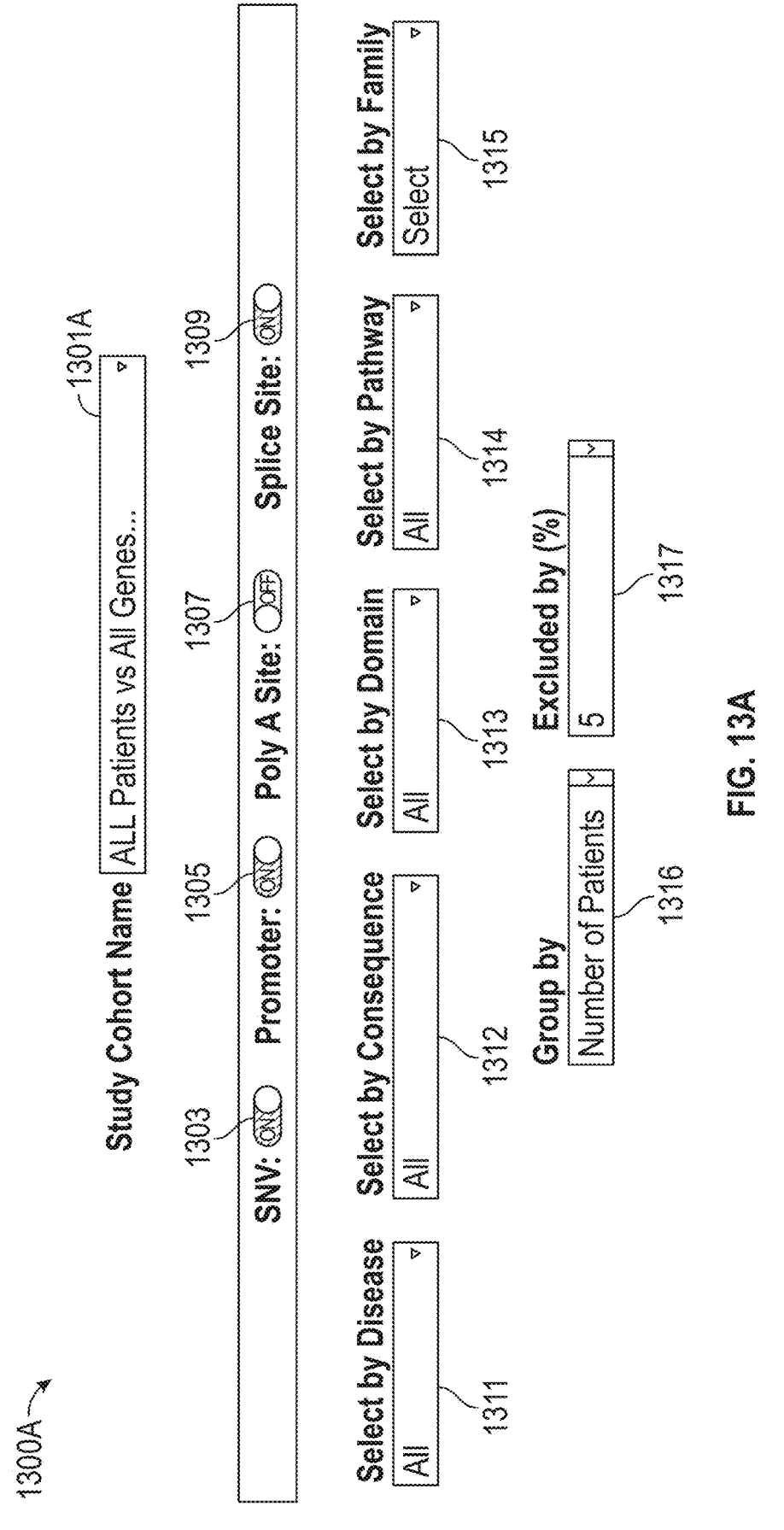

FIG. 13A includes framework 1300A, a study cohort name 1301A lists the patient datasets created for the analysis, for which genomic data visualization can be employed. Study cohort name 1301A selects lists of many of the patients involved in the selected module (e.g., cohort genomics module 260-6, or clinical trial module 260-7), and allows the user to select the patient of interest for viewing the Pathogenome of that patient. The patient selection enables the clinician and researcher to customize the tracks displayed in this section and thus helps to carry out various patient-centric analysis as the user desires in an interactive manner. The patient selection feature also helps to visualize the mutated genes identified in the selected patient, measured in a genomic scale. The bar plots displayed in this section are color-coded based on the pathogenicity and mutational consequences reported in the patient.

An SNV 1303 lists the genes identified with single nucleotide polymorphisms from the patient group. A promoter 1305 illustrates the genes identified with variants in their promoter regions (TATA box, CAAT box, Initiator box, and GC box) and the transcription initiation site, from the patient group. A Poly-A site 1307 illustrates the variants identified in the Poly-A sites from the patient group. A splice site 1309 lists the variants identified in the various splice sites (Real splice acceptor, Real splice donor, Cryptic splice acceptor, and Cryptic splice donor) from the patient group. A select by disease feature 1311 shows the genetic alterations identified in the genes associated with the selected disease panels. The feature integrates many of the oncology and inherited disorders; upon selection, the patient samples are scanned against the genes associated with these disease panels. This approach allows the clinicians and investigators to go beyond analyzing simple relationships and creating the potential to reveal the less obvious and indirect molecular causes of many diseases. A select by consequence feature 1312 illustrates the genomic data based on the mutation consequences identified in the patient group. In some embodiments, customizing framework 1300A also provides a consequence plot feature to visualize the consequences of the mutations with respect to the chromosomal positions, as selected by feature 1312. The gene name, consequence, number of patients, and the number of mutations are displayed on the mouse over of the bar plot. A select by domain feature 1313 illustrates the genomic data based on the affected protein domain identified in the patient group. A select by pathway feature 1314 illustrates the genomic data based on the impaired molecular pathways identified in the patient group. A select by family feature 1315 allows the user to select subjects that belong to the same family or cohort. A "group by" feature 1316 assists the researchers in visualizing the genomic data based on two different approaches: the number of mutations and the number of patients. An excluded by (%) feature 1317 helps to visualize the frequency plot above the cut-off value selected based on either a number of mutations or patients to refine the results. The cut-off value ranges, for example, from 1-10%.

Figure 13B:
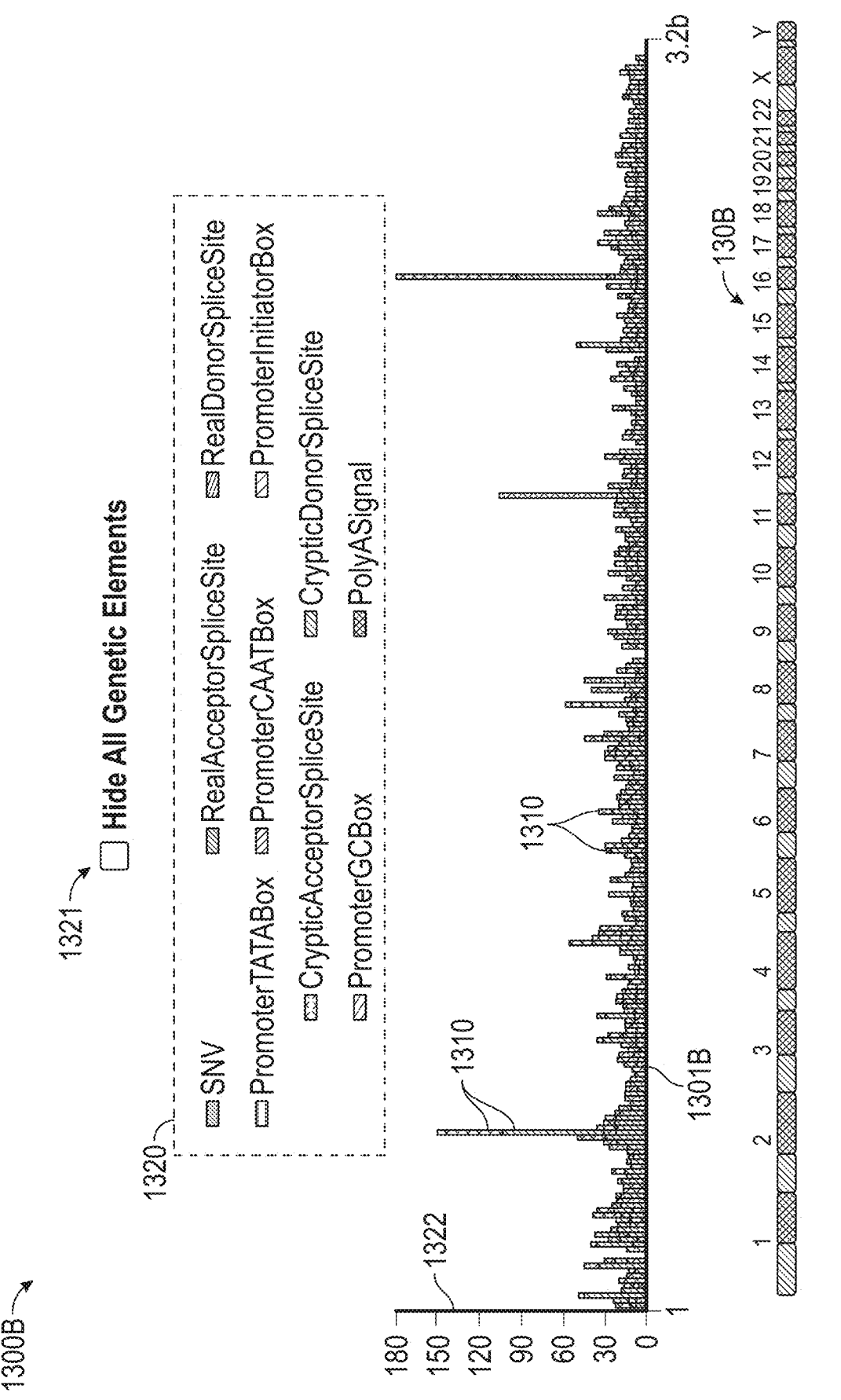

FIG. 13B includes cohort pathogenome frequency plot 1300B that illustrates top mutated genes (which can be grouped by either number of patients or number of mutations 1322) in a chromosome 1301B reported in a cohort. Chromosome 1301B is selected from a genome list 130B. On clicking stacked gene bars 1310, the related information like number of affected patients with affected domains, pathways, and related drug information are shown in the appropriate table. A color code 1320 for the stacked gene bars illustrates the different mutations found in a given gene in chromosome 1311 (e.g., SNV, Real Acceptor Splice site, Real Donor Splice Site, Cryptic Acceptor splice Site, Promoter TATA Box, Promoter CAAT Box, Promoter Initiator box, Promoter GC Box, and the like). The ordinate (Y-axis in cohort pathogenome frequency plot 1300B) indicates the number of individuals in the cohort having the associated mutated gene, wherein the mutation is indicated by color code 1320 and the gene is specified by its location in chromosome 130B (X-axis position). Cohort pathogenome frequency plot 1300B may include a box 1321 to hide/show genetic elements in the frequency chart.

Cohort pathogenome frequency plot 1300B facilitates the visualization of a frequency plot of every gene from the whole genome that is mutated across the cohort of patients, grouped by either number of patients or a number of mutations. This visualization technique is integrated with the identification and characterization of the different types of genomic alterations (e.g., SNVs, Promoters, Poly-A, and Splice sites) for every gene from the patient group. This visualization framework displays the mutated gene details like gene name, gene ID, start and end position of a gene, chromosome, and the mutation category on mouse over. The other visualization approaches employed in this pathogenome module are customized based on the selection of mutations in different features from a gene, such as real donor, cryptic acceptor, promoter, and many other coding and regulatory elements, from this section. This section thus opens unprecedented possibilities for understanding the characteristics and behavior of the molecular details in large patient groups, which aids in understanding and determining the causality of disease or drug response phenotypes. The whole genome is shown in the form of a chromosomal ideogram 130B of the human genome and shown in a horizontal view, where chromosomes are placed horizontally from chromosome 1 to 22, and the sex chromosomes. This feature is facilitated with selective focus on visualizing a particular chromosome and many of the genes with the identified mutations within the chromosome. Chromosomal ideogram 130B displays the chromosomes linked together end to end, to illustrate the whole genome in a horizontal view. Many of the genes and mutations are depicted on the genome-scale for visualization and analysis. In addition, selecting a specific chromosome will expand it and display many of the mutated genes present in that chromosome for a particular patient, or from the group of patients from Family, Cohort, or Clinical Trials, for a finer and more detailed analysis.

Figure 13C:
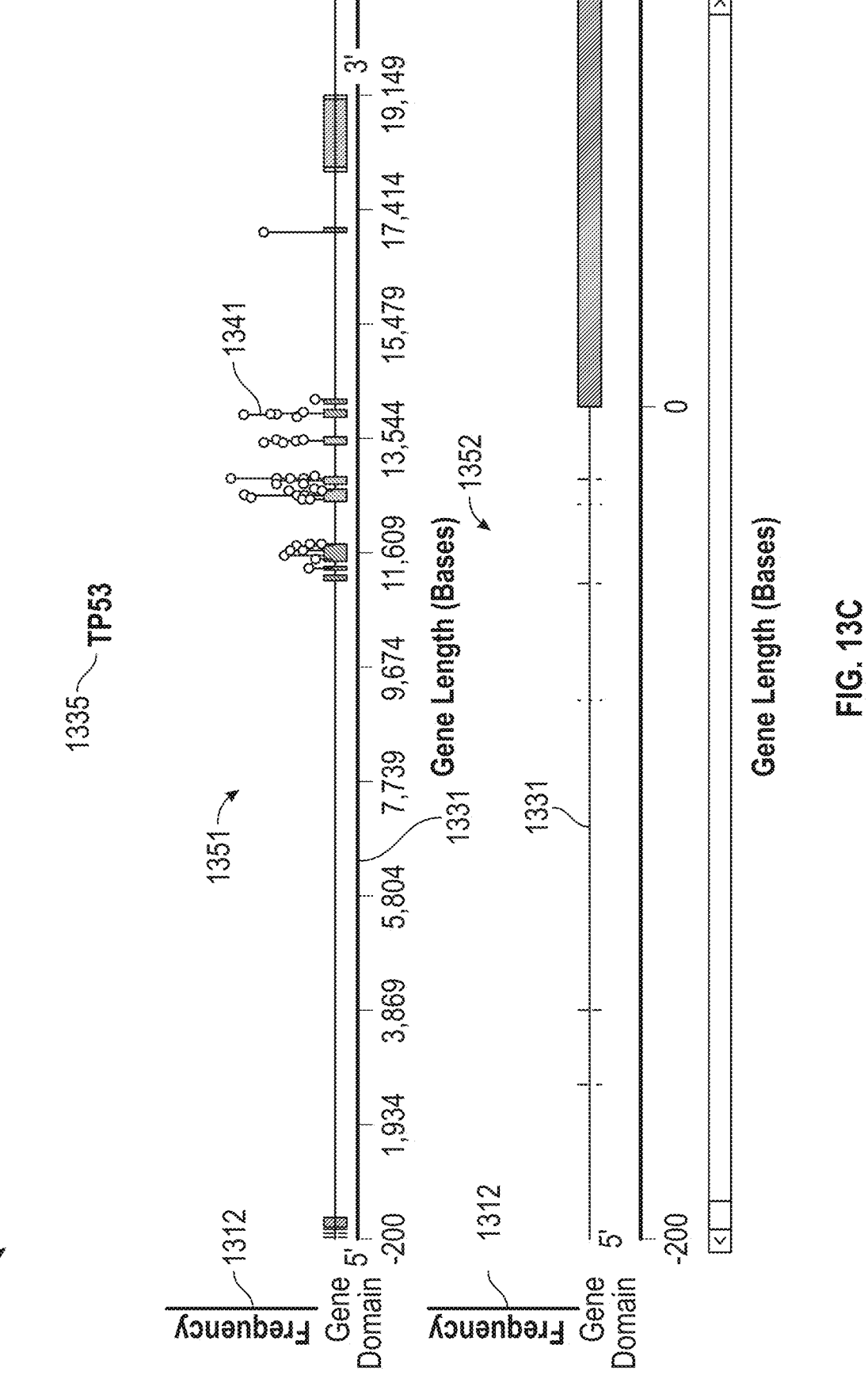

FIG. 13C includes pathogene frequency plot 1300C results, obtained by clicking on a chromosome in genome 1301A to illustrate a defect gene within cohort pathogenome frequency plot 1300B in detail.

Pathogene frequency plot 1300C facilitates the visualization of particular genes with mutations across the cohort of patients, with several details including gene length with the base position in a horizontal view, and the frequency of different types of mutations across the gene depicting them on the different regulatory and coding elements, including the promoters, transcription initiator, exons, introns, splice junctions, 5' and 3' UTRs, and poly-A regions. The exons are displayed on the gene view along with the encoded domains below the exons, and the mutations identified from the patient group as a frequency plot with the position of the mutation on the X-axis and the number of patients with the mutation on the Y-axis. The mutations are represented in the form of a needle which displays the mutation details like mutation position, exon number, amino acid change, the pathogenicity of the mutation, encoded domain id, and the number of patients and the mutations in popups on mouse over. Thus, this section empowers the clinicians and researchers with a deeper understanding of the identified gene, patient, domain, and several mutation details. The frequency plot can be initiated by selecting from the Pathogenome frequency plot, or from dropdowns on the Pathogene frequency plot window.

Frequency plot 1300C illustrates the positions 1331 and frequency 1312 of mutations 1341 reported in a selected gene 1335. Pathogenome frequency plot 1300C is a more finely granular view of the frequency plot 1300B, wherein the X-axis positions 1331 includes a fewer nucleotide basis. Accordingly, while frequency plot 1300B illustrates an entire chromosome, frequency plot 1300C indicates the same frequency values 1312 (Y-axis) for gene 1335, in either a compact view 1351 or an expanded view 1352.

In some embodiments, the gene is marked on the exact position 1331 of the selected chromosome to scale, indicating the number of patients with the specific mutation or specific genetic element types such as CDS or any of the regulatory elements. The gene and mutation details are displayed on mouse over. An ideogram of the selected chromosome is displayed in a compact view 1351 with the cytogenetic locations based on the bands and their chromosomal arm. An expanded view 1352 is displayed by clicking on the specific mutation position. Pathogene frequency plot 1300C enables the genes organized into gene families to be specifically displayed on the pathogenome view, and the genes that are mutated. Additional related information, like the number of affected patients (e.g., frequency 1322) with affected domains, pathways, and related drug information is also provided for the selected gene, or gene groups such as containing a specific domain, or genes that belong to a particular gene group such as a gene family or cell structure genes. Furthermore, each chromosome is shown in expanded view 1352 with many of the possibilities of illustrations and analytical capabilities described above.

Figure 13D:
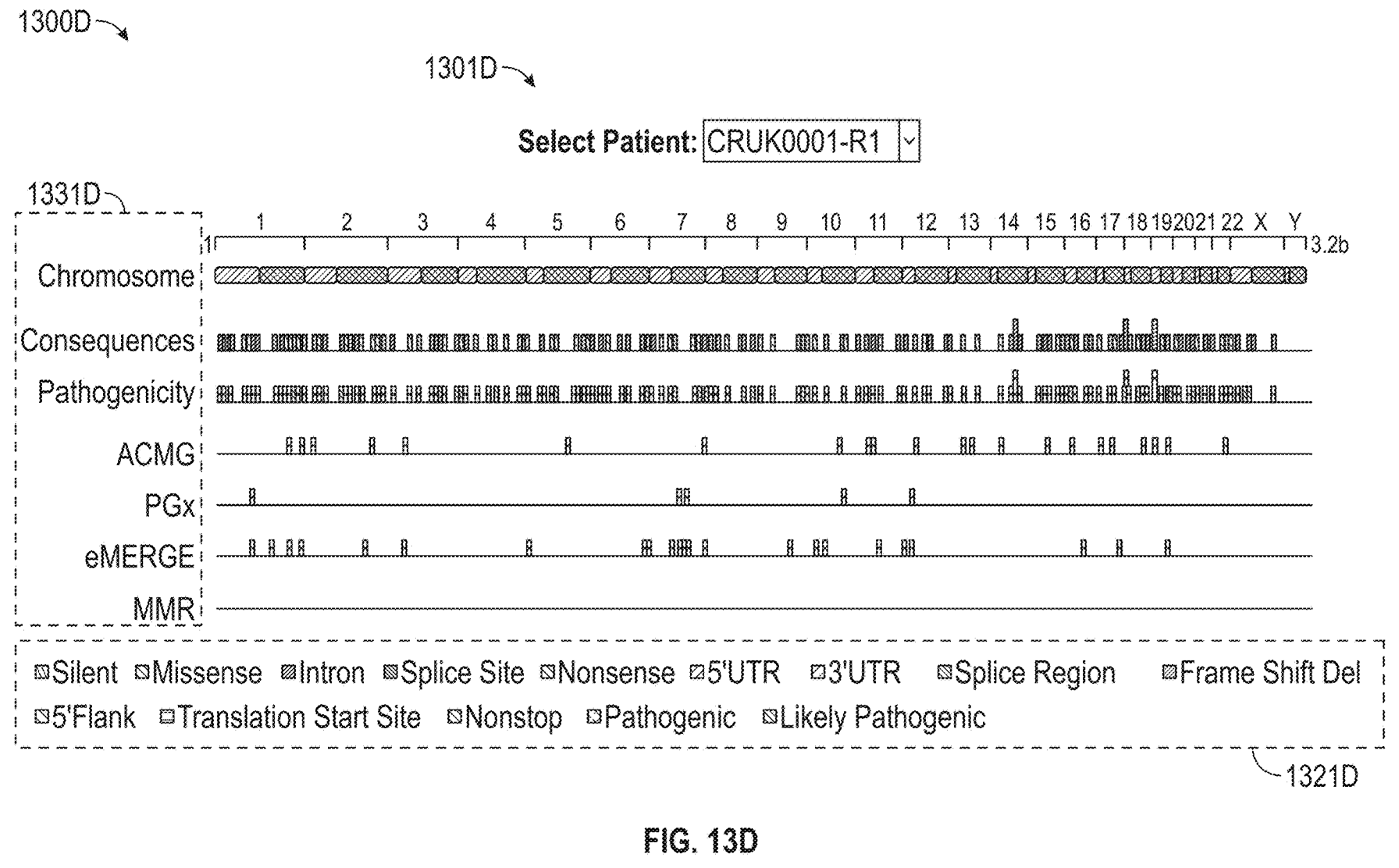

FIG. 13D includes pathogenome 1300D having several rows 1331D illustrating, along the entire genome of a selected patient 1301D, the chromosome, the consequences (color-coded as per a chart 1321D) of associated mutations, the pathogenicity of the mutation (color-coded green, for light or no pathogenicity, and red, dark red, or purple for high pathogenicity), ACMG, PGx, eMERGE, and MMR, among others. The ACMG, PGx, eMERGE, and MMR tracks indicate mutations identified in these various gene panels for the selected patient of the cohort. Chart 1321D may indicate the type of mutation (e.g., silent, missense, intron, splice site, nonsense, 5'UTR, 3'UTR, splice region, frameshift deletion, 5 flank, translation start site, nonstop, and the like).

Figure 14:
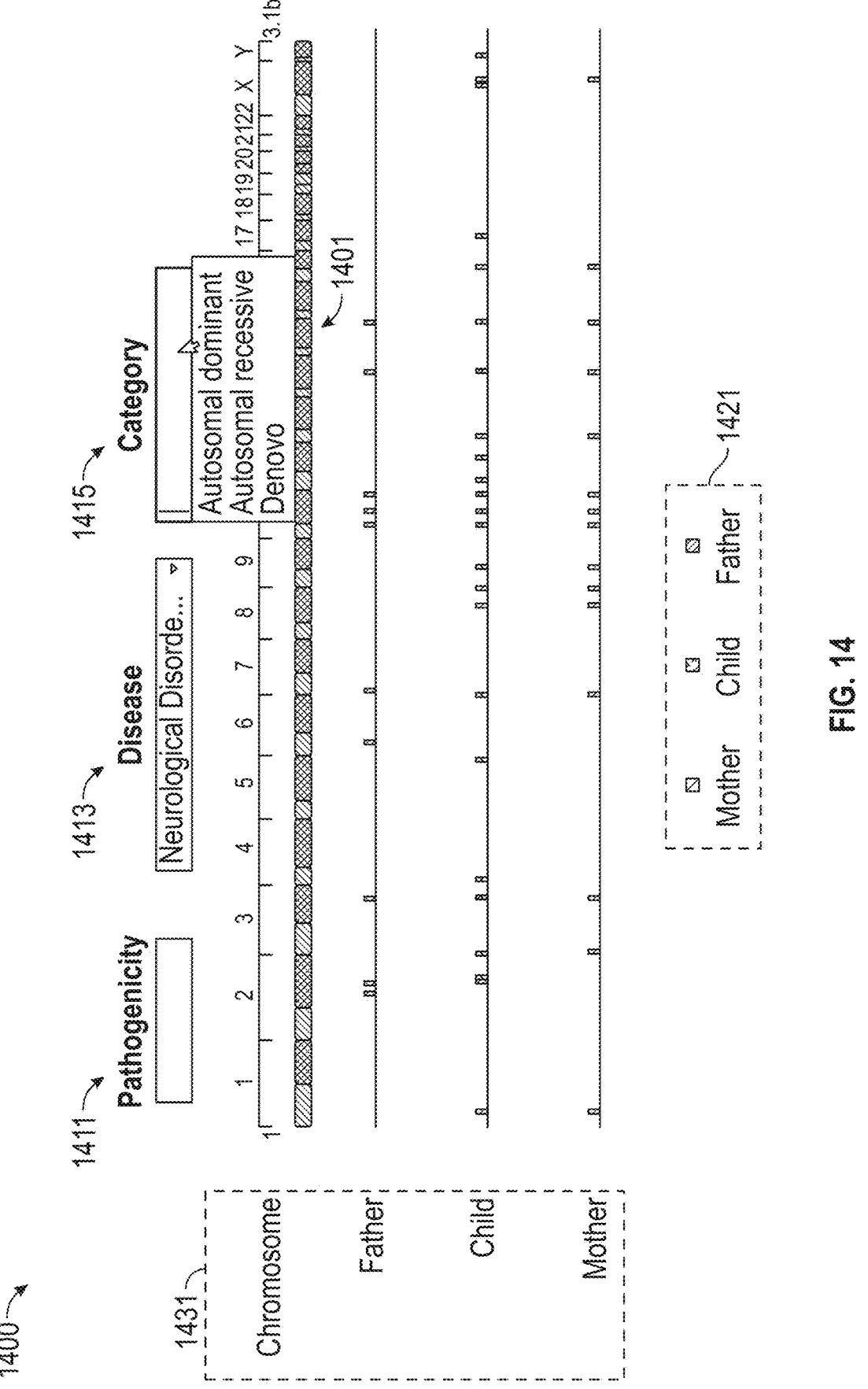
FIG. 14 illustrates portions of a family pathogenome, according to some embodiments.

FIG. 14 illustrates portions of a family pathogenome 1400, according to some embodiments. Family pathogenome 1400 facilitates the visualization and analysis of mutated genes identified across the family members. Family pathogenome 1400 is shown for father, mother, and child separately marked with the identified mutations. Family pathogenome 1400 aids in explaining genetic conditions by looking at differences in mutations between father, mother, and the affected child. This feature allows for the depiction of the pathogenome of additional family members including the siblings of the child, father, and mother as well as aunts, uncles, grandparents, and great grandparents of the child, and for the analysis of the relationship of each mutation and mutated gene across the family members, in addition to the zygosity and inheritance patterns. In some embodiments, family pathogenome 1400 illustrates the genes and mutations from the child and parents in a family genomics sub-module of a cohort genomics module (cf. cohort genomics module 260-6), depicting the consequences, inheritance, and pathogenicity for the identified mutations on the genomic scale.

The consequences and pathogenicity are shown on the genomic scale for the identified mutations. The module also aids the clinician and the researcher in identifying the commonly mutated genes and the inheritance patterns among the parents and the child, and in turn, facilitates in the interpretation of this analysis. Furthermore, it enables the illustration and analysis of genes and mutations from the child, siblings, parents, and uncles, aunts, and grandparents, and great grandparents on both sides. Pathogenome 1400 displays a pathogenome visualization plot for a patient selected from a group of patients in a cohort module or a clinical trials module (cf. cohort genomics module 260-6 and clinical trial module 260-7). A pathogenicity tab 1411, a disease tab 1413, and a category tab 1415 (e.g., autosomal dominant, autosomal recessive, denovo) provide more options for the user.

Pathogenome 1400 includes several rows 1431 illustrating, along the entire genome, the chromosome, and the parent (mother/father)-child mutation landscape. A color code 1421 indicates which mutation in the child comes from either parent (mother/father). A chromosomal ideogram 1401 illustrates the chromosomes in the human genome, laid horizontally, in sequence.

Figure 15:
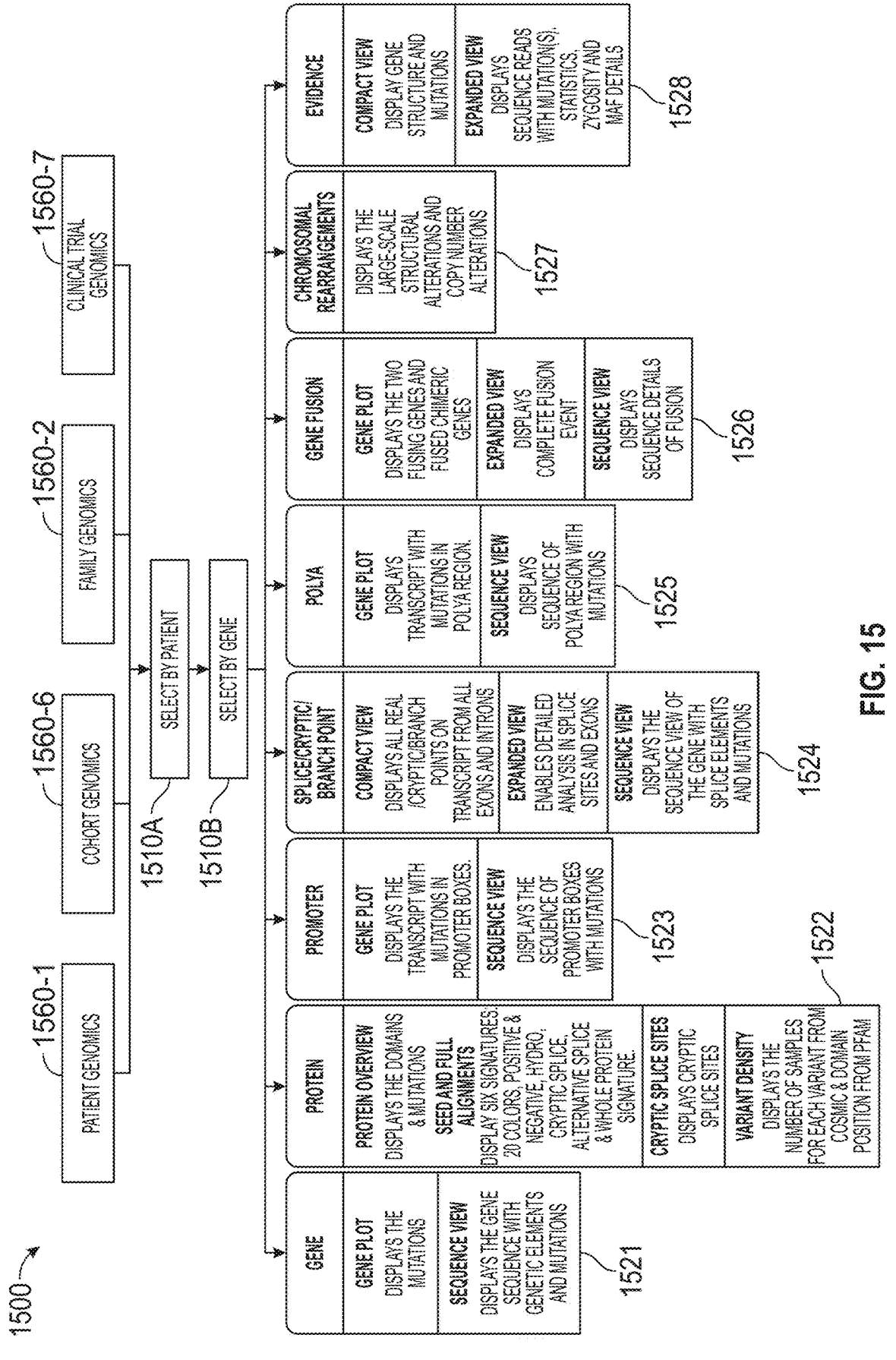
FIG. 15 illustrates a diagram of a pathogene module in a genome sequence analysis engine, according to some embodiments.

FIG. 15 illustrates a diagram 1500 of a pathogene module (cf. pathogene module 260-11) in a genome sequence analysis engine, according to some embodiments. Pathogenome module may include or interact with a patient genomics module 1560-1, a cohort genomics module 1560-6, a family genomics sub-module 1560-2, and a clinical trial genomics module 1560-7 (cf, cohort genomics module 260-6 and clinical trial module 260-7).

Select by Patient 1510A: This feature lists many of the patients present in the selected module. This helps in carrying out individual patient-centric analysis. Select by Gene 1510B: This feature lists many of the mutated genes identified in the selected patient. The feature applies to the visualization and analysis of Gene, Protein, UTR, Promoter, Poly-A, Real and Cryptic splice, branch, promoter, etc., sites, Gene Fusion, CNV, and many other genetic elements and Structural Variants, each provided under specialized modules. By selecting by gene, the pathogene module plots patient's mutations and known mutations from dbSNP, Clinvar, and COSMIC databases, among others. In some embodiments, the pathogene module categorized the mutations into clinical significance, molecular consequence, variation type, and pathogenicity or deleteriousness.

Gene 1521 displays the mutations. In some embodiments, gene 1521 includes a Sequence view that displays a gene sequence with genetic elements and mutations. This section assists in visualizing the mutations identified in the selected gene along with annotations from publicly available databases. Information related to the selected gene such as chromosome, Gene ID, symbol, length, and strand is displayed in this section. The gene ontology (molecular function, biological process, subcellular location) and the associated disease phenotype are provided to get complete knowledge on the characteristics of a gene before acquiring its role in regulating disease progression. This gene visualization module is similar for many modules (cf. modules 260).

Protein 1522 includes a protein overview that displays the domains and mutations in a protein. Protein 1522 also includes seed and full alignment views that display six signatures: 20 colors, positive and negative, hydro, cryptic splice, alternative splice, and whole protein signature. Protein 1522 also displays cryptic splice sites and the number of samples for each variant from a database (e.g., COSMIC) including domain position, to form a variant density plot.

Promoter 1523 includes a gene plot that displays the transcript with mutations in promoter boxes. In some embodiments, promoter 1523 displays a sequence view with the sequence of promoter boxes including mutations.

Splice/Cryptic/Branch point 1524 displays a compact view with real/cryptic/branch points on transcript from one or more exons and introns. In some embodiments, splice/cryptic/branch point 1524 displays an expanded view that enables detailed analysis in splice sites and exons. In some embodiments, splice/cryptic/branch point 1524 displays a sequence view with splice elements and mutations.

Poly-A 1525 includes a gene plot that displays a transcript with mutations in the Poly-A region. In some embodiments, Poly-A 1525 displays a sequence view of the Poly-A region with mutations.

Gene Fusion 1526 includes a gene plot that displays two fusing genes and fused chimeric genes. In some embodiments, gene fusion 1526 displays an expanded view of the complete fusion event. In some embodiments, gene fusion 1526 displays a sequence view including sequence details of the fusion event.

Chromosomal rearrangements 1527 displays a large-scale structural alteration and copy number alteration.

Evidence 1528 displays in a compact view a gene structure and mutations. In some embodiments, evidence 1528 includes an expanded view that displays sequence reads with mutations, statistics, zygosity, and mutation annotation format (MAF) file details.

FIG. 16A illustrates the structure of an entire gene 1600A in a compact view 1651 and in an expanded view 1652 provided by a genome sequence analysis engine, according to some embodiments. A select gene tab 1611 enables the user to select a gene. A general information table 1610 indicates the chromosome, a gene ID, a gene symbol, a gene length, and a strand for the selected gene. A mutation toggle 1603 and a view sequence toggle 1605 in a field 1620 enable the view of mutations and sequence for the user, respectively. This section displays the structure of the entire transcript including the promoter, coding, and non-coding regions, splicing sites, Poly-A sites, along with the mutations 1641 identified in the gene from the patient. The details are displayed on the mouse over of the mutation needles 1631 which are overlaid on the transcript in compact and expanded views, including a nucleotide number axis 1601A.

Figure 16B:
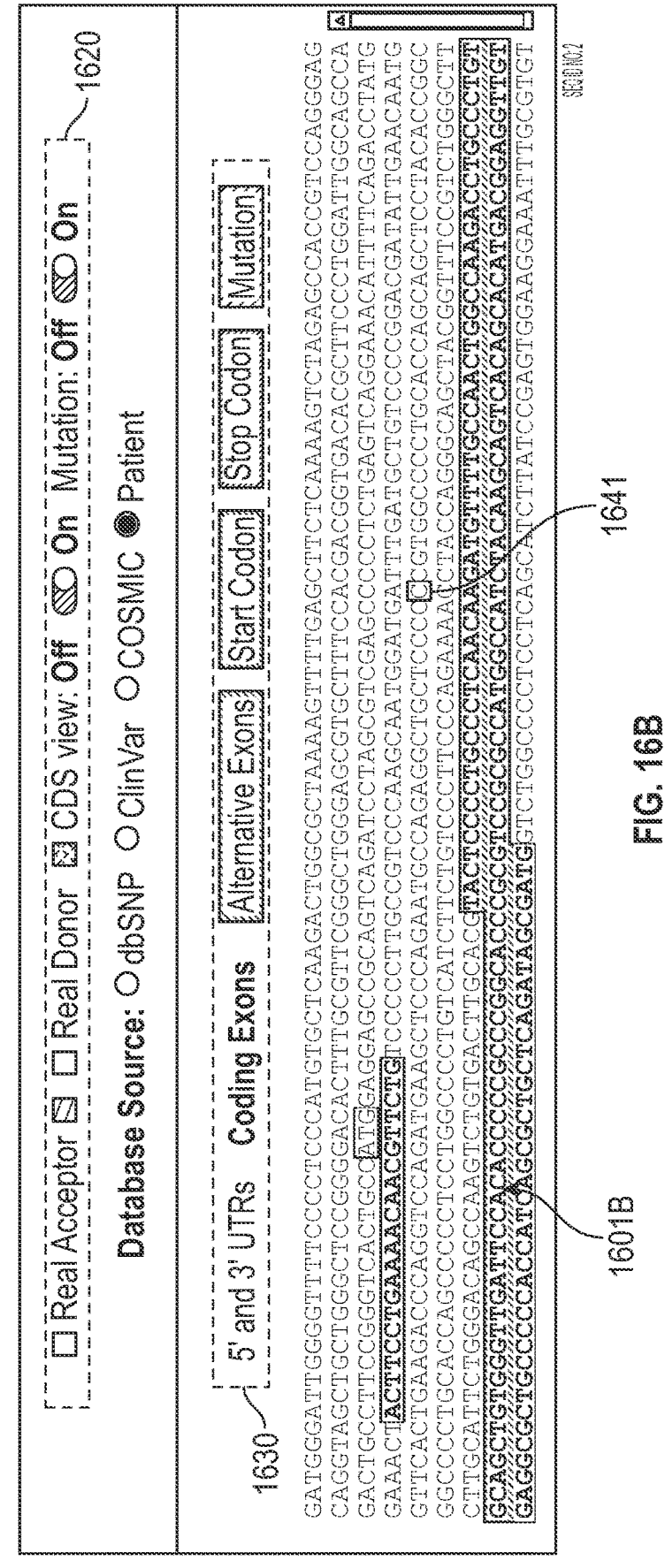

FIG. 16B illustrates a nucleotide sequence view 1600B of a genome, according to some embodiments. Sequence view 1600B displays the nucleotide sequence 1601B of the selected gene and shows the details of mutations 1641 identified in the gene in the patient on a user mouse over. In some embodiments, the specific location of a nucleotide (e.g., base number), may be indicated on a user mouse over of the nucleotide. A menu 1620 lists display options for the user, such as "real acceptor," "real donor," "CDS view" toggle, and "mutation" view toggle. A table 1630 indicates the graphical codes for the different elements illustrated, e.g., 5' and 3' UTRs, coding exons, alternative exons, start codons, stop codons, and mutations.

Figure 17:
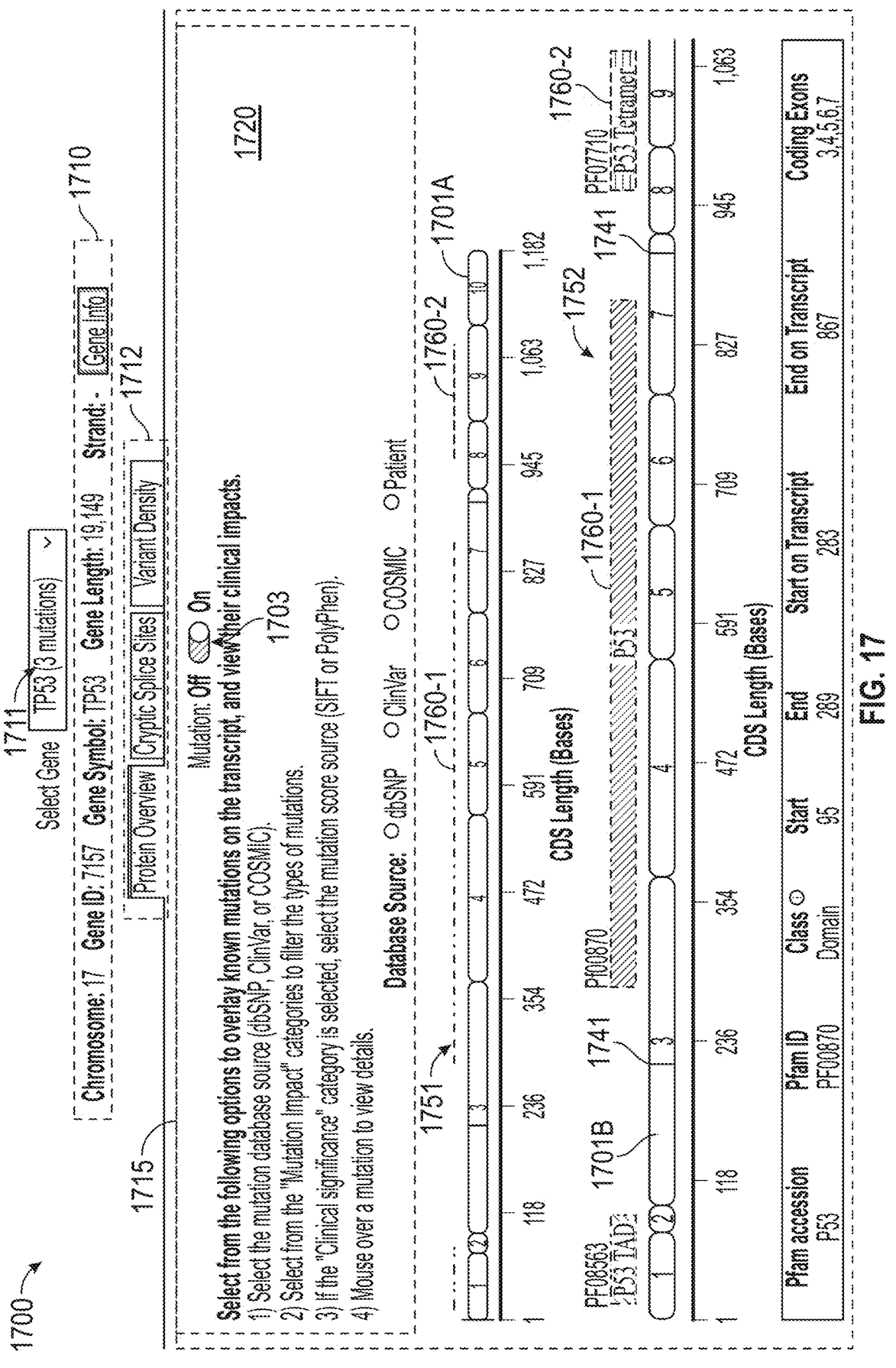
FIG. 17 illustrates a visual plot of genome mutations, according to some embodiments.

FIG. 17 illustrates a visual plot 1700 of genome mutations, according to some embodiments. Visual plot 1700 illustrates mutations found in the protein-coding regions of the genome and displaying the respective domains predicted by the selected algorithm. A gene selection tab 1711 enables the user to access a selected gene. A general information field 1710 includes a chromosome number, a gene ID, a gene symbol, a gene length (e.g., number of nucleotide bases), and the strand. The user may select in tab 1712 among several options such as protein overview, cryptic splice sites, and variant density.

A protein overview 1715 visualizes mutations 1741 which occur in the coding region of the genome, and their effect on the translated protein, per request by the user via a toggle 1703. A field 1720 lets the user select one or more database sources for searching mutations 1741 (e.g., dbSNP, ClinVar, COSMIC, Patient, and the like).

A compact view 1751 and an expanded view 1752 are available to the user. In some embodiments, coding exons of a selected transcript are depicted as grey ovals 1701A (compact view 1751) and 1701B (expanded view 1752). Structural regions 1760-1 and 1760-2 (hereinafter, collectively referred to as "structural regions 1760") of the encoded protein are predicted by an algorithm (cf. algorithm 250). Besides plotting patient mutations on the gene, the protein structure and sequence, the known mutations from the different databases such as dbSNP, ClinVar, and COSMIC depicting the CDS, and many of the regulatory elements are represented and categorized into clinical significance, molecular consequence, and variation type, and pathogenicity based on the SIFT and/or PolyPhen scores.

Protein overview 1715 may include two different alignments between an amino acid sequence in the protein and the nucleotide string in the coding gene. A seed alignment includes a set of curated amino acids that are matched to their corresponding nucleotide sequence in the genome. The seed alignment tends to have lesser amino acids compared with full alignment. A full alignment contains the set of amino acids produced by the algorithm or database selected (e.g., Pfam using Hidden-Markov models, and the like). The full alignment tends to have more amino acids when compared with the seed alignment. Both types of alignment may be visualized in different genomic signatures, per user selection, namely: 20 colors, Positive-Negative, Hydro, Cryptic splice, Alternative splice, and Whole protein signature. The 20 colors signature displays the amino acids of the selected domain in 20 different colors along with its positions and sequence. The hydro signature displays the amino acids of the selected domain based on the hydropathy of the individual amino acid. In some embodiments, the hydropathy signature may include a heat map like legend indicating color code and the hydropathy values for each of the 20 amino acids.

Figure 18:
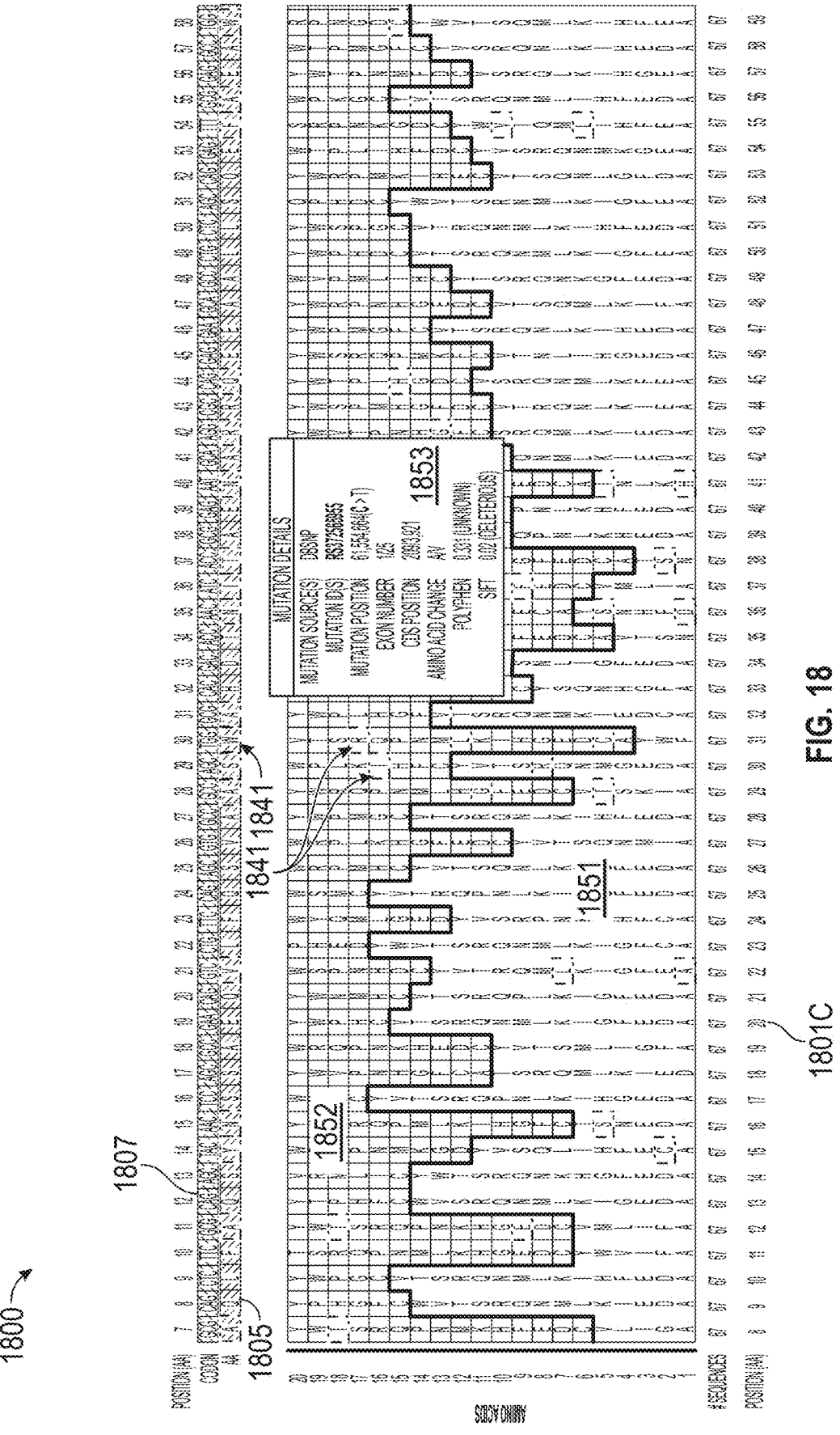
FIG. 18 illustrates a protein signature in a genome sequence analysis engine, according to some embodiments. Sequences, from top to bottom, are SEQ ID NOs: 3-24.

FIG. 18 illustrates a protein signature 1800 in a genome sequence analysis engine, according to some embodiments. When the image of a protein domain is clicked (e.g., structural regions 1760 in visual plot 1700), the variable amino acid sequence plot of the protein domain from the protein is displayed with color codes for the amino acids, which may be extracted from the PFAM multiple sequence alignment of the protein domain, or some other database. Protein signature 1800 displays the true amino acid 1805 (including the three basis coding the amino acid 1807) in any given position 1801C, and a list of allowed amino acids 1851 in one half (e.g., in green at the bottom) and the non-allowed amino acids 1852 above (in red). Mutations 1841 in an amino acid are shown in red if it is in the allowed or non-allowed portion. Protein signature 1800 allows the user to see if the mutation is truly deleterious 1852 or benign 1851. A window 1853 with mutation details may pop for display to the user upon mouse over of any of mutations 1841.

Figure 19A:
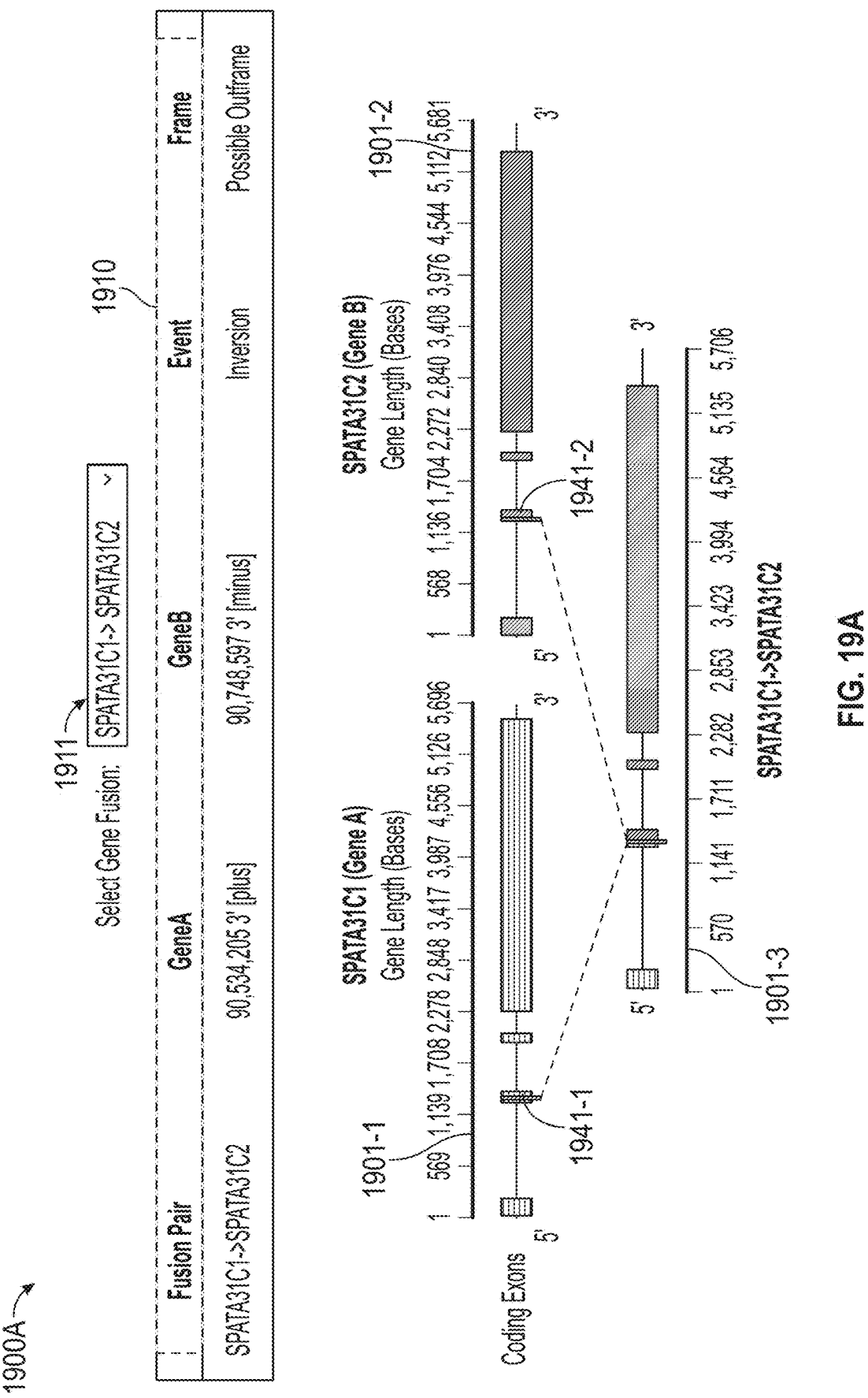
Figure 19B:
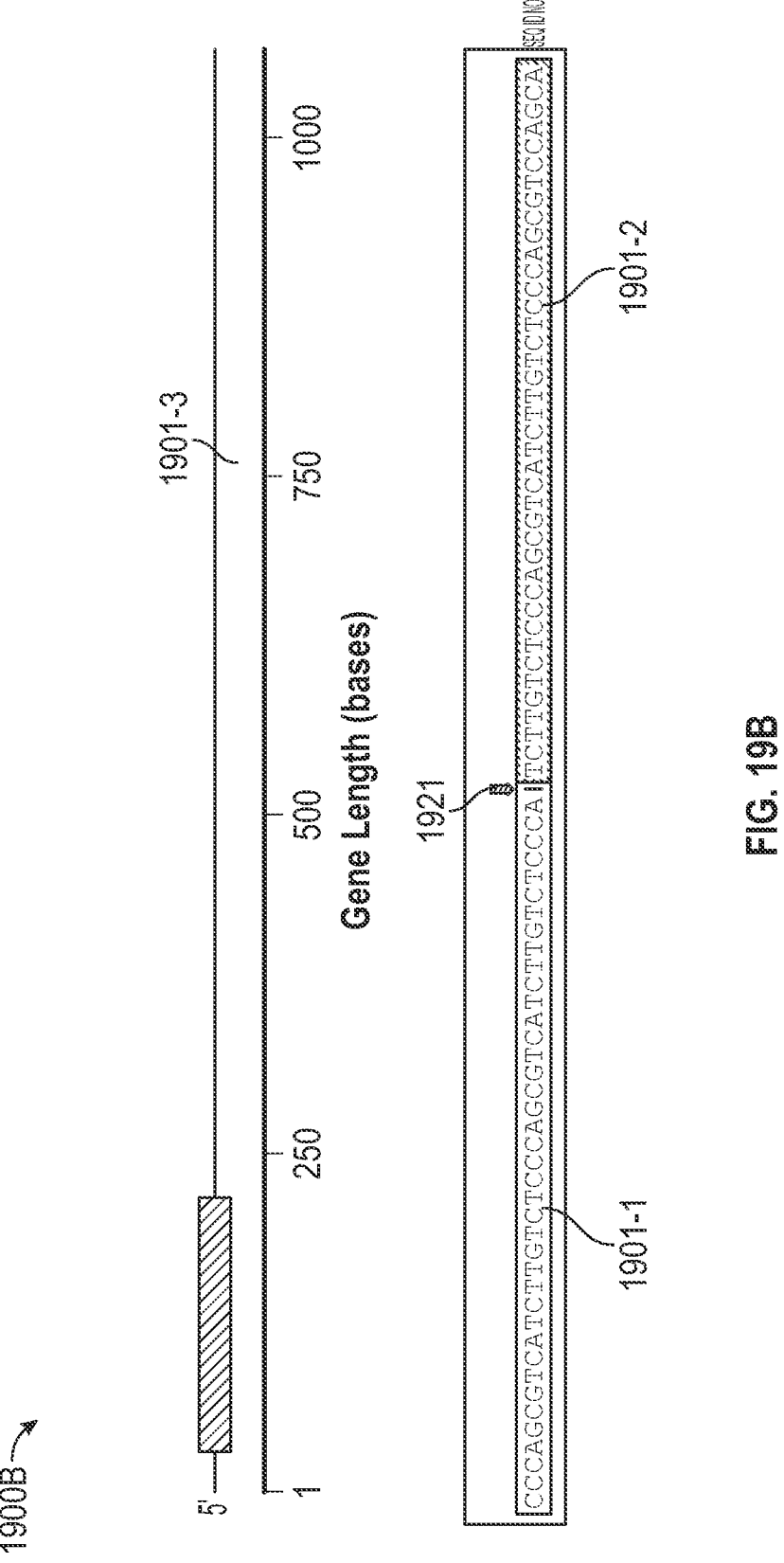
Figure 19:
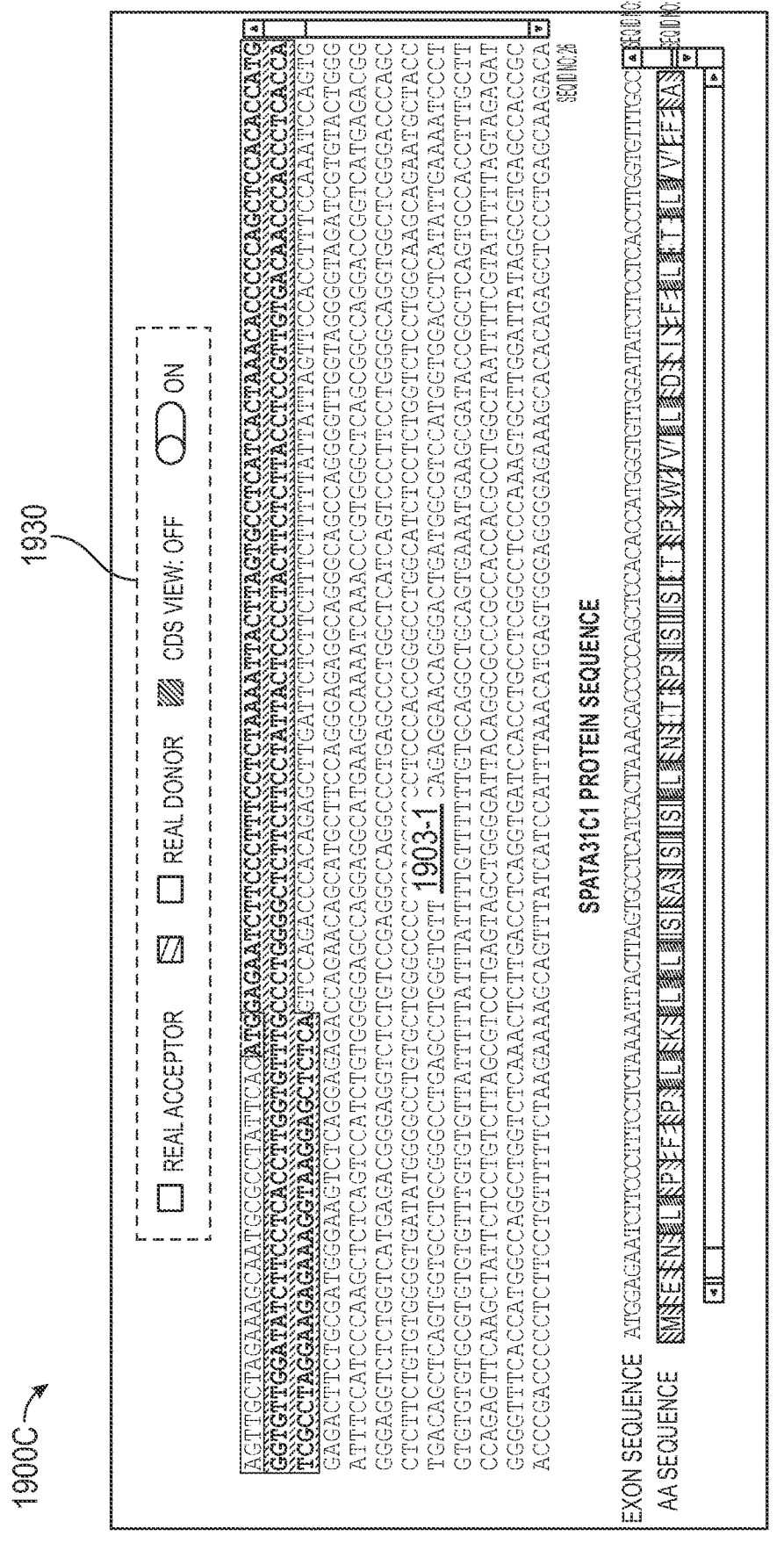
Figures 2, 19C:
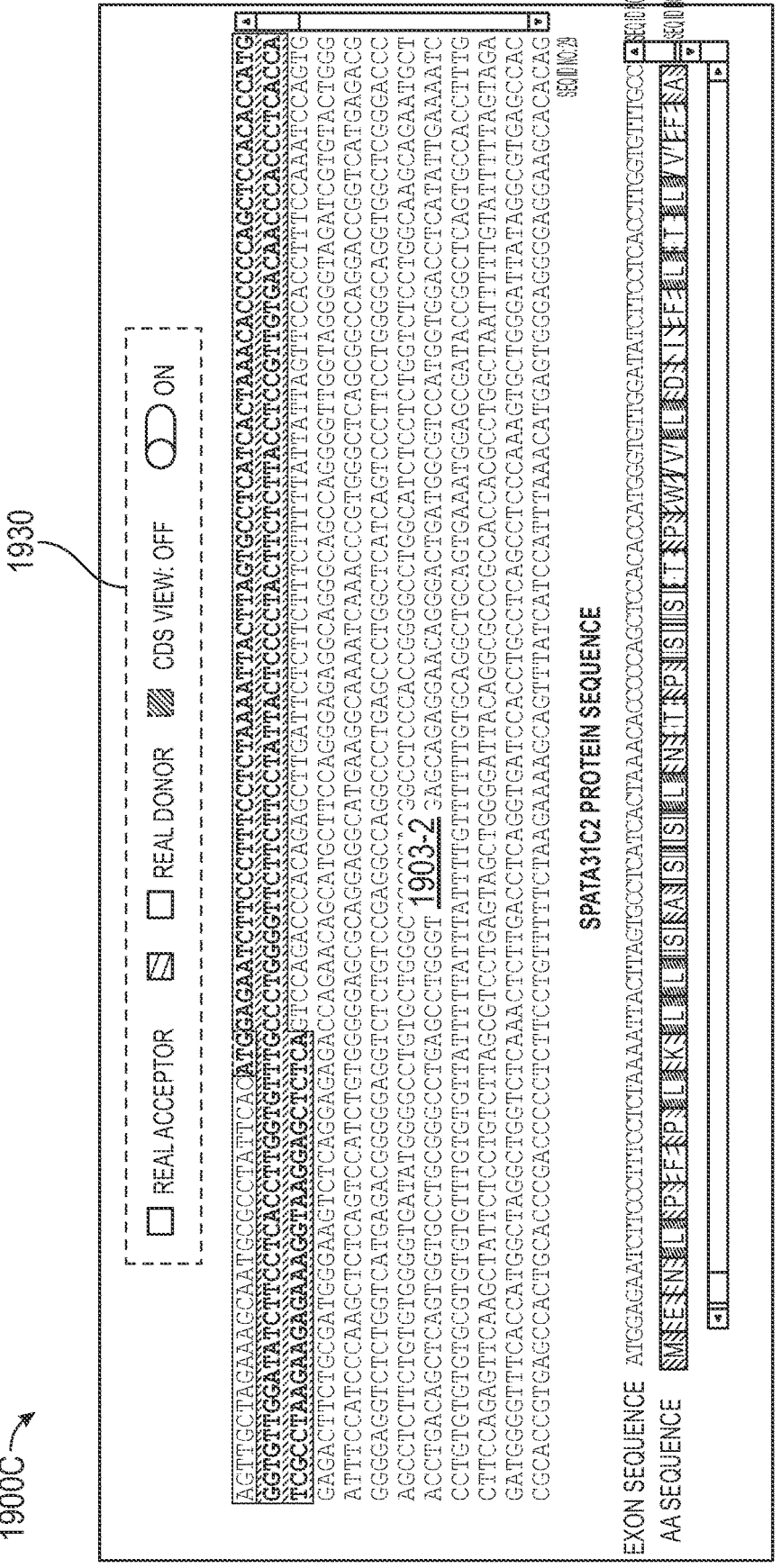
Figures 3, 19C:
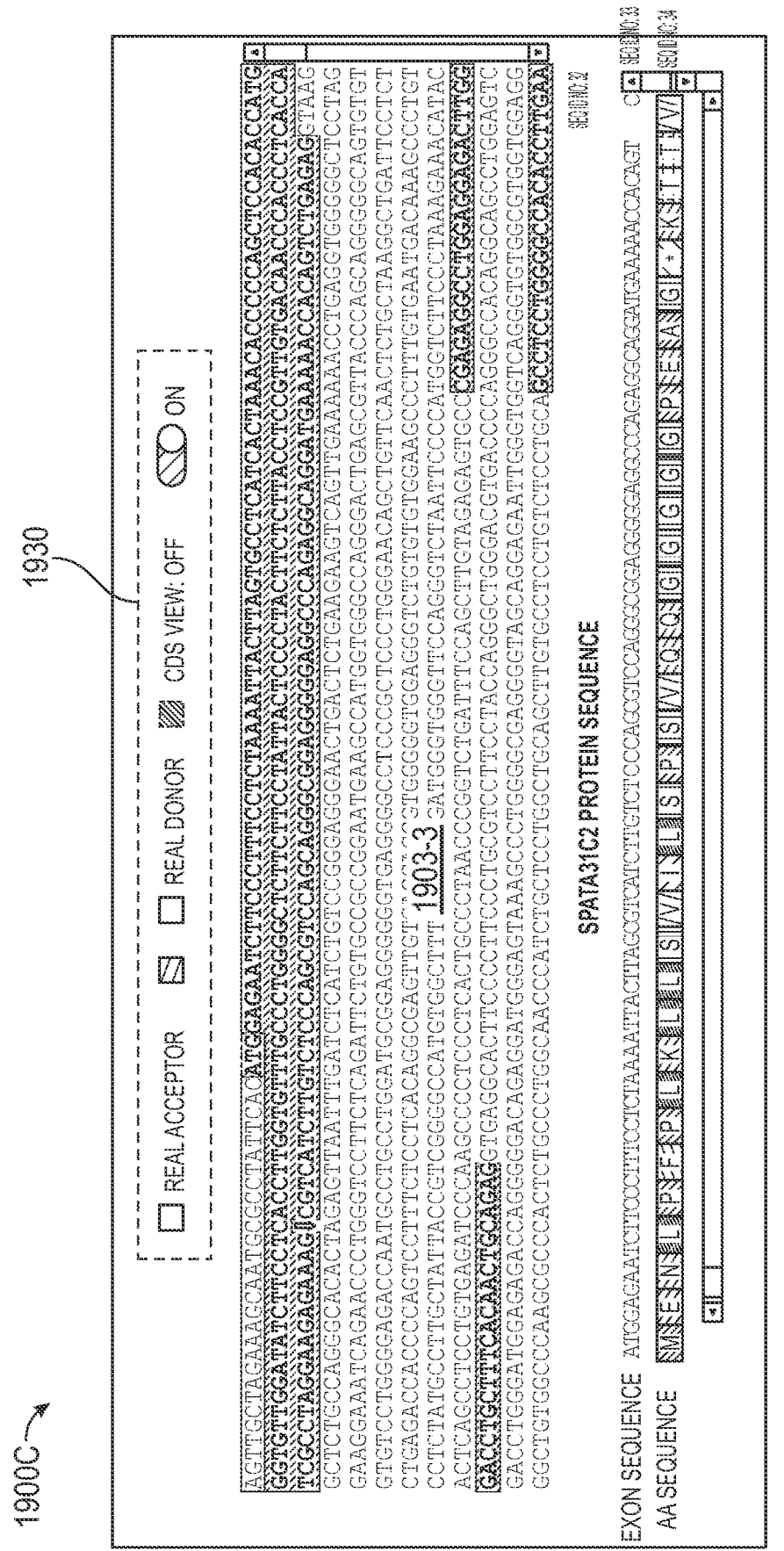

FIGS. 19A-C illustrate gene fusion mutation events in charts 1900A, 1900B, and 1900C (hereinafter, collectively referred to as "gene fusion charts 1900") leading to a chimeric gene, according to some embodiments for a selected gene fusion 1911. Gene fusion charts 1900 provide visualization of gene fusions, which are characterized as a phenomenon in which the whole or parts of two genes are juxtaposed and fused into a single chimeric gene. The fusion can result from different types of chromosomal aberrations, like translocations, inversion, amplification, or deletions.

FIG. 19A illustrates fusion chart 1900A including a gene plot for the visualization of the genes 1901-1 (gene A) and gene 1901-2 (gene B) involved in the fusion phenomenon and followed by the fused chimeric gene. A field 1910 indicates the fusion pair, the names or coordinates for gene A and gene B, the event and frame. The breakpoints 1941-1 and 1941-2 (hereinafter, collectively referred to as "breakpoints 1941") in both genes 1901 are highlighted (red) and on mouse over, the position of the breakpoint is displayed. The fused point on chimeric gene 1901-3 is highlighted with position and other details.

Fusion chart 1900A illustrates a nucleotide sequence 1901-1 from gene A that fuses with a nucleotide sequence 1901-2 from gene B to form a nucleotide sequence 1901-3 in the chimeric gene.

FIG. 19B illustrates fusion chart 1900B including an expanded view of fused genes in sequence 1901-3 from genes 1901-1 and 1901-2. A fusion point 1921 (possible out-frame) is illustrated. The details of fusion point 1921 may be displayed on a mouse over.

FIGS. 19C-1, 19C-2 and 19C-3 illustrate a fusion chart 1900C including a sequence view of the fusion event. This subsection aids in visualizing the nucleotide and protein sequences of the normal genes and fused chimeric genes. The sequences are marked with 5' and 3' UTRs, coding exons, alternative exons, start codons, and stop codons to visualize the nucleotide and amino acid sequences of the normal genes and fused chimeric gene. Fusion chart 1900C illustrates gene A sequence 1903-1, gene B sequence 1903-2, and fused gene sequence 1903-3 (hereinafter, collectively referred to as "nucleotide sequences 1903"). In nucleotide sequences 1903, a mouse over each nucleotide causes the display to indicate the position of the nucleotide in the genome. Fusion chart 1900C indicates real acceptor sites, real donor sites, alternative exons start codons, and stop codons by toggling a color indicator 1930 'on' or 'off.'

FIGS. 20A-G illustrate mutation visualizations 2000A, 2000B, 2000C, 2000D, 2000E, 2000F, and 2000G (hereinafter, collectively referred to as "visualizations 2000") provided by a genome sequence analysis engine, according to some embodiments. Visualizations 2000 enable the user to overlay known mutations on a gene transcript and view their clinical impacts. To do this, the user may select a mutation database source (e.g., dbSNP, ClinVar, COSMIC, or Patient), then select a "mutation impact" category to filter the types of mutations. When the clinical significance category is selected, the user may select a mutation score source (SIFT or PolyPhen) and view the details simply by mouse over. Visualizations 2000 may include a compact view 2051 and an expanded view 2052 of a nucleotide sequence 2001. In compact view 2051, an entire gene transcript is displayed, enabling quick access to cryptic sites and exons that occur within the gene. In expanded view 2052, the user may have a detailed analysis of cryptic sites and exons that occur within a selected portion of the gene. Moreover, the user may scroll to the left or right of nucleotide sequence 2001 using a sliding bar 2053, to scan the entire gene in expanded view 2052, if desired. By scrolling sliding bar 2053 to the left or right, the sequence position being analyzed in expanded view 2052 will be indicated in compact view 2051 with a grey bar.

Visualizations 2000 provide a summary and a view of the mutations identified in the promoter region of every gene from a particular patient, and from every patient in a cohort of patients. The promoter is defined as the region in the upstream portion of a gene, which helps in the initiation of transcription. Alterations in this region are said to cause changes in the protein-coding element (mRNA) and lead to a disease state. The potential promoter regions are predicted by employing an adaptation of the Shapiro-Senapathy algorithm suited to the sequence, PWM, and length of the different promoter elements. This module aids in visualizing the four different types of promoter boxes: TATA, GC, CAAT, and INIT (Initiator) boxes. This promoter visualization module is similar for four different objectives (comprehensive, cohort, trio, and clinical trials). Visualizations 2000 enable the clinician and researcher to visualize the entire transcript along with the mutations occurring in the promoter region. The different types of promoter boxes and exons are color-coded. On mouse over of the mutation needles, the mutation details are displayed.

Visualizations 2000 also provide a view of the promoter sequence along with the mutations occurring in this region. Besides plotting patient mutations, the mutations curated by databases like ClinVar, dbSNP, and COSMIC may be plotted, which are based on the mutation impact and clinical significance. Promoters identified in the selected gene are tabulated below the sequence view with the following information: the position, sequence, and the score for the respective promoter type, and mutation details. Visualizations 2000 also provide a view of the mutations identified in the poly-A region of every gene from a patient or group of patients. Poly-A sites are defined as those which are present in the downstream region of a gene and facilitate the regulation of transcription and gene expression. Aberrations in this region are said to have modulating effects leading to many different disease states. This poly-A visualization module is similar for many modules (cf. modules 260).

Visualizations 2000 also illustrate cryptic splice sites present in the particular gene. The coding exons for the selected transcript are depicted in the form of grey ovals, and the Pfam ID is overlaid as colored lines. Different color codes are given to represent different splice sites along with the scores, and they are as follows: cryptic acceptors in red, cryptic donors in green, and real sites in blue. It also provides a compact and expanded visualization that enables a detailed analysis of cryptic splice sites.

In some embodiments, visualizations 2000 may also display a variant density: This section aids in the visualization of the number of samples for each variant in the COSMIC database along with the domain position. According to the number of variants present in a position, the plot is color-coded, and on mouse over, the mutation details are displayed. (Positions with a single variant are depicted in red, and positions with more than one variant are depicted as follows: two variants→blue; three variants→green; four variants→yellow; more than four variants→magenta.)

Visualizations 2000 provide a gene plot and a sequence view. The gene plot aids in visualizing the entire transcript along with the mutations occurring in the Poly-A region. The different elements of Poly-A elements and exons are color-coded. On mouse over of the mutation needles, the mutation details are displayed in compact and expanded views. The sequence view facilitates visualizing the Poly-A sequence along with the mutations occurring in this region. Besides plotting patient mutations, the mutations curated by databases like ClinVar, dbSNP, and COSMIC are also plotted, which are based on the mutation impact and clinical significance. Visualizations 2000 also provides a visual interactive interface for the mutations identified in splice sites, cryptic splice sites, and cryptic exons. These abnormalities are now known to cause approximately 50% of diseases including major cancers and non-cancer disorders. Identifying and locating the mutations in those regulatory elements of a gene helps in understanding the importance of those regions across the whole genome and the occurrence of causative mutations in these regions contributes to the majority of human diseases. The potential cryptic splice sites identified using the Shapiro-Senapathy algorithm are scanned for the mutations from the patient data. This splice/cryptic visualization module is similar for many modules (cf. modules 260).

Figure 20A:
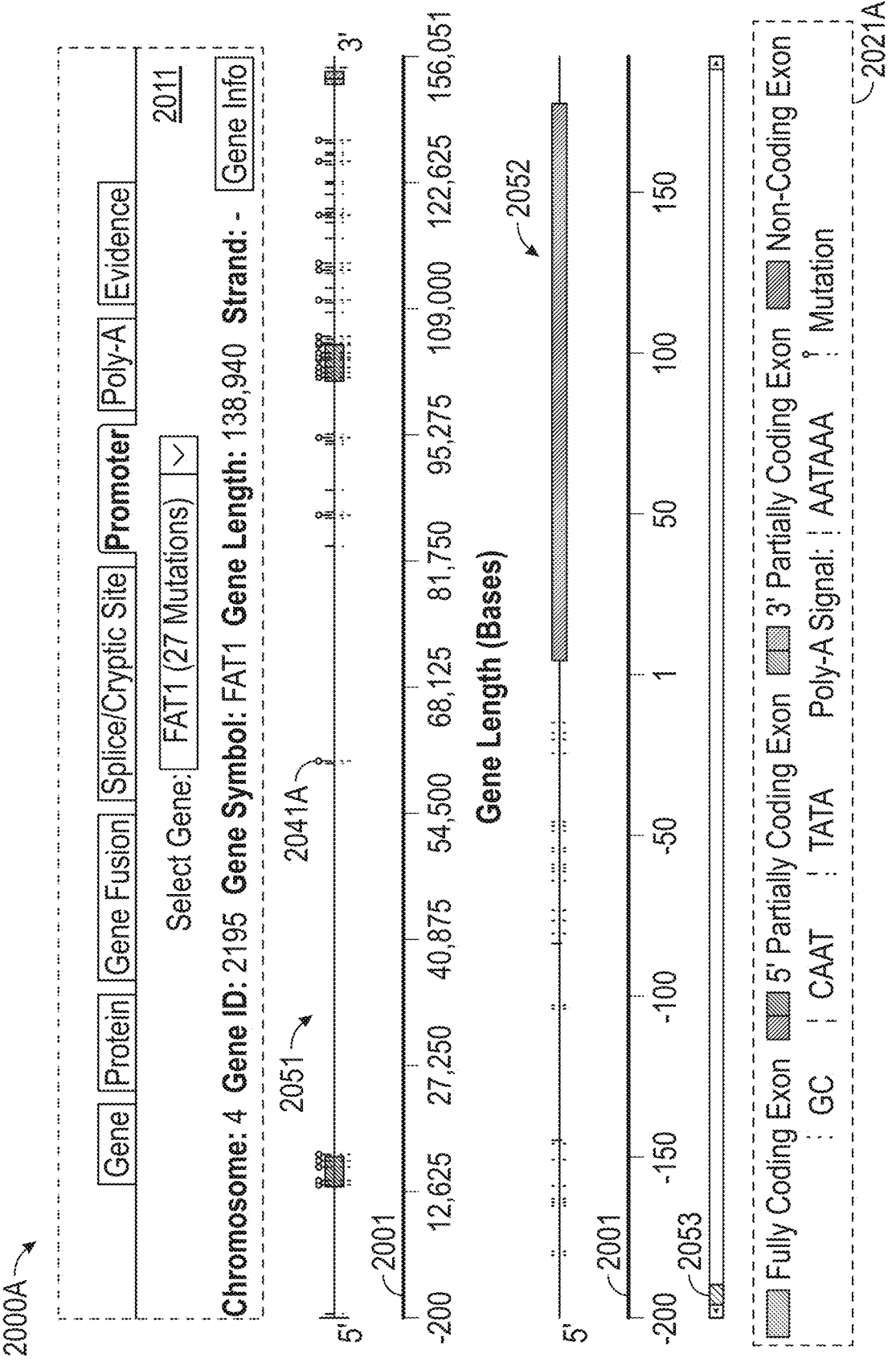

FIG. 20A illustrates visualization 2000A including a sequence view of an intron with the complete details of mutations identified within the splice sites in the patient. In some embodiments, visualizations 2000 also display evidence affirming the existence of the identified variants in the sequence reads from the NGS data. The coding exons are displayed on the canonical transcript with the identified mutations. The mutations are shown exactly in their respective position in the transcripts. The complete details of the mutations are also given along with supporting evidence. In some embodiments, visualizations 2000 also display the structure of a gene in a compact and expanded view with the identified mutations, with their evidence in sequence reads shown in a separate view. Besides, the sequenced reads from the case and control samples of the patient are aligned and scanned to derive the frequency of mutated bases within these reads. In some embodiments, visualizations 2000 include a complete color-coded visualization of these aligned reads against the human reference gene sequence and the frequency of alleles at the point of mutation is provided.

In some embodiments, visualizations 2000 enable the identification of the zygosity of a mutation and the gene with the following features, which adds to the complete details of the gene, variants, and associated phenotypes. In some embodiments, visualizations 2000 includes transcript details with CDS position and strand information, and variant details with the hgvsc codon and amino acid syntax along with variant type and variant quality information. In some embodiments, visualizations 2000 also display the pathogenicity of the variant with scores generated by multiple in-silico pathogenicity prediction algorithms. In some embodiments, visualizations 2000 displaying the frequency of the variant in healthy population databases (1KG, ESP, ExAC) is also determined, and the phenotypes sourced from public databases (HPO, MONDO) associated with the gene and variant.

Visualization 2000A identifies mutations in the promoter region of a selected gene from a particular patient, selected from a cohort. A menu 2011 enables the user to select between a gene, a protein, a gene fusion event, a splice/cryptic site, a promoter, a poly-A site, and evidence display. Visualization 2000A illustrates a promoter site and associated mutations 2041A over a nucleotide string 2001. The gene transcript is displayed in a compact view 2051 and in an expanded view 2052, enabling a quick scan of the real splice sites, cryptic sites, and exons that occur within it. In expanded view 2052, a slider 2053 allows the user to move easily along nucleotide string 2001. The different non-coding, partially coding, and coding exons are displayed with cryptic splice site acceptors, cryptic splice site donors, real splice site acceptors, real splice site donors, and cryptic exons. Visualization 2000A enables a quick view of real and cryptic splice sites, and cryptic exons, and mutations 2041A that occur within them per user selection in menu 2011, as indicated in table 2021A. Mutations 2041A are identified at the splice sites in the patient with complete details of the mutations upon mouse over. Interactive scaling and color coding allows the user to focus on a specific portion of the sequence and track the different types of splice regions in any part of the gene. Mutations 2041A may also include mutations from different publicly available databases.

Figure 20B:
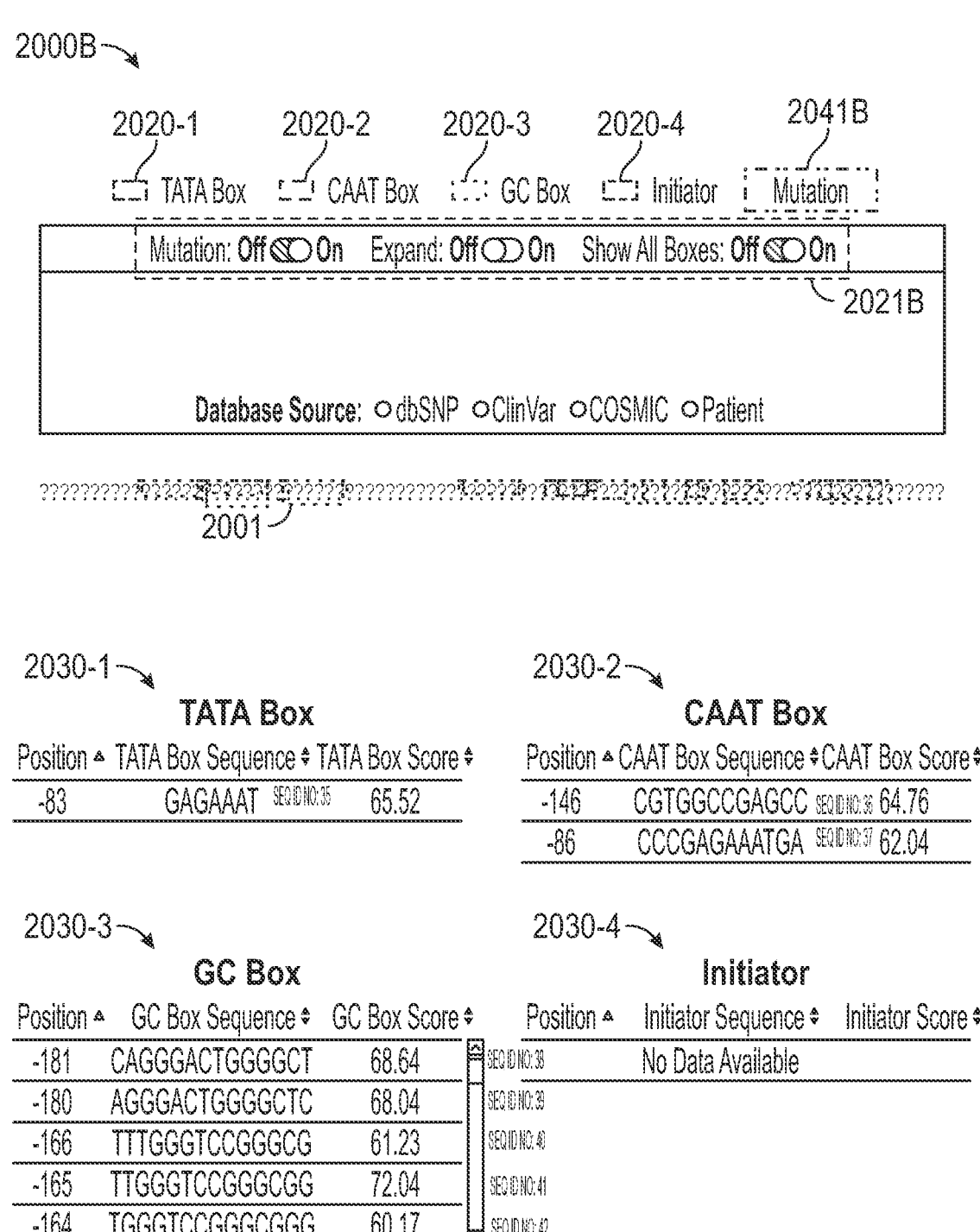

FIG. 20B illustrates mutation visualization 2000B including TATA boxes 2020-1, CAAT boxes 2020-2, GC boxes 2020-3, initiator boxes 2020-4, and promoter mutations 2041B within nucleotide sequence 2001. A control box 2021B allows the user to turn display functionalities "On/Off" such as "mutation," "sequence expand," "show all boxes," and the like. The user may also select a database source (dbSNP, ClinVar, COSMIC, Patient, and the like).

The promoter is identified as the region from −200 to +1 wherein +1 is the transcription start site. Any occurrences of the promoter boxes within this sequence that pass the selected score threshold are displayed within tables 2030-1, 2030-2, 2030-3, and 2030-4 (hereinafter, collectively referred to as "tables 2030"). TATA box (table 2030-1), CAAT box (table 2030-2), and GC box (table 2030-3) are derived from the region between −3 and −200. The initiator is shown at positions −2 to +6. By clicking on a sequence within any one of tables 2030, the user may view the sequence in the promoter sequence.

FIG. 20C illustrates mutation visualization 2000C including an mRNA nucleotide sequence 2023 wherein the strongest poly-A signal 2043C is AATAAA, and a mutation 2041C. A second signal ATTAAA may function at a similar strength as poly-A signal 2043C, and is illustrated in mutation visualization 2000C.

Figure 20D:
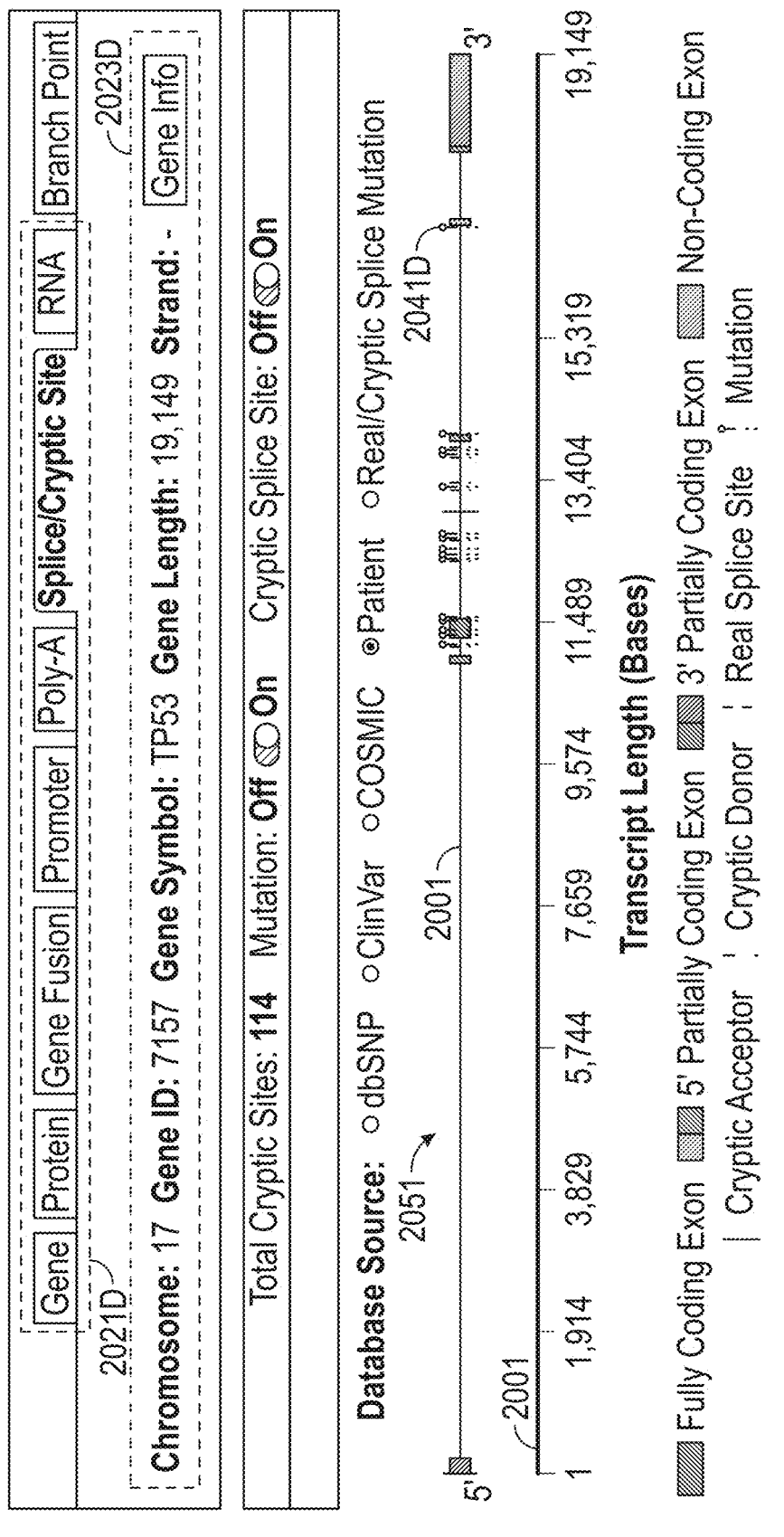
Figure 20D:
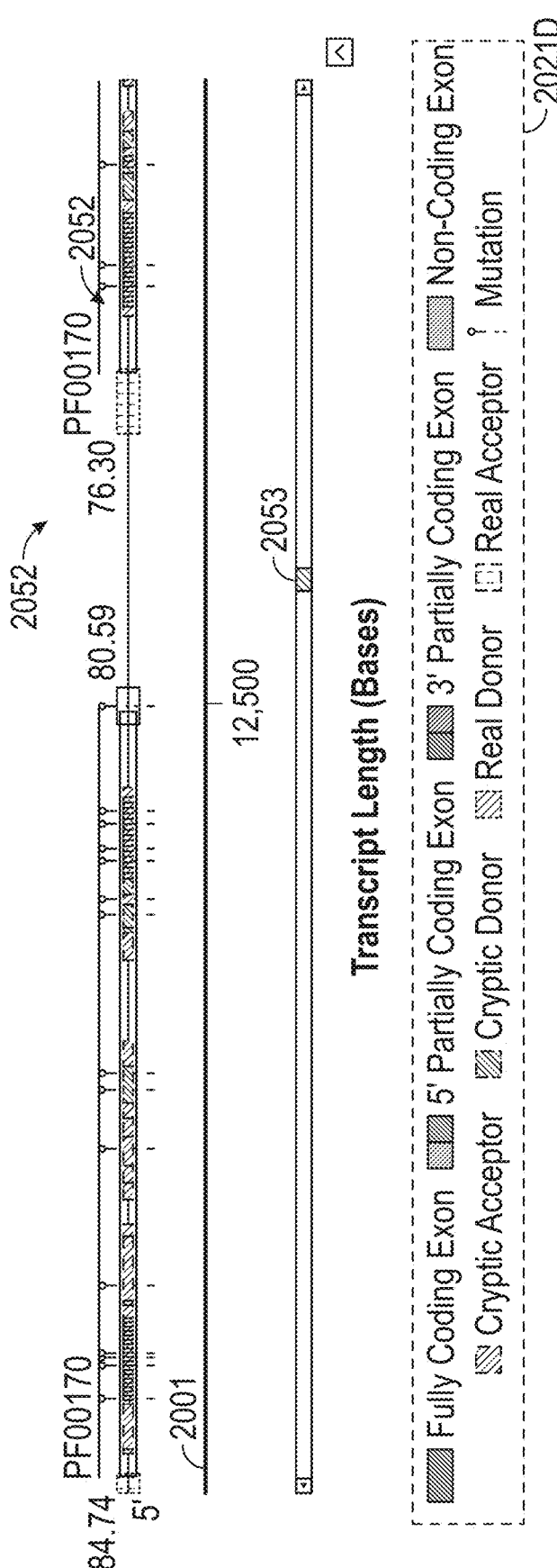

FIG. 20D illustrates mutation visualization 2000D including mutations 2041D in splice sites and cryptic splice sites, which are known to cause a large proportion of many diseases, including cancers and other diseases. A field 2023D indicates the chromosome, gene, gene symbol, gene length and strand of the selected gene. The Shapiro-Senapathy algorithm, among other algorithms, can be used to detect disease-causing mutations indicated in mutation visualization 2000D. When a splice site or a cryptic splice site mutation that is known to cause a disease occurs in a patient's genome sequence, it is identified using the Shapiro-Senapathy algorithm or some other algorithm and is displayed in mutation visualization 2000D in the gene structure and in the gene sequence.

Real exons and splice sites are displayed in the selected transcript as shown in key 2021D. Any cryptic splice site and cryptic exons that occur within the transcript are also displayed.

FIG. 20E illustrates mutation visualization 2000E including a sequence view 2003 of a selected intron, including real acceptor sites, real donor sites, cryptic acceptor sites, and cryptic donor sites (as indicated in table 2030).

Figure 20F:
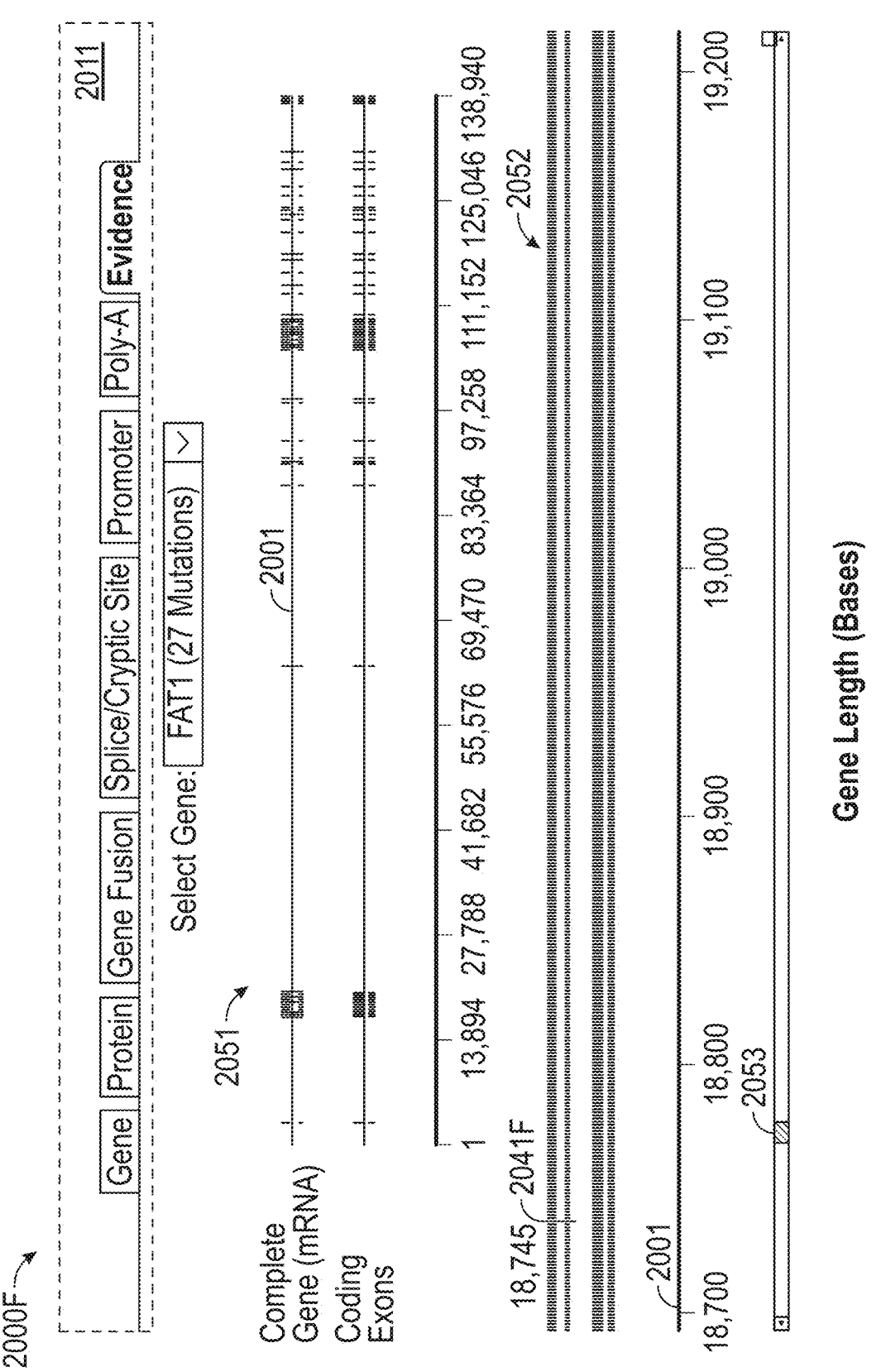

FIG. 20F illustrates mutation visualization 2000F including an evidence module to affirm the reported variants (including menu 2011). The first section shows the canonical transcript and coding exons of the selected gene. The mutations 2041F in the selected gene are represented in the form of red lines along with the exons showing the respective coordinates and mutation information on mouse over. Upon clicking the mutation of interest, a second section of the evidence block (the nucleotide view) displays the aligned mutations in case and control bands. Towards the left of the nucleotide view, the color key and the nucleotide composition for each mutation are displayed.

Figure 20G:
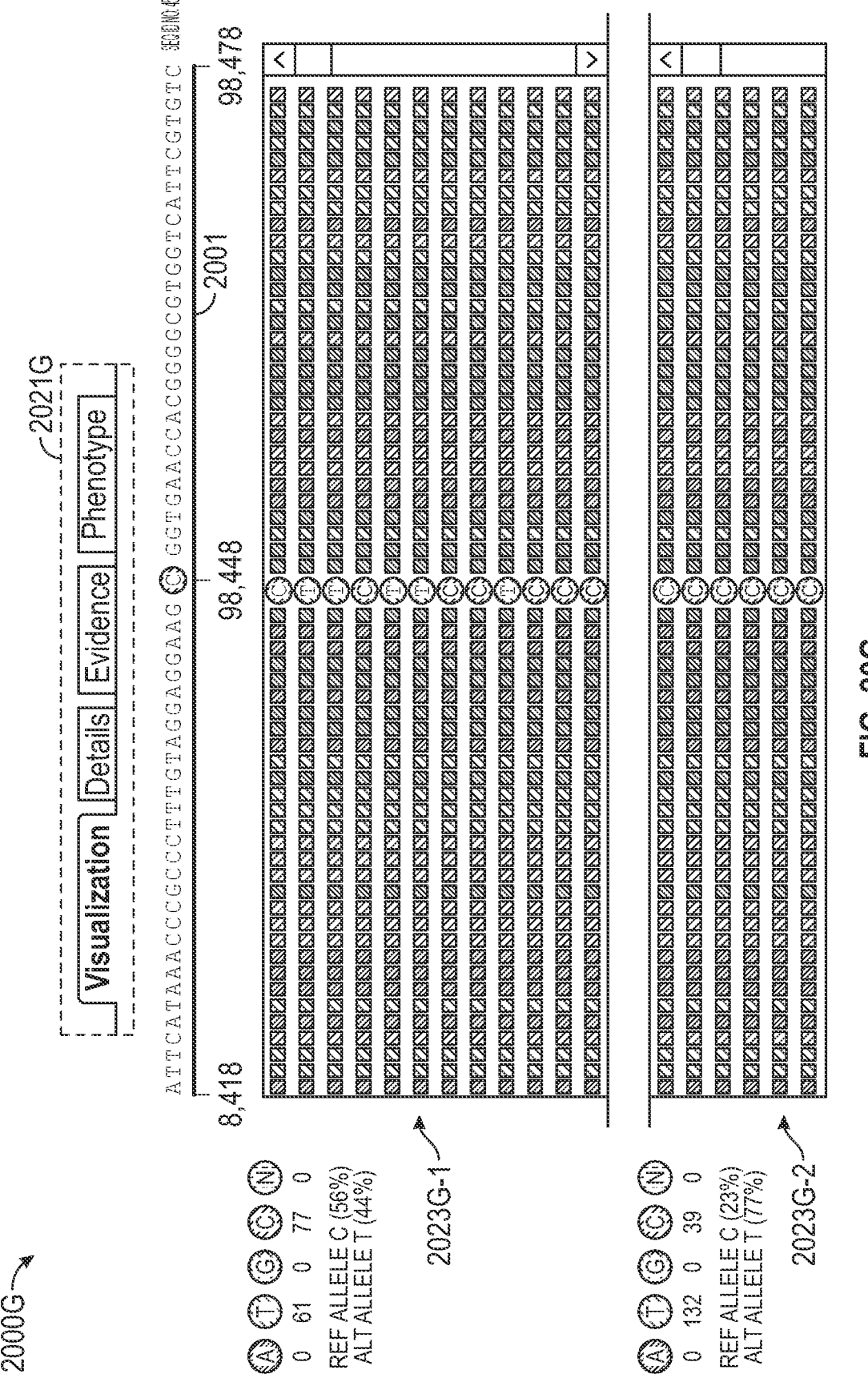

FIG. 20G illustrates mutation visualization 2000G, which displays the sequenced reads from the control sample 2023G-1 and case sample 2023G-2 of a patient, and aligns the sequence reads to illustrate and derive the frequency of mutated bases and other nucleotides within these reads. A menu 2021G allows the user to select between a visualization, details, evidence, and phenotype.

A missense single nucleotide mutation (chr4: 187,549, 428C>T) affecting the protein (ENSP00000406229-2: p.Ala1564Thr) is detected in the FAT1 gene of a subject. This mutation is classified as unknown due to variant consequences reviewed by ClinVar experts or having major consensus across most widely used in-silico pathogenicity prediction tools. This variant is not cited in PubMed clinical. The variant is not hitting any domain and is present in the conserved region. This is not reported in the ACMG list of incidental findings but reported in COSMIC-Cancer Gene Census. The variant is present in the healthy population databases such as 1000 Genomes, ExAC, or ESP with 0.256626074499 minor allele frequency.

Figure 21:
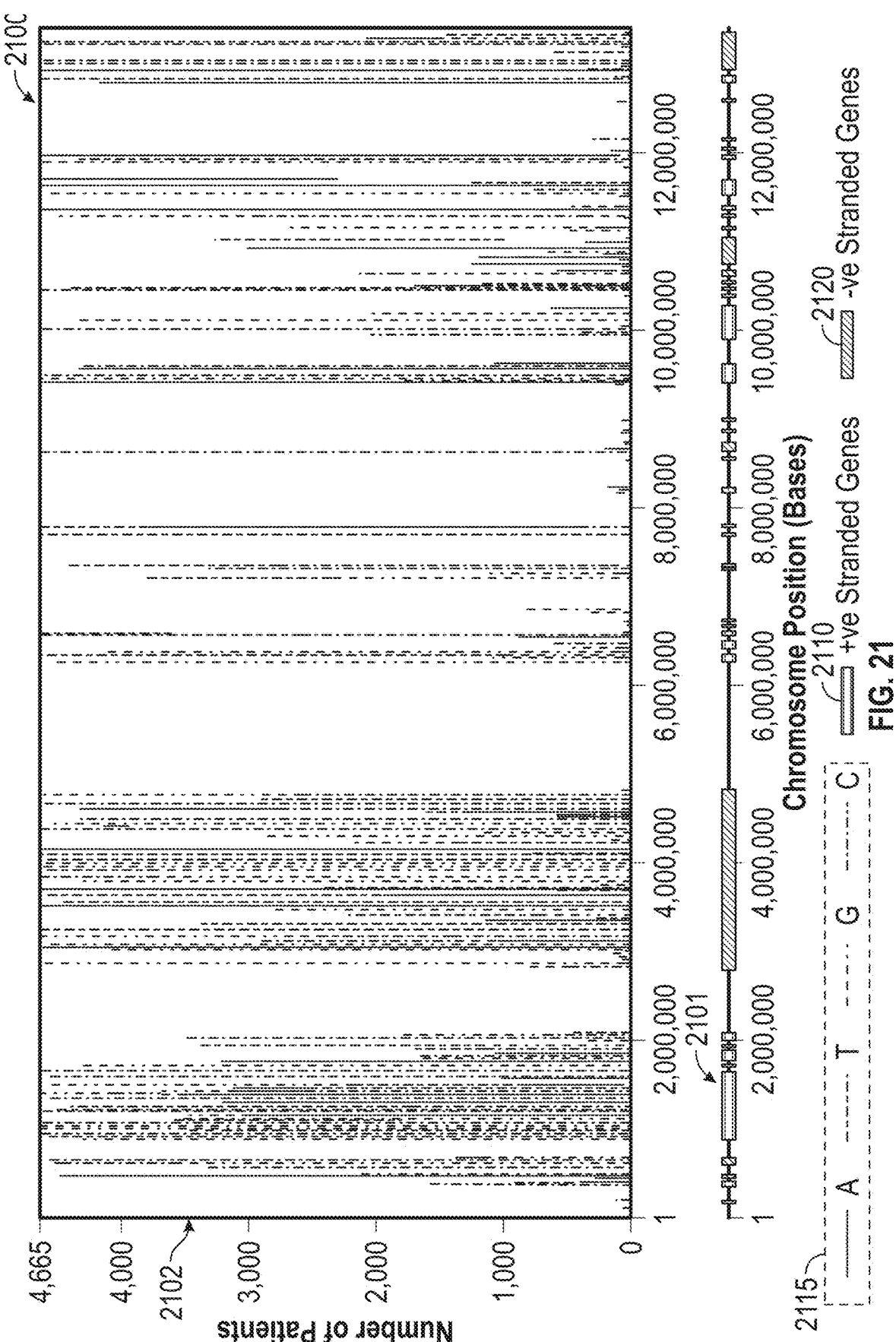
FIG. 21 illustrates a variant density plot in a chromosome with positive and negative strand genes, according to some embodiments.

FIG. 21 illustrates a variant density plot 2100 in a chromosome 2101 with positive 2110 and negative 2120 strand genes, according to some embodiments. A frequency value 2102 indicates the number of patients or subjects having a given base 2115 (e.g., A, T, G, C) for a given strand gene (positive or negative). The user may select the chromosome to inspect with variant plot 2100. Moreover, any portion of the genome can be magnified, revealing finer structures and details, including the regulatory and splicing patterns of the genes. Variant details such as reference and altered base 2115, type of variant, and variant position in chromosome 2101 are displayed within a block and are displayed on hovering a pointer over a desired variant. Variant density plot 2100 may be associated with a selected cohort of subjects or individuals selected by a cohort genomics module (e.g., cohort genomics module 260-6).

Figure 22:
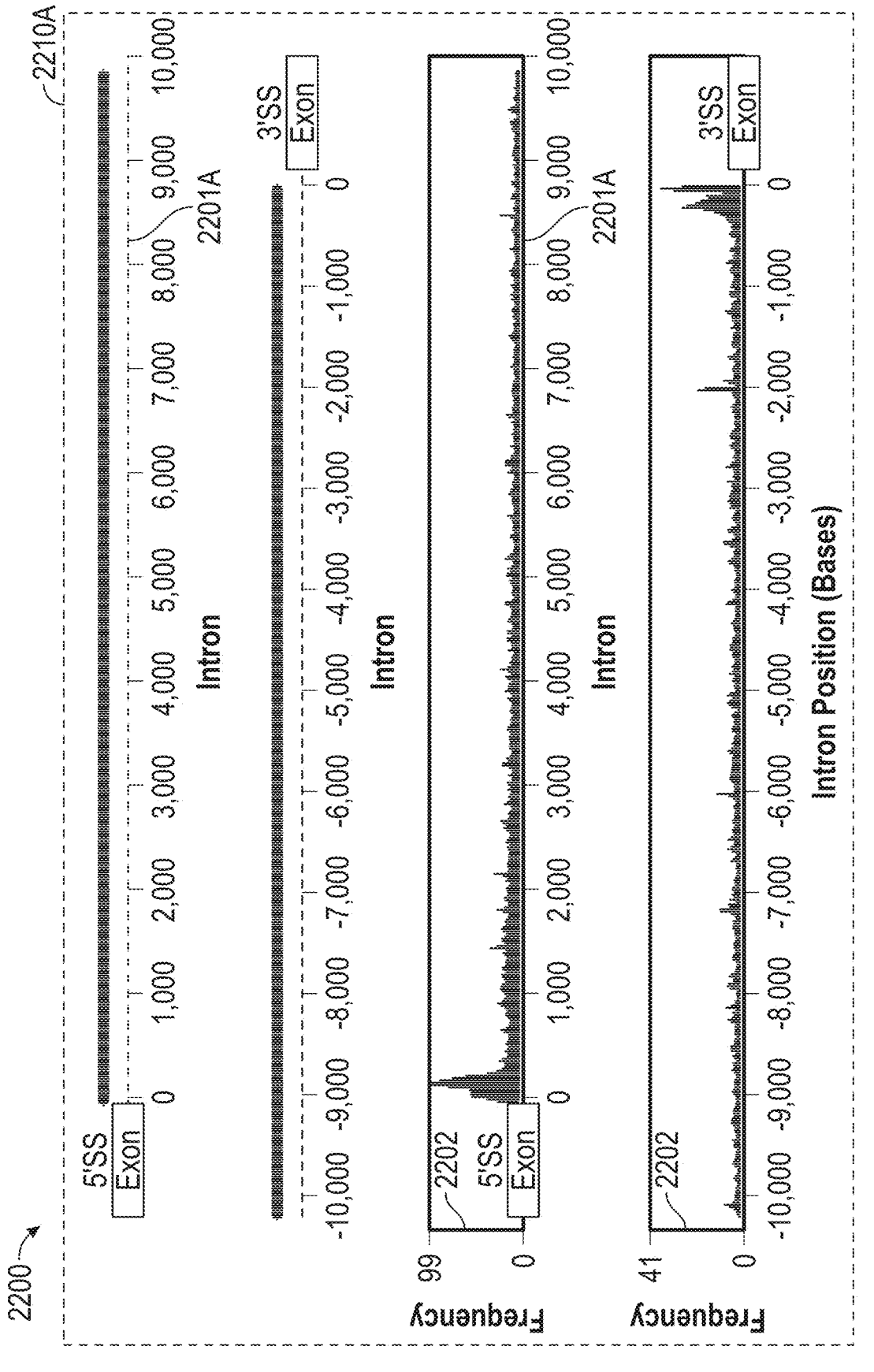
FIG. 22 illustrates a distribution of mutations in the introns and exons, according to some embodiments.
Figure 22:
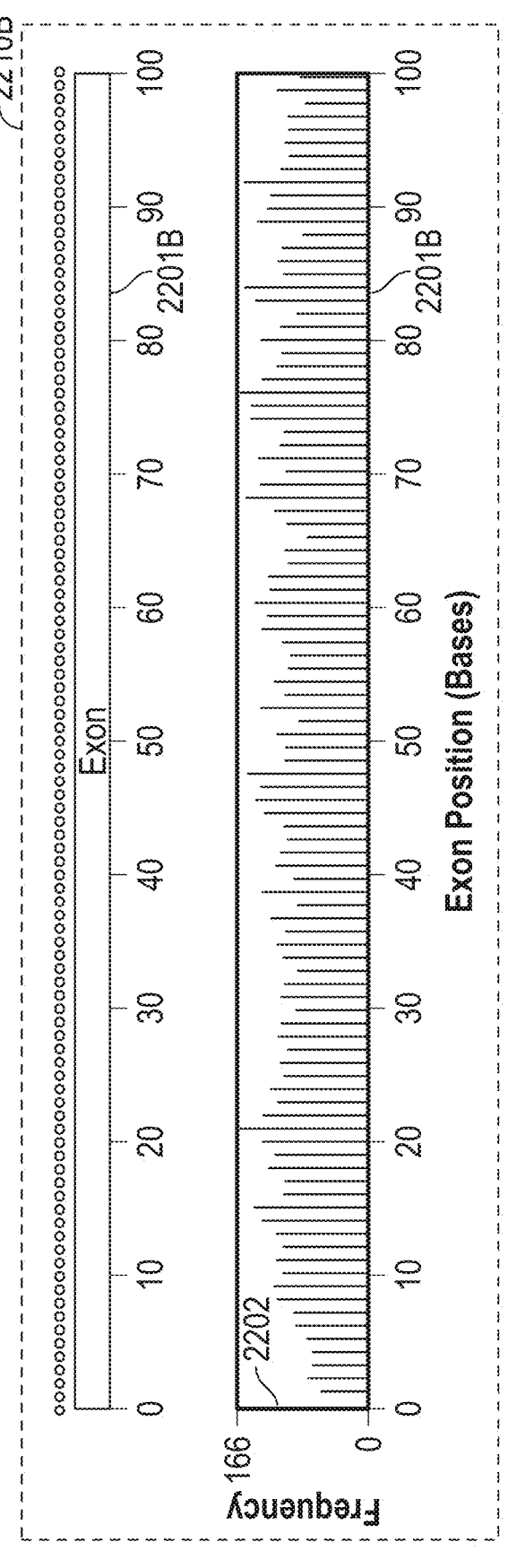

FIG. 22 illustrates a distribution 2200 of mutations in the introns 2210A and exons 2210B, representing a mutation distribution within an exon and an intron, according to some embodiments. Distribution 2200 indicates a frequency 2202 and an intron position 2201A or an exon position 2201B for a mutation. Frequency 2202 may be determined based on a subject population or cohort selected by a cohort genomics module (e.g., cohort genomics module 260-6).

Figure 23:
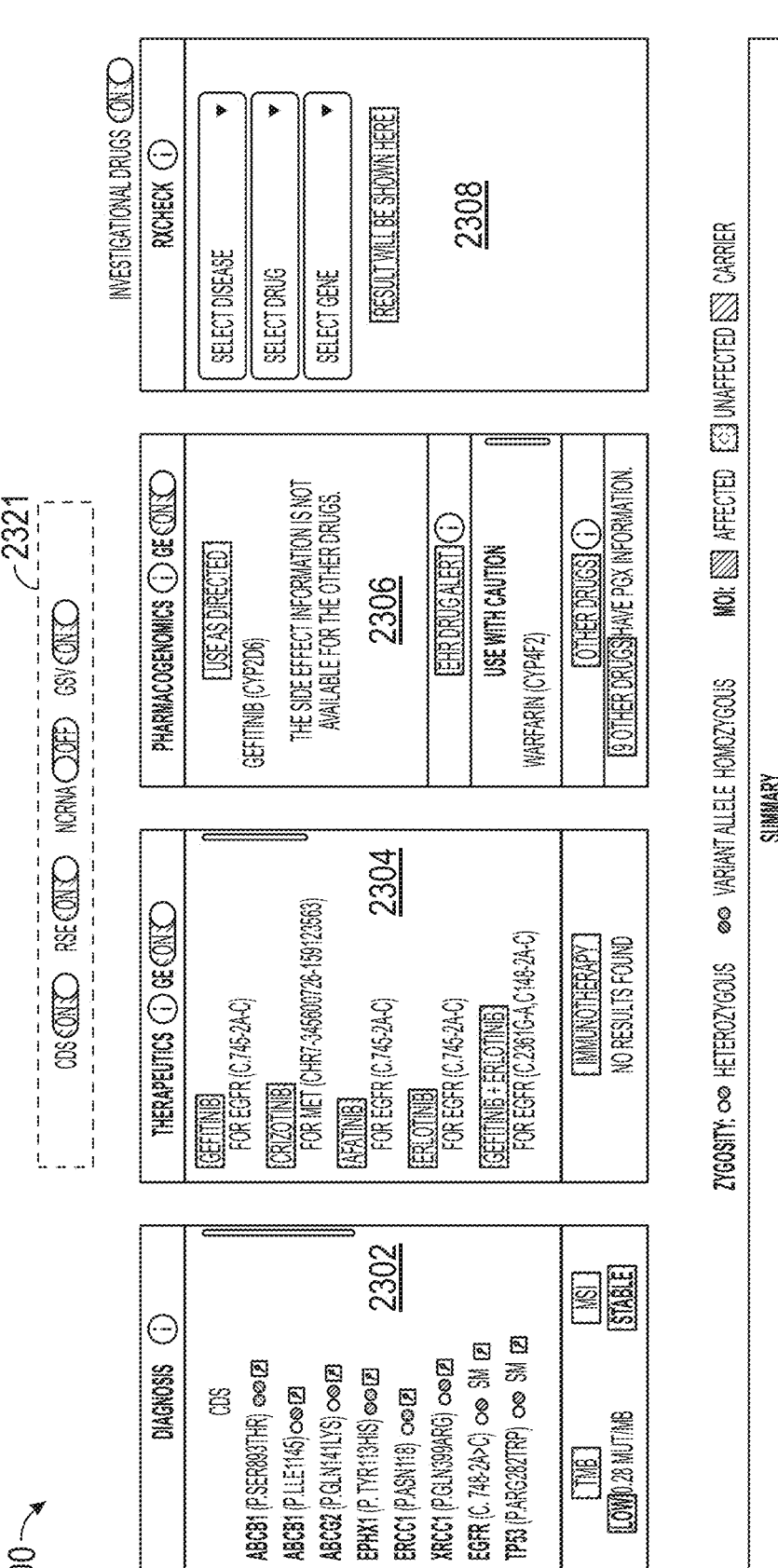
FIG. 23 illustrates a strip including an overview of diagnosis, therapeutics, pharmacogenomics and Rx check, according to some embodiments.

FIG. 23 illustrates a strip 2300 including an overview of diagnosis 2302, therapeutics 2304, pharmacogenomics 2306, and Rx check 2308, according to some embodiments. Toggles 2321 enable the user to select CDS, RSE, ncRNA, or GSV. In some embodiments, strip 2300 is configured to offer a simplified summary of a subject's genome analysis (e.g., "a 30 second summary").

Therapeutics block 2304 enables the display of therapeutic drugs based only on particular mutations of the genes (regardless of whether they are pathogenic or not) when it is turned off, and based only on the pathogenic mutations of genes, when it is turned on. Pharmacogenomics block 2306 enables the display of a pharmacogenomics report, where the pathogenic mutations in at least one of the genetic elements along with the zygosity information are considered to predict the adverse drug response phenotypes and recommendations. Pharmacogenomics block 2306 displays a pharmacogenomics reporting—the (*) nomenclature system—. In some embodiments, pharmacogenomics block 2306 may include an EHR Drug Alert. Accordingly, drugs being consumed by the patient and reported in the patient EHR metadata are processed by the pharmacogenomics module (e.g., pharmacogenomics module 260-5) to predict adverse drug reactions (drug response phenotypes). These drugs and their recommendations are reported within the EHR Drug Alert block. In some embodiments, pharmacogenomics block 2306 may report other drugs. Accordingly, drugs approved by FDA and other agencies, or under investigation, having pharmacogenomics recommendations based on the mutations in the drug metabolizing genes in the patient are shown in a separate section that can be accessed by clicking on the link provided.

A toggle menu 2321 enables the user to select a CDS, RSE, ncRNA, and GSV data. A summary block 2330. Summary block 2330 includes points from the clinical report blocks such as diagnosis, therapeutics, and pharmacogenomics is shown here for a quick perusal by the clinician or provider. A CDS block 2350 indicates, for the selected search from toggle menu 2321, the salient aspects of the genome analysis. For example, CDS block 2350 may indicate, as a diagnosis, that the patient has mutations in specific genes (further indicating the position and nature of the mutations), and that such mutation may be associated with certain disease (e.g., a type of cancer, and the like). In some embodiments, summary block 2350 may indicate, in therapeutics, a recommended type of drug, or a contraindicated drug (if available), or even if there are any investigational drugs that could potentially benefit the patient. Summary block 2350 may also include an immunotherapy recommendation and clinical trials that the patient may be able to participate in, based on therapeutics and immunotherapy recommendations.

In some embodiments, CDS block 2350 is displayed for a quick perusal by the clinician or provider. In some embodiments, summary block 2350 may include a report from a cohort genomics module (e.g., cohort genomics module 260-6, including a family genomics report), including various blocks for diagnosis, therapeutics, and pharmacogenomics. In these blocks, details such as the frequency of different alleles (RV, VV; R—Reference allele, V—Variant allele), samples, and patients for the genes are provided. Included is also a Summary block with clinically relevant information. In some embodiments, a clinical trial module (e.g., clinical trial module 260-7) may include blocks for high efficacy and high side effects, high efficacy and low side effects, low efficacy and high side effects, low efficacy and low side effects, high efficacy, low efficacy, high side effects, and low side effects are provided with information on frequency of different alleles (RV, VV), samples, and patients for the genes are provided.

FIG. 24 illustrates steps in a method 2400 for studying a disease or other inherited trait using a gene explorer platform, according to some embodiments. Each one or more of the steps in method 2400 may be performed at least partially by a processor executing instructions stored in a memory of a client device or a server communicatively coupled with each other via communications modules accessing a network, as disclosed herein (e.g., processors 212, memories 220, communications modules 218, client device 110, and server 130). In some embodiments, at least one or more of the steps in method 2400 may be performed by an application hosted by the server and installed in the client device, the application including a graphic display for illustrating the results of at least one or more of the steps in method 2400 (e.g., application 222 and graphic payload 225). In some embodiments, method 2400 may be at least partially performed by a genome analysis engine in the server, the genome sequence analysis engine including a sequence scoring tool, a mutation tool, a statistics tool, and an algorithm tool (e.g., genome sequence analysis engine 242, sequence scoring tool 244, mutation tool 246, statistics tool 248, and algorithm 250). Further, in some embodiments, one or more of the steps in method 2400 may be performed by a gene discovery module, an EHR module, a launch module, a report module, a pharmacogenomics module, a cohort module, a clinical trial module, a TMB/MSI module, a rearrangement module, a pathogenome module, a pathogene module, and a dark matter module interacting with a genome analysis engine, consistent with the present disclosure (e.g., genome analysis engine 255 and modules 260). In some embodiments, a method consistent with the present disclosure may include at least one of the steps in method 2400 performed in any order, simultaneously with one another, quasi-simultaneously, or overlapping in time.

Step 2402 includes receiving a nucleotide string including a plurality of nucleotides from at least a portion of one or more individual patients genome, wherein the portion of the genome includes at least one of the following elements: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a dark matter genome.

Step 2404 includes identifying a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof.

Step 2406 includes assigning each identified variant a score based on a location of a variant and a predicted functional consequence.

Step 2408 includes determining a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory.

Step 2410 includes identifying at least one phenotype such as a disease, a drug response, a therapeutic indication, and a harmful side effect of a medication or substance, based on the strength of the variation identified in one or more patients.

Step 2412 includes displaying, in a graphic unit interface of a client device, said nucleotide string, the identified variants, and the at least one phenotype, in one or more genetic elements for the one or more individual patients.

FIG. 25 illustrates steps in a method 2500 for applying a gene explorer platform to identify structural variants and phenotypic traits in a population cohort, according to some embodiments. Each one or more of the steps in method 2500 may be performed at least partially by a processor executing instructions stored in a memory of a client device or a server communicatively coupled with each other via communications modules accessing a network, as disclosed herein (e.g., processors 212, memories 220, communications modules 218, client device 110, and server 130). In some embodiments, at least one or more of the steps in method 2500 may be performed by an application hosted by the server and installed in the client device, the application including a graphic display for illustrating the results of at least one or more of the steps in method 2500 (e.g., application 222 and graphic display 225). In some embodiments, method 2500 may be at least partially performed by a genome sequence analysis engine in the server, the genome sequence analysis engine including a sequence scoring tool, a mutation tool, a statistics tool, and an algorithm tool (e.g., genome sequence analysis engine 242, sequence scoring tool 244, mutation tool 246, statistics tool 248, and algorithm 250). Further, in some embodiments, one or more of the steps in method 2500 may be performed by a gene discovery module, an EHR module, a launch module, a report module, a pharmacogenomics module, a cohort module, a clinical trial module, a TMB/MSI module, a rearrangement module, a pathogenome module, a pathogene module, and a dark matter module interacting with a genome analysis engine, consistent with the present disclosure (e.g., genome analysis engine 255 and modules 260). In some embodiments, a method consistent with the present disclosure may include at least one of the steps in method 2500 performed in any order, simultaneously with one another, quasi-simultaneously, or overlapping in time.

Step 2502 includes receiving a nucleotide string from a subject including multiple nucleotides forming at least one of an exon, at least two introns, at least two splice sites, a promoter site, a silencer site, an untranslated region, a poly-A site, a non-coding RNA site, a branching point site and optionally a cryptic version thereof.

Step 2504 includes identifying, in said nucleotide string, a structural variant based on one or more genes shared by a population of subjects.

Step 2506 includes identifying a phenotype trait based on the structural variant.

Step 2508 includes providing, to a graphic user interface in a client device, a display of the phenotype trait, the one or more genes, and the structural variant. In some embodiments, step 2508 includes identifying the structural variant as a gene fusion between two or more of the genes shared by the population of subjects.

FIG. 26 illustrates steps in a method for scoring the variants of a gene based on a subject response to a disease, according to some embodiments. Each one or more of the steps in method 2600 may be performed at least partially by a processor executing instructions stored in a memory of a client device or a server communicatively coupled with each other via communications modules accessing a network, as disclosed herein (e.g., processors 212, memories 220, communications modules 218, client device 110, and server 130). In some embodiments, at least one or more of the steps in method 2600 may be performed by an application hosted by the server and installed in the client device, the application including a graphic display for illustrating the results of at least one or more of the steps in method 2600 (e.g., application 222 and graphic payload 225). In some embodiments, method 2600 may be at least partially performed by a genome sequence analysis engine in the server, the genome sequence analysis engine including a sequence scoring tool, a mutation tool, a statistics tool, and an algorithm tool (e.g., genome sequence analysis engine 242, sequence scoring tool 244, mutation tool 246, statistics tool 248, and algorithm 250). Further, in some embodiments, one or more of the steps in method 2600 may be performed by a gene discovery module, an EHR module, a launch module, a report module, a pharmacogenomics module, a cohort module, a clinical trial module, a TMB/MSI module, a rearrangement module, a pathogenome module, a pathogene module, and a dark matter module interacting with the genome sequence analysis engine, consistent with the present disclosure (e.g., modules 260). In some embodiments, a method consistent with the present disclosure may include at least one of the steps in method 2600 performed in any order, simultaneously with one another, quasi-simultaneously, or overlapping in time.

Step 2602 includes receiving a nucleotide string from a subject, the nucleotide string including a plurality of nucleotides.

Step 2604 includes identifying, in said nucleotide string, a gene shared by a cohort of subjects sharing a phenotype trait associated with a disease.

Step 2606 includes identifying one or more variants of the gene within the cohort of subjects.

Step 2608 includes associating a score for each of the variants based on a response of the subject to the disease. In some embodiments, step 2608 includes determining a multiplicity of infection of the disease in the subject.

Step 2610 includes providing, to a graphic unit interface in a client device, a display of the gene, the one or more variants, and the scores for each of the variants.

Hardware Overview

Figure 27:
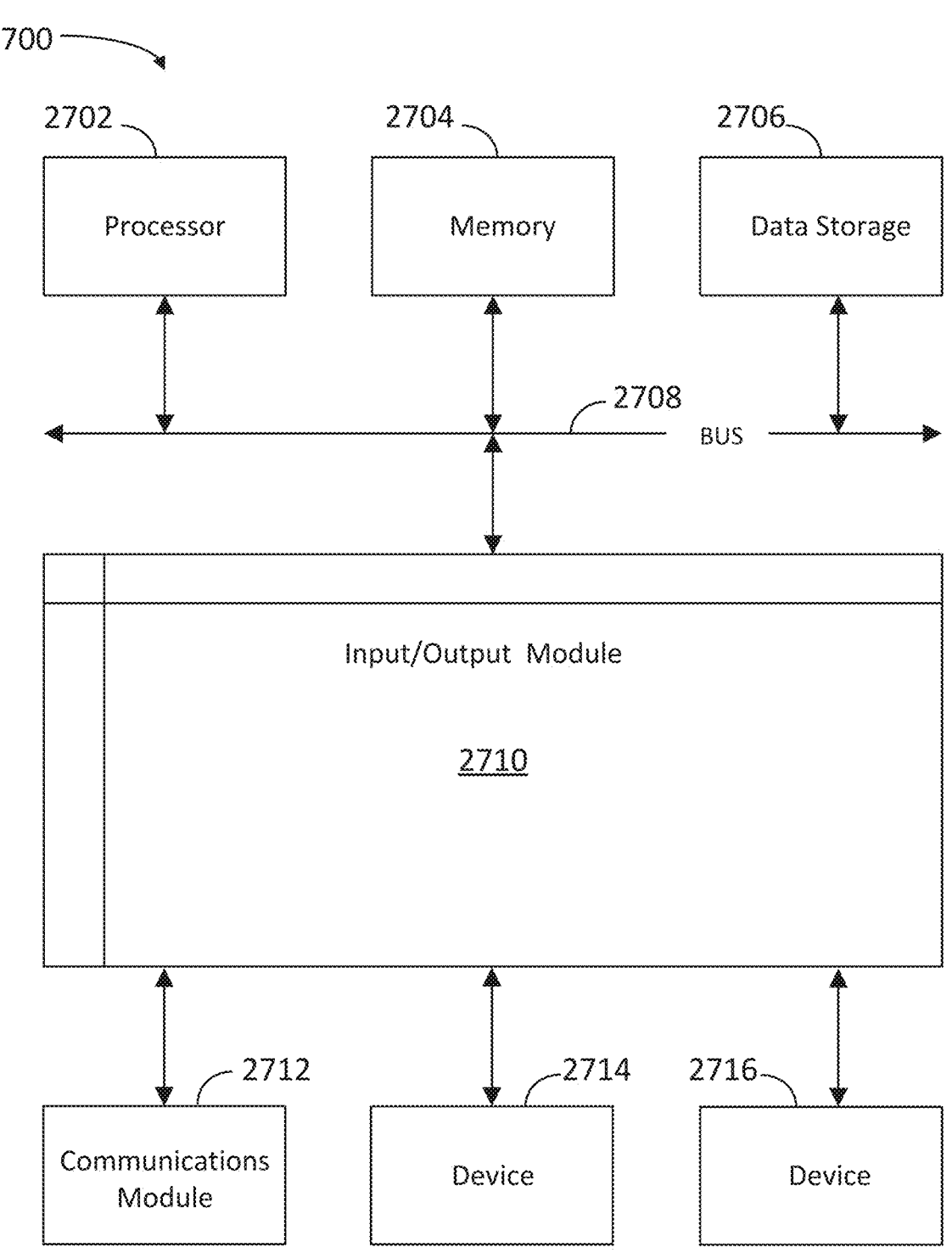
FIG. 27 is a block diagram illustrating an example computer system with which the client and server of FIGS. 1 and 2 and the methods of FIGS. 24, 25, and 26 can be implemented.

FIG. 27 is a block diagram illustrating an example computer system with which the client and server of FIGS. 1 and 2 and the methods of FIGS. 24, 25, and 26 can be implemented. In certain aspects, the computer system 2700 may be implemented using hardware or a combination of software and hardware, either in a dedicated server, or integrated into another entity, or distributed across multiple entities.

Computer system 2700 (e.g., client device 110 and server 130) includes a bus 2708 or other communication mechanism for communicating information, and a processor 2702 (e.g., processors 212) coupled with bus 2708 for processing information. By way of example, the computer system 2700 may be implemented with one or more processors 2702. Processor 2702 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 2700 can include, in addition to hardware, code that creates an execution environment for the computer program in question, e.g., code that constitutes processor firmware, a protocol stack, a database management system, an operating system, or a combination of one or more of them stored in an included memory 2704 (e.g., memories 220), such as a Random Access Memory (RAM), a flash memory, a Read-Only Memory (ROM), a Programmable Read-Only Memory (PROM), an Erasable PROM (EPROM), registers, a hard disk, a removable disk, a CD-ROM, a DVD, or any other suitable storage device, coupled with bus 2708 for storing information and instructions to be executed by processor 2702. The processor 2702 and the memory 2704 can be supplemented by, or incorporated in, special purpose logic circuitry.

The instructions may be stored in the memory 2704 and implemented in one or more computer program products, e.g., one or more modules of computer program instructions encoded on a computer-readable medium for execution by, or to control the operation of, the computer system 2700, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multi paradigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 2704 may also be used for storing temporary or other intermediate information during execution of instructions to be executed by processor 2702.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and inter-coupled by a communication network. The processes and logic flows described in this specification can be performed by one or more programmable processors executing one or more computer programs to perform functions by operating on input data and generating output.

Computer system 2700 further includes a data storage device 2706 such as a magnetic disk or optical disk, coupled with bus 2708 for storing information and instructions. Computer system 2700 may be coupled via input/output module 2710 to various devices. Input/output module 2710 can be any input/output module. Exemplary input/output modules 2710 include data ports such as USB ports. The input/output module 2710 is configured to connect to a communications module 2712. Exemplary communications modules 2712 (e.g., communications modules 218) include networking interface cards, such as Ethernet cards and modems. In certain aspects, input/output module 2710 is configured to connect to a plurality of devices, such as an input device 2714 (e.g., input device 214) and/or an output device 2716 (e.g., output device 216). Exemplary input devices 2714 include a keyboard and a pointing device, e.g., a mouse or a trackball, by which a user can provide input to the computer system 2700. Other kinds of input devices 2714 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 2716 include display devices, such as an LCD (liquid crystal display) monitor, for displaying information to the user.

According to one aspect of the present disclosure, the client device 110 and server 130 can be implemented using a computer system 2700 in response to processor 2702 executing one or more sequences of one or more instructions contained in memory 2704. Such instructions may be read into memory 2704 from another machine-readable medium, such as data storage device 2706. Execution of the sequences of instructions contained in main memory 2704 causes processor 2702 to perform the process steps described herein. One or more processors in a multi-processing arrangement may also be employed to execute the sequences of instructions contained in memory 2704. In alternative aspects, hard-wired circuitry may be used in place of or in combination with software instructions to implement various aspects of the present disclosure. Thus, aspects of the present disclosure are not limited to any specific combination of hardware circuitry and software.

The subject technology is illustrated, for example, according to various aspects described below. Various examples of aspects of the subject technology are described as numbered clauses (clause 1, 2, etc.) for convenience. These are provided as examples, and do not limit the subject technology.

In one aspect, a method may be an operation, an instruction, or a function and vice versa. In one aspect, a clause may be amended to include some or all of the words (e.g., instructions, operations, functions, or components) recited in other one or more clauses, one or more words, one or more sentences, one or more phrases, one or more paragraphs, and/or one or more clauses.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to many configurations of the subject technology. A disclosure relating to such phrase(s) may apply to many configurations, or one or more configurations.

A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Under-lined and/or italicized headings and subheadings are used for convenience only, do not limit the subject technology, and are not referred to in connection with the interpretation of the description of the subject technology. Relational terms such as first and second and the like may be used to distinguish one entity or action from another without nec-essarily requiring or implying any actual such relationship or order between such entities or actions. Many structural and functional equivalents to the elements of the various con-figurations described throughout this disclosure that are known or later come to be known to those of ordinary skill in the art are expressly incorporated herein by reference and intended to be encompassed by the subject technology. Moreover, nothing disclosed herein is intended to be dedi-cated to the public regardless of whether such disclosure is explicitly recited in the above description. No clause ele-ment is to be construed under the provisions of 35 U.S.C. § 112, sixth paragraph, unless the element is expressly recited using the phrase "means for" or, in the case of a method clause, the element is recited using the phrase "step for."

While this specification contains many specifics, these should not be construed as limitations on the scope of what may be described, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially described as such, one or more features from a described combination can in some cases be excised from the combination, and the described combination may be directed to a subcombination or variation of a subcombina-tion.

The subject matter of this specification has been described in terms of particular aspects, but other aspects can be implemented and are within the scope of the following clauses. For example, while operations are depicted in the drawings in a particular order, this should not be understood as requiring that such operations be performed in the par-ticular order shown or in sequential order, or that many illustrated operations be performed, to achieve desirable results. The actions recited in the clauses can be performed in a different order and still achieve desirable results. As one example, the processes depicted in the accompanying fig-ures do not necessarily require the particular order shown, or sequential order, to achieve desirable results. In certain circumstances, multitasking and parallel processing may be advantageous. Moreover, the separation of various system components in the aspects described above should not be understood as requiring such separation in many aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the clauses. In addition, in the detailed description, it can be seen that the description provides illustrative examples and the various features are grouped together in various implementations for the purpose of streamlining the disclosure. The method of disclosure is not to be interpreted as reflecting an intention that the described subject matter requires more features than are expressly recited in each clause. Rather, as the clauses reflect, inven-tive subject matter lies in less than all features of a single disclosed configuration or operation. The clauses are hereby incorporated into the detailed description, with each clause standing on its own as a separately described subject matter.

The clauses are not intended to be limited to the aspects described herein, but are to be accorded the full scope consistent with the language clauses and to encompass many legal equivalents. Notwithstanding, none of the clauses are intended to embrace subject matter that fails to satisfy the requirements of the applicable patent law, nor should they be interpreted in such a way.

RECITATION OF EMBODIMENTS

In a first embodiment, a computer-implemented method includes receiving a nucleotide string including a plurality of nucleotides from at least a portion of one or more individual patients genome, wherein the portion of the genome includes at least one of the following elements: a 5'-UTR, a promoter, an enhancer, a silencer, an exon, an intron, a coding sequence, a non-protein coding RNA, a splice accep-tor, a splice donor, a branch point site, a 3'-UTR, a poly-A addition site or signal, or a cryptic version thereof, from a known protein coding gene and a non-protein coding RNA gene, and within the genes not yet identified in a dark matter genome. The computer-implemented method also includes identifying a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof. The computer-implemented method also includes assigning each identified variant a score based on a location of a variant and a predicted functional conse-quence, determining a strength of a variation responsible for a trait or phenotypic manifestation of the variants based on a similarity score by executing instructions from an algo-rithm such as Shapiro-Senapathy algorithm, a MaxEntScan algorithm, and NNSplice algorithm, stored in a memory, identifying at least one phenotype such as a disease, a drug response, therapeutic indications, and harmful side effects of a medication or substance, based on the strength of the variation identified in one or more patients, and displaying, in a graphic unit interface of a client device, said nucleotide string, the identified variants, and the at least one phenotype, in one or more genetic elements for the one or more individual patients.

In a second embodiment, a computer-implemented method includes receiving a nucleotide string from a subject including a plurality of nucleotides wherein said nucleotide string includes at least one exon, at least two introns, at least two splice sites, a promoter site, a silencer site, an untranslated region, a poly-A site, a non-coding RNA site, a branching point site, and optionally a cryptic version thereof. The computer-implemented method may include identifying, in said nucleotide string, a structural variant based on one or more genes shared by a population of subjects, identifying a phenotype trait based on the structural variant, and providing, to a client device, a graphic display of the phenotype trait, the one or more genes, and the structural variant.

In a third embodiment, a computer-implemented method includes receiving a nucleotide string from a subject including a plurality of nucleotides, identifying, in said nucleotide string, a gene shared by a cohort of subjects sharing a phenotype trait associated with a disease, identifying one or more variants of the gene within the cohort of patients, associating a score for each of the variants based on a response of the subject to the disease, and providing, to a client device, a graphic display of the gene, the one or more variants, and the scores for each of the variants.

In a fourth embodiment, a system, includes one or more processors, and a memory storing instructions. When the instructions are executed by the one or more processors, they cause the system to: receive a nucleotide string comprising a plurality of nucleotides from at least a portion of one or more individual patients genome, wherein the portion of one or more individual patients genome includes at least one of: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a Dark Matter genome; identify a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof; assign each identified variant a score based on a location of a variant and a predicted functional consequence; determine a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory; identify at least one phenotype such as a disease, a drug response, a therapeutic indications, and a harmful side effects of a medication or substance, based on the strength of the variation identified in one or more patients; and display, in a graphic unit interface of a client device, said nucleotide string, the identified variants, and the at least one phenotype, in one or more genetic elements for one or more individual patients.

In a fifth embodiment, a non-transitory, computer readable medium storing instructions which, when executed by a processor, cause a computer to perform a method, the method includes: receiving a nucleotide string comprising a plurality of nucleotides from at least a portion of one or more individual patients genome, wherein the portion of one or more individual patients genome includes at least one of: a 5'-UTR, a promoter, an enhancer, a silencer, an exon, an intron, a coding sequence, a non-protein coding RNA, a splice acceptor, a splice donor, a branch point site, a 3'-UTR, a poly-A addition site or signal, or a cryptic version thereof, from a known protein coding gene and a non-protein coding RNA gene, and within the genes not yet identified in a Dark Matter genome; identifying a plurality of variants in said nucleotide string by comparing a sequence of said nucleotide string with at least one reference genome, wherein at least one of the variants is in at least one of the 5'-UTR, the promoter, the enhancer, the silencer, the exon, the intron, the non-protein coding RNA, the splice acceptor, the splice donor, the branch point site, the 3'-UTR, the poly-A addition site or signal, or the cryptic version thereof; assigning each identified variant a score based on a location of a variant and a predicted functional consequence; determining a strength of a variation responsible for a trait or phenotypic manifestation of the variants based on a similarity score by executing instructions from an algorithm such as Shapiro-Senapathy algorithm, a MaxEntScan algorithm, and NNSplice algorithm, stored in a memory; identifying at least one phenotype such as a disease, a drug response, a therapeutic indications, and a harmful side effects of a medication or substance, based on the strength of the variation identified in one or more patients; and displaying, in a graphic unit interface of a client device, said nucleotide string, the identified variants, and the at least one phenotype, in one or more genetic elements for one or more individual patients.

Element 1, further including enabling the visualization of many of the patients' meta information in tabular and graphical illustrations, and providing the ability to launch projects in the present disclosure. Element 2, further including providing the ability to automatically download any and many data from the IEHR into the GE EHR system that are relevant to genomics, and providing various kinds of analytical capabilities and metrics for the administration personnel and clinical researchers. Element 3, further including determining the frequency of mutations, and genes or patients with mutations in each of the coding sequence, non-coding sequence, regulatory and splicing elements in different protein coding genes, non-coding RNA genes, dark matter genes, individually or in combination, and depicting the frequencies and the details of their genetic and genomic locations for various genes for the different genetic elements in various tabular and graphical illustrations. Element 4, further including determining the frequency of patients including a defective domain due to mutations in at least one of the genetic elements in the genes coding for that domain, and depicting the frequencies and the details in various tabular and graphical illustrations. Element 5, further including determining the frequency of patients including defective domains and the genes containing them, due to mutations in at least one of the genetic elements in the genes coding for that domain, and depicting the frequencies and the details in various tabular and graphical illustrations. Element 6, further including determining the frequency of patients including defective genes within a gene family due to mutations in at least one of the genetic elements in the genes in the gene family, and depicting the frequencies and the details in various tabular and graphical illustrations. Element 7, further including determining the frequency of patients including of one or more defective pathways due to mutations in at least one of the genetic elements in the genes constituting the pathway, and depicting the frequencies and the details in various tabular and graphical illustrations. Element 8, further including graphically and tabularly depicting the statistics of frequencies of mutations, genes, or patients with mutations, and optionally mutated genes in gene families, in different protein coding genes, non-coding RNA genes, and dark matter genes affecting the domains and pathways, in various graphics and plots. Element 9, further including, determining the genes that exhibit high number of mutations across different genetic elements, individually or in combination, in one or more patients and graphically and tabularly depicting the statistics of frequencies of mutations, genes, or patients with mutations. Element 10, including, graphically plotting the mutation distribution within introns and exons within one or more genes from one or more patients represented by one exon for many exonic mutations, and one intron for many intronic mutations, and optionally whose lengths are normalized to a unit length (e.g., 100) and different possible variations in representing the distribution in one exon and two introns or one intron and two exons. Element 11, further including, detecting the genes including mutations in at least one of the genetic elements in two or more patients, based on the frequency of mutated genes, that are causal of a disease, therapeutic indications, or drug response phenotype. Element 12, further including, detecting the biochemical function whose defect or alteration caused a disease, based on highly mutated genes in at least one of the genetic elements in two or more patients, with the underlying disease. Element 13, further including, detecting the biochemical function whose defect or alteration caused a therapeutic indication or drug response phenotype, based on highly mutated genes in at least one of the genetic elements in two or more patients, with the underlying therapeutic indication or drug response phenotype. Element 14, further including, detecting a disease in an individual based on the presence of one or more genes from a set of highly mutated genes in at least one of the genetic elements in a cohort of patients with the same disease. Element 15, further including, detecting a therapeutic or drug response phenotype in a patient based on the presence of one or more genes from a set of highly mutated genes in at least one of the genetic elements in a cohort of patients with the same therapeutic or drug response phenotype. Element 16, further including, grouping the cohort of patients into various categories of drug response phenotypes, such as high, low, and medium levels of Adverse Drug Reactions (harmful side effects), or high, low, and medium levels of drug efficacy, and correlating the phenotypes with genes highly mutated in different genetic elements. Element 17, determining the likelihood of a splice site mutation to skip the exon based on the inherent score of a splice site and its neighboring cryptic splice sites, and the inherent score of an exon and the neighboring exons. Element 18, determining the likelihood of a protein becoming defective, based on the frequency of particular splice site mutations causing splicing aberrations in a large population of patients with an underlying disease, and the application of this information to predict a defective protein and causation of disease in a new patient. Element 19, including, determining the top ranking exons based on the scores of the likelihood of an exon to cause a defective protein, depending on the frequency of particular splice site mutations causing splicing aberrations in a large population of patients with an underlying disease, and the application of this information to predict a defective protein and causation of disease in a new patient. Element 20, further including, ascribing scores for deleteriousness of a mutation based on the invariability of the amino acid position at which a mutation occurs to determine the degree of deleteriousness of a patient mutation. Element 21, determining that mutations in different genes that fall into a minimal category of cellular roles, such as cell structure, cell function, and transcriptional regulation, are required to cause a disease or cancer in a patient, and developing a gene panel for each of these categories, and applying this information to identify the disease in a new patient. Element 22, including tabulating and graphically representing the genes from categories such as cell structure, cell function, and transcriptional regulation, including mutations across many of the genetic elements in one or more patients. Element 23, including determining a gene signature as a combination of genes from categories such as cell structure, cell function, and transcriptional regulation, including mutations in at least one of the genetic elements in one or more patients, and tabulating and graphically displaying them. Element 24, including determining that at least one gene from each of the categories such as cell structure, cell function, and transcriptional regulation, should be mutated to initiate and establish a cancer or disease in a patient, indicating a gene signature, and applying this signature to identify a cancer or a disease in a new patient. Element 25, including detecting cancer in a patient based on the mutations in at least one of the genes from each of the gene panels of categories such as cell structure, cell function, and transcriptional regulation, and tabulating and graphically displaying them. Element 26, wherein the initiation and establishment of a cancer or non-cancer disease, is dependent upon more than one gene being mutated. It indicates that minimal cell structure and functions has to be disruptive to achieve the disease. Based on the number of genes mutated from these categories, a score can be assigned for the likelihood of a disease in a patient, and using this score to determine and assign a likelihood for the occurrence of a disease in a new patient. Element 27, wherein the scores for different genes may vary depending on its importance in the cellular structure, function, and regulation. In addition, they can vary based on the frequency of these genes occurring in a large population exhibiting a disease. Element 28, including detecting a probability score of a cancer or disease in a patient based on the score for the likelihood of a cancer or disease determined from the number of mutated genes in a minimal category of cellular structure, function, and transcriptional regulation. Element 29, including detecting and predicting the possibility of a cancer or disease in a patient, based on the score for the likelihood of a cancer or disease determined from the number of mutated genes with affected status in a disease-gene-panel or within a gene signature. Element 30, including determining the frequency of combination of genes with mutations in at least one of the genes from the gene panel of a particular cancer type, in a large population of patients, and identifying the singlet, doublet, triplet, or higher number of combinations of genes that occur at a frequency greater than a threshold from the population of patients. Element 31, including determining the frequency of combination of genes with mutations in at least one of the genes from the gene panels of multiple cancer types, in a large population of patients, and identifying the singlet, doublet, triplet, or higher number of combinations of genes that occur at a frequency greater than a threshold from the population of patients. Element 32, including, determining the frequency of combination of genes with mutations in at least one of the genes from the gene panel of a particular disease (hypertrophic cardiomyopathy) or disease type (many cardiac diseases), in a large population of patients, and identifying the singlet, doublet, triplet, or higher number of combinations of genes that occur at a frequency greater than a threshold from the population of patients. Element 33, including developing a repository of combinations of genes with mutations from one or more gene panels for a disease, detected in a large population of patients, and using this repository to predict that disease in a new patient. Element 34, further including displaying by tabular and graphical illustrations the highly mutated genes in at least one of the genetic elements, in two or more patients exhibiting a particular disease. Element 35, further including displaying by tabular and graphical illustrations the highly mutated genes containing a defective domain due to mutations in at least one of the genetic elements, in two or more patients exhibiting a particular disease. Element 36, further including displaying by tabular and graphical illustrations the highly mutated genes involved in defective pathways due to mutations in at least one of the genetic elements, in two or more patients exhibiting a particular disease. Element 37, further including displaying by tabular and graphical illustrations the metrics, statistics, and patients' IDs containing mutated genes from the signatures of minimal sets of one to multiple genes, that are indicative of a disease. Element 38, further including displaying by tabular and graphical illustrations the metrics, statistics, and patients' IDs containing the mutations in at least one of the genetic elements causing aberrations such as exon skipping, intron retention, and cryptic exon creation, that are indicative of a disease. Element 39, further including displaying a concise description of a summary of many of the findings from cohort analysis. Element 40, including displaying the diagnostic, therapeutic, PGx genes in a cohort of patients with a particular disease, and the mutation and patient frequencies in different blocks in a single view. Element 41, further including displaying the findings from a cohort analysis in blocks visualizable within a single view, consisting of genes that are indicative of a disease, therapeutic drugs, and harmful side effects (pharmacogenomics), based on the highly mutated genes in at least one of the genetic elements from a cohort of two or more patients. Element 42, further including determining the genes that are highly mutated in the group of patients with high side effects and the genes that are highly mutated in the group of patients with least side effects, and determining the mutually exclusive genes from the two lists as the indicator of adverse effects or least side effects for that drug. Element 43, further including determining the genes that are highly mutated in the group of patients with high efficacy and the genes that are highly mutated in the group of patients with least efficacy, and determining the mutually exclusive genes from the two lists as the indicator of high or low efficacy for that drug. Element 44, further including determining the genes that are highly mutated in the group of patients with high side effects, as the indicator of adverse side effects for a drug. Element 45, further including determining the genes that are highly mutated in the group of patients with high side effects, and the presence of no mutations in these genes as the indicator of least side effects for a drug. Element 46, further including predicting or diagnosing the level of side effects for a drug in a patient, based on the presence of mutations in at least one of the genes from the highly mutated genes in the group of patients with high side effects. Element 47, further including, predicting or diagnosing the presence of no or least side effects in a patient for a drug, based on the presence of mutations in at least one of the genes from the highly mutated genes in the group of patients with least side effects, or the absence of mutations in at least one of the genes from the highly mutated genes in the group of patients with most side effects. Element 48, further including, predicting or diagnosing the presence of high efficacy in a patient for a drug, based on the presence of mutations in at least one of the genes from the highly mutated genes in the group of patients with high efficacy, or the absence of mutations in at least one of the genes from the highly mutated genes in the group of patients with least or no efficacy. Element 49, further including predicting or diagnosing the presence of least side effects for a drug in a patient, based on the presence of mutations in at least one of the genes from the least mutated genes in the group of patients with high side effects. Element 50, including graphically marking the mutations on the genome of the family members and tracing the inheritance pattern of disease-causing mutations in the patient/child. Element 51, wherein the multiple individuals include the father, mother, child, and other extended family members. Element 52, wherein the mutations, zygosity, mode of inheritance, and the traits are traced through the family members to detect a pattern of inheritance of the trait occurring in a child. Element 53, further including determining the causal gene(s) for a rare disease or a disease with unknown genes or known genes with unknown mutation, based on tracing the inheritance of the genes through each generation towards the direction of affected individual(s), whereby the number of causal genes is reduced by 50% by each parental or sibling relationship, or 25% by each relationship one step removed. Element 54, further including graphically displaying the pedigree chart for many of the members in the family and marking the affected members to demonstrate the tracing of disease through the relatives based on the different genetic elements of the genes, wherein tracing of each of the genetic elements can be shown by clicking a gene on the child's genome plot or tabular display. Element 55, including enabling the user to navigate through the application using voice commands Element 56, including enabling the user to go directly to a desired result swiftly based on voice commands by the user based on built-in data connections. Element 57, including enabling the user to use voice commands to know the details of any gene such as gene name, length, number of exons, number of domains, protein length, and gene function, and further enabling the user to stop or know more details of the same or different genes, mutations, disease, drugs, therapeutics, and harmful side effects. Element 58, including enabling a special clinical genomics intelligence to detect the appropriate commands with details of variant, mutation, disease, many different genetic elements, zygosity, MOI, cohort, clinical trials, Family genomics, drugs, therapeutics, PGx, side effects, dose, etc. Element 59, including enabling a special clinical genomics intelligence to detect the appropriate command from various types of commands used by various users, wherein they use different accents, use of words, and unnecessary words, and respond appropriately based on the command Element 60, including enabling the user to provide a voice command and receive an appropriate report that is read to the user by a voice through voice to text and text to voice functionalities. Element 61, including designing, implementing, and enabling clinic-centric, patient-centric, clinician-centric, and genome-centric questions and answers through voice navigation. Element 62, including detecting the occurrence of cancer in an individual, by giving a score for each of a set of genes based on the number of pathogenic mutations, in CDS and regulatory and splicing elements, within that gene in a set of patients (or samples) reported by a cancer gene database such as COSMIC. Element 63, further including, selecting a list of genes associated with cancer as the "master cancer gene set" (lookup). Element 64, including determining the number of patients (or samples) with pathogenic mutations in each gene from the cancer-gene lookup, calculated from a set of healthy individuals (say 1000) and a set of patients affected by cancer or any disease (say 1000). Element 65, including determining the total number of patients from many of the cancer genes occurring in the population of individuals from the healthy and cancer individuals. Element 66, including determining the cancer-gene score (%) for normal individuals=(total # of patients in many of the genes in the healthy population/# of genes)×100. Element 67, including determining the cancer-gene score (%) for cancer individuals= (total # of patients in many of the genes in the cancer population/# of genes)×100. Element 68, including determining the threshold indicator for a cancer to be a value above the value for normal individuals (or Normal value+ base) (e.g., if normal=40 & cancer=80, then any value >50 is cancer). Element 69, including normalizing the score between the normal population (say 40%) and the cancer population (say 80%) into 0% and 100%. Element 70, including determining the probability for an individual to have cancer from 0 to 100% based on where the individual's value falls in this spectrum of normalized score. Element 71, including determining the probability in another way by using the list of genes in a cancer type as a signature with their weights (i.e., # of patients for each gene) to compare the cancer genes from a patient and determine a cancer probability score for the patient by adding the weights for the patient genes. Element 72, including determining the threshold that will be the indicator of presence of a cancer, based on the scores for the genes from the gene lookup, calculated from healthy individuals and the patients affected by cancer. Element 73, including identifying the most frequently mutated genes from the cohort of patients with a disease by subtracting the genes from the gene panels of common diseases. Element 74, including determining the zygosity of these mutated genes in a population of patients with a disease. Element 75, including, when the zygosity of a highly frequent gene is mostly R/V, then the mode of inheritance of that gene will be autosomal dominant (AD). Element 76, including, when the zygosity of a highly frequent gene is mostly V/V, then the mode of inheritance of that gene will be autosomal recessive (AR). Element 77, further including identifying the most frequently mutated genes from the cohort of patients with a disease by subtracting the genes from the gene panels of common diseases, and determining the zygosity of each of these genes. Element 78, further including determining the inheritance pattern (MOI) of a gene based on the frequency of its zygosity (R/V or V/V), wherein a high frequency of R/V (e.g., in 80% of patients) would indicate the gene to be Autosomal Dominant (AD) and a high frequency of V/V (e.g., in 80% of patients) would indicate the gene to be Autosomal Recessive (AR). Element 79, further including, if the zygosity of a highly frequent gene is mostly V/V, then the mode of inheritance of that gene will be autosomal recessive (AR).

What is claimed is:

1. A computer-implemented method comprising:

receiving a nucleotide string comprising a plurality of nucleotides from at least a portion of one or more patients genome, wherein the portion of the genome includes at least one genetic element of: a 5'-UTR, a promoter, an enhancer, a silencer, an exon, an intron, a coding sequence, a splice acceptor, a splice donor, a branch point site, a 3'-UTR, a Kozak sequence, a poly-A addition site or signal, or a cryptic version thereof, from a known protein coding gene or a regulatory, splicing, or functional element of a non-protein coding RNA gene, and within genes not yet identified in a Dark Matter genome;

identifying a plurality of variants from the nucleotide string;

determining, from the plurality of variants, deleterious or strength altering variants, or variants of unknown significance (VUS) in at least one genetic element in at least one gene of the portion of the genome, by computing element-specific scores using position weight matrices (PWMs) and executing instructions from at least one of Shapiro-Senapathy, MaxEntScan, and NNSplice algorithms to assess a likelihood of functional changes in splice acceptor, splice donor, branch point, promoter, 5' and 3' UTR, and poly-A sites or signals, and classifying the variants based on differences between original and observed scores;

creating a user interface for summarily depicting details in a clinical genomic decision support system, wherein clinical genomic data comprising genes, genetic elements, mutations, pathogenicity, alleles, zygosity, mode of inheritance (MOI), domains, tumor mutation burden (TMB), microsatellite instability status (MSI), pathways, biochemical functions, or drugs, indicate at least one phenotype comprising disease causation, therapeutics, harmful side effects, in the one or more patients, wherein the user interface draws a chromosome or a genome on a single line drawn to scale and overlays interactive tracks, renders, on user interaction, aligned sequence read evidence from aligned sequence data (SAM/BAM) and variant call files (VCF), and automatically updates overlays and aligned-read evidence in real time responsive to user interactions and availability of updated analysis outputs; and presenting the details in the user interface based on different blocks in different graphical notations and color codes, and using scroll bars and sub blocks within each block, wherein the different blocks are displayable in a single view for a clinical decision, or in separate views for analysis.

2. The computer-implemented method of claim 1, wherein creating the user interface comprises:

identifying a mutated gene in the one or more patients from a disease gene panel as a causative gene, gene-drug panel as therapeutic or actionable drugs, or pharmacogene panel to determine a harmful side effect or a dosage of a drug; and representing the causative genes, actionable genes, mutations and drugs, or ADR causing pharmacogenes in separate blocks, in different graphical notations and color codes, and using scroll bars and sub blocks.

3. The computer-implemented method of claim 1, wherein creating the user interface comprises:

depicting in a graphical block of the user interface, the mutated gene, and representation of information such as MOI, zygosity, mutations, domains, pathways, biochemical functions, or effective drugs, contraindicated drugs, approved agencies, mechanism of action, or frequencies, in different graphical notations and color codes, and using scroll bars and sub blocks.

4. The computer-implemented method of claim 1, wherein creating the user interface comprises:

providing a clinical trials graphical block of the user interface for presenting available clinical trials information based on genetic information of the one or more patients, or clinically relevant information, in the different graphical notations and color codes, and using the scroll bars and sub blocks; and providing clinical trial information based on the pathogenicity or strength altering mutations in at least one of: coding, regulatory or splicing elements.

5. The computer-implemented method of claim 1, wherein creating the user interface comprises:

identifying an indication for a disease, via a first method based on a known mutation in a disease causing gene, or, if that mutation is pathogenic or a strength altering mutation, then, predicting, via a second method, similar pathogenic mutations or similar strength altering mutations throughout the disease causing gene as the indicator of the disease in the one or more patients;

depicting the indication for the disease such as causal genes, mutations, zygosity, MOI and other genetic or clinical features in a graphical block of the user interface using different graphical notations and color codes; and enabling one to choose between the first method and the second method of disease indication using toggle buttons.

6. The computer-implemented method of claim 1, wherein creating the user interface comprises:

identifying a therapeutic indication for a disease, via a first method based on a known mutation in a drug response gene, or, if that mutation is pathogenic or a strength altering mutation, then, predicting, via a second method, similar pathogenic mutations or similar strength altering mutations throughout the drug response gene as the therapeutic indication in the one or more patients; and depicting the therapeutic indication such as actionable genes, mutations, zygosity, MOI, and corresponding drugs, for the disease in a graphical block of the user interface using different graphical notations and color codes, and enabling one to choose between the first method and the second method of the therapeutic indication.

7. The computer-implemented method of claim 1, wherein creating the user interface comprises:

identifying a pharmacogenomics indication for a drug, via a * allele nomenclature method based on a combination of known variants and zygosity in a drug metabolizing gene, or, if any one of the plurality of variants is pathogenic or a strength altering mutation, then, predicting the same pharmacogenomic indication, via a non-nomenclature method, in one or more patients; and depicting the pharmacogenomics indication such as drug metabolizing genes, mutations, zygosity, MOI, and metabolizer status for drugs, in a graphical block of the user interface using different graphical notations and color codes, and enabling one to choose between the * allele nomenclature method and the non-nomenclature method of pharmacogenomics indication using toggle buttons.

8. The computer-implemented method of claim 1, wherein presenting the details in the user interface comprises:

enabling toggling of a summary view of a coding, a regulatory and splicing elements (RSE) of a protein-coding gene or a non-coding RNA gene, and/or a genomic structural variation (GSV) reports, within a diagnosis, therapeutics and pharmacogenomics blocks of the user interface, using toggle buttons;

displaying corresponding detailed reports in tab views, and combinations thereof; and visualizing and analyzing the details of a data element such as the genes, variants, genetic elements, mutations, domains, biochemical functions, drugs, or other genetic or clinical features, in tabular or graphical representations within a modal box, popover, mouseover or in other ways, from a report block, by clicking on the data element.

9. The computer-implemented method of claim 1, wherein presenting the details in the user interface comprises:

selecting a disease from a list of diseases;

generating a clinical genomics report for the selected disease;

providing the clinical genomics report within the user interface or in a downloadable file; and generating another clinical genomics report for each possible disease of the list of diseases with a highest probability of occurrence based on gene mutations in a patient, within the user interface or in a downloadable file.

10. The computer-implemented method of claim 1, wherein presenting the details in the user interface comprises:

enabling a clinician to obtain and review clinical genomics information of the one or more patients within a single view of the user interface such as a strip with multiple separate blocks, or individual block views; and displaying a summary clinical recommendation for the one or more patients such as genes, mutations, zygosity, or MOI, indicative of a disease, therapeutics, drug response phenotypes or the harmful side effects based on mutations in coding, a regulatory and splicing element (RSE), a non-coding RNA, and/or a genomic structural variation (GSV), in the one or more patients, in a single block of the user interface, using toggle buttons or other graphical notation.

11. The computer-implemented method of claim 1, further comprising, selecting a disease or a drug from a list, and displaying therapeutic or PGx gene details including mutations, and other genetic or clinical features, and drug recommendations for efficacy or harmful side effects, for that disease or drug, based on one or more patient's sequence, in a separate block in a same view of diagnosis, therapeutics and pharmacogenomics blocks, for clinician's quick decision making, or in different tabs for elaborate analysis.

12. The computer-implemented method of claim 1, further comprising:

representing novel causal genes specific for a disease, therapeutics and pharmacogenomics determined by analyzing individuals of a cohort with the disease, by subtracting genes for specific or common diseases, in a manner to enable visualization and analysis of clinically relevant data such as frequently mutated genes, variants in different genetic elements, pathogenicity, phenotypes, drugs, zygosity, domains, biochemical functions, pathways, or the one or more patients, or frequencies or statistics thereof, throughout the cohort.

13. The computer-implemented method of claim 1, further comprising:

representing data from different groups of individuals exhibiting varied phenotypes, such as high or low side effects, or high or low efficacy for a drug, of a clinical trial cohort to enable visualization and analysis of genetically or clinically relevant data throughout the clinical trial cohort, in separate blocks for various levels of drug response phenotypes, enabling analysis using Venn diagrams and other statistical and graphical representations, in a single view for quick clinical decision making or separate views for elaborate analysis.

14. A computer-implemented method comprising:

receiving a nucleotide string comprising a plurality of nucleotides from at least a portion of one or more individual patients genome, wherein the portion of the genome includes at least one of: a 5'-UTR, a promoter, an enhancer, a silencer, an exon, an intron, a coding sequence, a splice acceptor, a splice donor, a branch point site, a 3'-UTR, a Kozak sequence, a poly-A addition site or signal, or a cryptic version thereof, from a known protein coding gene or a non-protein coding RNA gene, and within genes not yet identified in a Dark Matter genome;

determining a representation of genetic features or elements of the known protein coding gene or the non-protein coding RNA gene on a gene structure in separate modules or tabs of a user interface, by one or more processors executing instructions from at least one of Shapiro-Senapathy, MaxEntScan, and NNSplice algorithms to compute scores for real and cryptic splice acceptor and donor sites, branch point sites, promoters, 5' and 3' UTRs, and poly-A sites or signals using PWMs;

overlaying, on the user interface, variants from the one or more individuals on each of the genetic elements depicted on the gene structure or in a sequence view, and rendering, on user interaction, aligned sequence read evidence with read counts and allele-frequency values from SAM/BAM and VCF files, and automatically updating overlays and evidence in real time responsive to user interactions and availability of updated analysis outputs; and, providing, on the user interface, a graphic depiction of a mutational impact comprising a defect in the genetic elements, domain, biochemical function, or protein structure, or a transcriptional, translational or splicing aberration in the gene structure or sequence, or a protein structure or sequence.

15. The computer-implemented method of claim 14, wherein overlaying variants comprises:

graphically displaying multiple details of a gene, protein, non-coding RNA functional element, the coding sequence, a real or the cryptic version of a splicing element or a regulatory element of the known protein coding gene or non-protein coding RNA gene, evidence for each of the variants based on next generation sequencing (NGS) read counts, in separate modules or tabs depicting structures and sequences, with corresponding mutations being overlaid.

16. The computer-implemented method of claim 14, wherein providing the graphic depiction of the mutational impact comprises:

graphically displaying mutations on a variable amino acid on a positive signature or a negative signature of a protein or its domains;

determining a deleteriousness corresponding to the variable amino acid based on a mutated amino acid occurring in the negative signature; and determining a strength alteration such as enhancement or reduction of a biochemical or biological activity due to a mutation based on a mutated amino acid occurring within the positive signature.

17. The computer-implemented method of claim 14, wherein providing the graphic depiction of the mutational impact comprises:

displaying a mutation within various genetic elements in the non-protein coding RNA gene, on the gene structure or sequence in the one or more patients; and depicting various steps in processing of a transcript from the non-protein coding RNA gene into an active RNA element, or elaborating the various steps in a structure or sequence view, indicating a step of the various steps at which an error occurs.

18. A computer-implemented method comprising:

receiving a nucleotide string comprising a plurality of nucleotides from at least a portion of one or more individual patients genome, wherein the portion of the genome includes at least one of: a 5'-UTR, a promoter, an enhancer, a silencer, an exon, an intron, a coding sequence, a splice acceptor, a splice donor, a branch point site, a 3'-UTR, a Kozak sequence, a poly-A addition site or signal, or a cryptic version thereof, from a known protein coding gene or a regulatory, splicing, or functional element of a non-protein coding RNA gene, and within the genes not yet identified in a Dark Matter genome;

providing, via a display, a first graphical representation of a chromosome or a genome on a single line drawn to scale within a view of a computer or expanded view;

providing, via the display, a second graphical representation of protein coding genes or non-protein coding RNA genes contained in a chromosome or a genome on the single line; and depicting, via the display, separate features comprising variations, mutations, consequences, genes, genetic elements, diseases, domains, biochemical functions, zygosity, or other genetically or clinically relevant features, details, or their frequencies, from the one or more individual patients in separate graphical notations, and overlaying, on multi-track genome-scale single lines, variants and rendering, in interactive popovers and mouseovers, aligned sequence read evidence with read counts and allele-frequency values from SAM/BAM and VCF files, and automatically updating overlays and evidence in real time responsive to user interactions and availability of updated analysis outputs.

19. The computer-implemented method of claim 18, further comprising, providing multiple single lines representing the chromosome or a genome drawn to scale to depict different themes such as pathogenicity, mutational consequence, diagnostic, therapeutic, or pharmacogenomic genes, biomarkers, drugs, genes that occur in various disease or drug response gene panels, gene family, domains, biochemical functions, mismatch repair (MMR) genes, tumor mutation burden (TMB), microsatellite instability status (MSI) status or immunotherapy, or their frequencies, in the one or more individual patients, enabling toggled depiction for different features;

graphically depicting a mutation or a frequency of different genetic or clinical features in the genetic elements including exons, introns, acceptors, donors, branch point sites, promoters, Kozaks, poly-A signals or sites, enhancers or silencers of regulatory or splicing elements, or cryptic versions thereof, in the genes, and corresponding themes on the chromosome or the genome drawn to scale, in the one or more individual patients.

20. The computer-implemented method of claim 18, further comprising:

graphically depicting a genetic or clinical feature, or frequency of patients or genes with mutations, in one or more coding, regulatory or splicing elements, or cryptic versions, in the known protein coding gene or the non-protein coding RNA gene, in the one or more individual patients, on the single line drawn to chromosome or genome scale;

customizing, on the display, visualizations using features such as table icons, bar plots, toggle buttons, lists, dropdowns, color codes, modal boxes, popovers, mouseovers, expandable or collapsible icons, auto-scaling, or graphical notations and techniques; and graphically displaying the protein coding or the non-protein coding RNA gene on a positive or a negative strand, intergenic regions, exons, introns, or the regulatory or splicing elements, or the cryptic versions thereof, drawn to the genome scale on the single line, below or above an illustration of details of variants, elements, or frequencies, in the genes, in the one or more individual patients, or enabling toggled depiction or expanded view.

21. The computer-implemented method of claim 18, further comprising, displaying a mutation in the genes, and associated genetic, genomic, clinical, or phenotypic details, from the chromosome or the genome on a single line drawn to scale, wherein chromosomes are linearly arranged by graphical elements such as ideograms to cover the genome, above or below the line representing the genome, within a view of the display.

22. The computer-implemented method of claim 18, further comprising:

displaying chromosomes linearly arranged on a genome scale, and by selection of an individual chromosome, graphically displaying the details of genes, mutations, and associated genetic, genomic, clinical, or phenotypic details, within the chromosome, within a view of a computer display.

23. The computer-implemented method of claim 18, further comprising:

overlaying genomic structural variations or aberrations on the chromosome or the genome drawn to scale on the single line in graphical illustration, such that the genomic structural variations or structural aberrations such as gene fusion, copy number variation, rearrangement, or structural variation are represented on successive lines, in a single view, or multiple views using toggle buttons.

24. The computer-implemented method of claim 18, further comprising, depicting, via the display, toggle buttons, lists, or drop down options to view various elements such as single nucleotide polymorphism (SNP),indel, the genetic elements, or their cryptic versions, disease panels such as a cancer, non-cancer, industrial panels, copy number variation (CNV), structural variation (SV), gene fusion, American College of Medical Genetics (ACMG) secondary findings, other diseases, rearrangement, gene family, immunotherapy, protein domains, mismatch repair (MMR) genes, or tumor mutation burden (TMB), positioned appropriately, and drawn to chromosome or genome scale successively in different groups of lines in a pathogenome graphical view to represent respective details.

25. The computer-implemented method of claim 18, further comprising providing statistical details such as frequency of variants including pathogenic, strength altering, drug response, pharmacogenomic, or metadata information concerning the one or more individual patients in a pathogenome graphical or tabular view of the display.

* * * * *